US011649285B2

(12) United States Patent
Kalabokis et al.

(10) Patent No.: US 11,649,285 B2
(45) Date of Patent: May 16, 2023

(54) IDENTIFICATION OF VSIG3/VISTA AS A NOVEL IMMUNE CHECKPOINT AND USE THEREOF FOR IMMUNOTHERAPY

(71) Applicant: BIO-TECHNE CORPORATION, Minneapolis, MN (US)

(72) Inventors: Vassilios Kalabokis, Fridley, MN (US); Jinghua Wang, Shoreview, MN (US); Guoping Wu, Blaine, MN (US); Jose Fernando Bazan, Stillwater, MN (US); Christopher Carlin Valley, Minnetonka, MN (US)

(73) Assignee: BIO-TECHNE CORPORATION, Minneapolis, MN (US)

( * ) Notice: Subject to any disclaimer, the term of this patent is extended or adjusted under 35 U.S.C. 154(b) by 663 days.

(21) Appl. No.: 16/322,268

(22) PCT Filed: Aug. 3, 2017

(86) PCT No.: PCT/US2017/045314
§ 371 (c)(1),
(2) Date: Jan. 31, 2019

(87) PCT Pub. No.: WO2018/027042
PCT Pub. Date: Feb. 8, 2018

(65) Prior Publication Data
US 2019/0194322 A1 Jun. 27, 2019

Related U.S. Application Data

(60) Provisional application No. 62/370,395, filed on Aug. 3, 2016.

(51) Int. Cl.
*C07K 16/28* (2006.01)
(52) U.S. Cl.
CPC ...... *C07K 16/2803* (2013.01); *C07K 16/2827* (2013.01); *C07K 2317/75* (2013.01); *C07K 2317/76* (2013.01)
(58) Field of Classification Search
CPC ............ C07K 16/2803; C07K 16/2827; C07K 2317/75; C07K 2317/76
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant, Jr. et al. | |
| 4,447,233 A | 5/1984 | Mayfield | |
| 4,486,194 A | 12/1984 | Josso et al. | |
| 4,487,603 A | 12/1984 | Harris | |
| 4,596,556 A | 6/1986 | Morrow et al. | |
| 4,741,900 A | 5/1988 | Alvarez et al. | |
| 4,790,824 A | 12/1988 | Morrow et al. | |
| 4,941,880 A | 7/1990 | Burn | |
| 5,064,413 A | 11/1991 | McKinnon et al. | |
| 5,223,409 A | 6/1993 | Ladner et al. | |
| 5,283,173 A | 2/1994 | Fields et al. | |
| 5,312,335 A | 5/1994 | McKinnon et al. | |
| 5,383,851 A | 1/1995 | McKinnon, Jr. et al. | |
| 5,399,163 A | 3/1995 | Peterson et al. | |
| 5,624,821 A | 4/1997 | Winter et al. | |
| 5,648,260 A | 7/1997 | Winter et al. | |
| 5,677,425 A | 10/1997 | Bodmer et al. | |
| 5,714,350 A | 2/1998 | Co et al. | |
| 5,869,045 A | 2/1999 | Hellstrom et al. | |
| 5,932,448 A | 8/1999 | Tso et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,277,375 B1 | 8/2001 | Ward | |
| 6,350,861 B1 | 2/2002 | Co et al. | |
| 6,562,576 B2 | 5/2003 | Manfredi | |
| 6,790,624 B2 | 9/2004 | Mayer | |
| 6,982,323 B1 | 1/2006 | Wang et al. | |

(Continued)

FOREIGN PATENT DOCUMENTS

| EP | 2275544 A2 | 1/2011 |
|---|---|---|
| EP | 1176195 B1 | 5/2013 |

(Continued)

OTHER PUBLICATIONS

Rudikoff et al. (Proc. Natl. Acad. Sci. USA, 79(6):1979-1983, Mar. 1982) (Year: 1982).*
Paul, Fundamental Immunology, 3rd Edition, 1993, pp. 292-295 (Year: 1993).*
Colman P. M. (Research in Immunology, 145:33-36, 1994) (Year: 1994).*
Bendig M. M. (Methods: A Companion to Methods in Enzymology, 1995; 8:83-93) (Year: 1995).*
Padlan (Advances in Protein Chemistry, 1996, 49:57-133) (Year: 1996).*
Watanabe (Cancer Sci. Aug. 2005;96(8):498-506, published Aug. 15, 2005) (Year: 2005).*
Berglund (Protein Science, 2008, 17:606-613) (Year: 2008).*
R&D Systems (Human/Mouse VSIG3 Antibody, AF4915; R&D Systems; commercially available Jul. 5, 2015) (Year: 2015).*
Murphy et al. (Journal of Immunological Methods, vol. 463, p. 127-133, 2018) (Year: 2018).*

(Continued)

*Primary Examiner* — Julie Wu
*Assistant Examiner* — Sung Min Yoon
(74) *Attorney, Agent, or Firm* — Mueting Raasch Group

(57) ABSTRACT

The ligand for VISTA is identified (VSIG3) as well as the use of this ligand and receptor interaction in the identification or synthesis of a VSIG3 agonist or antagonist compounds, preferably antibodies, polypeptides and fusion proteins which agonize or antagonize the effects of VSIG3 and/or VISTA and/or the VSIG3/VISTA interaction. These antagonists may be used to suppress VSIG3/VISTA's suppressive effects on T cell immunity, and more particularly used in the treatment of cancer, or infectious disease. These agonist compounds may be used to potentiate or enhance VSIG3/VISTA's suppressive effects on T cell immunity and thereby suppress T cell immunity, such as in the treatment of autoimmunity, allergy or inflammatory conditions. Screening assays for identifying these agonists and antagonist compounds are also provided.

21 Claims, 41 Drawing Sheets

Specification includes a Sequence Listing.

(56) References Cited

U.S. PATENT DOCUMENTS

| | | |
|---|---|---|
| 9,381,244 B2 | 7/2016 | Noelle |
| 2004/0110704 A1 | 6/2004 | Yamane et al. |
| 2006/0025576 A1 | 2/2006 | Miller et al. |
| 2006/0034852 A1 | 2/2006 | Rixon et al. |
| 2008/0069820 A1 | 3/2008 | Fuh et al. |
| 2014/0220012 A1 | 8/2014 | Noelle et al. |
| 2014/0341920 A1 | 11/2014 | Noelle |
| 2016/0083472 A1 | 3/2016 | Noelle et al. |
| 2016/0159927 A1 | 6/2016 | Molloy et al. |
| 2020/0362031 A1 | 11/2020 | Goetz et al. |

FOREIGN PATENT DOCUMENTS

| | | | |
|---|---|---|---|
| WO | WO 90/02809 A1 | 3/1990 | |
| WO | WO 91/17271 A1 | 11/1991 | |
| WO | WO 92/01047 A1 | 1/1992 | |
| WO | WO 92/01288 A1 | 1/1992 | |
| WO | WO 92/09690 A3 | 6/1992 | |
| WO | WO 92/15679 A1 | 9/1992 | |
| WO | WO 92/18619 A1 | 10/1992 | |
| WO | WO 92/20791 A1 | 11/1992 | |
| WO | WO 99/54342 A1 | 10/1999 | |
| WO | WO 00/42072 A3 | 7/2000 | |
| WO | WO 01/00814 A3 | 1/2001 | |
| WO | WO 02/043478 A2 | 6/2002 | |
| WO | WO 02/092780 A3 | 11/2002 | |
| WO | WO 03/035835 A2 | 5/2003 | |
| WO | WO 03/074679 A2 | 9/2003 | |
| WO | WO 06/050247 A2 | 5/2006 | |
| WO | WO 06/050262 A2 | 5/2006 | |
| WO | WO 13/184912 A2 | 12/2013 | |
| WO | 2015/097536 | 7/2015 | |
| WO | WO 2015/097536 A2 * | 7/2015 | ............ C07K 16/28 |
| WO | WO 18/027042 A1 | 2/2018 | |
| WO | WO 19/152810 A1 | 8/2019 | |

OTHER PUBLICATIONS

Wang J, Wu G, Manick B, et al. VSIG-3 as a ligand of VISTA inhibits human T-cell function. Immunology. 2019;156(1):74-85 (Year: 2019).*

Chen (Sci Adv. Apr. 1, 2020;6(14):eaaz7825) (Year: 2020).*

Yuan L, Tatineni J, Mahoney KM, Freeman GJ. VISTA: A Mediator of Quiescence and a Promising Target in Cancer Immunotherapy. Trends Immunol. Mar. 2021;42(3):209-227. doi: 10.1016/j.it.2020.12.008. Epub Jan. 23, 2021 (Year: 2021).*

Mehta N, Maddineni S, Kelly RL, Lee RB, Hunter SA, Silberstein JL, Parra Sperberg RA, Miller CL, Rabe A, Labanieh L, Cochran Jr. An engineered antibody binds a distinct epitope and is a potent inhibitor of murine and human VISTA. Sci Rep. Sep. 16, 2020;10(1):15171. (Year: 2020).*

Edwards BM et al. The remarkable flexibility of the human antibody repertoire; isolation of over one thousand different antibodies to a single protein, BLyS. J Mol Biol. Nov. 14, 2003;334(1):103-18 (Year: 2003).*

Justin Bryan Goh & Say Kong Ng (2018) Impact of host cell line choice on glycan profile, Critical Reviews in Biotechnology, 38:6, 851-867 (Year: 2018).*

Aalberse et al., IgG4 breaking the rules. *Immunology* 105, 9-19 (2002).

Ailan et al., Identification of target genes of transcription factor activator protein 2 gamma in breast cancer cells. *BMC Cancer* 9, 279 (2009).

Altschul et al., Basic local alignment search tool. *J Mol Biol* 215, 403-410 (1990).

Altschul et al., Gapped BLAST and PSI-BLAST: a new generation of protein database search programs. *Nucleic Acids Res* 25, 3389-3402 (1997).

Angal et al., A single amino acid substitution abolishes the heterogeneity of chimeric mouse/human (IgG4) antibody. *Mol Immunol* 30, 105-108 (1993).

Bork et al., The immunoglobulin fold. Structural classification, sequence patterns and common core. *J Mol Biol* 242, 309-320 (1994).

Bushell et al., Large-scale screening for novel low-affinity extracellular protein interactions. *Genome Res* 18, 622-630 (2008).

Chan et al., Therapeutic antibodies for autoimmunity and inflammation. *Nat Rev Immunol* 10, 301-316 (2010).

Chothia et al., Canonical structures for the hypervariable regions of immunoglobulins. *J Mol Biol* 196, 901-917 (1987).

Cox et al., A directory of human germ-line V kappa segments reveals a strong bias in their usage. *Eur J Immunol* 24, 827-836 (1994).

Eom et al., Melanophore migration and survival during zebrafish adult pigment stripe development require the immunoglobulin superfamily adhesion molecule Igsf11. *PLoS Genet* 8, e1002899 (2012).

Flies et al., Coinhibitory receptor PD-1H preferentially suppresses CD4(+) T cell-mediated immunity. *J Clin Invest* 124, 1966-1975 (2014).

Harvey et al., The Hippo pathway and human cancer. *Nat Rev Cancer* 13, 246-257 (2013).

Holliger et al., "Diabodies": small bivalent and bispecific antibody fragments. *Proc Natl Acad Sci U S A* 90, 6444-6448 (1993).

Horita et al., High-resolution crystal structure of the therapeutic antibody pembrolizumab bound to the human PD-1. *Sci Rep* 6, 35297 (2016).

International Search Report and Written Opinion for PCT/US17/45314 dated Nov. 6, 2017, 15 pages.

International Preliminary Report on Patentability for PCT/US17/45314 dated Feb. 14, 2019, 8 pages.

Jang et al., Synaptic adhesion molecule IgSF11 regulates synaptic transmission and plasticity. *Nat Neurosci* 19, 84-93 (2016).

Jones et al., Replacing the complementarity-determining regions in a human antibody with those from a mouse. *Nature* 321, 522-525 (1986).

Kohler et al., Continuous cultures of fused cells secreting antibody of predefined specificity. *Nature* 256, 495-497 (1975).

Kohler et al., Derivation of specific antibody-producing tissue culture and tumor lines by cell fusion. *Eur J Immunol* 6, 511-519 (1976).

Kostelny et al., Formation of a bispecific antibody by the use of leucine zippers. *J Immunol* 148, 1547-1553 (1992).

Lazar-Molnar et al., Crystal structure of the complex between programmed death-1 (PD-1) and its ligand PD-L2. *Proc Natl Acad Sci U S A* 105, 10483-10488 (2008).

Lin et al., The PD-1/PD-L1 complex resembles the antigen-binding Fv domains of antibodies and T cell receptors. *Proc Natl Acad Sci U S A* 105, 3011-3016 (2008).

Liu et al., Immune-checkpoint proteins VISTA and PD-1 nonredundantly regulate murine T-cell responses. *Proc Natl Acad Sci U S A* 112, 6682-6687 (2015).

Malashkevich et al., The crystal structure of a five-stranded coiled coil in COMP: a prototype ion channel? *Science* 274, 761-765 (1996).

Meyers et al. (Comput. Appl. Biosci., 4: 11-17 (1988)).

Mueller et al., Humanized porcine VCAM-specific monoclonal antibodies with chimeric IgG2/G4 constant regions block human leukocyte binding to porcine endothelial cells. *Mol Immunol* 34, 441-452 (1997).

Needleman et al., A general method applicable to the search for similarities in the amino acid sequence of two proteins. *J Mol Biol* 48, 443-453 (1970).

Nowak et al., Immunoregulatory functions of VISTA. *Immunol Rev* 276, 66-79 (2017).

Orlandi et al., Cloning immunoglobulin variable domains for expression by the polymerase chain reaction. *Proc Natl Acad Sci U S A* 86, 3833-3837 (1989).

Ozkan et al., An extracellular interactome of immunoglobulin and LRR proteins reveals receptor-ligand networks. *Cell* 154, 228-239 (2013).

Pan et al., 1L-1H, an interleukin 1-related protein that binds IL-18 receptor/IL-1Rrp. *Cytokine* 13, 1-7 (2001).

Presta, Molecular engineering and design of therapeutic antibodies. *Curr Opin Immunol* 20, 460-470 (2008).

(56) References Cited

OTHER PUBLICATIONS

Prodeus et al., VISTA.COMP—an engineered checkpoint receptor agonist that potently suppresses T cell-mediated immune responses. *JCI Insight* 2, (2017).
Ramos et al., "Mechanisms of Resistance to Immune Checkpoint Antibodies", *Handbook of Experimental Pharmacology*, (2017).
Rubinstein et al., Functional classification of immune regulatory proteins. *Structure* 21, 766-776 (2013).
Santus et al., "Osmotic drug delivery: a review of the patent literature" *J. Controlled Release*, 35(2):1-21 (1995).
Shields et al., High resolution mapping of the binding site on human IgG1 for Fc gamma RI, Fc gamma RII, Fc gamma RIII, and FcRn and design of IgG1 variants with improved binding to the Fc gamma R. *J Biol Chem* 276, 6591-6604 (2001).
Singer et al., Optimal humanization of 1B4, an anti-CD18 murine monoclonal antibody, is achieved by correct choice of human V-region framework sequences. *J Immunol* 150, 2844-2857 (1993).
Smith et al., Phage Display. *Chem Rev* 97, 391-410 (1997).
Smith and Waterman (1981) *Advances in Applied Mathematics* 2:482-489.
Songsivilai et al., Bispecific antibody: a tool for diagnosis and treatment of disease. *Clin Exp Immunol* 79, 315-321 (1990).
Stavenhagen et al., Fc optimization of therapeutic antibodies enhances their ability to kill tumor cells in vitro and controls tumor expansion in vivo via low-affinity activating Fcgamma receptors. *Cancer Res* 67, 8882-8890 (2007).
Stengel et al., Structure of TIGIT immunoreceptor bound to poliovirus receptor reveals a cell-cell adhesion and signaling mechanism that requires cis-trans receptor clustering. *Proc Natl Acad Sci U S A* 109, 5399-5404 (2012).
Swann et al., Considerations for the development of therapeutic monoclonal antibodies. *Curr Opin Immunol* 20, 493-499 (2008).
Takeda et al., Construction of chimaeric processed immunoglobulin genes containing mouse variable and human constant region sequences. *Nature* 314, 452-454 (1985).
Tomlinson et al., The repertoire of human germline VH sequences reveals about fifty groups of VH segments with different hypervariable loops. *J Mol Biol* 227, 776-798 (1992).
Traunecker et al., Bispecific single chain molecules (Janusins) target cytotoxic lymphocytes on HIV infected cells. *EMBO J* 10, 3655-3659 (1991).
Wang et al., "VSIG-3/IGSF11 is a ligand of VISTA/PD-1H and inhibits human T cell function", *J. Immunol*, 198 (1 Supplement) 154.1 (May 1, 2017).
Watanabe et al., Identification of immunoglobulin superfamily 11 (IGSF11) as a novel target for cancer immunotherapy of gastrointestinal and hepatocellular carcinomas. *Cancer Sci* 96, 498-506 (2005).
Yang et al., Construction of a versatile expression library for all human single-pass transmembrane proteins for receptor pairings by high throughput screening. *J Biotechnol* 260, 18-30 (2017).
Traunecker et al., Janusin: new molecular design for bispecific reagents. Int J Cancer Suppl 7, 51-52 (1992).
Wang et al., "VSIG-3/IGSF11 is a Ligand of VISTA/PD-1H and Inhibits Human T Cell Function" Abstract 154.1, presented at American Association of Immunology Conference, Washington DC, May 14, 2017; Retrieved from the Internet, Sep. 2021: app.core-apps.com/aai2017/abstract/9a14bff0a8f35af893c384cf61639cf1. 1 page.
Wang et al., "VSIG-3/IGSF11 is a Ligand of VISTA/PD-1H and Inhibits Human T Cell Function" Poster presented at American Association of Immunology conference, Washington DC, May 14, 2017, 1 page.
"Bio-Techne Corporation Brands" Retrieved on Jan. 19, 2022. Copyright 2022. Retrieved from: www.bio-techne.com/about/bio-techne-brands. 3 pages.
"About Us: R&D Systems" Retrieved on Jan. 19, 2022. Copyright 2022. Retrieved from: www.rndsystems.com/about-us. 2 pages.

\* cited by examiner

FIG. 6
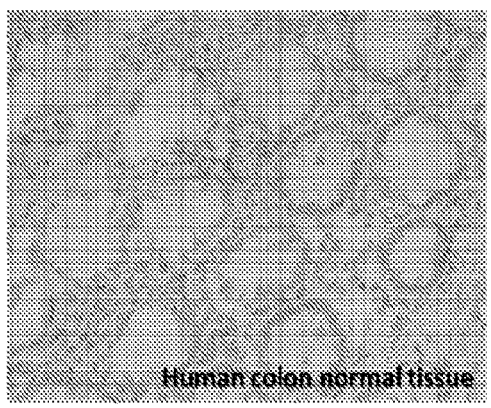
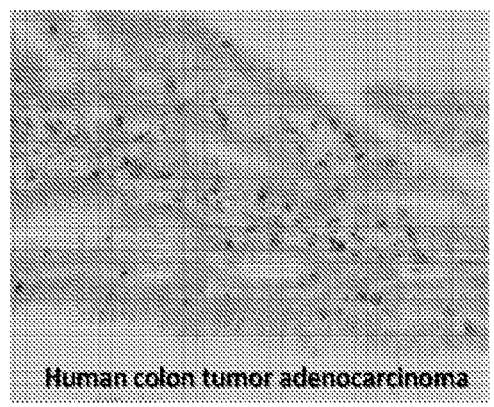

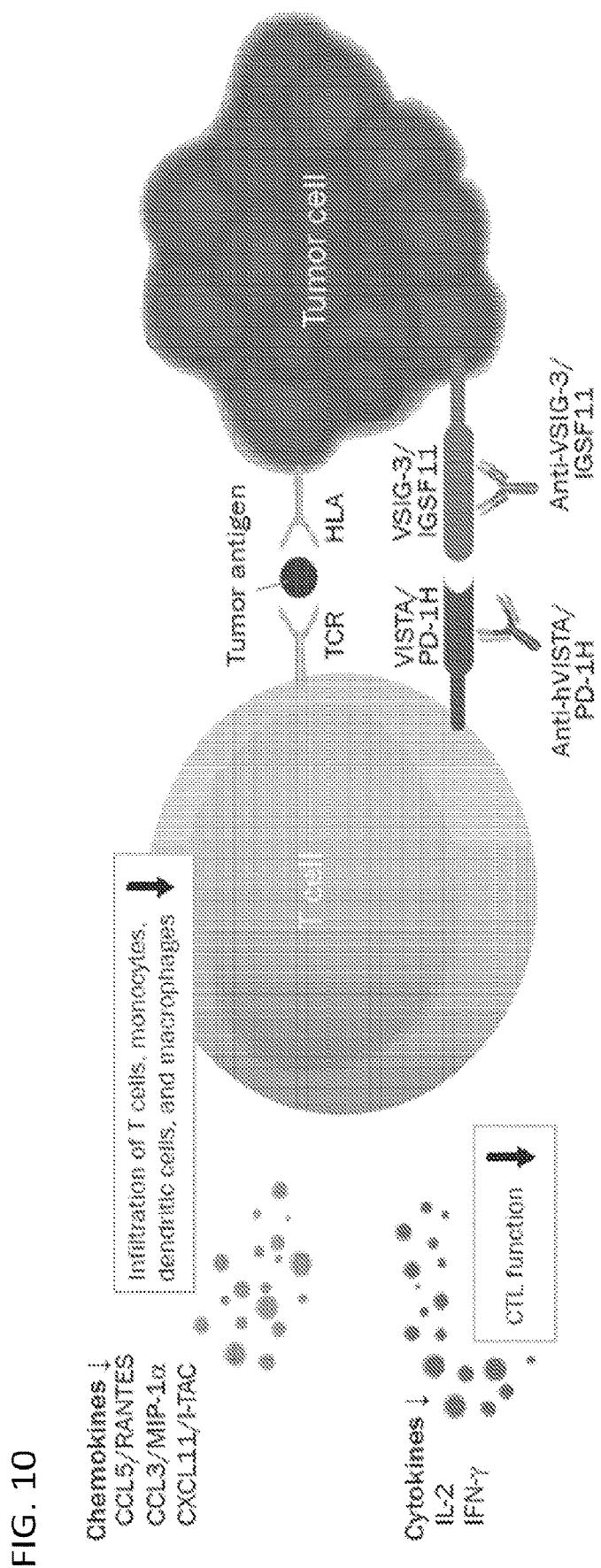

| | | |
|---|---|---|
| 774213R-LC_CDR1 | RASqdI-----hkYva | (SEQ ID NO:9) |
| 774221R-LC_CDR1 | RASenI-----NSYla | (SEQ ID NO:10) |
| 774226R-LC_CDR1 | RtSenI-----NSYla | (SEQ ID NO:11) |
| 973435R-LC_CDR1 | RASqSI-----Snnlh | (SEQ ID NO:17) |
| 973422R-LC_CDR1 | RASSSv------SYih | (SEQ ID NO:14) |
| 973428R-LC_CDR1 | RASkSv-stsGySYmh | (SEQ ID NO:15) |
| 774206R-LC_CDR1 | RASSSv------Symh | (SEQ ID NO:7) |
| 973401R-LC_CDR1 | sASSSv------Sfmh | (SEQ ID NO:12) |
| 973408R-LC_CDR1 | sASSSv------SYmh | (SEQ ID NO:13) |
| 973433R-LC_CDR1 | RsSqSIVhSNGNtYle | (SEQ ID NO:16) |
| 774208R-LC_CDR1 | RsSqSlldSDGktYlh | (SEQ ID NO:8) |
| | | |
| 774221R-LC_CDR2 | naktlae | (SEQ ID NO:21) |
| 774226R-LC_CDR2 | naktlae | (SEQ ID NO:22) |
| 774213R-LC_CDR2 | yaStlqp | (SEQ ID NO:20) |
| 973435R-LC_CDR2 | yasqsis | (SEQ ID NO:28) |
| 973433R-LC_CDR2 | kvSNrfS | (SEQ ID NO:27) |
| 774208R-LC_CDR2 | lvSkLdS | (SEQ ID NO:19) |
| 973428R-LC_CDR2 | laSNLeS | (SEQ ID NO:26) |
| 973401R-LC_CDR2 | lTSNLAS | (SEQ ID NO:23) |
| 973408R-LC_CDR2 | lTSNLAS | (SEQ ID NO:24) |
| 973422R-LC_CDR2 | aTSNLAS | (SEQ ID NO:25) |
| 774206R-LC_CDR2 | aTSNLAS | (SEQ ID NO:18) |
| | | |
| 774213R-LC_CDR3 | lQydNllfT | (SEQ ID NO:31) |
| 774221R-LC_CDR3 | QhhygtPpT | (SEQ ID NO:32) |
| 774226R-LC_CDR3 | QhhygtPpT | (SEQ ID NO:33) |
| 973428R-LC_CDR3 | QhsrelPyT | (SEQ ID NO:37) |
| 774208R-LC_CDR3 | wQgThfPyT | (SEQ ID NO:30) |
| 973433R-LC_CDR3 | fQgShvPpT | (SEQ ID NO:38) |
| 973401R-LC_CDR3 | QQwSSnPlT | (SEQ ID NO:34) |
| 973408R-LC_CDR3 | QQwSSnPlT | (SEQ ID NO:35) |
| 973422R-LC_CDR3 | QQwSSnPfT | (SEQ ID NO:36) |
| 774206R-LC_CDR3 | QQwSSdPpT | (SEQ ID NO:29) |
| 973435R-LC_CDR3 | QQsNSwPlT | (SEQ ID NO:39) |

FIG. 18B

| | | |
|---|---|---|
| 774213R-HC_CDR1 | -sfgmh | (SEQ ID NO:42) |
| 973435R-HC_CDR1 | -gYymh | (SEQ ID NO:50) |
| 973422R-HC_CDR1 | -sYsms | (SEQ ID NO:47) |
| 774206R-HC_CDR1 | -sYsms | (SEQ ID NO:40) |
| 774208R-HC_CDR1 | -sYsms | (SEQ ID NO:41) |
| 973428R-HC_CDR1 | -sYgms | (SEQ ID NO:48) |
| 973401R-HC_CDR1 | -tYtih | (SEQ ID NO:45) |
| 973408R-HC_CDR1 | -sYtmh | (SEQ ID NO:46) |
| 774221R-HC_CDR1 | SdYawn | (SEQ ID NO:43) |
| 774226R-HC_CDR1 | SdYawn | (SEQ ID NO:44) |
| 973433R-HC_CDR1 | -dYvit | (SEQ ID NO:49) |
| 774213R-HC_CDR2 | YIssGsttiYYaDTVKG | (SEQ ID NO:53) |
| 973428R-HC_CDR2 | iIssGgsTYYpDsVKG | (SEQ ID NO:59) |
| 973422R-HC_CDR2 | YInGgGsTYYpDTVKG | (SEQ ID NO:58) |
| 774206R-HC_CDR2 | YInGgGsTYYpDTVKG | (SEQ ID NO:51) |
| 774208R-HC_CDR2 | YInGgGspYYpDTVKG | (SEQ ID NO:52) |
| 973433R-HC_CDR2 | eIyprSGsTYYKnfKG | (SEQ ID NO:60) |
| 774221R-HC_CDR2 | YISy-SGYaiYKpslKs | (SEQ ID NO:54) |
| 774226R-HC_CDR2 | YISy-SGYtYKpslKs | (SEQ ID NO:55) |
| 973401R-HC_CDR2 | YInpsSGYTeYKqkfKd | (SEQ ID NO:56) |
| 973408R-HC_CDR2 | YInpsSGYTeYKqkfKd | (SEQ ID NO:57) |
| 973435R-HC_CDR2 | YIscsnGastYKqkfKG | (SEQ ID NO:61) |
| 774213R-HC_CDR3 | gSYyrydlyyamdY | (SEQ ID NO:64) |
| 973428R-HC_CDR3 | lSYyygSspyamdY | (SEQ ID NO:70) |
| 973401R-HC_CDR3 | ---revyGsgsmdY | (SEQ ID NO:67) |
| 973408R-HC_CDR3 | ---revyGsgamdY | (SEQ ID NO:68) |
| 973433R-HC_CDR3 | -----------gdY | (SEQ ID NO:71) |
| 973422R-HC_CDR3 | ---hgdgyypWFAY | (SEQ ID NO:69) |
| 774206R-HC_CDR3 | ---hdgnypWFAY | (SEQ ID NO:62) |
| 973435R-HC_CDR3 | ------SGetpFAY | (SEQ ID NO:72) |
| 774208R-HC_CDR3 | --lldsSGyvWFAY | (SEQ ID NO:63) |
| 774221R-HC_CDR3 | -------SGgsWFAY | (SEQ ID NO:65) |
| 774226R-HC_CDR3 | -------SGgsWFAY | (SEQ ID NO:66) |

FIG. 19A

```
973435 MvFtpQIlglmLf---wisaSRGDIVLTQSPAtLSvtPGdsVslSCRASqSi------snnl
973422 MDFQVQIFsFLLiSASVvMSRGqIVLsQSPAiLSASPGEKVTMtCRASSSV------SYi
973401 MDFQVQIFsFLLMSASViMSRGqIVLTQSPAlmSASPGEKVTMtCsASSSV------SFM
973408 MDFQVQIFsFLLMSASViMSRGqIVLTQSPAlmSASPGEKVTMtCsASSSV------SYM
973428 MEtdtlllwvLLL---wVpgStGDIVLTQSPAsLavSlGqRaTiSCRASkSV-sTSGySYM
973433 MklpVrllvlmf----wipaSssDvlmTQtPlsLpvSlGdqasiSCRsSqSivhSNGntYl 973435 HWYQQKsheSPrLLIkyaSqsiSGiPsRFSGSGSGTDFtLsInSVEtEDfgmYfCQQsnS
973422 HWYQQKPGSSPKpwIYaTSNLaSGVPARFSGSGSGTsySLTISrVEAEDAATYYCQQWSS
973401 YWYhQKPrSSPKpwIYlTSNLaSGVPARFSGSGSGTsySLTISSmEAEDAATYYCQQWSS
973408 nWYQQKPrSSPKpwIYlTSNLaSGVPARFSGSGSGTsySLTISSmEAEDAATYYCQQWSS
973428 HWYQQKPGqSPKLLIYlaSNLeSGVPARcSGSGSGTDFtLnIhpVEeEDAATYYCQhsre
973433 eWYlQKPGqSPKLLIYkvSNrfSGVPdRFSGSGSGTDFtLkISrVEAEDlgvYYCfQgSh 973435 wPlTFGAGTKLElKRADAAPTVSIFP    (SEQ ID NO:78)
973422 nPfTFasGTKLEIKRADAAPTVSIFP    (SEQ ID NO:75)
973401 nPlTFGAGTKLElKRADAAPTVSIFP    (SEQ ID NO:73)
973408 nPlTFGAGTKLElKRADAAPTVSIFP    (SEQ ID NO:74)
973428 lPyTFGgGTKLEIKRADAAPTVSIFP    (SEQ ID NO:76)
973433 vPpTFGgGTKLEIKRADAAPTVSIFP    (SEQ ID NO:77)
```

FIG. 19B

```
973422 Mnfgl-smiFLvlvlkGVlcEVkLveSGggLVqPGgSlKlSCaASGfTFsSYsMsWVrQt
973428 Mnfgl-sliFLalilkGVqcEVQLveSGgDLVKPGqSlKlSCaASGfTFnSYgMsWVrQt
973435 MgwiW-IFLFLLSgTAGVHSEVQvQQSGpELVKtGASVKiSCKASGYsFTgYyMHWVKQs
973401 MErhW-IFLFLLSvTAGVHSqVQLQQSaAELarPGASVKMSCKASGYTFaTYtiHWVKQR
973408 MErhW-IFLFLLSvTAGVHSqVQLQQSaAELarPGASVKMSCKASGYTFTSYtMHWVKQR
973433 --meWrIFLFiLSgTAGVHSqVQLQQSGpELVKPGASVKMSCKASGYTFTdYvitWVKQR 973422 PekrLEWvaYISnggGsTYYpdtvKGrfTIsrDnakNTlYlQMSSLkSEDtAmYYCAR---
973428 PdkrLEWvaiISsggsYTYYpdsvKGrfTIsrDnakNTlYlQMSSLkSEDtAmYYCARls
973435 hGmsLEWIGYIScSnGastYNQKFKGKaTfTvDtSSsTAYMQfnSLTSEDSAVYYCAR---
973401 PGQGLEWIGYINpSSGYTeYNQKFKdKtTLTADKSsTAYMQLSSLTSEDSAVYYCAR-R
973408 PGQGLEWIGYINpSSGYTeYNQKFKdKtTLTADKSsTAYMQLSSLTSEDSAVYYCAR-R
973433 tGQGLEWIGeIyprSGsTYYNenFKGKaTLTADKSSNTAYMQLSSLTSEDSAVYfCAR---

973422 --HGdGyYpwfaYWGQGTlVTVSaAKTTPPSVYPLAPGCgdtTGSsVTLGC    (SEQ ID NO:81)
973428 yyYGSspYa-MDYWGQGTSVTiSSAKTTPPSVYPLAPGsAAQTnSMVTLGC    (SEQ ID NO:82)
973435 --sGetp---faYWGQGTlVTVSaAKTTPPSVYPLAPGCgdtTGSsVTLGC    (SEQ ID NO:84)
973401 EVYGSGs----MDYWGQGTSVTVSSAKTTPPSVYPLAPGsAAQTnSMVTLGC    (SEQ ID NO:79)
973408 EVYGSGa----MDYWGQGTSVTVSSAKTTPPSVYPLAPGsAAQTnSMVTLGC    (SEQ ID NO:80)
973433 ----------gDYWGQGTTlTVSSAKTTPPSVYPLAPGCgdtTGSsVTLGC    (SEQ ID NO:83)
```

FIG. 19C

```
774213    MrpsIQfLgLLLfWlhg--aqcDIqmTQSPsSLSASlGgKVTITCKASqdI-hk----Yv
774221    MsvptQVLgLLLLWlTg--aRcDIqmTQSPASLSASvGEtVTITCRASenI-nS----YL
774226    MsvptQVLgLLLLWlTg--aRcDIqmTQSPASLSASvGEtVnITCRtSenI-nS----YL
774208    MmspaQfLfLLvLWire--tnGDvVmTQtPlTLSvtiGqpasIsCKsSqSlLdSdGkTYL
774206    MDFQVQIfSfLLIsASvIMSRGqIVLsQSPAiLSASPGEKVTmCRASSSv-S-----Ym 774213    aWYQhKPGkgPrLLIhyTStLqpGiPSRFSGSGSGsDySfsISNlEpaDiAsYYClQydN
774221    aWYQQKqGkSPqLLvYnaktLAeGVPSRFSGSGSGTqFSLkInSlqpEDfgsYYCQhhyg
774226    aWYQQKqGkSPqLLvYnaktLAeGVPSRFSGSGSGTqFSLkInSlqpEDfgsYYCQhhyg
774208    NWllQrPGqSPKrLIYlvSkLdSGVPdRFtGSGSGTDFtLkISrVEAEDlgvYYCwQgTh
774206    HWYQQKPGSSPKpwIYaTSNLASGVPARFSGSGSGTsySLTISrVEAEDAATYYCQQwSS 774213    llfTFGGGTKLEIKRADAAPTVSIFPPSSEQLTSGGASVVCFLNNFYPKDINVKWKIDGS
774221    tPpTFGGGTKLEIKRADAAPTVSIFPPSSEQLTSGGASVVCFLNNFYPKDINVKWKIDGS
774226    tPpTFGGGTKLEIKRADAAPTVSIFPPSSEQLTSGGASVVCFLNNFYPKDINVKWKIDGS
774208    fPyTFGGGTKLEIKRADAAPTVSIFPPSSEQLTSGGASVVCFLNNFYPKDINVKWKIDGS
774206    dPpTFGrGTKLEIKRADAAPTVSIFPPSSEQLTSGGASVVCFLNNFYPKDINVKWKIDGS 774213    ERQNGVLNSWTDQDSKDSTYSMSSTLTLTKDEYERHNSYTCEATHKTSTSPIVKSFNRNE
774221    ERQNGVLNSWTDQDSKDSTYSMSSTLTLTKDEYERHNSYTCEATHKTSTSPIVKSFNRNE
774226    ERQNGVLNSWTDQDSKDSTYSMSSTLTLTKDEYERHNSYTCEATHKTSTSPIVKSFNRNE
774208    ERQNGVLNSWTDQDSKDSTYSMSSTLTLTKDEYERHNSYTCEATHKTSTSPIVKSFNRNE
774206    ERQNGVLNSWTDQDSKDSTYSMSSTLTLTKDEYERHNSYTCEATHKTSTSPIVKSFNRNE 774213    (SEQ ID NO:87)
774221    (SEQ ID NO:88)
774226    (SEQ ID NO:89)
774208    (SEQ ID NO:86)
774206    (SEQ ID NO:85)
```

FIG. 19D

```
774213    MDsrLnLvFLVlILKGVqcdVQLvESGGGLVqPGGSrKLSCAASGfTFs-SfgMHWVRQa
774206    MNfgLswiFLVpVLKGVLcEVkLvESGrGLVqPGGSLKLSCAASGfTFs-SYsMsWVRQt
774226    -mrvLILLwLftafpGmLSdVQLQESGpGLVKPsqSLsLiCtvtGYsiTSdYawnWiRQf
774221    -mrvLILLwLftafpGiLSdVQLQESGpGLVKPsqSLsLtCtvtGYsiTSdYawnWiRQf
774208    MNfgLsLiFLVlVLKGVLcEVkLvESGGGLVqPGGSLKLSCAASGfTFs-SYsMsWVRlt 774213    PeKGLEWVaYISsGSttiYYaDTVKGRFTIsRDNpKNTLfLQmtSLrSEDTAMYYCtRgS
774206    PeKrLEWVaYISnGgGsTYYpDTVKGRFTIsRDNaKNTLYLQmSSLkSEDTAMYYCAR--
774226    PGnkLEWmGYISy-SGYTtYNpslKsRisITRDtSKNqffLQLnSvTtEDTAtYYCAi--
774221    PGnkLEWmGYISy-SGYaiYNpslKsRisITRDtSKNhffLQLnSvTtEDTAtYYCAR--
774208    PeKrLEWVaYISnGgGspYYpDTVKGRFTIsRDNanNTLYLQmSSLkSEDTAMYfCtRl- 774213    YYrydlyYa-mdYWGQGTsVTVSsAKTTPPSVYPLAPGCGDTTGSSVTLGCLVKGYFPES
774206    ---hdgnYpWFAYWGQGTLVTVSAAKTTPPSVYPLAPGCGDTTGSSVTLGCLVKGYFPES
774226    -----sGgsWFAYWGQGTLVTVSAAKTTPPSVYPLAPGCGDTTGSSVTLGCLVKGYFPES
774221    -----sGgsWFAYWGQGTLVTVSAAKTTPPSVYPLAPGsaaqTnSmVTLGCLVKGYFPEp
774208    --ldssGYvWFSYWGQGTLVTVSAAKTTPPSVYPLAPGsaaqTnSmVTLGCLVKGYFPEp 774213    LEPSGPISTINPCPPCKECHKCPAPNLEGGPSVFIFPPNIKDVLMISLTPKVTCVVVDVS
774206    LEPSGPISTINPCPPCKECHKCPAPNLEGGPSVFIFPPNIKDVLMISLTPKVTCVVVDVS
774226    LEPSGPISTINPCPPCKECHKCPAPNLEGGPSVFIFPPNIKDVLMISLTPKVTCVVVDVS
774221    ivPrd-----cgCkPC----iCtvPev---sSVFIFPPkpKDVLtItLTPKVTCVVVDiS
774208    ivPrd-----cgCkPC----iCtvPev---sSVFIFPPkpKDVLtItLTPKVTCVVVDiS 774213    EDDPDVQISWFVNNVEVHTAQTQTHREDYNSTIRVVSTLPIQHQDWMSGKEFKCKVNNKD
774206    EDDPDVQISWFVNNVEVHTAQTQTHREDYNSTIRVVSTLPIQHQDWMSGKEFKCKVNNKD
774226    EDDPDVQISWFVNNVEVHTAQTQTHREDYNSTIRVVSTLPIQHQDWMSGKEFKCKVNNKD
774221    kDDPeVQfSWFVddVEVHTAQTQpreEqfNSTfRsVSeLPImHQDWlnGKEFKCrVNsaa
774208    kDDPeVQfSWFVddVEVHTAQTQpreEqfNSTfRsVSeLPImHQDWlnGKEFKCrVNsaa 774213    LPSPIERTISKIKGLVRAPQVYILPPPAEQLSRKDVSLTCLVVGFNPGDISVEWTSNGHT
774206    LPSPIERTISKIKGLVRAPQVYILPPPAEQLSRKDVSLTCLVVGFNPGDISVEWTSNGHT
774226    LPSPIERTISKIKGLVRAPQVYILPPPAEQLSRKDVSLTCLVVGFNPGDISVEWTSNGHT
774221    fPaPIEkTISKtKGrpkAPQVYtiPPPkEQmakdkVSLTCmitdFfPeDItVEWqwNGqp
774208    fPaPIEkTISKtKGrpkAPQVYtiPPPkEQmakdkVSLTCmitdFfPeDItVEWqwNGqp 774213    EENYKDTAPVLDSDGSYFIYSKLNMKTSKWEKTDSFSCNVRHEGLKNYYLKKTISRSPGK
774206    EENYKDTAPVLDSDGSYFIYSKLNMKTSKWEKTDSFSCNVRHEGLKNYYLKxTISRSPGK
774226    EENYKDTAPVLDSDGSYFIYSKLNMKTSKWEKTDSFSCNVRHEGLKNYYLKKTISRSPGK
774221    aENYKnTqPimDtDGSYFvYSKLNvqkSnWEagntFtCsVlHEGLhNhhteKslSnSPGK
774208    aENYKnTqPimDtDGSYFvYSKLNvqkSnWEagntFtCsVlHEGLhNhhteKslShSPGK 774213    (SEQ ID NO:92)
774206    (SEQ ID NO:90)
774226    (SEQ ID NO:94)
774221    (SEQ ID NO:93)
774208    (SEQ ID NO:91)
```

FIG. 20A

```
973435    MvEtpQILgLmLfWisa--SRGDIVLTQSPATLSvtPGdsVslsCRASqSI-Sn----nL
774213    MrpsIQfLgLLLfWlhg--aqcDIqmTQSPsSLSASlGgKVTITCKASqdI-hk----Yv
774221    MsvptQVLgLLLIWlTg--aRcDIqmTQSPASLSASvGEtVTITCRASenI-nS----YL
774226    MsvptQVLgLLLIWlTg--aRcDIqmTQSPASLSASvGEtVnITCRtSenI-nS----YL
774208    MmspaQflfLLvIWire--tnGDvVmTQtPlTLSvtiGqpasIsCKsSqSlIdSdGkTYL
973433    MklpVrlL-vLmfWipa--SssDvlmTQtPlSLpvSlGdqasIsCRsSqSIVhSNGnTYL
973428    METdtlllwvLLlWvpg--StGDIVLTQSPASLavSlGqRaTIsCRASkSv-StsGysYm
973401    MDFQVQIfSfLLMsASvIMSRGqIVLTQSPAlmSASPGEKVTmICsASSSv-S-----fm
973408    MDFQVQIfSfLLMsASvIMSRGqIVLTQSPAlmSASPGEKVTmICsASSSv-S-----Ym
774206    MDFQVQIfSfLLIsASvIMSRGqIVLsQSPAiLSASPGEKVTmICRASSSv-S-----Ym
973422    MDFQVQIfSfLLIsASvvMSRGqIVLsQSPAiLSASPGEKVTmICRASSSv-S-----Yi 973435    HWYQQKsheSPrLLIkyaSqsiSGiPSRFSGSGSGTDFtLsInSVEtEDfgmYfCQQsNS
774213    aWYQhKPGkgPrLLIhyTStIqpGiPSRFSGSGSGsDySfsISNlEpaDiAsYYClQydN
774221    aWYQQKqGkSPqLLvYnaktLAeGVPSRFSGSGSGTqFSLkInSlqpEDfgsYYCQhhyg
774226    aWYQQKqGkSPqLLvYnaktLAeGVPSRFSGSGSGTqFSLkInSlqpEDfgsYYCQhhyg
774208    NWllQrPGqSPKrLLYlvSkLdSGVPdRFtGSGSGTDFtLkISrVEAEDlgvYYCwQgIh
973433    eWYlQKPGqSPKLLIYkvSNrfSGVPdRFSGSGSGTDFtLkISrVEAEDlgvYYCfQgSh
973428    HWYQQKPGqSPKLLIYlaSNLeSGVPARcSGSGSGTDFtLnIhpVEeEDAATYYCQhsre
973401    YWYhQKPrSSPKpwIYlTSNLASGVPARFSGSGSGTsySLTISSmEAEDAATYYCQQwSS
973408    NWYQQKPrSSPKpwIYlTSNLASGVPARFSGSGSGTsySLTISSmEAEDAATYYCQQwSS
774206    HWYQQKPGSSPKpwIYaTSNLASGVPARFSGSGSGTsySLTISrVEAEDAATYYCQQwSS
973422    HWYQQKPGSSPKpwIYaTSNLASGVPARFSGSGSGTsySLTISrVEAEDAATYYCQQwSS 973435    wPlTFGaGTKLElKRADAAPTVSIFPPSSEQLTSGGASVVCFLNNFYPKDINVKWKIDGS
774213    llfTFGGGTKLEIKRADAAPTVSIFPPSSEQLTSGGASVVCFLNNFYPKDINVKWKIDGS
774221    tPpTFGGGTKLEIKRADAAPTVSIFPPSSEQLTSGGASVVCFLNNFYPKDINVKWKIDGS
774226    tPpTFGGGTKLEIKRADAAPTVSIFPPSSEQLTSGGASVVCFLNNFYPKDINVKWKIDGS
774208    fPyTFGGGTKLEIKRADAAPTVSIFPPSSEQLTSGGASVVCFLNNFYPKDINVKWKIDGS
973428    lPyTFGGGTKLEIKRADAAPTVSIFPPSSEQLTSGGASVVCFLNNFYPKDINVKWKIDGS
973433    vPpTFGGGTKLEIKRADAAPTVSIFPPSSEQLTSGGASVVCFLNNFYPKDINVKWKIDGS
973401    nPlTFGaGTKLElKRADAAPTVSIFPPSSEQLTSGGASVVCFLNNFYPKDINVKWKIDGS
973408    nPlTFGaGTKLElKRADAAPTVSIFPPSSEQLTSGGASVVCFLNNFYPKDINVKWKIDGS
774206    dPpTFGrGTKLEIKRADAAPTVSIFPPSSEQLTSGGASVVCFLNNFYPKDINVKWKIDGS
973422    nPfTFasGTKLEIKRADAAPTVSIFPPSSEQLTSGGASVVCFLNNFYPKDINVKWKIDGS 973435    ERQNGVLNSWTDQDSKDSTYSMSSTLTLTKDEYERHNSYTCEATHKTSTSPIVKSFNRNE
774213    ERQNGVLNSWTDQDSKDSTYSMSSTLTLTKDEYERHNSYTCEATHKTSTSPIVKSFNRNE
774221    ERQNGVLNSWTDQDSKDSTYSMSSTLTLTKDEYERHNSYTCEATHKTSTSPIVKSFNRNE
774226    ERQNGVLNSWTDQDSKDSTYSMSSTLTLTKDEYERHNSYTCEATHKTSTSPIVKSFNRNE
774208    ERQNGVLNSWTDQDSKDSTYSMSSTLTLTKDEYERHNSYTCEATHKTSTSPIVKSFNRNE
973433    ERQNGVLNSWTDQDSKDSTYSMSSTLTLTKDEYERHNSYTCEATHKTSTSPIVKSFNRNE
973428    ERQNGVLNSWTDQDSKDSTYSMSSTLTLTKDEYERHNSYTCEATHKTSTSPIVKSFNRNE
973401    ERQNGVLNSWTDQDSKDSTYSMSSTLTLTKDEYERHNSYTCEATHKTSTSPIVKSFNRNE
973408    ERQNGVLNSWTDQDSKDSTYSMSSTLTLTKDEYERHNSYTCEATHKTSTSPIVKSFNRNE
774206    ERQNGVLNSWTDQDSKDSTYSMSSTLTLTKDEYERHNSYTCEATHKTSTSPIVKSFNRNE
973422    ERQNGVLNSWTDQDSKDSTYSMSSTLTLTKDEYERHNSYTCEATHKTSTSPIVKSFNRNE
```

FIG. 20B-1

```
774213   MDsrLnIvFLVlILKGVqcdVQLvESGGGLVqPGGSrKLSCAASGfTFs-SfgMHWVRQa
774206   MNfgLswiFLVpVLKGVLcEVkLvESGrGLVqPGGSLKLSCAASGfTFs-SYsMsWVRQt
973422   MNfgLsMiFLVlVLKGVLcEVkLvESGGGLVqPGGSLKLSCAASGfTFs-SYsMsWVRQt
774226   -mrvLILLwLftafpGmLSdVQLQESGpGLVKPsqSLsLiCtvtGYsiTSdYawnWiRQf
973433   Mewr-IfLFiLsgtaGVhSqVQLQqSGpeLVKPGaSvKmSCkASGYTFT-dYvitWVkQr
973435   MgwiwIfLFLLsgtaGVhSEVQvQqSGpeLVKtGaSvKiSCkASGYsFT-gYyMHWVkQs
774221   -mrvLILLwLftafpGiLSdVQLQESGpGLVKPsqSLsLtCtvtGYsiTSdYawnWiRQf
973401   MerhwIfLFLLsVtaGVhSqVQLQqSaaeLarPGaSvKmSCkASGYTFa-tYtiHWVkQr
973408   MerhwIfLFLLsVtaGVhSqVQLQqSaaeLarPGaSvKmSCkASGYTFT-SYtMHWVkQr
774208   MNfgLsLiFLVlVLKGVLcEVkLvESGGGLVqPGGSLKLSCAASGfTFs-SYsMsWVRlt
973428   MNfgLsLiFLalILKGVqcEVQLvESGGdLVKPGGSLKLSCAASGfTFn-SYgMsWVRQt 774213   PeKGLEWVaYISsGSttiYYaDTVKGRFTIsRDNpKNTLfLQmtSLrSEDTAMYYCtRgS
774206   PeKrLEWVaYISnGgGsTYYpDTVKGRFTIsRDNaKNTLYLQmSSLkSEDTAMYYCAR--
973422   PeKrLEWVaYISnGgGsTYYpDTVKGRFTIsRDNaKNTLYLQmSSLkSEDTAMYYCAR--
774226   PGnkLEWmGYISy-SGYTtYNpslKsRisITRDtSKNqffLQInSvTtEDTAtYYCAi--
973433   tGqGLEWIGeIyprSGsTYYNEnfKGkaTlTaDkSsNTaYmQLSSLTSEDsAvYfCAR--
973435   hGmsLEWIGYIScsnGastYNqkfKGkaTfTvDtSssTaYmQfnSLTSEDsAvYYCAR--
774221   PGnkLEWmGYISy-SGYaiYNpslKsRisITRDtSKNhffLQInSvTtEDTAtYYCAR--
973401   PGqGLEWIGYInpsSGYTeYNqkfKdktTlTaDkSssTaYmQLSSLTSEDsAvYYCAR--
973408   PGqGLEWIGYInpsSGYTeYNqkfKdktTlTaDkSssTaYmQLSSLTSEDsAvYYCAR--
774208   PeKrLEWVaYISnGgGspYYpDTVKGRFTIsRDNanNTLYLQmSSLkSEDTAMYfCtRl-
973428   PdKrLEWVaiISsGgsYTYpDsVKGRFTIsRDNaKNTLYLQmSSLkSEDTAMYYCARlS 774213   YYrydlyYa-mdYWGQGTsVTVSsAKTTPPSVYPLAPGCGDTTGSSVTLGCLVKGYFPES
774206   ---hdgnYpWFAYWGQGTLVTVSAAKTTPPSVYPLAPGCGDTTGSSVTLGCLVKGYFPES
973422   --hgdgyYpWFAYWGQGTLVTVSAAKTTPPSVYPLAPGCGDTTGSSVTLGCLVKGYFPES
774226   -----sGgsWFAYWGQGTLVTVSAAKTTPPSVYPLAPGCGDTTGSSVTLGCLVKGYFPES
973433   ----------gdYWGQGTtlTVSsAKTTPPSVYPLAPGCGDTTGSSVTLGCLVKGYFPES
973435   -----sGetpFAYWGQGTLVTVSAAKTTPPSVYPLAPGCGDTTGSSVTLGCLVKGYFPES
774221   -----sGgsWFAYWGQGTLVTVSAAKTTPPSVYPLAPGsaaqTnSmVTLGCLVKGYFPEp
973401   --revyGsgsmdYWGQGTsVTVSsAKTTPPSVYPLAPGsaaqTnSmVTLGCLVKGYFPEp
973408   --revyGsgamdYWGQGTsVTVSsAKTTPPSVYPLAPGsaaqTnSmVTLGCLVKGYFPEp
774208   --ldssGYvWFSYWGQGTLVTVSAAKTTPPSVYPLAPGsaaqTnSmVTLGCLVKGYFPEp
973428   YYygsspYa-mdYWGQGTsVTiSsAKTTPPSVYPLAPGsaaqTnSmVTLGCLVKGYFPEp 774213   VTVTWNSGSLSSSVHTFPALLQSGLYTMSSSVTVPSSTWPSQTVTCSVAHPASSTTVDKK
774206   VTVTWNSGSLSSSVHTFPALLQSGLYTMSSSVTVPSSTWPSQTVTCSVAHPASSTTVDKK
973422   VTVTWNSGSLSSSVHTFPALLQSGLYTMSSSVTVPSSTWPSQTVTCSVAHPASSTTVDKK
774226   VTVTWNSGSLSSSVHTFPALLQSGLYTMSSSVTVPSSTWPSQTVTCSVAHPASSTTVDKK
973433   VTVTWNSGSLSSSVHTFPALLQSGLYTMSSSVTVPSSTWPSQTVTCSVAHPASSTTVDKK
973435   VTVTWNSGSLSSSVHTFPALLQSGLYTMSSSVTVPSSTWPSQTVTCSVAHPASSTTVDKK
774221   VTVTWNSGSLSSgVHTFPAvLQSdLYTlSSSVTVPSSTWPSeTVTCnVAHPASSTkVDKK
973401   VTVTWNSGSLSSgVHTFPAvLQSdLYTlSSSVTVPSSTWPSeTVTCnVAHPASSTkVDKK
973408   VTVTWNSGSLSSgVHTFPAvLQSdLYTlSSSVTVPSSTWPSeTVTCnVAHPASSTkVDKK
774208   VTVTWNSGSLSSgVHTFPAvLQSdLYTlSSSVTVPSSTWPSeTVTCnVAHPASSTkVDKK
973428   VTVTWNSGSLSSgVHTFPAvLQSdLYTlSSSVTVPSSTWPSeTVTCnVAHPASSTkVDKK
```

FIG. 20B-2

```
774213    LEPSGPISTINPCPPCKECHKCPAPNLEGGPSVFIFPPNIKDVLMISLTPKVTCVVVDVS
774206    LEPSGPISTINPCPPCKECHKCPAPNLEGGPSVFIFPPNIKDVLMISLTPKVTCVVVDVS
973422    LEPSGPISTINPCPPCKECHKCPAPNLEGGPSVFIFPPNIKDVLMISLTPKVTCVVVDVS
774226    LEPSGPISTINPCPPCKECHKCPAPNLEGGPSVFIFPPNIKDVLMISLTPKVTCVVVDVS
973433    LEPSGPISTINPCPPCKECHKCPAPNLEGGPSVFIFPPNIKDVLMISLTPKVTCVVVDVS
973435    LEPSGPISTINPCPPCKECHKCPAPNLEGGPSVFIFPPNIKDVLMISLTPKVTCVVVDVS
774221    ivPrd-----cgCkPC----iCtvPev---sSVFIFPPkpKDVLtItLTPKVTCVVVDiS
973401    ivPrd-----cgCkPC----iCtvPev---sSVFIFPPkpKDVLtItLTPKVTCVVVDiS
973408    ivPrd-----cgCkPC----iCtvPev---sSVFIFPPkpKDVLtItLTPKVTCVVVDiS
774208    ivPrd-----cgCkPC----iCtvPev---sSVFIFPPkpKDVLtItLTPKVTCVVVDiS
973428    ivPrd-----cgCkPC----iCtvPev---sSVFIFPPkpKDVLtItLTPKVTCVVVDiS

774213    EDDPDVQISWFVNNVEVHTAQTQTHREDYNSTIRVVSTLPIQHQDWMSGKEFKCKVNNKD
774206    EDDPDVQISWFVNNVEVHTAQTQTHREDYNSTIRVVSTLPIQHQDWMSGKEFKCKVNNKD
973422    EDDPDVQISWFVNNVEVHTAQTQTHREDYNSTIRVVSTLPIQHQDWMSGKEFKCKVNNKD
774226    EDDPDVQISWFVNNVEVHTAQTQTHREDYNSTIRVVSTLPIQHQDWMSGKEFKCKVNNKD
973433    EDDPDVQISWFVNNVEVHTAQTQTHREDYNSTIRVVSTLPIQHQDWMSGKEFKCKVNNKD
973435    EDDPDVQISWFVNNVEVHTAQTQTHREDYNSTIRVVSTLPIQHQDWMSGKEFKCKVNNKD
774221    kDDPeVQfSWFVddVEVHTAQTQpreEqfNSTfRsVSeLPImHQDWlnGKEFKCrVNsaa
973401    kDDPeVQfSWFVddVEVHTAQTQpreEqfNSTfRsVSeLPImHQDWlnGKEFKCrVNsaa
973408    kDDPeVQfSWFVddVEVHTAQTQpreEqfNSTfRsVSeLPImHQDWlnGKEFKCrVNsaa
774208    kDDPeVQfSWFVddVEVHTAQTQpreEqfNSTfRsVSeLPImHQDWlnGKEFKCrVNsaa
973428    kDDPeVQfSWFVddVEVHTAQTQpreEqfNSTfRsVSeLPImHQDWlnGKEFKCrVNsaa 774213    LPSPIERTISKIKGLVRAPQVYILPPPAEQLSRKDVSLTCLVVGFNPGDISVEWTSNGHT
774206    LPSPIERTISKIKGLVRAPQVYILPPPAEQLSRKDVSLTCLVVGFNPGDISVEWTSNGHT
973422    LPSPIERTISKIKGLVRAPQVYILPPPAEQLSRKDVSLTCLVVGFNPGDISVEWTSNGHT
774226    LPSPIERTISKIKGLVRAPQVYILPPPAEQLSRKDVSLTCLVVGFNPGDISVEWTSNGHT
973433    LPSPIERTISKIKGLVRAPQVYILPPPAEQLSRKDVSLTCLVVGFNPGDISVEWTSNGHT
973435    LPSPIERTISKIKGLVRAPQVYILPPPAEQLSRKDaSLTCLVVGFNPGDISVEWTSNGHT
774221    fPaPIEkTISKtKGrpkAPQVYtiPPPkEQmakdkVSLTCmitdFfPeDItVEWqwNGqp
973401    fPaPIEkTISKtKGrpkAPQVYtiPPPkEQmakdkVSLTCmitdFfPeDItVEWqwNGqp
973408    fPaPIEkTISKtKGrpkAPQVYtiPPPkEQmakdkVSLTCmitdFfPeDItVEWqwNGqp
774208    fPaPIEkTISKtKGrpkAPQVYtiPPPkEQmakdkVSLTCmitdFfPeDItVEWqwNGqp
973428    fPaPIEkTISKtKGrpkAPQVYtiPPPkEQmakdkVSLTCmitdFfPeDItVEWqwNGqp 774213    EENYKDTAPVLDSDGSYFIYSKLNMKTSKWEKTDSFSCNVRHEGLKNYYLKKTISRSPGK
774206    EENYKDTAPVLDSDGSYFIYSKLNMKTSKWEKTDSFSCNVRHEGLKNYYLKxTISRSPGK
973422    EENYKDTAPVLDSDGSYFIYSKLNMKTSKWEKTDSFSCNVRHEGLKNYYLKKTISRSPGK
774226    EENYKDTAPVLDSDGSYFIYSKLNMKTSKWEKTDSFSCNVRHEGLKNYYLKKTISRSPGK
973433    EENYKDTAPVLDSDGSYFIYSKLNMKTSKWEKTDSFSCNVRHEGLKNYYLKKTISRSPGK
973435    EENYKDTAPVLDSDGSYFIYSKLNMKTSKWEKTDSFSCNVRHEGLKNYYLKKTISRSPGK
774221    aENYKnTqPimDtDGSYFvYSKLNvqkSnWEagntFtCsVlHEGLhNhhteKslSnSPGK
973401    aENYKnTqPimDtDGSYFvYSKLNvqkSnWEagntFtCsVlHEGLhNhhteKslShSPGK
973408    aENYKnTqPimDtDGSYFvYSKLNvqkSnWEagntFtCsVlHEGLhNhhteKslShSPGK
774208    aENYKnTqPimDtDGSYFvYSKLNvqkSnWEagntFtCsVlHEGLhNhhteKslShSPGK
973428    aENYKnTqPimDtDGSYFvYSKLNvqkSnWEagntFtCsVlHEGLhNhhteKslShSPGK
```

IDENTIFICATION OF VSIG3/VISTA AS A NOVEL IMMUNE CHECKPOINT AND USE THEREOF FOR IMMUNOTHERAPY

CONTINUING APPLICATION DATA

This application is the § 371 U.S. National Stage of International Application No. PCT/US2017/045314, filed Aug. 3, 2017, which claims the benefit of U.S. Provisional Application Ser. No. 62/370,395, filed Aug. 3, 2016, the disclosures of which are incorporated by reference herein in their entireties.

SEQUENCE LISTING

This application contains a Sequence Listing electronically submitted to the United States Patent and Trademark Office via EFS-Web as an ASCII text file entitled "0541_000007US01_ST25.txt" having a size of 111 kilobytes and created on Sep. 9, 2022. Due to the electronic filing of the Sequence Listing, the electronically submitted Sequence Listing serves as both the paper copy required by 37 CFR § 1.821 (c) and the CRF required by § 1.821 (e). The information contained in the Sequence Listing is incorporated by reference herein.

BACKGROUND

V-region Immunoglobulin-containing Suppressor of T cell Activation (referred to herein as "VISTA," and also known as PD-1H, Gi24 or B7-H5) is a receptor that mediates T cell suppression. However, it is difficult to identify ligands of VISTA. It would be desirable to identify a ligand of VISTA as blocking the ligand/VISTA signaling, which can allow for the development of immunotherapies for cancer. It would also be desirable to identify compounds that agonize/antagonize the interaction of a new ligand of VISTA with VISTA to produce immunotherapeutic effects.

SUMMARY

Herein experimental methods which have identified that "V-Set and Immunoglobulin domain containing 3" (referred to herein as "VSIG3" or "VSIG-3," also known as IGSF11) as a ligand for VISTA are presented. Also disclosed are assays that validate that VSIG3 specifically interacts with VISTA in vitro and that the interaction of VSIG3 with VISTA has a suppressive effect on T cell activation, T cell proliferation, and/or T cell cytokine or chemokine production. The identification of VSIG3 as the ligand for VISTA has much clinical and scientific promise particularly in the development of VSIG3 agonists and VSIG3 antagonists.

Therefore, molecules (e.g., antibodies) which block or inhibit the VSIG3/VISTA interaction may be effective in treating oncology and infectious disease. Particularly, VSIG3/VISTA antagonists which block or inhibit the VSIG3/VISTA interaction may be useful in the treatment of cancer or infectious diseases. By contrast, VSIG3/VISTA agonists which promote or enhance the VSIG3/VISTA binding interaction may be useful in the treatment of autoimmune, allergic, and inflammatory indications, GVHD, transplant or other indications wherein the suppression of T cell activation, T cell proliferation or cytokine production is desired.

Some embodiments provide a compound that agonizes or antagonizes a VSIG3-VISTA interaction. In some embodiments, such agonism or antagonism may modulate immunity. Certain embodiments provide a compound that antagonizes a VSIG3-VISTA interaction. Such a compound is referred to as a VSIG3/VISTA antagonist. Such antagonization can include, for example, inhibition of signaling of VSIG3 and/or VISTA. Certain embodiments provide a compound that agonizes the VSIG3/VISTA interaction Such a compound is referred to as a VSIG3/VISTA agonist. Such agonism can include, for example, enhancing the signaling of VSIG3 and/or VISTA.

In some embodiments, antagonism of VISTA signaling can include antagonism of CD3-induced cytokine signals. For example, antagonism of VISTA signaling can include abrogation of at least one of CD3-induced IL-2 production, CD3-induced IFN-γ production, CD3-induced RANTES production, CD3-induced MIP-1 alpha production, CD3-induced IL-17 production, and CD3-induced CXCL11 production.

In some embodiments, the VISTA and/or VSIG3 agonized or antagonized by the compound may be expressed on the surface of a cell. In some embodiments, a VSIG3/VISTA agonist or a VSIG3/VISTA antagonist agonizes or antagonizes the interaction of VSIG3 and VISTA. In some embodiments, a VSIG3/VISTA agonist or a VSIG3/VISTA antagonist agonizes or antagonizes the interaction of VSIG3 and VISTA when at least one of VSIG3 and VISTA is expressed on the surface of a cell. In some embodiments, a VSIG3/VISTA agonist or a VSIG3/VISTA antagonist can agonize or antagonize the multimerization of VSIG3. The multimerization of VSIG3 may include homodimerization of VSIG3 and/or heterodimerization of VSIG3 including, for example, with VSIG8.

In some embodiments, a compound that agonizes or antagonizes a VSIG3-VISTA interaction includes an antibody. An antibody can include an antigen binding fragment of an antibody. In some embodiments, an antibody includes an anti-VSIG3 antibody. Examples of such antibodies are provided herein. In some embodiments, an antibody includes an anti-VISTA antibody.

In some embodiments, a compound that agonizes or antagonizes a VSIG3-VISTA interaction includes a VSIG3 polypeptide. A VSIG3 polypeptide can include a soluble fragment of VSIG3 and/or the extracellular region of VSIG3.

In some embodiments, a compound that agonizes or antagonizes a VSIG3-VISTA interaction includes a VISTA polypeptide. A VISTA polypeptide can include a soluble fragment of VISTA and/or the extracellular region of VISTA.

In some embodiments, a compound that agonizes or antagonizes a VSIG3-VISTA interaction includes a fusion protein. A fusion protein can include an Fc domain.

In some embodiments, a compound that agonizes or antagonizes a VSIG3-VISTA interaction includes a protein having at least 80% sequence identity to SEQ ID NO: 1, SEQ ID NO: 2, SEQ ID NO:3, SEQ ID NO: 4, SEQ ID NO: 5, or SEQ ID NO:6. In some embodiments, a compound that agonizes or antagonizes a VSIG3-VISTA interaction includes a protein including SEQ ID NO: 1, SEQ ID NO: 2, SEQ ID NO:3, SEQ ID NO: 4, SEQ ID NO: 5, or SEQ ID NO:6.

Other embodiments include methods of agonizing or antagonizing a VSIG3-VISTA interaction and method of using a compound that agonizes or antagonizes a VSIG3-VISTA interaction. For example, such a compound maybe administered to a subject in a therapeutically effective amount. In some embodiments, VSIG3 may be overexpressed in a sample obtained from the subject. In some embodiments, the subject may have been diagnosed with cancer including, for example, colon cancer or liver cancer.

In some cases, the VSIG3/VISTA antagonist is used to inhibit or block VISTA-associated suppression of T cell activation. In other cases, the VSIG3/VISTA antagonist is used to inhibit or block VISTA-associated suppression of CD3+ T cell activation. In other cases, the VSIG3/VISTA antagonist is used to inhibit or block VISTA-associated suppression of cytokine production.

The VSIG3/VISTA antagonist or VSIG3/VISTA agonist can include but is not limited to an anti-VSIG3 antibody (including a fragment or derivative thereof), a VSIG3 polypeptide (including a fragment or derivative thereof), a VSIG3 fusion protein (including a fragment or derivative thereof), an anti-VISTA antibody (including a fragment or derivative thereof), a VISTA polypeptide (including a fragment or derivative thereof), a VISTA fusion protein (including a fragment or derivative thereof). In some embodiments, the VSIG3/VISTA antagonist or VSIG3/VISTA agonist may be provided as part of a composition that can be administered to a subject. In some embodiments, the VSIG3/VISTA antagonist or VSIG3/VISTA agonist may be provided as part of a kit. In some embodiments, the VSIG3/VISTA antagonist or VSIG3/VISTA agonist is attached to a detectable label, linker or a therapeutic moiety.

Other embodiments provide methods of using a VSIG3/VISTA antagonist to inhibit interaction of VSIG3 and VISTA. In some embodiments, such inhibition may be used to treat a disease. In some embodiments, the VSIG3/VISTA antagonist is used to inhibit or block VISTA-associated suppression of T cell activation. In certain cases, the VSIG3/VISTA antagonist is used to inhibit or block VISTA-associated suppression of CD3+ T cell activation. In some embodiments, the VSIG3/VISTA antagonist is used to inhibit or block VISTA-associated suppression of cytokine production. In some cases, the disease is cancer. In other cases, the disease is an infectious disease. The infectious disease can be a viral, bacterial, protozoan, yeast or fungal, or parasitic disease.

Other embodiments provide methods of using a VSIG3/VISTA agonist to enhance interaction of VSIG3 and VISTA to treat a disease. In some embodiments, the VSIG3/VISTA agonist is used to enhance the interaction of VSIG3 and VISTA and thereby potentiate VISTA-associated suppression of T cell activation. In certain cases, the VSIG3/VISTA agonist is used to potentiate VISTA-associated suppression of CD3+ T cell activation. In some embodiments, the VSIG3 agonist is used to potentiate VISTA-associated suppression of cytokine production. In some cases, the disease is an autoimmune, allergic or inflammatory disease.

Some embodiments provide a screening assay to identify VSIG3/VISTA agonists or VSIG3/VISTA antagonists, preferably a binding assay or cell based assay that identifies compounds that interact with VSIG3 or VISTA and inhibit the VSIG3/VISTA interaction or compounds that potentiate the VSIG3/VISTA interaction.

Other embodiments provide a composition that includes at least two anti-VSIG3 antibodies. In some embodiments, the anti-VSIG3 antibodies bind to different epitopes. Additional embodiments provide a composition that includes an anti-VSIG3 antibody and an anti-VISTA antibody.

BRIEF DESCRIPTION OF DRAWINGS

FIG. 3(A-B) shows the effect of rhVSIG3 on anti-CD3-induced RANTES, MIP-1 alpha, IL-17 and CXCL11 production in human PBMCs.

FIG. 6 shows VSIG3 is overexpressed in human colon cancer relative to normal human colon tissue. VSIG-3 transcript levels were detected using RNAscope 2.0 HD red detection kit (Advanced Cell Diagnostics, Newark, Calif.) following kit instructions.

FIG. 8(A-B) shows rhVSIG3 IgG1Fc inhibits anti-CD3 induced human CD3+ T cell proliferation in a dose- and time-dependent manner.

FIG. 9(A-B) shows anti-CD3-activated T cells but not resting T cells express VISTA and VSIG-3 protein binds to anti-CD3 activated T cells. Human CD3+ T cells were isolated from PMBCs and then incubated with immobilized mouse anti-human CD3 epsilon monoclonal antibody (1 μg/mL) or media only for 24 hours to provide activated or resting T cells, respectively.

FIG. 10 shows an illustration of an exemplary interaction between VSIG3 and VISTA.

FIG. 11(A-B) shows the interaction of VSIG3 and VISTA inhibits IFN-γ secretion in human T cells. Human CD3+ T cells were transfected with human VISTA or negative control siRNA. Transfected T cells were treated with 1 μg/mL plate-bound anti-human CD3 and 10 μg/mL rhVSIG-3 or rhIgG1Fc proteins.

FIG. 13(A-C) shows an exemplary avidity-based extracellular interaction screen (AVEXIS) modified to test for blocking antibodies against VSIG3.

FIG. 14(B-F). The affinity of each blocking antibody (774206.111, 774208.111, 774213.111, 774221.111, 774226.111, 973401, 973404, 973422, 973423, 973428, and 973436) was determined using single-cycle kinetic titration. Data were fit using a 1:1 Langmuir model and demonstrate that antibodies bind VSIG3 with a range of affinities between 1.5 nM and 65 nM.

FIG. 15(B-F) The affinity of the blocking antibodies 774206.111, 774208.111, 774213.111, 774221.111, and 774226.111 was determined using single-cycle kinetic titration. Data were fit using a 1:1 Langmuir model and demonstrate that antibodies bind VSIG3 with a range of affinities between ~5-40 nM.

FIG. 16 shows an exemplary avidity-based extracellular interaction screen (AVEXIS) modified to test for blocking antibodies against VSIG3.

FIG. 17(A-F) shows exemplary schematic models of VSIG3-VISTA interactions and complexes of related compounds.

FIG. 18A shows light chain CDR alignments for antibodies from clones #774206, #774208, #774213, #774221, #774226, #973401, #973408, #973422, #973428, #973433, and #973435. FIG. 18B shows heavy chain CDR alignments for antibodies from clones #774206, #774208, #774213, #774221, #774226, #973401, #973408, #973422, #973428, #973433, and #973435. Highly conserved residues are shaded in light gray; medium conserved residues are shaded in dark gray.

FIG. 19A shows light chain alignments for antibodies from clones #973401, #973408, #973422, #973428, #973433, and #973435. FIG. 19B shows heavy chain alignments for antibodies from clones #973401, #973408, #973422, #973428, #973433, and #973435. FIG. 19C shows light chain alignments for antibodies from clones #774206, #774208, #774213, #774221, and #774226. FIG. 19D shows heavy chain alignments for antibodies from clones #774206, #774208, #774213, #774221, and #774226.

FIG. 20A shows light chain alignments for antibodies from clones #774206 (SEQ ID NO: 85), #774208 (SEQ ID NO:86), #774213 (SEQ ID NO:87), #774221 (SEQ ID NO:88), #774226 (SEQ ID NO:89), #973401 (SEQ IO NO: 95), #973408 (SEQ ID NO: 96), #973422 (SEQ ID NO: 97), #973428 (SEQ ID NO:98), #973433 (SEQ ID NO:99), and #973435 (SEQ ID NO: 100). FIG. 20B shows heavy chain alignments for antibodies from clones #774206 (SEQ ID NO:90), #774208 (SEQ ID NO:91), #774213 (SEQ ID NO:92), #774221 (SEQ ID NO:93), #774226 (SEQ ID NO:94), #973401 (SEQ ID NO: 101), #973408 (SEQ ID NO: 102), #973422 (SEQ ID NO:103), #973428 (SEQ ID NO:104), #973433 (SEQ ID NO: 105), and #973435 (SEQ ID NO: 106). Highly conserved residues are shaded in light gray; medium conserved residues are shaded in dark gray.

DETAILED DESCRIPTION

Figure 1A:
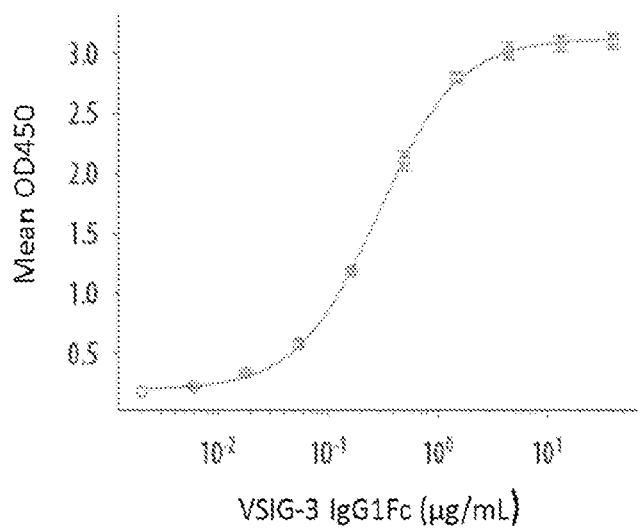
FIG. 1A shows a recombinant human VSIG3 Fc chimera ("rhVSIG3") specifically binds to a recombinant human VISTA Fc chimera ("rhVISTA") in an exemplary functional enzyme-linked immunosorbent assay (ELISA) binding assay.

Unless defined otherwise, all technical and scientific terms used herein have the same meaning as those commonly understood by one of ordinary skill in the art to which this invention belongs. Although methods and materials similar or equivalent to those described herein may be used in the invention or testing, suitable methods and materials are described herein. The materials, methods and examples are illustrative only, and are not intended to be limiting. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used in the description herein and throughout the claims that follow, the meaning of "a," "an," and "the" includes plural reference unless the context clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

"Activating receptor," as used herein, refers broadly to immune cell receptors that bind antigen, complexed antigen (e.g., in the context of MHC molecules), Ig-fusion proteins, ligands, or antibodies. Activating receptors include but are not limited to T cell receptors (TCRs), B cell receptors (BCRs), cytokine receptors, lipopolysaccharide (LPS) receptors, complement receptors, and Fc receptors. T cell activation via the TCR results in numerous changes, e.g., protein phosphorylation, membrane lipid changes, ion fluxes, cyclic nucleotide alterations, RNA transcription changes, protein synthesis changes, and cell volume changes.

"Adjuvant" as used herein, refers to an agent used to stimulate the immune system and increase the response to a vaccine, without having any specific antigenic effect in itself.

"Allergic disease," as used herein, refers broadly to a disease involving allergic reactions. More specifically, an "allergic disease" is defined as a disease for which an allergen is identified, where there is a strong correlation between exposure to that allergen and the onset of pathological change, and where that pathological change has been proven to have an immunological mechanism. Herein, an immunological mechanism means that leukocytes show an immune response to allergen stimulation.

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified (e.g., hydroxyproline, γ-carboxyglutamate, and O-phosphoserine.) Amino acid analogs refers to compounds that have the same basic chemical structure as a naturally occurring amino acid (i. e., a carbon that is bound to a hydrogen, a carboxyl group, an amino group), and an R group (e.g., homoserine, norleucine, methionine sulfoxide, methionine methyl sulfonium.) Analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Anergy" or "tolerance," or "prolonged antigen-specific T cell suppression" or "prolonged immunosuppression" as used herein refers broadly to refractivity to activating receptor-mediated stimulation. Refractivity is generally antigen-specific and persists after exposure to the tolerizing antigen has ceased. For example, anergy in T cells may be characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer. Modulation of a costimulatory signal results in modulation of effector function of an immune cell.

The term "antibody" as used herein refers to a molecule that contains at least one antigen binding site that immunospecifically binds to a particular antigen target of interest. The term "antibody" thus includes but is not limited to a full length antibody and/or its variants, a fragment thereof including an antigen-binding fragment thereof, peptibodies and variants thereof, monoclonal antibodies (including full-length monoclonal antibodies), polyclonal antibodies, multispecific antibodies (for example, bispecific antibodies) formed from at least two intact antibodies, human antibodies, humanized antibodies, and antibody mimetics that mimic the structure and/or function of an antibody or a specified fragment or portion thereof, including single chain antibodies and fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. An antibody of the present disclosure thus encompasses antibody fragments including antibody fragments capable of binding to a biological molecule (such as an antigen or receptor) or portions thereof, including but not limited to Fab, Fab' and F(ab')2, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody may be of any isotype (for example, IgG, IgE, IgM, IgD, IgA and IgY), class (for example, IgG1, IgG2, IgG3, IgG4, IgA1 and IgA2), or subclass. The antibody may be from any source including, for example, human, rodent, rabbit, cow, sheep, pig, dog, other mammals, chicken, other avians, etc.

An intact antibody molecule has two heavy (H) chain variable regions (abbreviated herein as VH or $V_H$) and two light (L) chain variable regions (abbreviated herein as VL or $V_L$). The VH and VL regions can be further subdivided into regions of hypervariability, termed "complementarity determining regions" ("CDRs"), interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242, and Chothia et al., J. Mol. Biol. 1987; 196: 901-917). Each VH and $V_L$ is composed of three CDRs and four FRs, arranged from amino-terminus to carboxy-terminus in the following order: FR1, CDR1, FR2, CDR2, FR3, CDR3, FR4.

The term "monoclonal antibody" as used herein refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. The monoclonal antibodies may be synthesized by hybridoma cells uncontaminated by other immunoglobulin producing cells. Alternatively, the monoclonal antibody may be produced recombinantly including, for example, by cells stably or transiently transfected with the heavy and light chain genes encoding the monoclonal antibody.

The modifier "monoclonal" indicates the character of the antibody as being obtained from a substantially homogeneous population of antibodies, and is not to be construed as requiring engineering of the antibody by any particular method. In some embodiments, the term "monoclonal" is used herein to refers to an antibody that is derived from a clonal population of cells, including any eukaryotic, prokaryotic, or phage clone, and not the method by which the antibody was engineered.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens.

"Antigen presenting cell," as used herein, refers broadly to professional antigen presenting cells including, for example, B lymphocytes, monocytes, dendritic cells, and Langerhans cells, as well as other antigen presenting cells including, for example, keratinocytes, endothelial cells, astrocytes, fibroblasts, and oligodendrocytes.

"Apoptosis," as used herein, refers broadly to programmed cell death which can be characterized using techniques which are known in the art. Apoptotic cell death can be characterized by cell shrinkage, membrane blebbing, and chromatin condensation culminating in cell fragmentation. Cells undergoing apoptosis may also display a characteristic pattern of internucleosomal DNA cleavage.

"Autoimmunity" or "autoimmune disease or condition," as used herein, refers broadly to a disease or disorder arising from an immune response directed against an individual's own tissues or a co-segregate or manifestation thereof or resulting condition therefrom. Herein autoimmune conditions include inflammatory or allergic conditions, e.g., chronic diseases characterized by a host immune reaction against self-antigens potentially associated with tissue destruction such as rheumatoid arthritis.

"B cell receptor" (BCR)," as used herein, refers broadly to the complex between membrane Ig (mIg) and other transmembrane polypeptides (e.g., IgA and Ig) found on B cells. The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

"Cancer" as used herein, refers broadly to any neoplastic disease (whether invasive or metastatic) characterized by abnormal and uncontrolled cell division causing malignant growth or tumor. Cancers include but are not limited to, carcinoma, lymphoma, blastoma, sarcoma, and leukemia or lymphoid malignancies. More particular examples of such cancers include colorectal cancer, bladder cancer, ovarian cancer, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; multiple myeloma and post-transplant lymphoproliferative disorder (PTLD), as well as abnormal vascular proliferation associated with phakomatoses, edema (such as that associated with brain tumors), and Meigs' syndrome.

"Cancer therapy" herein refers to any method which prevents or treats cancer or ameliorates one or more of the symptoms of cancer.

"Chimeric antibody," as used herein, refers broadly to an antibody molecule in which the constant region, or a portion thereof, is altered, replaced, or exchanged so that the antigen-binding site (variable region) is linked to a constant region of a different or altered class, effector function and/or species, or an entirely different molecule which confers new properties to the chimeric antibody (including, for example, an enzyme, toxin, hormone, growth factor, drug).

"Coding region," as used herein, refers broadly to regions of a nucleotide sequence comprising codons which are translated into amino acid residues, whereas the term "non-coding region" refers to regions of a nucleotide sequence that are not translated into amino acids (e.g., 5' and 3' untranslated regions).

"Conservatively modified variants," as used herein with respect to particular nucleic acid sequences, refers to nucleic acid sequences which encode identical or essentially identical amino acid sequences, or, where the nucleic acid does not encode an amino acid sequence, to essentially identical sequences. Because of the degeneracy of the genetic code, a large number of functionally identical nucleic acids may encode any given protein. "Silent variations" are one species of conservatively modified nucleic acid variations. Unless otherwise indicated, every nucleic acid sequence herein that encodes a polypeptide also includes every possible silent variation of the nucleic acid sequence. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarity determining regions (CDRs) found in the variable regions of light or heavy chains of an antibody. These expressions include the hypervariable regions as defined by Kabat, et al. (1983) Sequences of Proteins of Immunological Interest, U. S. Dept. of Health and Human Services or the hypervariable loops in 3-dimensional structures of antibodies. The CDRs in each chain may be held in close proximity by framework regions and, with the CDRs from the other chain, may contribute to the formation of the antigen-binding site.

"B7" polypeptide, as used herein, refers to a member of the B7 family of proteins that costimulate T cells including but not limited to B7-1, B7-2, B7-DC, B7-H5, B7-H1, B7-H2, B7-H3, B7-H4, B7-H6, and B7-S3, and biologically active fragments and/or variants thereof.

"Diagnostic," as used herein, refers broadly to identifying the presence or nature of a pathologic condition.

"Diagnosing," or "aiding in the diagnosis" as used herein refers broadly to classifying a disease or a symptom, and/or determining the likelihood that an individual has a disease condition; determining a severity of the disease, monitoring disease progression, forecasting an outcome of a disease and/or prospects of recovery. The term "detecting" may also optionally encompass any of the foregoing. Diagnosis of a disease according to the present disclosure may, in some embodiments, be affected by determining a level of a polynucleotide or a polypeptide in a biological sample obtained from the subject, wherein the level determined can be correlated with predisposition to, or presence or absence of the disease. It should be noted that a "biological sample obtained from the subject" may include a sample that has not been physically removed from the subject.

"Effective amount," as used herein, refers broadly to the amount of a compound, antibody, antigen, or cells that, when administered to a patient for treating a disease, is sufficient to affect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or affect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this disclosure. For example, the term "therapeutically effective amount" may refer to an amount of agent that is effective to treat a disease or disorder in a mammal.

"Extracellular domain," "ectodomain," or "ECD," as used herein refers broadly to the portion of a protein that extends from the surface of a cell into the extracellular space.

"Expression vector," as used herein, refers broadly to any recombinant expression system for the purpose of expressing a nucleic acid sequence in vitro or in vivo, constitutively or inducibly, in any cell, including prokaryotic, yeast, fungal, plant, insect, or mammalian cell. The term includes linear or circular expression systems. The term includes expression systems that remain episomal or integrate into the host cell genome. The expression systems can have the ability to self-replicate or not, i. e., drive only transient expression in a cell. The term includes recombinant expression cassettes which contain only the minimum elements needed for transcription of the recombinant nucleic acid.

"Family," as used herein, refers broadly to two or more polypeptide or nucleic acid molecules having a common structural domain or motif and having sufficient amino acid or nucleotide sequence homology as defined herein. Family members can be naturally or non-naturally occurring and can be from either the same or different species. For example, a family can contain a first polypeptide of human origin, as well as other, distinct polypeptides of human origin or alternatively, can contain homologues of non-human origin (e.g., monkey polypeptides). Members of a family may also have common functional characteristics.

"Fc receptor" (FcR), as used herein, refers broadly to cell surface receptors for the Fc portion of immunoglobulin molecules (Igs).

"Framework region" or "FR," as used herein, refers broadly to one or more of the framework regions within an antibody. These regions include those amino acid sequence regions interposed between the CDRs within the variable regions of the light and heavy chains of an antibody.

"Heterologous," as used herein, when referring to portions of a nucleic acid, indicates that the nucleic acid comprises two or more subsequences that are not found in the same relationship to each other in nature. For instance, a heterologous nucleic acid is typically recombinantly produced, having two or more sequences from unrelated genes arranged to make a new functional nucleic acid (e.g., a promoter from one source and a coding region from another source). Similarly, when referring to portions of a protein, a "heterologous," as used herein, indicates that the protein comprises two or more subsequences that are not found in the same relationship to each other in nature (e.g., a fusion protein).

"High affinity," as used herein, refers broadly to an antibody or fusion protein having a $K_D$ of less than $10^{-6}$ M, more preferably less than $10^{-7}$ M, even more preferably less than $10^{-8}$M and even more preferably less than $10^{-9}$M, less than $10^{-10}$ M, less than $10^{-11}$ M, or less than $10^{-12}$ M for a target antigen or receptor. With particular respect to antibodies, "high affinity" binding can vary for different antibody isotypes. For example, "high affinity" binding for an IgM isotype refers to an antibody having a $K_D$ of $10^{-7}$ M or less, more preferably $10^{-8}$M or less.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that a nucleic acid or amino acid sequence is identical to the reference nucleic acid or reference amino acid sequence. A partially homologous nucleic acid or amino acid sequence is one that is not identical to the reference nucleic acid or reference amino acid sequence. The degree of homology can be determined by sequence comparison, for example using BlastP software of the National Center of Biotechnology Information (NCBI) using default parameters. The term "sequence identity" may be used interchangeably with "homology."

"Host cell," as used herein, refers broadly to refer to a cell into which a nucleic acid molecule, such as a recombinant expression vector, has been introduced. Host cells may be prokaryotic cells (e.g., *E. coli*), or eukaryotic cells such as yeast, insect (e.g., SF9), amphibian, or mammalian cells such as CHO, HeLa, HEK-293, e.g., cultured cells, explants, and cells in vivo. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, progeny may not, in fact, be identical to the parent cell, but are still included within the scope of the term as used herein.

"Humanized antibody," as used herein, refers broadly to include antibodies that have been altered to more closely resemble human antibodies. For example, by altering the non-human antibody amino acid sequence to incorporate amino acids found in human germline immunoglobulin sequences. The humanized antibodies may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

"IgV domain" and "IgC domain" as used herein, refer broadly to immunoglobulin (Ig) superfamily member domains.

"Immune cell," as used herein, refers broadly to cells that are of hematopoietic origin and that play a role in the immune response. Immune cells include but are not limited to lymphocytes, such as B cells and T cells; natural killer (NK) cells; dendritic cells; monocytes; macrophages; eosinophils; mast cells; basophils; and granulocytes.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Immune related disease," "Immune related disorder," or "Immune related condition" as used herein should be understood to encompass any disease disorder or condition selected from the group including but not limited to autoimmune diseases, inflammatory disorders, and immune disorders associated with graft transplantation rejection, such as acute and chronic rejection of organ transplantation, allogenic stem cell transplantation, autologous stem cell transplantation, bone marrow transplantation, and graft versus host disease.

"Immune response," as used herein, refers broadly to T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "downmodulation" with reference to the immune response includes a diminution in any one or more immune responses, while the term "upmodulation" with reference to the immune response includes an increase in any one or more immune responses. It will be understood that upmodulation of one type of immune response may lead to a corresponding downmodulation in another type of immune response. For example, upmodulation of the production of certain cytokines (e.g., IL-10) can lead to downmodulation of cellular immune responses.

"Immunologic", "immunological" or "immune" response herein refer to the development of a humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T cells. Without wishing to be limited by a single hypothesis, a cellular immune response is elicited by the presentation of polypeptide epitopes in association with Class II or Class I MHC molecules to activate antigen-specific $CD4^+$ T helper cells and/or $CD8^+$ cytotoxic T cells, respectively. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T cells from an immunized syngeneic animal and measuring protective or therapeutic effect in a second subject.

"Immunogen," as used herein, is a moiety capable of inducing an immunological response against itself on administration to a mammal, optionally in conjunction with an adjuvant.

"Infectious agent," as used herein, refers to any pathogen or agent that infects mammalian cells, preferably human cells and causes a disease condition. Examples thereof include bacteria, yeast, fungi, protozoans, *mycoplasma*, viruses, prions, and parasites. Examples of such infectious agents include by way of example those involved in (a) viral diseases such as, for example, diseases resulting from infection by an adenovirus, a herpesvirus (e.g., HSV-I, HSV-II, CMV, or VZV), a poxvirus (e-g-, an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenza virus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV); (b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella*; (c) other infectious diseases, such *chlamydia*, fungal diseases including but not limited to candidiasis, aspergillosis, histoplasmosis, cryptococcal meningitis, parasitic diseases including but not limited to malaria, *Pneumocystis* carnii pneumonia, leishmaniasis, cryptosporidiosis, toxoplasmosis, and trypanosome infection and prions that cause human disease such as Creutzfeldt-Jakob Disease (CJD), variant Creutzfeldt-Jakob Disease (vCJD), Gerstmann-Straussler-Scheinker syndrome, Fatal Familial Insomnia and kuru.

"Infectious agent antigen," as used herein, means a compound, e.g., peptide, polypeptide, glycopeptide, glycoprotein, and the like, or a conjugate, fragment or variant thereof, which compound is expressed by a specific infectious agent and which antigen may be used to elicit an immune response. In some embodiments, the antigen will comprise a moiety, e.g., polypeptide or glycoprotein expressed on the surface of the virus or other infectious agent, such as a capsid protein or other membrane protein.

"Inflammatory bowel disease" herein comprises any inflammatory bowel condition and includes inflammatory bowel disease, Crohn's disease, ulcerative colitis (UC), collagenous colitis, lymphocytic colitis, ischemic colitis, diversion colitis, Behcet's disease, and indeterminate colitis.

"Inflammatory disorders" or "inflammatory conditions" as used interchangeably herein, refers broadly to chronic or acute inflammatory diseases, and expressly includes inflammatory autoimmune diseases and inflammatory allergic conditions. These conditions include by way of example inflammatory abnormalities characterized by dysregulated immune response to harmful stimuli, such as pathogens, damaged cells, or irritants. Inflammatory disorders underlie a vast variety of human diseases. Non-immune diseases with etiological origins in inflammatory processes include cancer, atherosclerosis, and ischemic heart disease. Examples of disorders associated with inflammation include: chronic prostatitis, glomerulonephritis, hypersensitivities, pelvic inflammatory disease, reperfusion injury, sarcoidosis, vasculitis, interstitial cystitis, normocomplementemic urticarial vasculitis, pericarditis, myositis, anti-synthetase syndrome, scleritis, macrophage activation syndrome, Behcet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

"Inhibitory signal," as used herein, refers broadly to a signal transmitted via an inhibitory receptor molecule on an immune cell. An inhibitory signal may antagonize a signal via an activating receptor (e.g., via a TCR, CD3, BCR, or Fc molecule). An inhibitory signal can result in the development of anergy; the failure of the immune cell to produce mediators (e.g., cytokines (e.g., IL-2) and/or mediators of allergic responses); or in inhibition of, for example, second messenger generation; proliferation; or effector function in the immune cell, e.g., reduced phagocytosis, antibody production, or cellular cytotoxicity.

"Isolated," as used herein, refers broadly to material removed from its original environment in which it naturally occurs, and thus is altered by the hand of man from its natural environment and includes "recombinant" polypeptides. Isolated material may be, for example, exogenous nucleic acid included in a vector system, exogenous nucleic acid contained within a host cell, or any material which has been removed from its original environment and thus altered by the hand of man (e.g., "isolated antibody"). For example, "isolated" or "purified," as used herein, refers broadly to a protein, DNA, antibody, RNA, or biologically active portion thereof, that is substantially free of cellular material or other contaminating proteins from the cell or tissue source from which the biological substance is derived, or substantially free of chemical precursors or other chemicals when chemically synthesized. As used herein the term "isolated" refers to a compound of interest (for example a polynucleotide or a polypeptide) that is in an environment different from that in which the compound naturally occurs e.g., separated from its natural milieu such as by concentrating a peptide to a concentration at which it is not found in nature. "Isolated" includes compounds that are within samples that are substantially enriched for the compound of interest and/or in which the compound of interest is partially or substantially purified. A nucleic acid may be "isolated" when purified away from other cellular components or other contaminants, e.g., other cellular nucleic acids or proteins, by standard techniques, including alkaline/SDS treatment, CsCl banding, column chromatography, agarose gel electrophoresis, and others.

"Isolated antibody", as used herein, is intended to refer to an antibody that is substantially free of other antibodies having different antigenic specificities (e.g., an isolated antibody that specifically binds VSIG3 is substantially free of antibodies that specifically bind antigens other than VSIG3). Moreover, an isolated antibody may be substantially free of other cellular material and/or chemicals.

"Isotype" herein refers to the antibody class that is encoded by the heavy chain constant region genes.

"K-assoc" or "$k_a$", as used herein, refers broadly to the association rate of a particular antibody-antigen interaction, whereas the term "$k_a$," as used herein, refers to the dissociation rate of a particular antibody-antigen interaction.

The term "$K_D$", as used herein, is intended to refer to the dissociation constant, which is obtained from the ratio of $k_d$ to $k_a$ (i. e., $k_d/k_a$) and is expressed as a molar concentration (M). $K_D$ values for antibodies can be determined using methods well established in the art such as plasmon resonance (for example, BIACORE), ELISA and KINEXA. A preferred method for determining the $K_D$ of an antibody is by using surface Plasmon resonance, preferably using a biosensor system such as a BIACORE system or by ELISA.

"Label" or a "detectable moiety" as used herein, refers broadly to a composition detectable by, for example, spectroscopic, photochemical, biochemical, immunochemical, chemical, or other physical means.

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof and complementary sequences, as well as the sequence explicitly indicated. A nucleic acid may include a gene, a cDNA, an mRNA, an oligonucleotide, and/or a polynucleotide.

"Operatively linked", as used herein, refers broadly to when two DNA fragments are joined such that the amino acid sequences encoded by the two DNA fragments remain in-frame.

"Patient," or "subject" or "recipient", "individual", or "treated individual" refer broadly to any human or nonhuman animal. The animal may be in need of treatment either to alleviate a disease state or to prevent the occurrence or reoccurrence of a disease state. Also, "patient" as used herein, refers broadly to any animal that has risk factors of a disease; a history of disease; susceptibility, symptoms, and signs of a disease; was previously diagnosed with a disease; is at risk for a disease; or is a member of a population at risk for a disease.

"Polypeptide," "peptide," and "protein," are used interchangeably and refer broadly to a polymer of amino acid residues, regardless of modification (e.g., phosphorylation or glycosylation). The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" may include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

"Recombinant" as used herein with reference to a product, e.g., to a cell, or nucleic acid, peptide, or vector, indicates that the cell, nucleic acid, peptide or vector, has been modified by the introduction of a heterologous nucleic acid or peptide or the alteration of a native nucleic acid or peptide or that the cell is derived from a cell so modified. Thus, for example, recombinant cells express genes that are not found within the native (non-recombinant) form of the cell or express native genes that are otherwise abnormally expressed, under expressed or not expressed at all.

"Signal sequence" or "signal peptide," as used herein, refers broadly to a peptide including 15 or more amino acids at the N-terminus of secretory and membrane bound polypeptides. Typically, the amino acids include a large number of hydrophobic amino acids. For example, a signal sequence may contain at least 10-30 amino acids and may have at least 35-65% hydrophobic amino acids (including, for example, Valine, Leucine, Isoleucine or Phenylalanine). A signal sequence may serve to direct a polypeptide containing such a sequence to a lipid bilayer, and a signal sequence may be cleaved in secreted polypeptides.

"Specifically binds," as used herein, refers broadly to a peptide, that in some embodiments, under designated immunoassay conditions, binds to another peptide at least two times greater than the background, at least 10 times greater than the background, or at least 20 times greater than the background.

"Complementary" as used herein, refers broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. A percent complementarity indicates the percentage of contiguous residues in a nucleic acid molecule that can form hydrogen bonds (e.g., Watson-Crick base pairing) with a second nucleic acid sequence (e.g., at least 5, 6, 7, 8, 9, 10 out of 10 being at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence.

"Signs" of disease, as used herein, refers broadly to any abnormality indicative of disease, discoverable on examination of the patient; an objective indication of disease, in contrast to a symptom, which is a subjective indication of disease.

"Soluble VSIG3 or VISTA protein(s)/molecule(s)" as used herein means non-cell-surface-bound VSIG3 and/or VISTA molecules or any portion thereof, including, but not limited to: VSIG3 and/or VISTA fusion proteins or VSIG3 ECD-Ig and/or VISTA ECD-Ig fusion proteins, wherein the extracellular domain of VSIG3 and/or VISTA or fragment thereof is fused to an immunoglobulin (Ig) moiety rendering the fusion molecule soluble, or fragments and derivatives thereof, proteins with the extracellular domain of VSIG3 and/or VISTA fused or joined with a portion of a biologically active or chemically active protein such as the papillomavirus E7 gene product, melanoma-associated antigen p97 or HIV env protein, or fragments and derivatives thereof; hybrid (chimeric) fusion proteins such as VSIG3 and/or VISTA-Ig, or fragments and derivatives thereof. Such fusion proteins are described in greater detail herein. "Soluble VSIG3 or VISTA protein(s)/molecule(s)," as used herein also include VSIG3 or VISTA molecules with the transmembrane domain removed to render the protein soluble, or fragments and derivatives thereof; fragments, portions or derivatives thereof, and soluble VSIG3 or VISTA mutant molecules. The soluble VSIG3 or VISTA molecules used in the methods according to at least some embodiments may or may not include a signal (leader) peptide sequence.

"Substantially free of chemical precursors or other chemicals," as used herein, refers broadly to preparations of a protein (including, for example, VSIG3 or VISTA) in which the protein is separated from chemical precursors or other chemicals which are involved in the synthesis of the protein.

"Symptoms" of disease as used herein, refers broadly to any morbid phenomenon or departure from the normal in structure, function, or sensation, experienced by the patient and indicative of disease.

"T cell," as used herein, refers broadly to CD3+ T cells. The term T cell includes both T helper 1 type T cells and T helper 2 type T cells.

"Therapy," "therapeutic," "treating," or "treatment", as used herein, refer broadly to treating a disease, arresting, or reducing the development of the disease or its clinical symptoms, and/or relieving the disease, causing regression of the disease or its clinical symptoms. Therapy may encompass an alleviation of signs and/or symptoms of disease in patients with ongoing disease signs and/or symptoms (e.g., inflammation, pain). Therapy may include treating or preventing relapses or recurrent signs and/or symptoms (e.g., inflammation, pain). The term "reduced", for purpose of therapy, refers broadly to the clinical significant reduction in signs and/or symptoms. Therapy may encompass prophylaxis and/or precluding the appearance of signs of disease as well as reducing existing signs of disease and eliminating existing signs signs of disease. Therapy may include treating chronic disease ("maintenance") and acute disease.

"Treg cell" (sometimes also referred to as suppressor T cells or inducible Treg cells or iTregs) as used herein refers to a subpopulation of T cells which modulate the immune system and maintain tolerance to self-antigens and can abrogate autoimmune diseases.

"Transmembrane domain," as used herein, refers broadly to an amino acid sequence that spans the plasma membrane. A transmembrane domain may include at least 15, at least 20, at least 25, at least 30, at least 35, at least 40, or at least 45 amino acids.

"Transgenic animal," as used herein, refers broadly to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

"Tumor," as used herein, refers broadly to at least one cell or cell mass in the form of a tissue neoformation, in particular in the form of a spontaneous, autonomous and irreversible excess growth, which is more or less disinhibited, of endogenous tissue, which growth is as a rule associated with the more or less pronounced loss of specific cell and tissue functions. This cell or cell mass is not effectively inhibited, in regard to its growth, by itself or by the regulatory mechanisms of the host organism, e.g., colorectal cancer, melanoma or carcinoma.

"Vaccine" as used herein, refers to a biological preparation that improves immunity to a particular disease, including, for example, cancer or an infectious disease, wherein the vaccine includes a disease specific antigen, for example, a cancer antigen or infectious agent antigen, against which immune responses are elicited. A vaccine may include an adjuvant as immune potentiator to stimulate the immune system. This includes prophylactic (which prevent disease) and therapeutic vaccines (which treat the disease or its symptoms).

"Variable region" or "$V_R$," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein.

Herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

VSIG3-VISTA Interaction

Described herein is evidence of a newly observed interaction between VSIG3 and VISTA. For example, data presented herein provides evidence for the molecular association between VSIG3 and VISTA, and indicates that VSIG3 modulates T cell activation, T cell proliferation, and/or cytokine secretion through an interaction with VISTA.

Also described herein is evidence that VSIG3 is highly expressed in certain types of cancer including, for example, colon cancer, indicating that modulation of the VSIG3/VISTA pathway may be used for cancer immunotherapy.

Without wishing to be bound by theory, it is believed that, in some embodiments, the VSIG3/VISTA interaction described herein may include a multimerized complex. For example, FIG. 17 shows a predicted, minimal VISTA-VSIG3 binding assembly that is consistent with the avidity-based extracellular interaction screen (AVEXIS) interaction assay results shown in FIG. 12, FIG. 13, and FIG. 16, and how the assembly of such a complex could be disrupted by the binding of anti-VSIG3 antibodies. The AVEXIS screen showed that a multimerized VISTA ECD could bind a dimer of VSIG3 ECDs—but in the converse situation, pitting a penta-VSIG3 against a VISTA dimer, a binding event was not detected.

Without wishing to be bound by theory, these results are suggestive of a 4:2 stoichiometry between VISTA and VSIG3 molecules, wherein four VISTA ECDs engage two VSIG3 ECDs. This interaction is reminiscent of the binding complex captured by X-ray crystallography of the PVR-TIGIT structure (Stengel et al., Proc. Natl. Acad. Sci. USA 109 (2012) 5399-5404. doi:10.1073/pnas.1120606109) which shows a 2:2 stoichiometry of stably bound PVR and TIGIT ECDs, as shown in FIG. 17C. The PVR-TIGIT complex illustrates that the immunoglobulin (Ig) domains of TIGIT first need to associate as a homodimer in a back-to-back fashion, employing the 'ABE' or back face of the Ig domain β-sandwich (that is typically comprised of seven to nine β-strands, labeled A-G) (Bork et al., J. Molec. Biol. 242 (1994) 309-320. doi:10.1006/jmbi.1994.1582). The TIGIT ECD homodimer can then bind a pair of PVR ECDs, via respective front-to-front or 'GFC' face interactions. These GFC face-mediated Ig domain interactions are the most common way for Ig domains to bind, and have been captured by X-ray crystallography, in nearly every minimal binding complex between cell surface immunoregulatory receptors (Stengel et al., Proc. Natl. Acad. Sci. USA 109 (2012) 5399-5404. doi:10.1073/pnas.1120606109), and even antibodies and T-cell receptor (TCR) complexes (Lin et al., Proc. Natl. Acad. Sci. USA 105 (2008) 3011-3016. doi:10.1073/pnas.0712278105).

Figure 17A:
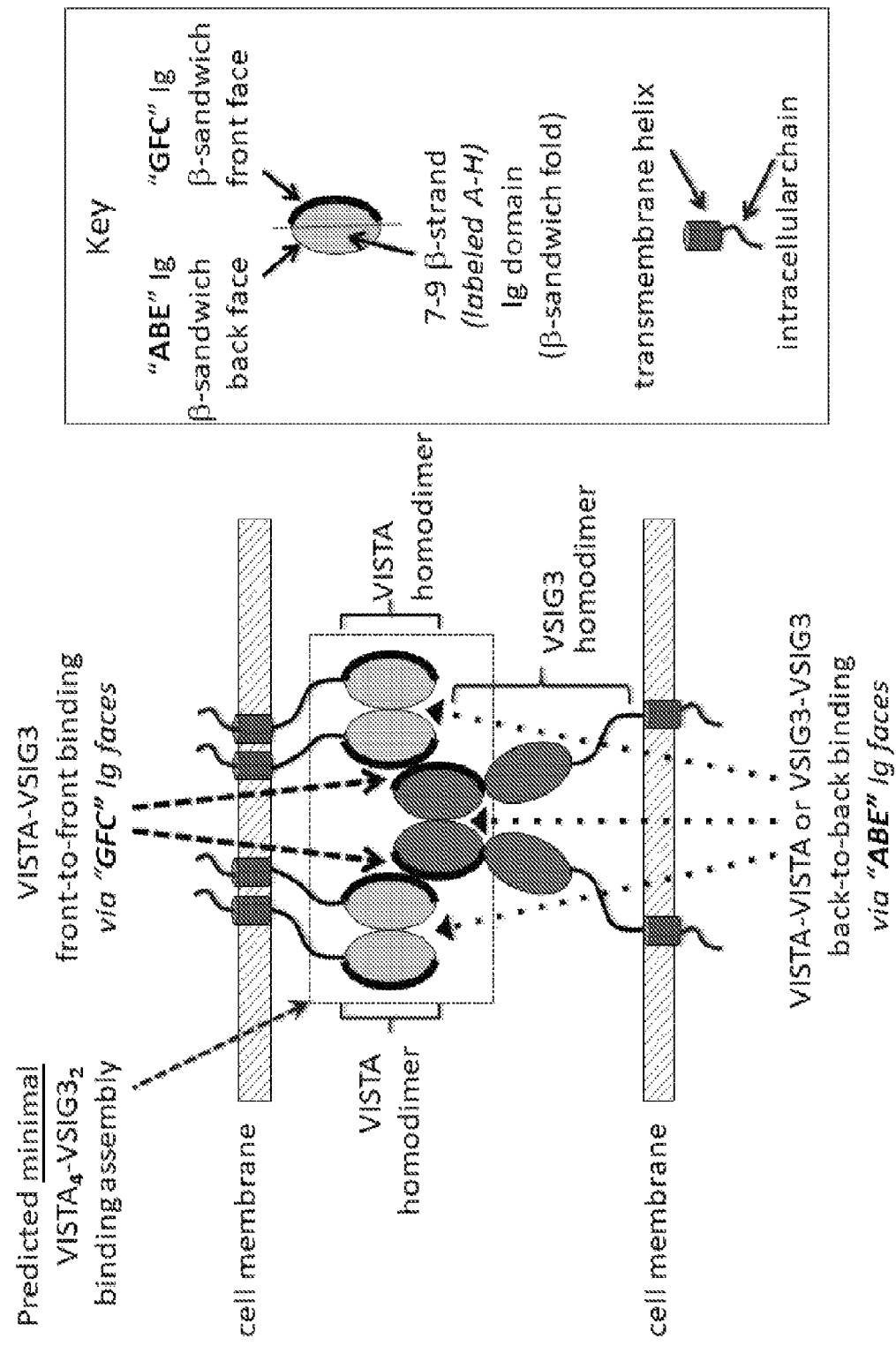
FIG. 17A shows a VISTA-VSIG3 complex having a 4:2 molecular stoichiometry.
Figure 17B:
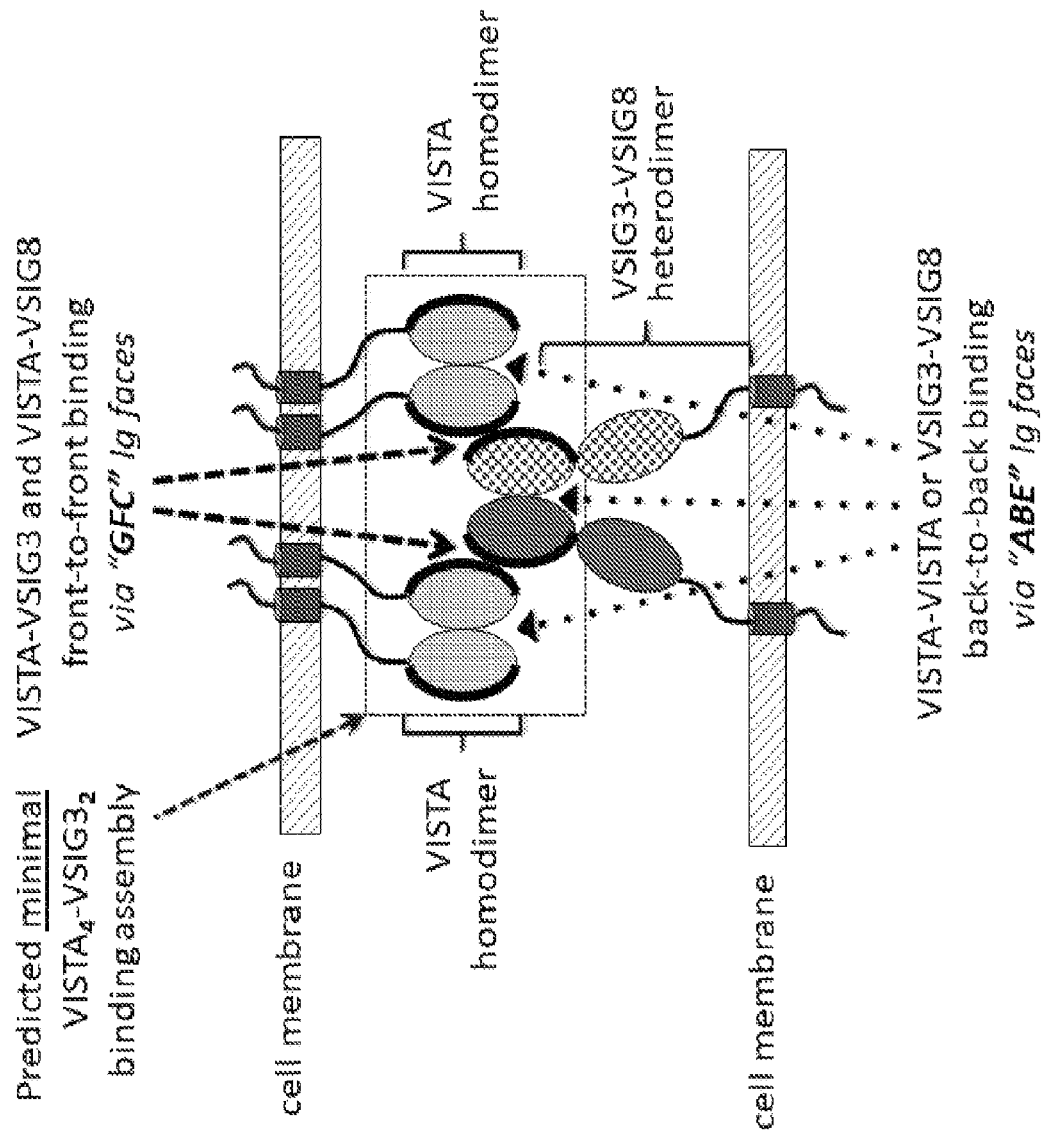
FIG. 17B shows a VISTA-VSIG3 complex including a VSIG3-VSIG8 heterodimer.
Figure 17C:
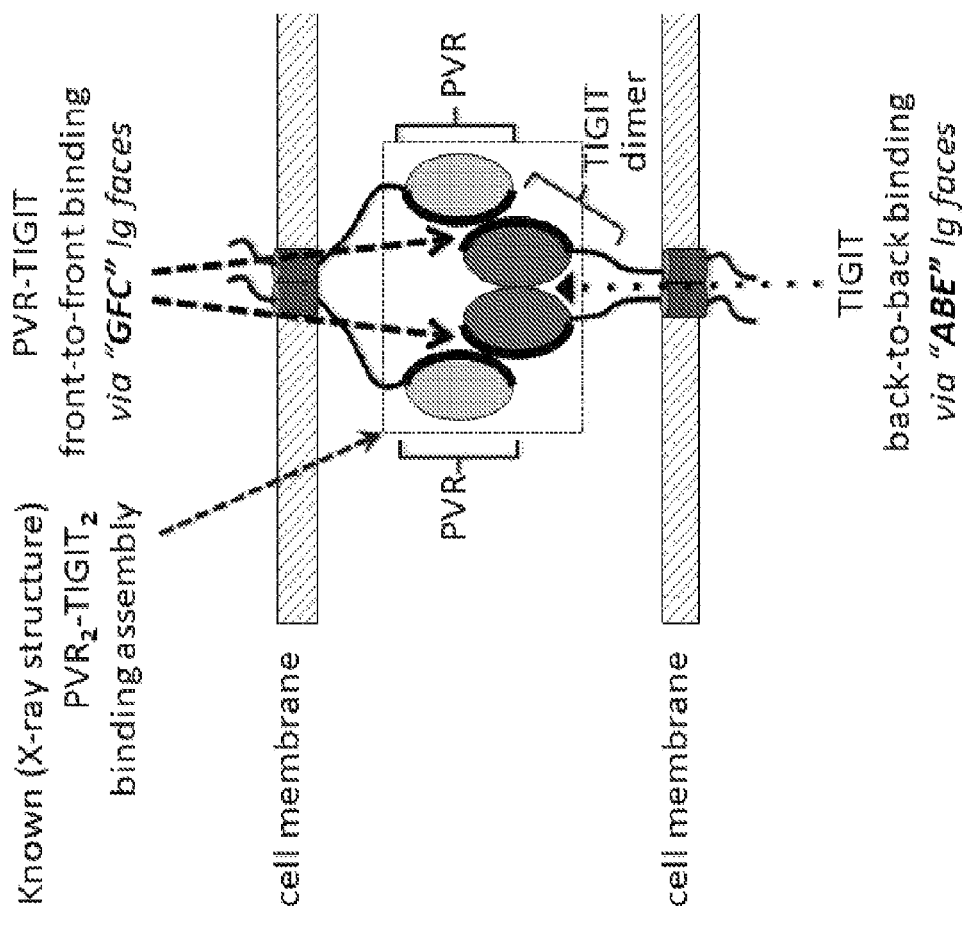
FIG. 17C shows the stoichiometry of a PVR-TIGIT complex.
Figure 17D:
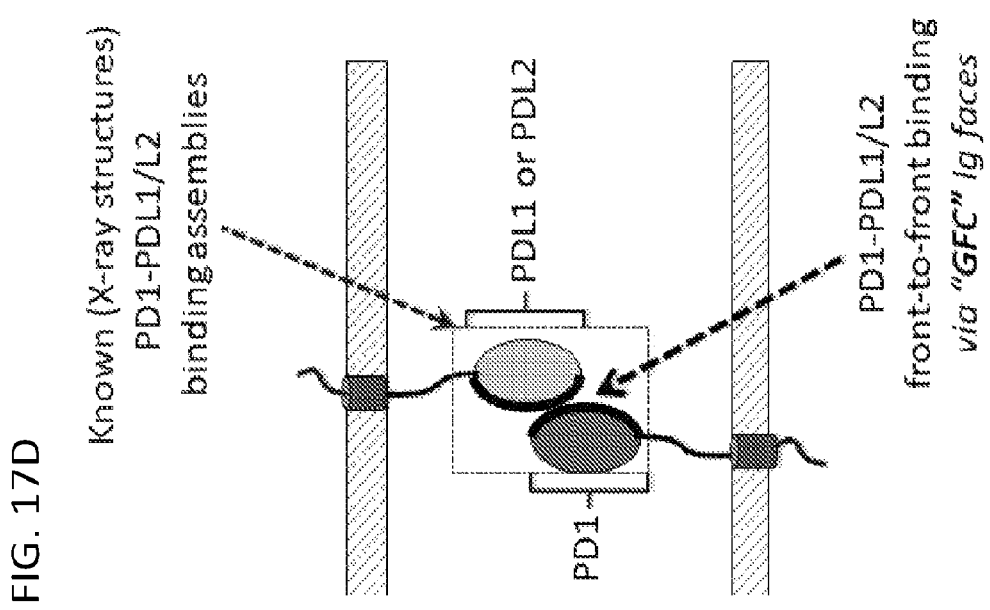
FIG. 17D shows the stoichiometry of a PDL1-PD1 or PDL2-PD1 complex.

Similarly, FIG. 17D shows the 1:1 binding complex between PD-1 and both of its ligands, PD-L1 and PD-L2, that respectively utilize the same front-to-front (or GFC) faces of interacting Ig ECDs (Lin et al., Proc. Natl. Acad. Sci. USA 105 (2008) 3011-3016. doi:10.1073/pnas.0712278105; Lazar-Molnar et al., Proc. Natl. Acad. Sci. USA 105 (2008) 10483-10488. doi:10.1073/pnas.0804453105).

By analogy, VSIG3 may first form a back-to-back (ABE face) homodimer, as shown in FIG. 17A, or possibly a VSIG3-VSIG8 heterodimer, as shown in FIG. 17B (when both are present on the same cell surface). VSIG3 and VSIG8 are Ig superfamily proteins with very similar architectures (both of their respective ECDs reveal a pair of Ig domains, where only their N-terminal domains are predicted to be involved in intercellular binding to the VISTA ECD), and both cluster close together in the same Ig subfamily, drawing from a sensitive sequence-based classification of Ig immuoregulatory proteins (Rubinstein et al., Structure (2013) 766-776, doi:10.1016/j.str.2013.02.022). This close sequence and structural relationship between VSIG3 and VSIG8 could allow their heterodimer formation and joint VISTA binding. As seen with PVR-TIGIT, the central VSIG3 homodimer engages VISTA ECDs through a front-to-front (or GFC face) interaction, shown in FIG. 17A and FIG. 17B. Differently from PVR-TIGIT, however, VISTA does not appear to engage VSIG3 as a monomer, but perhaps due to its unusual, nearly 20 amino acid insert in the middle of its Ig domain (which could destablize the folding of the VISTA Ig β-sandwich) (Nowak et al., Immunol. Rev. 276 (2017) 66-79, doi:10.1111/imr.12525), needs to itself be stabilized via a back-to-back VISTA homodimer—and therefore four VISTA ECDs (in two pairs of back-to-back homodimers) are minimally used to grasp the VSIG3 homodimer (or VSIG3-VSIG8 heterodimer) in respective front-to-front interactions, as shown in FIG. 17A and FIG. 17B. By contrast, as shown in FIG. 17C, PVR is stable as a monomer ECD with a conventional Ig structure, and therefore only two PVRs are needed to engage the TIGIT homodimer.

Figure 17E:
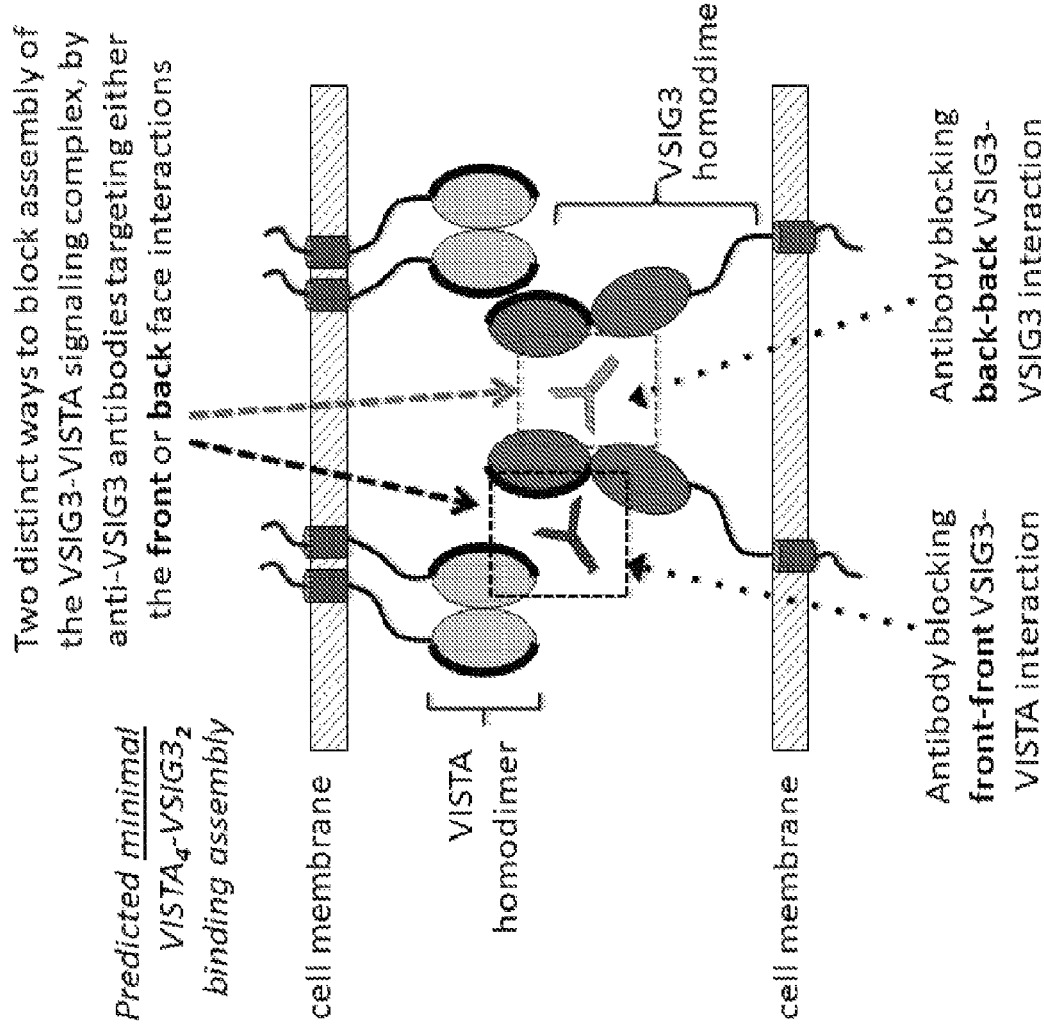
FIG. 17E shows a model of ways to block assembly of a VISTA-VSIG3 complex.

Thus, as further described herein, blocking antibodies directed against VISTA or VSIG3 may, in some embodiments disrupt the assembly of a 4:2 VISTA-VSIG3 complex (or VISTA$_4$-VSIG3$_2$, as shown in FIG. 17A). However, the nature of the minimal binding complex suggests (for the specific case of VSIG3, but applicable also in the case of VISTA or VSIG8 ECDs) as shown in FIG. 17E that anti-VSIG3 antibodies could prevent productive formation of the minimal binding complex by targeting epitopes either on the 'ABE' or back face of VSIG3 (critical to VSIG3-VSIG3 homodimer, or VSIG3-VSIG8 heterodimer formation), or on the 'GFC' or front face of VSIG3—which is uniquely used to bind a VISTA homodimer through a front-to-front VSIG3-VISTA interaction. An antibody that directly and sterically blocks or prevents VSIG3-VISTA binding may target a front face epitope, while an antibody that interferes with VSIG3-VISTA complex formation by destabilizing the core VSIG3 homodimer (or VSIG3-VSIG8 heterodimer) formation, may bind a back face epitope. Antibodies that target the minimal 1:1 binding interactions between immunregulatory receptor and ligand, as seen in FIG. 17D, typically bind the front face, so that the antibody epitope competes exactly with the pair molecule binding. For instance, such face-specific binding is seen for an anti-PD-1 antibody that blocks interaction with both PD-L1 and PD-L2 (Horita et al., Sci. Rep. 13; 6 (2016) 35297. doi:10.1038/srep35297). The anti-PD-1 pembrolizumab antibody targets the front or GFC face of PD-1 receptor, that is used to bind PD-L1/L2 ligands. In some embodiments, therefore, an anti-VSIG3 thats block VISTA interaction in a minimal complex, may fall both in a front-face targeting category, and also in a back-face binding category.

Figure 17F:
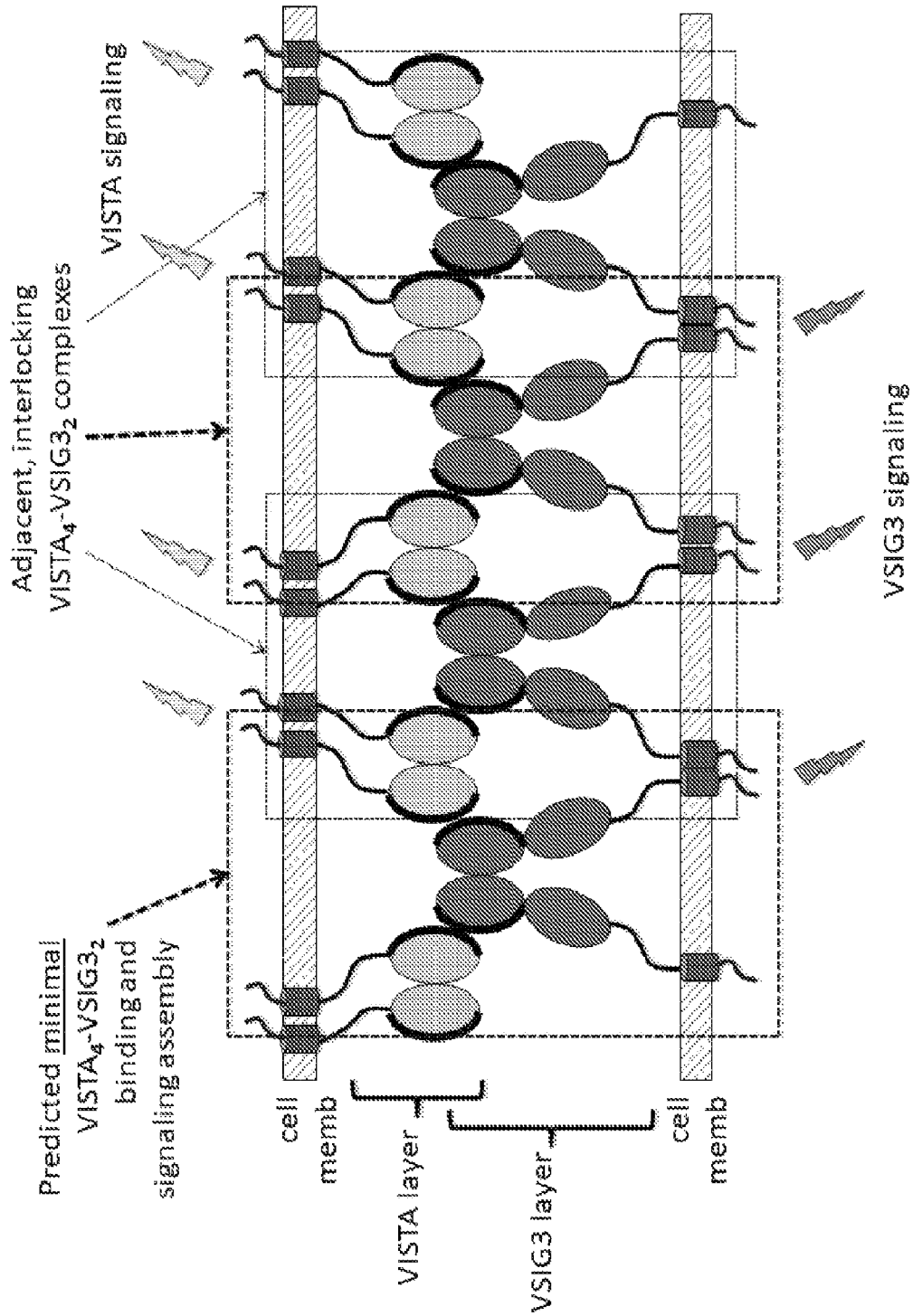
FIG. 17F shows a predicted minimal VISTA-VSIG3 complex having a 4:2 molecular stoichiometry bridging two cell membranes; without wishing to be bound by theory, such a theoretical complex is believed to be able to nucleate a field of adjacent and interlocking VISTA-VSIG3 complexes.

FIG. 17F shows how a predicted minimal VISTA$_4$-VSIG3$_2$ complex, stretching between two cell membranes in the tight confines of a synapse, could nucleate a field of adjacent and interlocking VISTA-VSIG3 complexes. This 'zipper' model could provide a signaling rationale for the complex assembly, since individual VSIG3 molecules from adjacent complexes could form transmembrane helix and intracellular signaling chain dimers. Conversely, the VISTA homodimers present in every complex would themselves already be adjacent, providing a signal into the opposing cell interior, as depicted in FIG. 17F. Looking at this immune synapse cross-section, a VISTA layer of ECDs may engage a VSIG3 layer of ECDs (or mixed VSIG3s and VSIG8s, in heterodimer pairs). Consequently, anti-VSIG3 antibodies could disrupt the formation of this complex, as would anti-VISTA antibodies.

Identification and Methods of Using a VSIG3/VISTA Agonist and/or a VSIG3/VISTA Antagonist The VSIG3/VISTA interaction described herein can be used to identify agonists or antagonists that agonize or antagonize binding of VISTA and VISIG and/or agonize or antagonize an effect of a VSIG3/VISTA interaction. In some embodiments, the VSIG3/VISTA interaction is a VSIG3/VISTA interaction on T cell immunity. In some embodiments, the VSIG3/VISTA interaction includes VISTA signaling. In certain cases, a VSIG3/VISTA antagonist will substantially inhibit or prevent the suppressive effects of VISTA on immunity. In certain cases, a VSIG3 and/or VISTA antagonist will substantially inhibit or prevent the interaction of VSIG3 and VISTA. In certain cases, a VSIG3 and/or VISTA antagonist will result in inhibition of CD3-induced MIP-1 alpha, CD3-induced Rantes (CCL5), CD3- induced CXCL11, CD3-induced Interferon (IFN)-γ, and/or IL-17 (also known as IL-17A) production. Such production may be decreased in peripheral blood mononuclear cells (PBMCs) and/or T cells. This inhibition may be detected using in vitro cell based assays with cells that express VISTA and/or VSIG3. Conversely, in certain cases, a VSIG3/VISTA agonist will substantially potentiate or enhance the suppressive effects of VISTA on immunity. This potentiation can also be detected using in vitro using cell based assays with cells that express VISTA and/or VSIG3.

In some embodiments, a VSIG3/VISTA agonist or a VSIG3/VISTA antagonist agonizes or antagonizes the interaction of VSIG3 and VISTA. In some embodiments, a VSIG3/VISTA agonist or a VSIG3/VISTA antagonist agonizes or antagonizes the interaction of VSIG3 and VISTA when at least one of VSIG3 and VISTA is expressed on the surface of a cell. In some embodiments, a VSIG3/VISTA agonist or a VSIG3/VISTA antagonist can agonize or antagonize the multimerization of VSIG3. The multimerization of VSIG3 may include homodimerization of VSIG3 and/or heterodimerization of VSIG3 including, for example, with VSIG8.

In some embodiments, an VSIG3/VISTA agonist or VSIG3/VISTA antagonist can include an antibody. The antibody can be obtained by in vivo or in vitro immunization using a VSIG3 polypeptide or VISTA polypeptide or a fragment or conjugate thereof as an immunogen. In some embodiments, the antibody includes a human, humanized, primatized, or chimeric antibody. In some embodiments, the antibody includes an antibody fragment. In some embodiments, the antibody fragment includes an Fab, a Fab', a scFv, a (Fab)$_2$, an IgNar, a metMab, etc. In some embodiments, the VSIG3/VISTA agonist or VSIG3/VISTA antagonist includes an anti-VISTA antibody. In some embodiments, the VSIG3/VISTA agonist or VSIG3/VISTA antagonist includes an anti-VSIG3 antibody.

In some embodiments, the VSIG3/VISTA agonists or VSIG3/VISTA antagonists can include a polypeptide. In some cases, the polypeptide may comprise all or a portion of the extracellular region of VSIG3. In certain cases, the polypeptide comprises at least 80, 90, 95 or 99% sequence identity to the extracellular region of VSIG3 or VISTA or a portion thereof such as an IgV domain or IgC domain therein. In certain cases, the polypeptide can also be fused to another polypeptide such as an Ig constant region, e.g., an IgG1, IgG2, IgG3 or IgG4 constant region which optionally may be mutagenized to enhance or inhibit FcR and/or complement binding or other effector function. Also, in some cases, the VSIG3/VISTA agonists or VSIG3/VISTA antagonists can comprise one or more copies of a VSIG3 polypeptide or a fragment thereof or VISTA polypeptide or a fragment thereof. In other words, the VSIG3/VISTA agonists or VSIG3/VISTA antagonists can be multimeric and copies of the VSIG3 polypeptide or a fragment thereof or the VISTA polypeptide or a fragment thereof can be intervened by a linker. In some cases, the linker can be a long, flexible peptide such as one which is at least 15-25 amino acids and containing one or more serine residues.

VSIG3/VISTA agonists and VSIG3/VISTA antagonists can be formulated for use in human therapy. For example, in some cases, a composition can be provided that includes a VSIG3/VISTA agonist or VSIG3/VISTA antagonist in combination with one or more suitable stabilizers, excipients or carriers. In addition, the VSIG3/VISTA agonist or VSIG3/VISTA antagonist in the composition can be modified to enhance in vivo stability. For example, in some cases, the VSIG3/VISTA agonist or VSIG3/VISTA antagonist can be attached to one or more desired moieties such as one or more water-soluble polymers such as polyethylene glycol polymers. Also, in some cases, the composition can include more than one VSIG3/VISTA agonist or VSIG3/VISTA antagonist.

In some cases, compositions are provided containing a VSIG3/VISTA agonist to inhibit T cell immunity in conditions where this is therapeutically desirable, such as autoimmunity, allergy or inflammatory conditions. Such compositions can comprise an amount of a VSIG3/VISTA agonist effective to suppress T cell activation or proliferation in a subject in need thereof. Exemplary autoimmune, inflammatory and allergic conditions include but are not limited to arthritic conditions such as RA, psoriatic arthritis, scleroderma, multiple sclerosis, lupus, IBD, ITP, diabetes, sarcoidosis, allergic asthma, and the like.

In other cases, compositions are provided containing a VSIG3/VISTA antagonist to promote T cell immunity and to treat conditions where this is therapeutically desirable, such as cancer and infectious disease conditions. Such compositions can comprise an amount of an antagonist effective to promote T cell activation or proliferation in a subject in need thereof, e.g. a subject with a cancer.

The VSIG3/VISTA antagonist can be provided in compositions used to treat a cancer. The cancer can include but is not limited to melanoma, lymphoma, leukemia, lung cancer, ovarian cancer, cervical cancer, testicular cancer, digestive cancers, esophageal cancer, liver cancers, pancreatic cancer, kidney cancer and skin cancer. Applicant has also discovered that VSIG3 is highly expressed in colon cancer tissue and liver cancer tissue compared to healthy tissue. Thus, in some cases, a VSIG3/VISTA antagonist can be provided in compositions used to treat colon cancer. Also, in some cases, a VSIG3/VISTA antagonist can be provided in compositions used to treat liver cancer. In certain cases, a VSIG3/VISTA antagonist can be provided in compositions used to treat cancer by blocking interaction of VSIG3 and VISTA to prevent inhibition of MIP-1 alpha, Rantes (CCL5), CXCL11, and IL-17 secretion in PBMCs, which in turn allows for infiltration of T cells, monocytes, dendritic cells and macrophages into cancerous tissues.

Cancers include cancers that express or do not express VSIG3 and/or VISTA and further include non-metastatic or non-invasive as well as invasive or metastatic cancers wherein VSIG3 and/or VISTA expression by immune, stromal or diseased cells suppress antitumor responses and anti-invasive immune responses, and those characterized by vascularized tumors.

The VSIG3/VISTA antagonist can also be provided in compositions used to treat infectious diseases including but not limited to viral diseases such as HIV, HPV, EBV, encephalitis, herpes, other pox viruses, and other known human viruses, parasitic diseases, bacterial diseases, fungal or yeast associated diseases.

It should be understood that the disease conditions identified herein are intended to be exemplary and not exhaustive. In addition, the VSIG3/VISTA agonist or VSIG3/VISTA antagonist can be combined with other therapeutics which can be administered in the same or different compositions, at the same or different time. For example, the VSIG3/VISTA agonist or VSIG3/VISTA antagonist can be administered in a therapeutic regimen that includes the administration of a PD-1 or PD-L1 agonist or antagonist, CTLA4-Ig, a cytokine, a cytokine agonist or antagonist, or another receptor agonist or antagonist.

Antibodies and Homologous Antibodies

Certain embodiments provide an anti-VSIG3 or an anti-VISTA antibody. In some embodiments, the antibody is a monoclonal antibody. In some embodiments, an anti-VSIG3 antibody includes an antibody produced by at least one of the clones listed in Table 2. In some embodiments, an anti-VSIG3 antibody includes an antibody that binds to the same VSIG3 epitope as an antibody produced by at least one of the following clones: #774206, #774208, #774211, #774213, #774220, #774221, #774225, #774226, #774232, and #774234. In some embodiments, an anti-VSIG3 antibody includes an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an antibody can contain one, two, three, four, five, six, or more amino acid substitutions relative to the antibodies identified above which do not substantially affect binding of the antibody to VSIG3 and/or the function of the antibody.

In some embodiments, an anti-VSIG3 antibody includes an antibody having the same heavy chain as an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an anti-VSIG3 antibody includes an antibody having the same light chain as an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an anti-VSIG3 antibody includes an antibody having the same heavy chain and the same light chain as an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an antibody can contain one, two, three, four, five, six, or more amino acid substitutions in the heavy chain and/or the light chains identified above which do not substantially affect binding of the antibody to VSIG3 and/or the function of the antibody.

In some embodiments, an anti-VSIG3 antibody includes an antibody having the same heavy chain variable region ($V_H$ domain) as an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an anti-VSIG3 antibody includes an antibody having the same light chain variable region (VL domain) as an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an anti-VSIG3 antibody includes an antibody having the same $V_H$ domain and the same VL domain as an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an anti-VSIG3 antibody can contain one, two, three, four, five, six, or more amino acid substitutions in the $V_H$ domains and/or the VL domains identified above which do not substantially affect binding of the antibody to VSIG3.

In some embodiments, an anti-VSIG3 antibody includes an antibody having at least one CDR, at least two CDRs, or at least 3 CDRs from the heavy chain of an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an anti-VSIG3 antibody includes an antibody having at least one CDR, at least two CDRs, or at least 3 CDRs from the light chain of an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436. In some embodiments, an anti-VSIG3 antibody includes an antibody having at least one CDR, at least two CDRs, or at least 3 CDRs from the heavy chain and at least one CDR, at least two CDRs, or at least 3 CDRs from the light chain of an antibody produced by at least one of the following clones: #774206, #774208, #774211, #774213, #774220, #774221, #774225, #774226, #774232, #774234, #973401, #973404, #973408, #973422, #973423, #973428, #973433, #973435, and #973436.

In some embodiments, an anti-VSIG3 antibody can contain one, two, three, four, five, six, or more amino acid substitutions in one or more CDRs identified above which do not substantially affect binding of the antibody to VSIG3. In some embodiments, an anti-VSIG3 antibody can contain one, two, three, four, five, six, or more amino acid substitutions in a frameword regions. In some embodiments, amino acid substitutions in the frameword regions do not substantially affect binding of the antibody to VSIG3.

In some embodiments, an anti-VSIG3 antibody includes a light chain variable region including at least one of the sequences of FIG. 19A. In some embodiments, an anti-VSIG3 antibody includes a light chain variable region including at least one SEQ ID NOs:73-78. In some embodiments, an anti-VSIG3 antibody includes a heavy chain variable region including at least one of the sequences of FIG. 19B. In some embodiments, an anti-VSIG3 antibody includes a heavy chain variable region including at least one of SEQ ID NOs:79-83.

In some embodiments, an anti-VSIG3 antibody includes a light chain variable region including at least one of the sequences of FIG. 19C. In some embodiments, an anti-VSIG3 antibody includes a light chain variable region including at least one SEQ ID NOs:85-89. In some embodiments, an anti-VSIG3 antibody includes a heavy chain variable region including at least one of the sequences of FIG. 19D. In some embodiments, an anti-VSIG3 antibody includes a heavy chain variable region including at least one of SEQ ID NOs:90-94.

In some embodiments, an anti-VSIG3 antibody includes a light chain variable region including at least one of the sequences of FIG. 18A. In some embodiments, an anti-VSIG3 antibody includes a light chain variable region including at least one SEQ ID NOs:7-33. In some embodiments, an anti-VSIG3 antibody includes a heavy chain variable region including at least one of the sequences of FIG. 18B. In some embodiments, an anti-VSIG3 antibody includes a heavy chain variable region including at least one of SEQ ID NOs:40-72.

In some embodiments, an anti-VSIG3 antibody includes an antibody that interacts with an ABE Ig face of VSIG3. In some embodiments, an anti-VSIG3 antibody includes an antibody that interacts with an GFC Ig face of VSIG3.

The anti-VSIG3 antibody or anti-VISTA antibody can comprise a heavy chain variable region from a particular germline heavy chain immunoglobulin gene and/or a light chain variable region from a particular germline light chain immunoglobulin gene. For example, the anti-VSIG3 antibody or anti-VISTA antibody can comprise or consist of a human antibody comprising heavy or light chain variable regions that are the product of or derived from a particular germline sequence if the variable regions of the antibody are obtained from a system that uses human germline immunoglobulin genes. Such systems include immunizing a transgenic mouse carrying human immunoglobulin genes with an antigen of interest or screening a human immunoglobulin gene library displayed on phage with an antigen of interest. A human antibody that is the product of or derived from a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody.

A human antibody that is the product of or derived from a particular human germline immunoglobulin sequence can contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, 96%, 97%, 98%, or 99%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

In certain embodiments, the anti-VSIG3 antibody or anti-VISTA antibody comprises heavy and light chain variable regions comprising amino acid sequences that are homologous to isolated anti-VSIG3 amino acid sequences of preferred anti-VSIG3 antibodies, respectively, or isolated anti-VISTA amino acid sequences of preferred anti-VISTA antibodies, respectively, wherein the antibodies retain the desired functional properties of the parent antibodies. In some cases, the anti-VSIG3 antibody or anti-VISTA antibody has a percent homology between two amino acid sequences that is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4: 11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available commercially), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, protein sequences can further be used as a "query sequence" to perform a search against public databases to, for example, identify related sequences. Such searches can be performed using the XBLAST program (version 2.0) of Altschul, et al. (1990) J Mol. Biol. 215:403-10. BLAST protein searches can be performed with the XBLAST program, score=50, word-length=3 to obtain amino acid sequences homologous to the antibody molecules according to at least some embodiments. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

In certain embodiments, an anti-VSIG3 antibody or anti-VISTA antibody comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on a preferred anti-VSIG3 antibody or anti-VISTA antibody isolated and produced using methods herein, or conservative modifications thereof. Such an anti-VSIG3 antibody or anti-VISTA antibody produced therein retains desired functional properties of the preferred anti-VSIG3 antibody or the preferred anti-VISTA antibody. The anti-VSIG3 antibody or anti-VISTA antibody can be a human antibody, a humanized antibody or a chimeric antibody. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody according to at least some embodiments by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Thus, one or more amino acid residues within the CDR regions of an antibody according to at least some embodiments can be replaced with other amino acid residues from the same side chain family and the altered antibody can be tested for retained function (i.e., the functions set forth in (c) through j) above) using the functional assays described herein.

Anti-VSIG3 Antibodies or Anti-VISTA Antibodies that Bind to the Same Epitope

Certain embodiments provide an anti-VSIG3 antibody or anti-VISTA antibody that binds to the same epitope as another selected antibody. Such an anti-VSIG3 antibody or anti-VISTA antibody possesses desired functional properties such as modulation of immune stimulation and related functions. Other antibodies with the same epitope specificity may be selected and will have the ability to cross-compete for binding to VSIG3 antigen (or to VISTA antigen) with the desired antibodies. Alternatively, the epitopic specificity of a desired antibody may be determined using a library of overlapping peptides.

Engineered and Modified Antibodies

Other embodiments provide a modified anti-VSIG3 antibody or anti-VISTA antibody. Such a modified anti-VSIG3 antibody or anti-VISTA antibody is engineered such that it has altered properties from a desired starting anti-VSIG3 antibody or anti-VISTA antibody. In some cases, the modified anti-VSIG3 antibody or anti-VISTA antibody has one or more of the VH and/or $V_L$ sequences derived from a starting anti-VSIG3 antibody or anti-VISTA antibody but has altered properties from the starting anti-VSIG3 antibody or anti-VISTA antibody. In some cases, the modified anti-VSIG3 antibody or anti-VISTA antibody can be engineered by modifying one or more residues within one or both variable regions (i.e., VH and/or VL) of a starting anti-VSIG3 antibody or anti-VISTA antibody, for example within one or more CDR regions and/or within one or more framework regions. Additionally or alternatively, the modified anti-VSIG3 antibody or anti-VISTA antibody can be engineered by modifying residues within the constant regions of a starting anti-VSIG3 antibody or anti-VISTA antibody, for example to alter the effector functions of the starting anti-VSIG3 antibody or anti-VISTA antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties Suitable framework sequences can be obtained from public DNA databases or published references that include germline antibody gene sequences. For example, germline DNA sequences for human heavy and light chain variable region genes can be found in the "VBase" human germline sequence database (available on the Internet), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J Immunol. 24:827-836; the contents of each of which are expressly incorporated herein by reference.

Another type of variable region modification is to mutate amino acid residues within the VH and/or $V_L$ CDR 1, CDR2 and/or CDR3 regions to thereby improve one or more binding properties (e.g., affinity) of the starting anti-VSIG3 antibody or anti-VISTA antibody. Site-directed mutagenesis or PCR-mediated mutagenesis can be performed to introduce the mutations and the effect on antibody binding, or other functional property of interest, can be evaluated in appropriate in vitro or in vivo assays. Preferably conservative modifications (as discussed herein) are introduced. The mutations may be amino acid substitutions, additions or deletions, but are preferably substitutions. Moreover, typically no more than one, two, three, four or five residues within a CDR region are altered.

Modified anti-VSIG3 antibodies or anti-VISTA antibodies can also include those in which modifications have been made to framework residues within VH and/or VL, e.g. to improve the properties of the starting anti-VSIG3 antibody or starting anti-VISTA antibody. Typically such framework modifications are made to decrease the immunogenicity of the starting anti-VSIG 3 antibody or starting anti-VISTA antibody. For example, one approach is to "backmutate" one or more framework residues to the corresponding germline sequence. For example, a modified anti-VSIG3 antibody that has undergone somatic mutation may contain framework residues that differ from the germline sequence from the starting anti-VSIG3 antibody. Such residues can be identified by comparing the antibody framework sequences to the germline sequences from the starting anti-VSIG3 antibody.

In addition or alternative to modifications made within the framework or CDR regions, a modified anti-VSIG3 antibody or modified anti-VISTA antibody can be engineered to include modifications within the Fc region, typically to alter one or more functional properties of the starting anti-VSIG3 antibody or starting anti-VISTA antibody, such as serum half-life, complement fixation, Fc receptor binding, and/or antigen-dependent cellular cytotoxicity. Furthermore, a modified anti-VSIG3 antibody or modified anti-VISTA antibody can be chemically modified (e.g., one or more chemical moieties can be attached to the starting anti-VSIG3 antibody or starting anti-VISTA antibody) or be modified to alter its glycosylation, again to alter one or more functional properties of the starting anti-VSIG3 antibody or starting anti-VISTA antibody. Such embodiments are described further below. The numbering of residues in the Fc region is that of the EU index of Kabat.

In one embodiment, the hinge region of CH1 in a starting anti-VSIG3 antibody or starting anti-VISTA antibody is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the starting anti-VSIG3 antibody or starting anti-VISTA antibody.

In another embodiment, the Fc hinge region of a starting anti-VSIG3 antibody or starting anti-VISTA antibody is mutated to decrease the biological half-life. More specifically, one or more amino acid mutations are introduced into the CH2-CH3 domain interface region of the Fc-hinge fragment to produce a modified anti-VSIG3 antibody or modified anti-VISTA antibody impaired Staphylococcal protein A (SpA) binding relative to native Fc-hinge domain SpA binding. This approach is described in further detail in U.S. Pat. No. 6,165,745.

In another embodiment, the starting anti-VSIG3 antibody or starting anti-VISTA antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the starting anti-VSIG3 antibody or starting anti-VISTA antibody can be altered within the $C_{H1}$ or $C_L$ region to contain a salvage receptor binding epitope taken from two loops of a $C_{H2}$ domain of an Fc region of an IgG, as described in U.S. Pat. Nos. 5,869,046 and 6,121,022.

In yet other embodiments, the Fc region in a starting anti-VSIG3 antibody or starting anti-VISTA antibody is altered by replacing at least one amino acid residue with a different amino acid residue to alter the effector functions. For example, one or more amino acids selected from amino acid residues 234, 235, 236, 237, 297, 318, 320 and 322 can be replaced with a different amino acid residue such that the modified anti-VSIG3 antibody or modified anti-VISTA antibody has an altered affinity for an effector ligand but retains the antigen-binding ability of the starting anti-VSIG3 antibody or starting anti-VISTA antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the modified anti-VSIG3 antibody or modified anti-VISTA antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the starting anti-VSIG3 antibody or starting anti-VISTA antibody to fix complement. This approach is described further in PCT Publication WO 94/29351 by Bodmer et al.

In yet another example, the Fc region is modified to increase the ability of the starting anti-VSIG3 antibody or starting anti-VISTA antibody to mediate antibody dependent cellular cytotoxicity (ADCC) and/or to increase the affinity of the starting anti-VSIG3 antibody or starting anti-VISTA antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 are shown to improve binding to FcγRIII. Additionally, the following combination mutants are shown to improve FcγRIII binding: T256A/S298A, S298A/E333A, S298A/K224A and S298A/E333A/K334A. Furthermore, mutations such as M252Y/S254T/T256E or M428L/N434S improve binding to FcRn and increase antibody circulation half-life (see Chan C A and Carter P J (2010) Nature Rev Immunol 10:301-316).

In still another embodiment, the starting anti-VSIG3 antibody or starting anti-VISTA antibody can be modified to abrogate in vivo Fab arm exchange. Specifically, this process involves the exchange of IgG4 half-molecules (one heavy chain plus one light chain) between other IgG4 antibodies that effectively results in b specific antibodies which are functionally monovalent. Mutations to the hinge region and constant domains of the heavy chain can abrogate this exchange (see Aalberse, R C, Schuurman J., 2002, Immunology 105:9-19).

In still another embodiment, the glycosylation of a starting anti-VSIG3 antibody or starting anti-VISTA antibody is modified. For example, an aglycosylated modified anti-VSIG3 antibody or anti-VISTA antibody can be made (i.e., the antibody lacks glycosylation). Glycosylation can be altered to, for example, increase the affinity of the starting anti-VSIG3 antibody or starting anti-VISTA antibody for antigen. Such carbohydrate modifications can be accomplished by, for example, altering one or more sites of glycosylation within the starting anti-VSIG3 antibody or anti-VISTA antibody sequence. For example, one or more amino acid substitutions can be made that result in elimination of one or more variable region framework glycosylation sites to thereby eliminate glycosylation at that site. Such aglyclosylation may increase the affinity of the starting anti-VSIG3 antibody or starting anti-VISTA antibody for antigen. Such an approach is described in further detail in U.S. Pat. Nos. 5,714,350 and 6,350,861.

Additionally or alternatively, a modified anti-VSIG 3 antibody or modified anti-VISTA antibody can be made that has an altered type of glycosylation, such as a hypofucosylated anti-VSIG 3 antibody or anti-VISTA antibody having reduced amounts of fucosyl residues or a modified anti-VSIG 3 antibody or anti-VISTA antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of to thereby produce a modified anti-VSIG 3 antibody or anti-VISTA antibody with altered glycosylation. For example, the cell lines Ms704, Ms705, and Ms709 lack the fucosyltransferase gene, FUT8 (a (1,6) fucosyltransferase), such that antibodies expressed in the Ms704, Ms705, and Ms709 cell lines lack fucose on their carbohydrates. The Ms704, Ms705, and Ms709 FUT8 cell lines are created by the targeted disruption of the FUT8 gene in CHO/DG44 cells using two replacement vectors (see U.S. Patent Publication No. 20040110704 by Yamane et al. and Yamane-Ohnuki et al. (2004) Biotechnol Bioeng 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the a 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell. PCT Publication WO 99/54342 by Umana et al. describes cell lines engineered to express glycoprotein-modifying glycosyl transferases (e.g., P(1,4)-N-acetylglucosaminyltransferase III (GnTIII)) such that antibodies expressed in the engineered cell lines exhibit increased bisecting GlcNac structures which results in increased ADCC activity of the antibodies. Alternatively, the fucose residues of the starting anti-VSIG 3 antibody or anti-VISTA antibody may be cleaved off using a fucosidase enzyme. For example, the fucosidase a-L-fucosidase removes fucosyl residues from antibodies.

Another modification of a starting anti-VSIG 3 antibody or anti-VISTA antibody can include pegylation or addition of other water soluble moieties, typically polymers, e.g., in order to enhance half-life. A starting anti-VSIG 3 antibody or anti-VISTA antibody can be pegylated to, for example, increase the biological (e.g., serum) half-life. To pegylate a starting anti-VSIG 3 or anti-VISTA antibody, the starting anti-VSIG 3 antibody or anti-VISTA antibody, or fragment thereof, typically is reacted with polyethylene glycol (PEG), such as a reactive ester or aldehyde derivative of PEG, under conditions in which one or more PEG groups become attached to the starting anti-VSIG 3 antibody or anti-VISTA antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (Ci-Cio) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments.

Methods of Engineering Antibodies

In certain embodiments, a starting anti-VSIG3 antibody or anti-VISTA antibody having $V_H$ and $V_L$ sequences can be used to create a modified anti-VSIG3 antibody or anti-VISTA antibody, respectively, by modifying the $V_H$ and/or $V_L$ sequences, or the constant regions attached thereto. Thus, in some cases, the structural features of an starting anti-VSIG3 antibody or anti-VISTA antibody is used to create a structurally related modified anti-VSIG3 antibody or anti-VISTA antibody that retains at least one functional property, such as binding to human VSIG3. For example, one or more CDR regions of a starting anti-VSIG 3 antibody or anti-VISTA antibody or mutations thereof can be combined recombinantly with known framework regions and/or other CDRs to create a modified anti-VSIG3 antibody or anti-VISTA antibody. Other types of modifications include those described in the previous section.

In some cases, the starting material engineering a modified anti-VSIG 3 antibody or anti-VISTA antibody is one or more of the $V_H$ and/or $V_L$ sequences provided herein, or one or more CDR regions thereof. To create the modified anti-VSIG 3 antibody or anti-VISTA antibody, it is not necessary to actually prepare (i.e., express as a protein) an antibody having one or more of the $V_H$ and/or $V_L$ sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence. Preferably, the anti-VSIG3 antibody or anti-VISTA antibody encoded by the altered antibody sequences is one that retains one, some or all of the functional properties of the starting anti-VSIG3 antibody or anti-VISTA antibody. In some cases, the functional properties include binding to VSIG3 antigen or VISTA antigen with a specific KD level or less and/or modulating immune responses and/or selectively binding to desired target cells such as for example that express VSIG3 antigen or VISTA antigen.

The functional properties of the modified anti-VSIG3 antibody or anti-VISTA antibody can be assessed using standard assays available in the art and/or described herein. In certain embodiments, mutations can be introduced randomly or selectively along all or part of an anti-VSIG3 antibody or anti-VISTA antibody coding sequence and the resulting modified anti-VSIG3 antibody or anti-VISTA antibody can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

VSIG3 Polypeptides, VISTA Polypeptides, and Fragments Thereof

Certain embodiments provide a VSIG3 polypeptide. In some cases, the VSIG3 polypeptide is a polypeptide or fragment thereof. In some embodiments, a fragment includes a soluble fragment. In some cases, the VSIG3 polypeptide is a polypeptide or fragment thereof corresponding to the polypeptide sequence listed in any one of SEQ ID NOs: 1 or 2, and/or variants thereof possessing at least 80% sequence identity, more preferably at least 90% sequence identity therewith and even more preferably at least 95, 96, 97, 98 or 99% sequence identity therewith, and/or fusions and or conjugates thereof, and/or polynucleotides encoding same.

Certain embodiments provide a VSIG3 fusion protein. In some cases, the VSIG3 fusion protein is a polypeptide or fragment thereof. In some embodiments, a fragment includes a soluble fragment. In some cases, the VSIG3 fusion protein is a polypeptide or fragment thereof corresponding to the polypeptide sequences listed in SEQ ID NO: 3, and/or variants thereof possessing at least 80% sequence identity, more preferably at least 90% sequence identity therewith and even more preferably at least 95, 96, 97, 98 or 99% sequence identity therewith, and/or fusions and or conjugates thereof, and/or polynucleotides encoding same. In some cases, the VSIG3 fusion protein includes an Fc domain.

Certain embodiments provide a VISTA polypeptide. In some cases, the VISTA polypeptide is a polypeptide or fragment thereof. In some embodiments, a fragment includes a soluble fragment. In some cases, the VISTA polypeptide is a polypeptide or fragment thereof corresponding to the polypeptide sequences listed in any one of SEQ ID NOs: 4 or 5, and/or variants thereof possessing at least 80% sequence identity, more preferably at least 90% sequence identity therewith and even more preferably at least 95, 96, 97, 98 or 99% sequence identity therewith, and/or fusions and or conjugates thereof, and/or polynucleotides encoding same.

Certain embodiments provide a VISTA fusion protein. In some cases, the VISTA fusion protein is a polypeptide or fragment thereof. In some embodiments, a fragment includes a soluble fragment. In some cases, the VISTA fusion protein is a polypeptide or fragment thereof corresponding to the polypeptide sequences listed in SEQ ID NO: 6, and/or variants thereof possessing at least 80% sequence identity, more preferably at least 90% sequence identity therewith and even more preferably at least 95, 96, 97, 98 or 99% sequence identity therewith, and/or fusions and or conjugates thereof, and/or polynucleotides encoding same. In some cases, the VISTA fusion protein includes an Fc domain.

In some embodiments, a VSIG3 polypeptide or VISTA polypeptide can include a soluble protein including, for example, a soluble fragment of VSIG3 or of VISTA, and/or the ECD of VSIG3 or of VISTA. In some embodiments, an ECD of VSIG3 or of VISTA includes an IgV domain of VSIG3 or VISTA.

The VSIG3 proteins or VISTA proteins can contain an immunoglobulin domain within the extracellular domain, the IgV domain (or V domain), which is related to the variable domain of antibodies. The IgV domain may be responsible for receptor binding, by analogy to the other B7 family members. The Ig domain of the extracellular domain includes one disulfide bond formed between intra domain cysteine residues, as is typical for this fold and may be important for structure-function.

In one embodiment, there is provided a soluble fragment of VSIG3 or VISTA; as described in greater detail below with regard to the section on fusion proteins, such a soluble fragment may optionally be described as a first fusion partner. Useful fragments are those that alone or when comprised in fusion proteins or multimerized retain the ability to bind to their natural receptor or receptors, e.g., expressed on T and NK cells, and/or which modulate (inhibit or promote) T cell and/or NK cell activation. A VSIG3 polypeptide or VISTA polypeptide that is a fragment of full-length VSIG3 or VISTA typically has at least 20 percent, 30 percent, 40 percent, 50 percent, 60 percent, 70 percent, 80 percent, 90 percent, 95 percent, 98 percent, 99 percent, 100 percent, or even more than 100 percent of the ability to bind its natural receptor(s) and/or the modulation (agonism or antagonism) of one or more of the functional effects of VSIG3 or VISTA on immunity and on specific immune cells as compared to full-length VSIG3 or VISTA. Soluble VSIG3 or VISTA polypeptide fragments are fragments of VSIG3 or VISTA polypeptides that may be shed, secreted or otherwise extracted from the producing cells. In other embodiments, the soluble fragments of VSIG3 or VISTA polypeptides include fragments of the VSIG3 or VISTA extracellular domain that retain VSIG3 or VISTA biological activity, such as fragments that retain the ability to bind to their natural receptor or receptors and/or which modulate (inhibit or promote) T or NK cell activation. The extracellular domain can include 1, 2, 3, 4, or 5 contiguous amino acids from the transmembrane domain, and/or 1, 2, 3, 4, or 5 contiguous amino acids from the signal sequence. Alternatively, the extracellular domain can have 1, 2, 3, 4, 5 or more amino acids removed from the C-terminus, N-terminus, or both.

In some embodiments, the VSIG3 extracellular domain polypeptide comprises the amino acid sequence of the IgV domain as set forth in SEQ ID NO: 2, or fragments or variants thereof. In other embodiments, the VSIG3 extracellular domain polypeptide consists essentially of the amino acid sequence of the IgV domain as set forth SEQ ID NO: 1.

In some embodiments, the VISTA extracellular domain polypeptide comprises the amino acid sequence of the IgV domain as set forth in SEQ ID NO: 5, or fragments or variants thereof.

The VSIG3 or VISTA polypeptide fragments may be expressed from a nucleic aci. In some embodiments, the nucleic acid encoding a VSIG3 or VISTA polypeptide fragment may include a sequence that encode a signal sequence. The signal sequence can be generally cleaved from the immature polypeptide to produce the mature polypeptide lacking the signal sequence. The signal sequence of VSIG3 or VISTA can be replaced by the signal sequence of another polypeptide using standard molecule biology techniques to affect the expression levels, secretion, solubility, or other property of the polypeptide. The signal peptide sequence that is used to replace the VSIG3 or VISTA signal peptide sequence can be any known in the art.

In some embodiments, a VSIG3 or VISTA polypeptide fragment including, for example, a soluble portion thereof, will modulate (agonize or antagonize) one or more of VSIG3's effects on immunity and specific types of immune cells such as cytotoxic or effector T cells, Tregs, and NK cells.

Modified Polypeptides

Certain embodiments provide a modified VSIG3 or VISTA polypeptide. In some cases, the modified VSIG3 or VISTA polypeptide has an increased biological activity or an increased half-life or increased stability as compared to a starting VSIG3 or VISTA polypeptide. In some cases, the starting VSIG3 or VISTA polypeptide can be a VSIG3 or VISTA protein or a fragment thereof or a fusion VSIG3 or VISTA protein having VSIG3 or VISTA protein activity. In some cases, a VSIG3 or VISTA protein or fusion VSIG3 or VISTA protein is modified with at least one amino acid substitution, deletion, or insertion that increases the binding of the molecule to an immune cell, for example a T cell, and transmits an inhibitory signal into the T cell. In certain cases, the VSIG3 or VISTA protein or fusion VSIG3 or VISTA protein comprises at least one half-life extending moiety. A half-life extending moiety can include but is not limited to polyethylene glycol (PEG), monomethoxy PEG (mPEG), an XTEN molecule, an rPEG molecule, an adnectin, a serum albumin, human serum albumin, immunoglobulin constant region or fragment thereof, or acyl group. In some cases, the half-life extending moiety can increase the in vivo half-life of the VSIG3 or VISTA polypeptide or VSIG3 or VISTA fusion protein by at least 2-fold, at least 3-fold, at least 4-fold, at least 5-fold, at least 10-fold, or more compared to an otherwise identical molecule that lacks the half-life extending moiety.

In other cases, the modified VSIG3 polypeptide or VISTA polypeptide can be engineered to preferentially bind to one type of T cell versus other immune cells or to NK cells. For example, the modified VSIG3 polypeptide or VISTA polypeptide can be engineered to preferentially bind to Tregs, Th0, Th1, Th17, Th2 or Th22 cells or to NK cells. Preferential binding refers to binding that is at least 10%, 20%, 30%, 40%, 50%, 60%, 70%, 80%, 90%, 95%, or greater for one type of cell over another type of cell. In other cases, the modified VSIG3 polypeptide or VISTA polypeptide can be engineered to have reduced binding to immune cells relative to wild-type VSIG3 protein or VISTA protein, respectively. Such a modified VSIG3 polypeptide or VISTA polypeptide can be used in combination with another modified VSIG3 or VISTA polypeptide having a stronger binding property to modulate the immune response with a more moderate impact.

In other cases, the modified VSIG3 or VISTA polypeptide can be engineered to have an increased half-life relative to a wild-type VSIG3 or VISTA polypeptide. In some cases, the modified VSIG3 or VISTA polypeptide is modified to resist enzymatic degradation. Exemplary modifications include modified amino acid residues and modified peptide bonds that resist enzymatic degradation.

Fusion Polypeptides

Some embodiments provide a VSIG3 or VISTA fusion polypeptide. In certain cases, the VSIG3 or VISTA fusion polypeptide is a VSIG3 or VISTA fusion protein. In some cases, the VSIG3 or VISTA fusion polypeptide includes a first VSIG3 or VISTA polypeptide fused to a second polypeptide. The first VSIG3 or VISTA polypeptide can be from a VSIG3 or VISTA protein in some cases. Likewise, the second polypeptide can be from a protein in some cases. The first VSIG3 or VISTA polypeptide can be fused to the second polypeptide directly or via a linker peptide sequence or a chemical linker. The presence of the second polypeptide can alter the solubility, stability, affinity and/or valency of the VSIG3 or VISTA polypeptide. As used herein, "valency" refers to the number of binding sites available per molecule. In some cases, the second polypeptide is a polypeptide from a different protein than the first VSIG3 or VISTA polypeptide.

In some embodiments, the second polypeptide contains one or more domains of an immunoglobulin heavy chain constant region, preferably having an amino acid sequence corresponding to a hinge, Cm and Cm regions of a human immunoglobulin Cy1, Cy2, Cy3 or Cy4 chain or to a hinge, Cm and Cm regions of a murine immunoglobulin Cy2a chain. According to some embodiments, the VSIG3 or VISTA fusion protein is a dimeric VSIG3 or VISTA fusion protein which optionally is capable of cross-linking two or more targets. In a dimeric VSIG3 or VISTA fusion protein, the dimer results from the covalent bonding of Cys residue in the hinge region of two of the Ig heavy chains that are the same Cys residues that are disulfide linked in dimerized normal Ig heavy chains. In one embodiment, the immunoglobulin heavy chain constant region can contain one or more amino acid insertions, deletions or substitutions that enhance or decrease binding to specific cell types, increase the bioavailability, or increase the stability of the VSIG3 or VISTA fusion polypeptide. Suitable amino acid substitutions include conservative and non-conservative substitutions.

The VSIG3 or VISTA fusion protein optionally contains a domain that functions to dimerize or multimerize two or more fusion proteins. The peptide/polypeptide linker domain can either be a separate domain, or alternatively can be contained within one of the other domains (VSIG3 or VISTA polypeptide or second polypeptide) of the VSIG3 or VISTA fusion protein. Similarly, the domain that functions to dimerize or multimerize the fusion proteins can either be a separate domain, or alternatively can be contained within one of the other domains. In one embodiment, the dimerization/multimerization domain and the peptide/polypeptide linker domain are the same.

Fusion proteins disclosed herein according to at least some embodiments are of formula I: N-R1-R2-R3-C wherein "N" represents the N-terminus of the fusion protein, "C" represents the C-terminus of the fusion protein. In the further embodiment, "RI" is a VSIG3 polypeptide, "R2" is an optional peptide/polypeptide or chemical linker domain, and "R3" is a second polypeptide. Alternatively, R3 may be a VSIG3 polypeptide and RI may be a second polypeptide.

In some cases, a VSIG3 or VISTA fusion protein is provided comprising a VSIG3 or VISTA polypeptide fused by a linker peptide of one or more amino acids (e.g. GS) to one or more "half-life extending moieties". A "half-life extending moiety" is any moiety, for example, a polypeptide, small molecule or polymer, that, when appended to protein, extends the in vivo half-life of that protein in the body of a subject (e.g., in the plasma of the subject). For example, a half-life extending moiety is, in an embodiment, polyethylene glycol (PEG), monomethoxy PEG (mPEG), XTEN molecule, an rPEG molecule, an adnectin, a serum albumin, human serum albumin, immunoglobulin constant region or fragment thereof, or acyl group. In an embodiment, PEG is a 5, 10, 12, 20, 30, 40 or 50 kDa moiety or larger or comprises 12000 ethylene glycol units (PEG12000).

Half-life extending moieties include PEGs, an XTEN molecule, an rPEG molecule, an adnectin, a serum albumin, human serum albumin, immunoglobulin constant region or fragment thereof, or acyl group. In some embodiments, the half-life extending moiety can increase the in vivo half-life of the VSIG3 or VISTA polypeptide by at least 2-fold, at least 3-fold, at least 4-fold, at least 5-fold, at least 10-fold, or more compared to an otherwise identical molecule that lacks said half-life extending moiety.

In some embodiments, a VSIG3 or VISTA fusion protein may be prepared by fusion of a VSIG3 or VISTA protein with a portion of an immunoglobulin comprising a constant region of an immunoglobulin. The portion of the immunoglobulin comprises a heavy chain constant region. In some embodiments, the heavy chain constant region is a human heavy chain constant region. Also, in some embodiments, the heavy chain constant region is an IgG heavy chain constant region. Further, the IgG heavy chain can be a Fc chain. The Fc chain may optionally be a known or "wild type" Fc chain, or alternatively may be mutated or truncated. The Fc chain can also optionally be varied by isotype or subclass, may be a chimeric or a hybrid, and/or may be modified, for example to improve effector functions, control of half-life, tissue accessibility, augment biophysical characteristics such as stability, and improve efficiency of production. Many modifications useful in construction of fusion proteins and methods for making them are known in the art, see for example Mueller, et al, Mol. Immun., 34(6):441-452 (1997), Swann, et al., Curr. Opin. Immun., 20:493-499 (2008), and Presta, Curr. Opin. Immun. 20:460-470 (2008). In some embodiments, the Fc region is the native IgG1, IgG2, IgG3 or IgG4 Fc region. In some embodiments the Fc region is a hybrid, for example a chimeric consisting of IgG2/IgG4 Fc constant regions.

Modifications to the Fc region include, but are not limited to, IgG4 modified to prevent binding to Fcγ receptors and complement, IgG1 modified to improve binding to one or more Fcγ receptors, IgG1 modified to minimize effector function (amino acid changes), IgG1 with altered/no glycan (typically by changing expression host or substituting the Asn at position 297), and IgG1 with altered pH-dependent binding to FcRn. The Fc region may include the entire hinge region, or less than the entire hinge region. In another embodiment, the Fc region may contain one or more amino acid insertions, deletions or substitutions that reduce binding to the low affinity inhibitory Fc receptor CD32B (FcγRIIB) and retain wild-type levels of binding to or enhance binding to the low affinity activating Fc receptor CD16A (FcγRIIIA).

Another embodiment includes IgG2-4 hybrids and IgG4 mutants that have reduced binding to FcR (Fc receptor)

which increase their half-life. Representative IgG2-4 hybrids and IgG4 mutants are described in Angal, S. et al., Molecular Immunology, 30(1):105-108 (1993); Mueller, J. et al, Molecular Immunology, 34(6): 441-452 (1997); and U.S. Pat. No. 6,982,323 to Wang et al. In some embodiments the IgG1 and/or IgG2 domain is deleted; for example, Angal et al. Molecular Immunology, 30(1): 105-108 (1993) describe IgG1 and IgG2 having serine 241 replaced with a proline.

In a further embodiment, the Fc domain contains amino acid insertions, deletions or substitutions that enhance binding to CD16A. A large number of substitutions in the Fc domain of human IgG1 that increase binding to CD16A and reduce binding to CD32B are described in Stavenhagen, et al., Cancer Res., 57(18):8882-90 (2007). Exemplary variants of human IgG1 Fc domains with reduced binding to CD32B and/or increased binding to CD16A contain F243L, R929P, Y300L, V305I or P296L substitutions. These amino acid substitutions may be present in a human IgG1 Fc domain in any combination.

In one embodiment, the human IgG1 Fc domain variant contains a F243L, R929P and Y300L substitution. In another embodiment, the human IgG1 Fc domain variant contains a F243L, R929P, Y300L, V305I and P296L substitution. In another embodiment, the human IgG1 Fc domain variant contains an N297A/Q substitution, as these mutations abolish FcγR binding. Non-limiting, illustrative, exemplary types of mutations are described in US Patent Application No. 20060034852, published on Feb. 16, 2006, hereby Incorporated by reference as if fully set forth herein.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the VSIG or VISTA fusion protein include the following changes (given with regard to the Fc sequence nomenclature as given by Kabat, from Kabat E A et al: Sequences of Proteins of Immunological Interest, US Department of Health and Human Services, NIH, (1991)): 220C->S; 233-238 ELLGGP->EAEGAP; 265D->A, preferably in combination with 434N->A; 297N->A (for example to block N-glycosylation); 318-322 EYKCK->AYACA; 330-331AP->SS; or a combination thereof (see for example M. Clark, Chemical Immunol and Antibody Engineering, pp 1-31 for a description of these mutations and their effect). The construct for the Fc chain which features the above changes optionally and preferably comprises a combination of the hinge region with the Cm and Cm domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions). Substitution of 331 proline for serine may block the ability to activate complement, which may optionally be considered an undesired function. Changing the alanine to serine at position 330 in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function. Residue 220 is normally a cysteine for Fc from IgG1, which is the site at which the heavy chain forms a covalent linkage with the light chain. Optionally, this residue may be changed to another amino acid residue (e.g., serine), to avoid any type of covalent linkage or by deletion or truncation.

The above changes to residues 265 and 434 may optionally be implemented to reduce or block binding to the Fc receptor, which may optionally block undesired functionality of Fc related to its immune system functions.

The above changes are intended as illustrations only of optional changes and are not meant to be limiting in any way. Furthermore, the above explanation is provided for descriptive purposes only, without wishing to be bound by a single hypothesis. In a further embodiment, the fusion protein includes the extracellular domain of VSIG3 or VISTA or a fragment thereof fused to an Ig Fc region. Recombinant Ig VSIG3 or VISTA polypeptides, fragments or fusion proteins thereof fusion proteins can be prepared by fusing the coding region of the extracellular domain of VSIG3 or a fragment thereof to the Fc region of human IgG1 or mouse IgG2a Optionally, VSIG3 ECD or VISTA ECD refers also to a fusion protein comprising an amino acid sequence of human VSIG3 ECD or human VISTA ECD fused to human immunoglobulin Fc. In some embodiments, the fusion protein includes the amino acid sequence of VSIG3 ECD set forth in SEQ ID NO: 2 or a fragment thereof or the amino acid sequence of VISTA ECD set forth in SEQ ID NO: 5 or a fragment thereof. In some embodiments, said fusion protein includes the amino acid sequence of VSIG3 ECD fused to human immunoglobulin Fc set forth in SEQ ID NO:3 or a fragment thereof or the amino acid sequence of VISTA ECD fused to human immunoglobulin Fc set forth in SEQ ID NO: 6 or a fragment thereof.

In another embodiment, the second polypeptide may have a conjugation domain through which additional molecules can be bound to the VSIG3 or VISTA fusion proteins. In one such embodiment, the conjugated molecule is capable of targeting the fusion protein to a particular organ or tissue; further specific, illustrative, non-limiting examples of such targeting domains and/or molecules are given below.

In another such embodiment, the conjugated molecule is another immunomodulatory agent that can enhance or augment the effects of the VSIG3 or VISTA fusion protein. In another embodiment, the conjugated molecule is Polyethylene Glycol (PEG). In some embodiments VSIG3 or VISTA polypeptides or fusion proteins will comprise a binding domain, wherein the binding protein is capable of cross-linking two or more targets. In some embodiments, VSIG3 or VISTA polypeptides or fusion proteins will comprise another binding moiety, wherein the binding moiety targets a tumor cell, infectious agent, e.g., a virus, bacterium, mycoplasm, fungus, yeast or parasite, or cell infected thereby, an immune cell, or a disease site.

In some embodiments, the VSIG3 or VISTA polypeptide comprises at least one heterologous polypeptide which may be a receptor, hormone, cytokine, antigen, B-cell target, NK cell target, T cell target, TNF receptor superfamily member, Hedgehog family member, a receptor tyrosine kinase, a proteoglycan-related molecule, a TGF-β superfamily member, a Wnt-related molecule, a receptor ligand, a Dendritic cell target, a myeloid cell target, a monocyte/macrophage cell target or an angiogenesis target.

In some embodiments, the VSIG3 or VISTA polypeptide comprises at least one antigen, e.g., a tumor antigen, autoantigen, allergen, or an infectious agent antigen.

In some embodiments, the VSIG3 or VISTA polypeptide comprises a T cell target selected from the group consisting of 2B4/SLAMF4, IL-2 Ra, 4-1BB/TNFRSF9, IL-2Rb, ALCAM, B7-1/CD80, IL-4R, B7-H3, BLAME/SLAMF8, BTLA, IL-6R, CCR3, IL-7 Ra, CCR4, CXCRI/IL-8 RA, CCR5, CCR6, IL-10 R a, CCR7, IL-10 R, CCR8, IL-12 Rβ1, CCR9, IL-12 Rβ2, CD2, IL-13Ral, IL-13, CD3, CD4, ILT2/CD85j, ILT3/CD85k, ILT4/CD85d, ILT5/CD85a, Integrin a 4/CD49d, CD5, IntegrinaE/CD103, CD6, Integrin a M/CDI Ib, CD8, Integrin a X/CD 11c, Integrin 2/CD18, KIR/CD158, CD27/TNFRSF7, KIR2DL1, CD28, KIR2DL3, CD30/TNFRSF8, KIR2DL4/CD158d, CD31/PECAM-1, KIR2DS4, CD40 Ligand/TNFSF5, LAG-3, CD43, LAIR1, CD45, LAIR2, CD83, Leukotriene B4 RI, CD84/SLAMF5, NCAM-LI, CD94, NKG2A, CD97, NKG2C, CD229/SL AMF3, NKG2D, CD2F-10/SLAMF9, NT-4, CD69, NTB-A/SLAMF6, Common γ Chain/IL-2 Rγ, Osteopontin, CRACC/SLAMF7, PD-1, CRT AM, PSGL-1, CTLA-4, RANK/TNFRSF11 A, CX3CR1, CX3CL1, L-Selectin, CXCR3, SIRP βi, CXCR4, SLAM, CXCR6, TCCRAVSX-1, DNAM-1, Thymopoietin, EMMPRIN/CD 147, TIM-1, EphB6, TIM-2, Fas/TNFRSF6, TIM-3, Fas Ligand/TNFSF6, TIM-4, Fcγ RIII/CD16, TIM-6, GITR/TNFRSF18, TNF RI/TNFRSFIA, Granulysin, TNF R11/TNFRSF1B, H VEM/TNFRSF 14, TRAIL R1/TNFRSF10A, ICAM-1/CD54, TRAIL R2/TNFRSF10B, ICAM-2/CD102, TRAIL R3/TNFRSF10C, IFN-yRI, TRAIL R4/TNFRSF10D, IFN-yR2, TSLP, IL-1 RI and TSLP R.

In some embodiments, the VSIG3 or VISTA polypeptide comprises at least one monocyte/macrophage cell target selected from the group consisting of B7-1/CD80, ILT4/CD85d, B7-H1, ILT5/CD85a, Common (3 Chain, Integrin a 4/CD49d, BLAME/SLAMF8, Integrin a X/CD1 Ic, CCL6/C10, Integrin β2/CD18, CD155/PVR, Integrin β3/CD61, CD31/PECAM-1, Latexin, CD36/SR-B3, Leukotriene B4 RI, CD40/TNFRSF5, LIMPII/SR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD 147, MGL2, Endoglin/CD105, Osteoactivin/GPNMB, Fc yRI/CD64, Osteopontin, Fc y RIIB/CD32b, PD-L2, Fc yRIIC/CD32c, Siglec-3/CD33, Fcγ RIIA/CD32a, SIGNR1/CD209, Fcγ RIII/CD16, SLAM, GM-CSF R a, TCCR/WSX-1, ICAM-2/CD102, TLR3, IFN-y RI, TLR4, IFN-y R2, TREM-1, IL-1 RII, TREM-2, ILT2/CD85j, TREM-3, ILT3/CD85k, TREMLI/TLT-1, 2B4/SLAMF4, IL-10 R a, ALCAM, IL-10 R (3, Aminopeptidase N/ANPEP, ILT2/CD85j, Common β Chain, ILT3/CD85k, Clq R1/CD93, ILT4/CD85d, CCR1, ILT5/CD85a, CCR2, Integrin a 4/CD49d, CCR5, Integrin a M/CD I ib, CCR8, Integrin a X/CD 11c, CD155/PVR, Integrin β2/CD18, CD14, Integrin β3/CD61, CD36/SR-B3, LAIR1, CD43, LAIR2, CD45, Leukotriene B4 RI, CD68, LIMPII/SR-B2, CD84/SLAMF5, LMIR1/CD300A, CD97, LMIR2/CD300c, CD163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD 147, MMR, Endoglin/CD105, NCAM-L1, Fc γ R1/CD64, PSGL-1, Fc Y RIII/CD16, RP105, G-CSF R, L-Selectin, GM-CSF R a, Siglec-3/CD33, H VEM/TNFRSF 14, SLAM, ICAM-1/CD54-ICAM-2/CD102, TREM-1, IL-6 R, TREM-2, CXCRI/IL-8 RA, TREM-3 and TREMLI/TLT-1.

In some embodiments, the VSIG3 or VISTA polypeptide comprises at least one Dendritic cell target is selected from the group consisting of CD36/SR-B3, LOX-1/SR-E1, CD68, MARCO, CD1863, SR-AI/MSR, CD5L, SREC-I, CL-P 1/COLEC 12, SREC-II, LIMPII/SR-B2, RP105, TLR4, TLRI, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, Integrin a 4/CD49d, Aag, Integrin β2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB, CCR7, LMIR6/CD300LE, CD40/TNFRSF5, MAG/Siglec-4a, CD43, MCAM, CD45, MD-1, CD68, MD-2, CD83, MDL-1/CLEC5A, CD84/SLAMF5, MMR, CD97, NCAM-L1, CD2F-10/SLAMF9, Osteoactivin/GPNMB, Chem 23, PD-L2, CLEC-1, RP105, CLEC-2, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD148, SIGNR4, DLEC, SLAM, EMMPRIN/CD 147, TCCR/WSX-1, Fc γ R1/CD64, TLR3, Fc γ RIIB/CD32b, TREM-1, Fc γ RIIC/CD32c, TREM-2, Fcy RIIA/CD32a, TREM-3, Fc γ RIII/CD16, TREMLI/TLT-1, ICAM-2/CD102 and Vanilloid RI.

In some embodiments, the VSIG3 or VISTA polypeptide comprises at least one TNF receptor superfamily member selected from the group consisting of 4-1BB/TNFRSF9, NGF R/TNFRSF16, BAFF R/TNFRSF13C, Osteoprotegerin/TNFRSFI IB, B CMA/TNFRSF 17, OX40/TNFRSF4, CD27/TNFRSF7, RANK/TNFRSF11 A, CD30/TNFRSF8, RELT/TNFRSF19L, CD40/TNFRSF5, T ACI/TNFRSF 13B, DcR3/TNFRSF6B, TNF RI/TNFRSF1A, DcTRAIL R1/TNFRSF23, TNF RII/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF 10D, Fas/TNFRSF6, TRO Y/TNFRSF 19, GITR/TNFRSF18, TWEAK R/TNFRSF12, HVEM/TNFRSF14, XEDAR, Lymphotoxin β R/TNFRSF3, 4-1BB Ligand/TNFSF9, Lymphotoxin, APRIL/TNFSF 13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF-/TNFSFIB, EDA-A2, TRAIL/TNFSFIO, Fas Ligand/TNFSF6, TR ANCE/TNFSF 11, GITR Ligand/TNFSF18, TWEAK/TNFSFI 2 and LIGHT/TNFSF14.

In some embodiments, the VSIG3 or VISTA polypeptide comprises at least one Hedgehog family member selected from the group consisting of patched and smoothened.

In some embodiments, the VSIG3 or VISTA polypeptide comprises at least one receptor tyrosine kinase selected from the group consisting of Axl, FGF R4, Clq R1/CD93, FGF R5, DDR1, Flt-3, DDR2, HGF R, Dtk, IGF-I R, EGF R, IGF-II R, Eph, INSRR, EphAI, Insulin R/CD220, EphA2, M-CSF R, EphA3, Mer, EphA4, MSP R/Ron, EphA5, MuSK, EphA6, PDGF R a, EphA7, PDGF R β, EphA8, Ret, EphBI, RORI, EphB2, ROR2, EphB3, SCF R/c-kit, EphB4, Tie-1, EphB6, Tie-2, ErbB2, TrkA, ErbB3, TrkB, ErbB4, TrkC, FGF RI, VEGF RI/Flt-1, FGF R2, VEGF R2/Flk-1, FGF R3 and VEGF R3/Flt-4.

In some embodiments, the VSIG3 or VISTA polypeptide comprises at least one Transforming Growth Factor (TGF)-superfamily member selected from the group consisting of Activin RIA/ALK-2, GFR a-1, Activin RIB/ALK-4, GFR a2, Activin RIIA, GFR a-3, Activin RIIB, GFR a-4, ALK-1, MIS RII, ALK-7, Ret, BMPR-IA/ALK-3, TGF-beta RI/ALK-5, BMPR-IB/ALK-6, TGF-β RII, BMPR-II, TGF-β RIIb, Endoglin/CD 105 and TGF-βRIII.

In some embodiments, the VSIG3 or VISTA polypeptide comprises at least one Wnt-related molecule selected from the group consisting of Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP, LRP 5, LRP 6, Wnt-1, Wnt-8a, Wnt-3a, Wnt-10b, Wnt-4, Wnt-11, Wnt-5a, Wnt-9a and Wnt-7a.

In some embodiments, the VSIG3 or VISTA polypeptide comprises at least one receptor ligand selected from the group consisting of 4-1BB Ligand/TNFSF9, Lymphotoxin, APRIL/TNFSF 13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF-β/TNFSF 1 B, EDA-A2, TRAIL/TNFSF10, Fas Ligand/TNFSF6, RANCE/TNFSFI I, GITR Ligand/TNFSF18, TWEAK TNFSF12, LIGHT/TNFSF14, Amphiregulin, NRG1 isoform GGF2, Betacellulin, NRG1 Isoform SMDF, EGF, NRGI-a HRGI-a, Epigen, NRGI-β I/HRGI-β1, Epiregulin, TGF-a, HB-EGF, TMEFFI/Tomoregulin-1, Neuregulin-3, TMEFF2, IGF-I, IGF-II, Insulin, Activin A, Activin B, Activin AB, Activin C, BMP-2, BMP-7, BMP-3, BMP-8, BMP-3b/GDF-10, BMP-9, BMP-4, BMP-15, BMP-5, Decapentaplegic, BMP-6, GDF-1, GDF-8, GDF-3, GDF-9, GDF-5, GDF-11, GDF-6, GDF-15, GDF-7, Artemin, Neurturin, GDNF, Persephin, TGF-β, TGF-β2, TGF-β1, TGF-β3, LAP (TGF-β1), TGF-β5, Latent TGF-β1, Latent TGF-β bpl, TGF-β1.2, Lefty, Nodal, MIS/AMH, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, Neuropilin-1, P1GF, Neuropilin-2, P1GF-2, PDGF, PDGF-A, VEGF, PDGF-B, VEGF-B, PDGF-C, VEGF-C, PDGF-D, VEGF-D and PDGF-AB.

In some embodiments, the VSIG3 or VISTA polypeptide comprises at least one tumor antigen selected from the group consisting of Squamous Cell Carcinoma Antigen 1 (SCCA-1), (PROTEIN T4-A), Squamous Cell Carcinoma Antigen 2 (SCCA-2), Ovarian carcinoma antigen CA125 (1A1-3B; KIAA0049), MUCIN 1 (TUMOR-ASSOCIATED MUCIN; Carcinoma-Associated Mucin; Polymorphic Epithelial Mucin; PEM; PEMT; EPISIALIN; Tumor-Associated Epithelial Membrane Antigen; EMA; H23AG; Peanut-Reactive Urinary Mucin; PUM; and Breast Carcinoma-Associated Antigen DF3), CTCL tumor antigen sel-1, CTCL tumor antigen se14-3, CTCL tumor antigen se20-4, CTCL tumor antigen se20-9, CTCL tumor antigen se33-I, CTCL tumor antigen se37-2, CTCL tumor antigen se57-I, CTCL tumor antigen se89-I, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B 1 ANTIGEN (MAGE-XP Antigen; DAM10), MAGE-B2 Antigen (DAME), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, Tumor-Associated Antigen CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195 and L6.

In some embodiments, the VSIG3 or VISTA polypeptide comprises at least one B cell target selected from the group consisting of CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138 and CDw150.

In some embodiments, the VSIG3 or VISTA polypeptide comprises at least one angiogenesis target is selected from the group consisting of Angiopoietin-1, Angiopoietin-like 2, Angiopoietin-2, Angiopoietin-like 3, Angiopoietin-3, Angiopoietin-like 7/CDT6, Angiopoietin-4, Tie-1, Angiopoietin-like 1, Tie-2, Angiogenin, iNOS, Coagulation Factor III/Tissue Factor, nNOS, CTGF/CCN2, NOV/CCN3, DANCE, OSM, EDG-1, Plfr, EG-VEGF/PK1, Proliferin, Endostatin, ROB 04, Erythropoietin, Thrombospondin-1, Kininostatin, Thrombospondin-2, MFG-E8, Thrombospondin-4, Nitric Oxide, VGSQ, eNOS, EphAI, EphA5, EphA2, EphA6, EphA3, EphA7, EphA4, EphA8, EphBI, EphB4, EphB2, EphB6, EphB3, Ephrin-AI, Ephrin-A4, Ephrin-A2, Ephrin-A5, Ephrin-A3, Ephrin-BI, Ephrin-B3, Ephrin-B2, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, FGF RI, FGF R4, FGF R2, FGF R5, FGF R3, Neuropilin-1, Neuropilin-2, Semaphorin 3A, Semaphorin 6B, Semaphorin 3C, Semaphorin 6C, Semaphorin 3E, Semaphorin 6D, Semaphorin 6A, Semaphorin 7 A, MMP, MMP-11, MMP-1, MMP-12, MMP-2, MMP-13, MMP-3, MMP-14, MMP-7, MMP-15, MMP-8, MMP-16/MT3-MMP, MMP-9, MMP-24/MT5-MMP, MMP-10, MMP-25/MT6-MMP, TIMP-1, TIMP-3, TIMP-2, TIMP-4, ACE, IL-13 R a 1, IL-13, Clq R1/CD93, Integrin a 4/CD49d, VE-Cadherin, Integrin β2/CD18, CD31/PECAM-1, KLF4, CD36/SR-B3, LYVE-1, CD151, MCAM, CL-P1/COLEC12, Nectin-2/CD112, Coagulation Factor III/Tissue Factor, E-Selectin, D6, P-Selectin, DC-SIGNR/CD299, SLAM, EMMPRIN/CD 147, Tie-2, Endoglin/CD105, TNF RI/TNFRSF1A, EPCR, TNF RII/TNFRSF1B, Erythropoietin R, TRAIL R1/TNFRSF10A, ESAM, TRAIL R2/TNFRSF10B, FABP5, VCAM-1, ICAM-1/CD54, VEGF R2/Flk-1, ICAM-2/CD102, VEGF R3/Flt-4, IL-1 RI and VGSQ.

In some embodiments, VSIG3 or VISTA polypeptides or fusion proteins will comprise a VSIG3 or VISTA polypeptide and at least one heterologous polypeptide and/or or binding moiety or VSIG3 or VISTA polypeptides are linked to one another by an amino acid spacer.

In some embodiments, VSIG3 or VISTA polypeptides or fusion proteins will a VSIG3 or VISTA polypeptide and at least one heterologous polypeptide and/or or binding moiety or VSIG3 or VISTA polypeptides are linked to one another by an amino acid spacer of sufficient length of amino acid residues so that the different moieties can successfully bind to their individual targets.

In some embodiments, VSIG3 or VISTA polypeptides or fusion proteins will comprise one or more VSIG3 or VISTA polypeptide(s) and at least one heterologous polypeptide optionally intervened by a heterologous linker which optionally comprises a polypeptide that is not a fragment of a VSIG3 or VISTA polypeptide.

In some embodiments, VSIG3 or VISTA polypeptides or fusion proteins can comprise a linker which is a peptide comprising 5-50 amino acid residues, more preferably 5-25 amino acid residues.

In some embodiments, VSIG3 or VISTA polypeptides or fusion proteins can comprise a linker which comprises, consists essentially of, glycine, serine, and/or alanine residues.

In some embodiments, VSIG3 or VISTA polypeptides or fusion proteins will comprise a linker which comprises 5-50, 5-25, 5-15, 4-14, 4-12, or more amino acid residues, e.g., which may include or consist of glycine, serine, and/or alanine residues.

Linker Domains

VSIG3 or VISTA fusion proteins optionally may contain a peptide or polypeptide linker domain that separates the VSIG3 or VISTA polypeptide from the second polypeptide. Various non-limiting examples of such linker domains are described herein. In one embodiment, the linker domain contains the hinge region of an immunoglobulin. In a further embodiment, the hinge region is derived from a human immunoglobulin. Suitable human immunoglobulins that the hinge can be derived from include IgG, IgD and IgA. In a further embodiment, the hinge region is derived from human IgG. Amino acid sequences of immunoglobulin hinge regions and other domains are well known in the art. In another embodiment, the linker domain optionally contains a hinge region of an immunoglobulin as described above, and further includes one or more additional immunoglobulin domains.

Other suitable peptide/polypeptide linker domains optionally include naturally occurring or non-naturally occurring peptides or polypeptides. Peptide linker sequences are at least 2 amino acids in length. Optionally the peptide or polypeptide domains are flexible peptides or polypeptides. A "flexible linker" herein refers to a peptide or polypeptide containing two or more amino acid residues joined by peptide bond(s) that provides increased rotational freedom for two polypeptides linked thereby than the two linked polypeptides would have in the absence of the flexible linker. Such rotational freedom allows two or more antigen binding sites joined by the flexible linker to each access target antigen(s) more efficiently.

Exemplary flexible peptides/polypeptides include, but are not limited to, the amino acid sequences Gly-Ser, Gly-Ser-Gly-Ser, Ala-Ser, Gly-Gly-Gly-Ser, Gly4-Ser, (Gly4-Ser)2, (Gly4-Ser)3, (Gly4-Ser)4, [Gly4-Set]2 Gly-Ala-Gly-Ser-Gly4-Ser Gly-(Gly4-Ser)2, Gly4-Ser-Gly, Gly-Ser-Gly2 and Gly-Ser-Gly2-Ser.

Other suitable peptide linker domains optionally include the TEV linker ENLYFQG, a linear epitope recognized by the Tobacco Etch Virus protease. Exemplary peptides/polypeptides include, but are not limited to, GSENLYFQGSG and helix forming linkers such as Ala-(Glu-Ala-Ala-Ala-Lys)n-Ala (n=1-5).

In some optionally embodiments, VSIG3 or VISTA fragments, e.g., ECD fragments, are linked to each other (multimers) and/or one or more VSIG3 or VISTA fragments, e.g., ECD fragments, are linked to a heterologous polypeptide such as an immunoglobulin or fragment thereof, especially an immunoglobulin heavy chain or fragment thereof by a peptide linker, preferably a "flexible linker" sequence. The linker sequence should allow effective positioning of the VSIG3 or VISTA fragments and the heterologous polypeptide such as an immunoglobulin polypeptide or domains thereof to allow functional activity of both moieties and the domains thereof. Successful presentation of the polypeptide fusion can modulate the activity of a cell either to induce or to inhibit T-cell proliferation, or to initiate or inhibit an immune response to a particular site. This can be determined in appropriate assays such as disclosed herein below, including the in vitro assays that includes sequential steps of culturing T cells to proliferate same, and contacting the T cells with a fusion polypeptide or a cell expressing same and then evaluating whether the fusion polypeptide promotes or inhibits T cell proliferation.

As used herein, the phrase "effective positioning of the heterologous polypeptide and the VSIG3 or VISTA polypeptide", or other similar phrase, is intended to mean that the domains of these moieties are positioned so that VSIG3 or VISTA domains and heterologous polypeptide domains are capable of interacting with immune or other target cells, e.g., cancer or other VSIG3 or VISTA expressing cells to initiate or inhibit an immune reaction, or to inhibit or stimulate cell development.

With respect to VSIG3 or VISTA fusion proteins the linker sequence also preferably permits effective positioning of the Fc domain and VSIG3 or VISTA domains to allow functional activity of each domain. In certain embodiments, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences are discussed supra in connection with fusion proteins. Linker sequences can optionally be used to link two or more VSIG3 or VISTA polypeptides of the biologically active polypeptide to generate a single-chain molecule with the desired functional activity. In some embodiments, the linker sequence comprises from 5 to 20 amino acids, more preferably from 7 or 8 to 16 amino acids. The linker sequence can be flexible so as not hold the VSIG3 or VISTA polypeptide and moiety linked thereto, e.g., an effector molecule in a single undesired conformation. The linker sequence can be used, e.g., to space the recognition site from the fused molecule. Specifically, the peptide linker sequence can be positioned between the biologically active VSIG3 or VISTA polypeptide and the effector molecule, e.g., to chemically cross-link same and to provide molecular flexibility. The linker in some embodiments can predominantly comprise amino acids with small side chains, such as glycine, alanine and serine, to provide for flexibility. Preferably 80 or 90 percent or greater of the linker sequence comprise glycine, alanine or serine residues, particularly glycine and serine residues. Other suitable linker sequences include flexible linker designs used successfully to join antibody variable regions together. In some examples, for covalently linking an effector molecule to a VSIG3 or VISTA molecule, the amino sequence of the linker should be capable of spanning a suitable distance from the C-terminal residue of the VSIG3 or VISTA polypeptide to the N-terminal residue of the effector molecule. Suitable linker sequences can be readily identified empirically. Additionally, suitable size and sequences of linker sequences also can be determined by known computer modeling techniques based on the predicted size and shape of the fusion polypeptide.

Optionally a polypeptide as described herein may comprise 2-20 VSIG3 or VISTA ECD polypeptide fragments linked together. Optionally the fragments are intervened by a heterologous linker which optionally comprises a polypeptide that is not a fragment of a VSIG3 or VISTA polypeptide.

Optionally the linker is a peptide comprising 5-50 amino acid residues, more preferably 5-25 amino acid residues. Optionally the linker comprises, consists essentially of, or consists of 4-12 glycine, serine, and/or alanine residues.

Dimerization, Multimerization, and Oligomerization Domains

VSIG3 or VISTA fusion proteins disclosed herein optionally contain a dimerization or multimerization or oligomerization domain that functions to dimerize, oligomerize or multimerize two or more fusion proteins, which may be the same or different (heteromultimers or homomultimers). For example, a VSIG3 or VISTA fusion protein may be attached to another VSIG3 or VISTA fusion protein or another moiety, e.g. another costimulatory fusion protein. The domain that functions to dimerize or multimerize the fusion proteins can either be a separate domain, or alternatively can be contained within one of the other domains (VSIG3 or VISTA polypeptide, second polypeptide, or peptide/polypeptide linker domain) of the fusion protein.

Dimerization or multimerization can occur between or among two or more fusion proteins through dimerization or multimerization domains. Alternatively, dimerization or multimerization of fusion proteins can occur by chemical crosslinking. The dimers or multimers that are formed can be homodimeric/homomultimeric or heterodimeric/heteromultimeric. The second polypeptide "partner" in the VSIG3 or VISTA fusion polypeptides may be comprised of one or more other proteins, protein fragments or peptides as described herein, including but not limited to any immunoglobulin (Ig) protein or portion thereof, preferably the Fc region, or a portion of a biologically or chemically active protein such as the papillomavirus E7 gene product, melanoma-associated antigen p97), and HIV env protein (gp120). The "partner" is optionally selected to provide a soluble dimer/multimer and/or for one or more other biological activities as described herein.

A "dimerization domain" is formed by the association of at least two amino acid residues or of at least two peptides or polypeptides (which may have the same, or different, amino acid sequences). The peptides or polypeptides may interact with each other through covalent and/or non-covalent associations). Optional dimerization domains contain at least one cysteine that is capable of forming an intermolecular disulfide bond with a cysteine on the partner fusion protein. The dimerization domain can contain one or more cysteine residues such that disulfide bond(s) can form between the partner fusion proteins. In one embodiment, dimerization domains contain one, two or three to ten cysteine residues. In a further embodiment, the dimerization domain is the hinge region of an immunoglobulin.

Additional exemplary dimerization domains can be any known in the art and include, but are not limited to, coiled coils, acid patches, zinc fingers, calcium hands, a $C_{H1}$-$C_L$ pair, an "interface" with an engineered "knob" and/or "protuberance" as described in U.S. Pat. No. 5,821,333, leucine zippers (e.g., from jun and/or fos) (U.S. Pat. No. 5,932,448), and/or the yeast transcriptional activator GCN4, SH2 (src homology 2), SH3 (src Homology 3), phosphotyrosine binding, an isoleucine zipper, a receptor dimer pair (e.g., interleukin-8 receptor (IL-8R), and integrin heterodimers such as LFA-I and GPIIIb/IIIa), or the dimerization region(s) thereof, dimeric ligand polypeptides (e.g., nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576. Affinities between a pair of interacting domains can be determined using methods known in the art. Alternatively, a library of peptide sequences can be screened for heterodimerization, for example, using the methods described in WO 01/00814. Useful methods for protein-protein interactions are also described in U.S. Pat. No. 6,790,624.

A "multimerization domain" or "oligomerization domain," as used herein, refers to a domain that causes three or more peptides or polypeptides to interact with each other through covalent and/or non-covalent association(s). Suitable multimerization or oligomerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, He, Leu, Met, Tyr, Phe and Trp. "Mainly hydrophobic" means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-I and TSP-2) or five (TSP-3, TSP-4 and TSP-5) chains are connected, or from COMP (COMPcc) which folds into a parallel five-stranded coiled coil. Additional non-limiting examples of coiled-coil domains derived from other proteins, and other domains that mediate polypeptide multimerization are known in the art such as the vasodilator-stimulated phosphoprotein (VASP) domain, matrilin-1 (CMP), viral fusion peptides, soluble NSF (N-ethylmaleimide-sensitive factor) Attachment Protein receptor (SNARE) complexes, leucine-rich repeats, certain tRNA synthetases, are suitable for use in the disclosed fusion proteins.

In another embodiment, VSIG3 or VISTA polypeptides, fusion proteins, or fragments thereof can be induced to form multimers by binding to a second multivalent polypeptide, such as an antibody. Antibodies suitable for use to multimerize VSIG3 or VISTA polypeptides, fusion proteins, or fragments thereof include, but are not limited to, IgM antibodies and cross-linked, multivalent IgG, IgA, IgD, or IgE complexes.

Dimerization or multimerization can occur between or among two or more fusion proteins through dimerization or multimerization domains, including those described above. Alternatively, dimerization or multimerization of fusion proteins can occur by chemical crosslinking. Fusion protein dimers can be homodimers or heterodimers. Fusion protein multimers can be homomultimers or heteromultimers.

Fusion protein dimers as disclosed herein are of formula II: N-R1-R2-R3-C, N-R4-R5-R6-C or, alternatively, are of formula III: N-R1-R2-R3-C, C-R4-R5-R6-N wherein the fusion proteins of the dimer provided by formula II are defined as being in a parallel orientation and the fusion proteins of the dimer provided by formula III are defined as being in an antiparallel orientation. Parallel and antiparallel dimers are also referred to as cis and trans dimers, respectively. "N" and "C" represent the N- and C-termini of the fusion protein, respectively. The fusion protein constituents "RI", "R2" and "R3" are as defined above with respect to formula I. With respect to both formula II and formula III, "R4" is a VSIG3 or VISTA polypeptide or a second polypeptide, "R5" is an optional peptide/polypeptide linker domain, and "R6" Is a VSIG3 or VISTA polypeptide or a second polypeptide, wherein "R6" is a VSIG3 or VISTA polypeptide when "R4" is a second polypeptide, and "R6" is a second polypeptide when "R4" is a VSIG3 or VISTA polypeptide. In one embodiment, "RI" is a VSIG3 or VISTA polypeptide, "R4" is also a VSIG3 or VISTA polypeptide, and "R3" and "R6" are both second polypeptides.

Fusion protein dimers of formula II are defined as homodimers when "RI"="R4", "R2"="R5" and "R3"="R6". Similarly, fusion protein dimers of formula III are defined as homodimers when "RI"="R6", "R2"="R5" and "R3"="R4". Fusion protein dimers are defined as heterodimers when these conditions are not met for any reason. For example, heterodimers may contain domain orientations that meet these conditions (i. e., for a dimer according to formula II, "RI" and "R4" are both VSIG3 polypeptides, "R2" and "R5" are both peptide/polypeptide linker domains and "R3" and "R6" are both second polypeptides), however the species of one or more of these domains is not identical. For example, although "R3" and "R6" may both be VSIG3 or VISTA polypeptides, one polypeptide may contain a wild-type VSIG3 or VISTA amino acid sequence while the other polypeptide may be a variant VSIG3 or VISTA polypeptide. An exemplary variant VSIG3 or VISTA polypeptide is a VSIG3 or VISTA polypeptide that has been modified to have increased or decreased binding to a target cell, increased activity on immune cells, increased or decreased half-life or stability. Dimers of fusion proteins that contain either a Cm or CL region of an immunoglobulin as part of the polypeptide linker domain preferably form heterodimers wherein one fusion protein of the dimer contains a Cm region and the other fusion protein of the dimer contains a CL region.

Fusion proteins can also be used to form multimers. As with dimers, multimers may be parallel multimers, in which all fusion proteins of the multimer are aligned in the same orientation with respect to their N- and C-termini. Multimers may be antiparallel multimers, in which the fusion proteins of the multimer are alternatively aligned in opposite orientations with respect to their N- and C-termini. Multimers (parallel or antiparallel) can be either homomultimers or heteromultimers. The fusion protein is optionally produced in dimeric form; more preferably, the fusion is performed at the genetic level as described below, by joining polynucleotide sequences corresponding to the two (or more) proteins, portions of proteins and/or peptides, such that a joined or fused protein is produced by a cell according to the joined polynucleotide sequence. A description of preparation for such fusion proteins is described with regard to U.S. Pat. No. 5,851,795 to Linsley et al, which is hereby incorporated by reference as if fully set forth herein as a non-limiting example only.

Targeting Domains

The VSIG3 or VISTA polypeptides and fusion proteins can contain a targeting domain to target the molecule to specific sites in the body. Optional targeting domains target the molecule to areas of inflammation. Exemplary targeting domains are antibodies, or antigen binding fragments thereof that are specific for inflamed tissue or to a proinflammatory cytokine including but not limited to IL17, IL-4, IL-6, IL-12, IL-21, IL-22, IL-23, MIF, TNF-a, and TNF-β and combinations thereof. In the case of neurological disorders such as multiple sclerosis, the targeting domain may target the molecule to the CNS or may bind to VCAM-I on the vascular epithelium. Additional targeting domains can be peptide aptamers specific for a proinflammatory molecule. In other embodiments, the VSIG3 or VISTA fusion protein can include a binding partner specific for a polypeptide displayed on the surface of an immune cell, for example a T cell. In still other embodiments, the targeting domain specifically targets activated immune cells. Optional immune cells that are targeted include Th0, Th1, Th17, Th2 and Th22 T cells, other cells that secrete, or cause other cells to secrete inflammatory molecules including, but not limited to, IL-Iβ, TNF-a, TGF-β, IFN-y, IL-17, IL-6, IL-23, IL-22, IL-21, and MMPs, and Tregs. For example, a targeting domain for Tregs may bind specifically to CD25.

Addition of Groups

If a protein is a linear molecule, it is possible to place various functional groups at various points on the linear molecule which are susceptible to or suitable for chemical modification. Functional groups can be added to the termini of linear forms of the protein. In some embodiments, the functional groups improve the activity of the protein with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions according to at least some embodiments will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, (1991), the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein RI is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO, iso-propyl-O—CO, n-butyl-O—CO, sec-butyl-O—CO, t-butyl-O—CO, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbornane, or Z-caproic. In order to facilitate the N-acylation, one to four glycine residues can be present in the N-terminus of the molecule.

The carboxyl group at the C-terminus of the compound can be protected, for example, by a group including but not limited to an amide (i. e., the hydroxyl group at the C-terminus is replaced with —NH 2, —NHR2 and —NR2R3) or ester (i. e., the hydroxyl group at the C-terminus is replaced with —OR2). R2 and R3 are optionally independently an aliphatic, substituted aliphatic, benzyl, substituted benzyl, aryl or a substituted aryl group. In addition, taken together with the nitrogen atom, R2 and R3 can optionally form a C4 to C8 heterocyclic ring with from 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —NH$_2$, —NHCH3, —N(CH$_3$)$_2$, —NH(ethyl), —N(ethyl)$_2$, —N(methyl) (ethyl), —NH(benzyl), —N(C1-C4 alkyl)(benzyl), —NH(phenyl), —N(C1-C4 alkyl) (phenyl), —OCH3-O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in a composition both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to some embodiments, one or more peptidomimetics are selected such that a composition at least substantially retains its physiological activity as compared to the native protein.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol, isosteres of amide bonds, and LL-3-amino-2-propenidone-6-carboxylic acid (LL-Acp). Further suitable exemplary peptidomimetics include hydroxy-1,2,3,4-tetrahydroisoquinoline-3-carboxylate, 1,2,3,4-tetrahydro-isoquinoline-3-carboxylate, histidine isoquinolone carboxylic acid (HIC), (2S,S)-methyl-phenylalanine, (2S,3R)-methyl-phenylalanine, (2R,3S)-methyl-phenylalanine and (2R,3R)-methyl-phenylalanine.

Exemplary, illustrative but non-limiting non-natural amino acids include β-amino acids (β3 and β2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA).

Chemical Modifications

In some embodiments, any part of a protein may optionally be chemically modified, for example by adding functional groups. In one example, the side amino acid residues appearing in a native sequence may optionally be modified. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar. Acetal and ketal bonds can also optionally be formed between amino acids and carbohydrates. Fatty acid acyl derivatives can optionally be made, for example, by acylation of a free amino group (e.g., lysine).

As used herein the term "chemical modification", when referring to a protein or peptide, refers to a protein or peptide where at least one of its amino acid residues is modified either by natural processes, such as processing or other post-translational modifications, or by chemical modification techniques. Examples of the numerous known modifications typically include, but are not limited to: acetylation, acylation, amidation, ADP-ribosylation, glycosylation, GPI anchor formation, covalent attachment of a lipid or lipid derivative, methylation, myristoylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Proteins may also be modified to have an altered glycosylation pattern (i. e., altered from the original or native glycosylation pattern). As used herein, "altered" means having one or more carbohydrate moieties deleted, and/or having at least one glycosylation site added to the original protein. Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to proteins is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

Removal of any carbohydrate moieties present on proteins may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Nucleic Acid Molecules Encoding Antibodies

The invention further provides nucleic acids which encode an anti-VSIG3 antibody, or a fragment or conjugate thereof. The nucleic acids may be present in whole cells, in a cell lysate, or in a partially purified or substantially pure form. The nucleic acids may be isolated. The nucleic acid according to at least some embodiments can be, for example, DNA or RNA and may or may not contain intronic sequences. In one embodiment, the nucleic acid is a cDNA molecule.

Nucleic acids according to at least some embodiments can be obtained using molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. "Operatively linked", means that that the two DNA fragments are joined such that the amino acid sequences encoded by the two DNA fragments remain in-frame.

The isolated DNA encoding the VH region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1, IgG2 or IgG4 constant region. For a Fab fragment heavy chain gene, the Vn-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$—The sequences of human light chain constant region genes are known in the art and DNA fragments encompassing these regions can be obtained by standard PCR amplification. The light chain constant region can be a kappa (K) or lambda (λ) constant region.

To create a scFv gene, the $V_R$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker.

Antibody Production

Anti-VSIG3 or VISTA monoclonal antibodies (mAbs)—including antigen-binding fragments thereof—can be produced by a variety of techniques, including conventional monoclonal antibody methodology e.g., the standard somatic cell hybridization technique of Kohler and Milstein (1975) Nature 256:495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions. To create a humanized antibody, the murine CDR regions can be inserted into a human framework.

According to at least some embodiments, the anti-VSIG3 or VISTA antibodies are human monoclonal antibodies. Such human monoclonal antibodies directed against VSIG3 or VISTA can be generated using transgenic or transchromosomic mice carrying parts of the human immune system rather than the mouse system. These transgenic and transchromosomic mice include mice referred to herein as the HuMAb Mouse™ and KM Mouse™, respectively, and are collectively referred to herein as "human Ig mice." The HuMAb Mouse™ (Medarex Inc.) contains human immunoglobulin gene miniloci that encode unrearranged human heavy μ and γ and K light chain immunoglobulin sequences, together with targeted mutations that inactivate the endogenous μ and K chain loci. Accordingly, the mice exhibit reduced expression of mouse IgM or K and in response to immunization, the introduced human heavy and light chain transgenes undergo class switching and somatic mutation to generate high affinity human IgG K monoclonal.

In another embodiment, anti-VSIG3 or anti-VISTA human antibodies can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-VSIG3 or anti-VISTA human antibodies. For example, an alternative transgenic system referred to as the Xenomouse (Abgenix, Inc.) can be used.

Moreover, alternative transchromosomic animal systems expressing human immunoglobulin genes are available in the art and can be used to raise anti-VSIG3 or anti-VISTA human antibodies according to at least some embodiments. For example, mice carrying both a human heavy chain transchromosome and a human light chain transchromosome, referred to as "TC mice" can be used. Furthermore, cows carrying human heavy and light chain transchromosomes can be used to raise anti-VSIG3 or anti-VISTA antibodies.

Human monoclonal anti-VSIG3 or anti-VISTA antibodies can also be prepared using phage display methods for screening libraries of human immunoglobulin genes. Human monoclonal anti-VSIG3 or anti-VISTA antibodies can also be prepared using SCID mice into which human immune cells have been reconstituted such that a human antibody response can be generated upon immunization.

Immunization

In some embodiments, human Ig mice are used to raise human anti-VSIG3 or anti-VISTA antibodies, e.g., by immunizing such mice with a purified or enriched preparation of VSIG3 or VISTA antigen and/or recombinant VSIG3 or VISTA, or VSIG3 or VISTA fusion protein. In some cases, the mice will be 6-16 weeks of age upon the first infusion. For example, a purified or recombinant preparation (5 μg to 50 μg) of VSIG3 antigen and/or VISTA antigen can be used to immunize the human Ig mice intraperitoneally.

In general, transgenic mice respond when initially immunized intraperitoneally with antigen in complete Freund's adjuvant, followed by every other week intraperitoneal immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA, and mice with sufficient titers of anti-VSIG3 or anti-VISTA human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo 12). Alternatively or additionally, the KM Mouse™ strain can be used.

Generation of Hybridomas

In certain embodiments, hybridomas producing a human monoclonal anti-VSIG3 or anti-VISTA antibody may be generated using splenocytes and/or lymph node cells from immunized mice and can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and IX HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas

In certain embodiments, an anti-VSIG3 or anti-VISTA antibody can be produced in a host cell transfectoma using, for example, a combination of recombinant DNA techniques and gene transfection methods.

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segments within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Characterization of Antibodies

In certain embodiments, the binding specificity of an anti-VSIG3 or anti-VISTA antibody is determined by known antibody binding assay techniques such as ELISA. In an exemplary ELISA, microtiter plates are coated with a purified antigen at 0.25 µg/ml in PBS, and then blocked with 5% bovine serum albumin in PBS. Dilutions of antibody (e.g., dilutions of plasma from-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay can also be used to screen for hybridomas that show positive reactivity with VSIG3 or VISTA immunogen. Hybridomas that bind with high avidity to VSIG3 or VISTA are subcloned and further characterized. One clone from each hybridoma, which retains the reactivity of the parent cells (by ELISA), can be chosen for making a 5-10 vial cell bank stored at −140° C., and for antibody purification.

To purify anti-VSIG3 or anti-VISTA antibodies, selected hybridomas can be grown in two-liter spinner-flasks for monoclonal antibody purification. Supernatants can be filtered and concentrated before affinity chromatography with protein A-Sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-VSIG3 or anti-VISTA monoclonal antibodies bind to unique epitopes, each antibody can be biotinylated using commercially available reagents. Competition studies using unlabeled monoclonal antibodies and biotinylated monoclonal antibodies can be performed using VSIG3 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-VSIG3 or anti-VISTA human IgGs can be further tested for reactivity with VSIG3 or VISTA antigen, respectively, by Western blotting. Briefly, VSIG3 or VISTA antigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets.

Alternative Scaffolds

Certain embodiments provide an antigen-binding construct comprising a protein scaffold which is linked to one or more epitope-binding domains. Such engineered protein scaffolds are usually obtained by designing a random library with mutagenesis focused at a loop region or at an otherwise permissible surface area and by selection of variants against a given target via phage display or related techniques. Some embodiments provide alternative scaffolds including, but not limited to, anticalins, DARPins, Armadillo repeat proteins, protein A, lipocalins, fibronectin domain, ankyrin consensus repeat domain, thioredoxin, chemically constrained peptides and the like. Other embodiments provide alternative scaffolds that are used as therapeutic agents for treatment of cancer, autoimmune, infectious diseases, sepsis, or for inhibiting an undesirable immune activation that follows gene therapy, as well as for in vivo diagnostics. Some embodiments provide a pharmaceutical composition comprising an antigen-binding construct as described herein a pharmaceutically acceptable carrier.

The term "protein scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. Such protein scaffolds may comprise antigen-binding sites in addition to the one or more constant regions, for example where the protein scaffold comprises a full IgG. Such protein scaffolds will be capable of being linked to other protein domains, for example protein domains which have antigen-binding sites, for example epitope-binding domains or ScFv domains.

In some embodiments, a domain includes a folded protein structure which has tertiary structure independent of the rest of the protein. Generally, domains are responsible for discrete functional properties of proteins and in many cases may be added, removed or transferred to other proteins without loss of function of the remainder of the protein and/or of the domain.

Loops corresponding to CDRs of antibodies can be substituted with heterologous sequence to confer different binding properties i.e. Evibodies. Lipocalins are a family of extracellular proteins which transport small hydrophobic molecules such as steroids, bilins, retinoids and lipids. They have a rigid secondary structure with a number of loops at the open end of the conical structure which can be engineered to bind to different target antigens. Anticalins are between 160-180 amino acids in size, and are derived from lipocalins. An affibody is a scaffold derived from Protein A of Staphylococcus aureus which can be engineered to bind to antigen. The domain consists of a three-helical bundle of approximately 58 amino acids. Libraries have been generated by randomization of surface residues. Avimers are multidomain proteins derived from the A-domain scaffold family. The native domains of approximately 35 amino acids adopt a defined disulphide bonded structure. Diversity is generated by shuffling of the natural variation exhibited by the family of A-domains.

A transferrin is a monomeric serum transport glycoprotein. Transferrins can be engineered to bind different target antigens by insertion of peptide sequences in a permissive surface loop. Examples of engineered transferrin scaffolds include the Trans-body.

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α helices and a β turn. They can be engineered to bind different target antigens by randomizing residues in the first α-helix and a β-turn of each repeat. Their binding interface can be increased by increasing the number of modules (a method of affinity maturation).

Fibronectin is a scaffold which can be engineered to bind to antigen. Adnectins consists of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest.

Peptide aptamers are combinatorial recognition molecules that consist of a constant scaffold protein, typically thioredoxin (TrxA) which contains a constrained variable peptide loop inserted at the active site.

Microbodies are derived from naturally occurring microproteins of 25-50 amino acids in length which contain 3-4 cysteine bridges—examples of microproteins include KalataBI and conotoxin and knottins. The microproteins have a loop which can be engineered to include up to 25 amino acids without affecting the overall fold of the microprotein.

Other epitope binding domains include proteins which have been used as a scaffold to engineer different target antigen-binding properties include human β-crystallin and human ubiquitin (affilins), Kunitz type domains of human protease inhibitors, PDZ-domains of the Ras-binding protein AF-6, scorpion toxins (charybdo toxin) and C-type lectin domain (tetranectins). Epitope binding domains can be derived from any of these alternative protein domains.

Conjugates or Immunoconjugates

Some embodiments provide conjugates of VSIG3 or VISTA antigen for use in immune therapy comprising the VSIG3 or VISTA antigen and soluble portions thereof including the ectodomain or portions or variants thereof. For example, some embodiments provide conjugates wherein the ECD of the VISTA or VSIG3 antigen is attached to an immunoglobulin or fragment thereof. The conjugates can be used for promoting or inhibiting VSIG3 or VISTA antigen activities such as immune stimulation and the use thereof in treating transplant, autoimmune, and cancer indications.

Other embodiments provide antibody-drug conjugates (ADCs), used for example for treatment of cancer, consisting of an antibody (or antibody fragment such as a single-chain variable fragment (scFv) linked to a payload drug (often cytotoxic). The antibody causes the ADC to bind to the target cancer cells. Often the ADC is then internalized by the cell and the drug is released into the cell. Because of the targeting, the side effects are lower and give a wider therapeutic window. Hydrophilic linkers (e.g., PEG4Mal) help prevent the drug being pumped out of resistant cancer cells through MDR (multiple drug resistance) transporters.

Other embodiments provide immunoconjugates comprising an anti-VSIG3 or anti-VISTA antibody, or a fragment thereof, conjugated to a therapeutic agent, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody include duocarmycins, calicheamicins, maytansines and auristatins, and derivatives thereof. An example of a calicheamicin antibody conjugate is commercially available (Mylotarg.™. Wyeth).

Cytotoxins can be conjugated to antibodies using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

Antibodies also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Methods for preparing radioimmunconjugates are established in the art. Radioimmunoconjugates are commercially available, including ZEVALIN (BiogenIDEC) and BEXXAR (Corixa Pharmaceuticals), and similar methods can be used to prepare radioimmunoconjugates using the antibodies according to at least some embodiments.

The antibodies or fusion proteins disclosed herein or conjugates according to at least some embodiments can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Multispecific Molecules

Other embodiments provide a multispecific anti-VSIG3 or anti-VISTA antibody. Multispecific antibodies are monoclonal antibodies that have binding specificities for at least two different sites. Other embodiments provide bispecific molecules comprising an anti-VSIG3 or anti-VISTA antibody, or a fragment thereof. An antibody or antigen-binding portions thereof can be derivatized or linked to another functional molecule, e.g., another peptide or protein (e.g., another antibody or ligand for a receptor) to generate a bispecific molecule that binds to at least two different binding sites or target molecules. The antibody may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule according to at least some embodiments, an antibody can be functionally linked (e.g., by chemical coupling, genetic fusion, noncovalent association or otherwise) to one or more other binding molecules, such as another antibody, antibody fragment, peptide or binding mimetic, such that a bispecific molecule results. In certain embodiments, one of the binding specificities of the bispecific antibodies is for VSIG3 or VISTA and the other is for any other antigen. In certain embodiments, bispecific antibodies may bind to two different epitopes of VSIG3 or VISTA. Bispecific antibodies may also be used to localize cytotoxic agents to cells which express VSIG3 or VISTA. Bispecific antibodies can be prepared as full length antibodies or antibody fragments.

A bispecific antibody according to at least some embodiments is an antibody which can bind simultaneously to two targets which are of different structure. Bispecific antibodies (bsAb) and bispecific antibody fragments (bsFab) according to at least some embodiments have at least one arm that specifically binds to a B-cell antigen or epitope and at least one other arm that specifically binds a targetable conjugate.

Some embodiments provide a fusion antibody protein, which is a recombinantly produced antigen-binding molecule in which two or more different single-chain antibody or antibody fragment segments with the same or different specificities are linked. A variety of bispecific fusion antibody proteins can be produced using molecular engineering. In one form, the bispecific fusion antibody protein is monovalent, consisting of, for example, a sent with a single binding site for one antigen and a Fab fragment with a single binding site for a second antigen. In another form, the bispecific fusion antibody protein is divalent, consisting of, for example, an IgG with two binding sites for one antigen and two scFv with two binding sites for a second antigen.

Some embodiments provide engineered antibodies with three or more functional antigen-binding sites, including "Octopus antibodies" (see, e.g. US 2006/0025576A1), and "Dual Acting FAb" or "DAF" antibodies comprising an antigen-binding site that binds to VSIG3 as well as another, different antigen (see e.g. US 2008/0069820).

Accordingly, some embodiments provide bispecific molecules comprising at least one first binding specificity for VSIG3 or VISTA and a second binding specificity for a second target epitope. In some cases, the second target epitope is an Fc receptor, e.g., human FcγRI (CD64) or a human Fcα receptor (CD89). Therefore, some embodiments provide bispecific molecules capable of binding both to FcγR, FcαR or FcεR expressing effector cells (e.g., monocytes, macrophages or polymorphonuclear cells (PMNs)), and to target cells expressing VSIG3 or VISTA, respectively. These bispecific molecules target VSIG3 or VISTA expressing cells to effector cell and trigger Fc receptor-mediated effector cell activities, such as phagocytosis of VSIG3 or VISTA expressing cells, antibody dependent cell-mediated cytotoxicity (ADCC), cytokine release, or generation of superoxide anion.

In some cases in which the bispecific molecule is multispecific, the molecule can further include a third binding specificity, in addition to an anti-Fc binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In some cases, the bispecific molecules comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which are expressly incorporated by reference.

In one embodiment, the binding specificity for a Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fc γ receptor is a human high affinity FcγRI. The human FcγRI is a 72 kDa molecule, which shows high affinity for monomeric IgG. These antibodies bind to an epitope of FcγRI, FcγRII or FcγRIII at a site which is distinct from the Fcγ binding site of the receptor and, thus, their binding Is not blocked substantially by physiological levels of IgG. Specific anti-FcγRI antibodies that may be useful include, for example, mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The H22 antibody producing cell line is deposited at the American Type Culture Collection under the designation HA022CL1 and has the accession no. CRL 11177.

In other embodiments, the binding specificity for an Fc receptor is provided by an antibody that binds to a human IgA receptor, e.g., an Fc-a receptor (FcαRI(CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 10 kDa. FcαRI (CD89) is constitutively expressed on monocytes/macrophages, eosinophilic and neutrophilic granulocytes, but not on non-effector cell populations. FcαRI has medium affinity (approximately $5\times10^{-7}$ $M^{-1}$) for both IgAI and IgA2, which is increased upon exposure to cytokines such as G-CSF or GM-CSF. Four FcαRI-specific monoclonal antibodies, identified as A3, A59, A62 and A77, which bind FcαRI outside the IgA ligand binding domain, have been described.

FcαRI and FcγRI are preferred trigger receptors for use in the bispecific molecules according to at least some embodiments because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

While human monoclonal antibodies are preferred, other antibodies which can be employed in the bispecific molecules according to at least some embodiments are murine, chimeric and humanized monoclonal antibodies.

The bispecific molecules can be prepared by conjugating the constituent binding specificities using methods known in the art. For example, the binding specificity of each bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyld-ithio propionate (SPDP), and sulfosuccinimidyl 4-(N-maleimidomethyl)cyclohaxane-1-carboxylate (sulfo-SMCC). Preferred conjugating agents are SATA and sulfo-SMCC, both available from Pierce Chemical Co. (Rockford, Ill.). When the binding moieties are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF (ab')2 or ligand XFab fusion protein. A bispecific molecule can be a single chain molecule comprising one single chain antibody and a binding determinant, or a single chain bispecific molecule comprising two binding determinants. Bispecific molecules may comprise at least two single chain molecules.

Techniques for making multispecific antibodies include, but are not limited to, recombinant co-expression of two immunoglobulin heavy chain-light chain pairs having different specificities and "knob-in-hole" engineering. Multispecific antibodies may also be made by engineering electrostatic steering effects for making antibody Fc-heterodimeric molecules, controlled Fab-arm exchange, cross-linking two or more antibodies or fragments, using leucine zippers to produce bi-specific antibodies, using "diabody" technology for making bispecific antibody fragments, using single-chain Fv (sFv) dimers, and preparing trispecific antibodies.

Binding of the bispecific molecules to their specific targets can be confirmed by, for example, enzyme-linked immunosorbent assay (ELISA), radioimmunoassay (MA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (MA). The radioactive isotope can be detected by such means as the use of a γ counter or a scintillation counter or by autoradiography.

Cancer Immunotherapy

Unlike tumor-targeted therapies, which are aimed at inhibiting molecular pathways that are crucial for tumor growth and development, and/or depleting tumor cells, cancer immunotherapy is aimed to stimulate the patient's own immune system to eliminate cancer cells, providing long-lived tumor destruction. Various approaches can be used in cancer immunotherapy, among them are therapeutic cancer vaccines to induce tumor-specific T cell responses, and immunostimulatory antibodies (i.e. antagonists of inhibitory receptors=immune checkpoints) to remove immunosuppressive pathways.

Clinical responses with targeted therapy or conventional anti-cancer therapies tend to be transient as cancer cells develop resistance, and tumor recurrence takes place. However, the clinical use of cancer immunotherapy in the past few years has shown that this type of therapy can have durable clinical responses, showing dramatic impact on long term survival. However, although responses are long term, only a small number of patients respond (as opposed to conventional or targeted therapy, where a large number of patients respond, but responses are transient).

By the time a tumor is detected clinically, it has already evaded the immune-defense system by acquiring immunoresistant and immunosuppressive properties and creating an immunosuppressive tumor microenvironment through various mechanisms and a variety of immune cells. Thus, in cancer immunotherapy it is becoming increasingly clear that a combination of therapies is required for clinical efficacy.

Combination approaches are needed and expected to increase the number of patients benefiting from immunotherapy and expand the number and types of cancers that are responsive, expanding the potential cancer indications for checkpoint agents well beyond the initial indications currently showing efficacy of immune checkpoint blockade as monotherapy. The combination of immunomodulatory approaches is meant to maximize the outcomes and overcome the resistance mechanisms of most tumors to a single approach. Thus, tumors traditionally thought of as non-immunogenic can likely become immunogenic and respond to immunotherapy though co-administration of pro-immunogenic therapies designed to increase the patient's anti-tumor immune responses. Potential priming agents are detailed herein below.

The underlying scientific rationale for the dramatic increased efficacy of combination therapy claims that immune checkpoint blockade as a monotherapy will induce tumor regressions only when there is pre-existing strong anti-tumor immune response to be 'unleashed' when the pathway is blocked. According to some embodiments, VSIG3-specific or VISTA-specific antibodies, antibody fragments, conjugates and compositions comprising same, are used for treatment of all types of cancer in cancer immunotherapy in combination therapy.

For example, immunostimulatory anti-VSIG3 antibodies may promote T cell or NK or cytokine immunity against target cells, e.g., cancer, infected or pathogen cells and thereby treat cancer or infectious diseases by depleting the cells involved in the disease condition. Conversely, immunoinhibitory anti-VSIG3 antibodies may reduce T cell or NK activity and/or or the secretion of proinflammatory cytokines which are involved in the disease pathology of some immune disease such as autoimmune, inflammatory or allergic conditions and thereby treat or ameliorate the disease pathology and tissue destruction that may be associated with such conditions (e.g., joint destruction associated with rheumatoid arthritis conditions).

The therapeutic agents can be provided to the subject alone, or as part of a pharmaceutical composition where they are mixed with a pharmaceutically acceptable carrier.

According to at least some embodiments, a therapeutic agent can include a VSIG3/VISTA agonist or a VSIG3/VISTA antagonist. In some embodiments, the VSIG3/VISTA agonist or a VSIG3/VISTA antagonist may be administered in a therapeutically effective amount. In some embodiments, the subject may exhibit overexpression of VSIG3 in a tissue relative to a control or relative to a subject not having a disease. In some embodiments, VSIG3 may be overexpressed in a biological sample obtained from the subject. In some embodiments, the subject may have been diagnosed with cancer including, for example, colon cancer or liver cancer.

In some embodiments, an anti-VSIG3 or anti-VISTA antibody; a VSIG3 and/or VISTA polypeptide; a VSIG3 and/or VISTA a VSIG3 and/or VISTA fusion protein; a VSIG3 and/or VISTA conjugate; a VSIG3 and/or VISTA multimer (e.g., a homomultimer or heteromultimer); a VSIG3 and/or VISTA fragment or a conjugate thereof; and/or a pharmaceutical composition comprising same, can be administered. In some embodiments, the composition may be administered in combination therapy, i.e., combined with other potentiating agents and/or other therapies. According to at least some embodiments, the anti-VSIG3 or anti-VISTA antibody or VSIG3 fusion protein or VISTA fusion protein disclosed herein could be used in combination with a cancer therapy. Such cancer therapies can be found, for example, on the world wide web at cancer.gov/cancer-topics. Such therapies may additionally or alternatively include chemotherapy or radiotherapy or other biologics. Any chemotherapeutic agent exhibiting anticancer activity may be used. In some cases, the chemotherapeutic agent may include alkylating agents, antimetabolites, folic acid analogs, pyrimidine analogs, purine analogs and related inhibitors, *vinca* alkaloids, epipodophyllotoxins, antibiotics, L-Asparaginase, topoisomerase inhibitor, interferons, platinum coordination complexes, anthracenedione substituted urea, methyl hydrazine derivatives, adrenocortical suppressant, adrenocorticosteroids, progestins, estrogens, antiestrogen, androgens, antiandrogen, and gonadotropin-releasing hormone analog. In certain cases, the chemotherapeutic agent may be selected from the group consisting of 5-fluorouracil (5-FU), leucovorin (LV), irinotecan, oxaliplatin, capecitabine, paclitaxel, and docetaxel. Two or more chemotherapeutic agents can be used in a cocktail to be administered in combination. A biologic can be another immune potentiator including, for example, antibodies to PD-L1, PD-L2, CTLA-4, or VISTA; PD-L1, PD-L2, CTLA-4, or VISTA fusion proteins; cytokines; growth factor antagonists and agonists; hormones; and anti-cytokine antibodies. In some embodiments, the combination therapy can include a therapeutic or immune modulatory agent, other compounds or immunotherapies, or an immuno stimulatory strategy.

According to at least some embodiments, therapeutic agents that can be used in combination with anti-VSIG3 or anti-VISTA antibodies are potentiating agents that enhance anti-tumor responses.

Various strategies are available for combining an anti-VSIG3 or anti-VISTA immuno stimulatory antibody or VSIG3 or VISTA fusion proteins disclosed herein with potentiating agents for cancer immunotherapy. According to at least some embodiments, anti-VSIG3 antibody for cancer immunotherapy is used in combination with potentiating agents that are primarily geared to increase endogenous anti-tumor responses, such as radiotherapy, cryotherapy, conventional/classical chemotherapy potentiating anti-tumor immune responses, targeted therapy potentiating anti-tumor immune responses, anti-angiogenic therapy, therapeutic agents targeting immunosuppressive cells such as Tregs and MDSCs, immuno stimulatory antibodies, cytokine therapy, therapeutic cancer vaccines and adoptive cell transfer.

One rationale behind the combined use with some chemotherapy or anti-cancer conventional drugs is that cancer cell death, a consequence of the cytotoxic action of most chemotherapeutic compounds, may result in increased levels of tumor antigen leading to enhanced antigen presentation and stimulation of anti-tumor immune responses (i.e. immunogenic cell death), resulting in potentiating effects with the anti-VSIG3 or anti-VISTA antibody. Other combination therapies that may potentiate anti-tumor responses through tumor cell death are radiotherapy, cryotherapy, surgery, and hormone deprivation. Each of these cancer therapies creates a source of tumor antigen in the host.

According to at least some embodiments, anti-VSIG3 or anti-VISTA antibodies or VSIG3 or VISTA fusion proteins disclosed herein for cancer immunotherapy is used in combination with bisphosphonates, especially amino-bisphosphonates (ABP), which have shown to have anti-cancer activity. Some of the activities associated with ABPs are on human $\gamma\Delta T$ cells that straddle the interface of innate and adaptive immunity and have potent anti-tumour activity.

Targeted therapies can also stimulate tumor-specific immune response by inducing the immunogenic death of tumor cells or by engaging immune effector mechanisms.

According to at least some embodiment, targeted therapies used as agents for combination with anti-VSIG3 or anti-VISTA antibodies for treatment of cancer are as described herein.

Other cancer immunotherapies that also increase endogenous anti-tumor responses could also potentiate the effect of the anti-VSIG3 or anti-VISTA antibodies or VSIG3 or VISTA proteins disclosed herein by enhancing immune effector mechanisms, such as adoptive T cell therapy, therapeutic cancer vaccines, reduced immune suppressive cells and their function, cytokine therapy, or immuno stimulatory antibodies.

According to at least some embodiments, anti-VSIG3 or anti-VISTA antibodies or VSIG3 or VISTA fusion proteins disclosed herein for cancer immunotherapy is used in combination with therapeutic agents targeting regulatory immunosuppressive cells such as regulatory T cells (Tregs) and myeloid derived suppressor cells (MDSCs). A number of commonly used chemotherapeutics exert non-specific targeting of Tregs and reduce the number or the immunosuppressive capacity of Tregs or MDSCs. In this regard, metronomic therapy with some chemotherapy drugs results in immuno stimulatory rather than immunosuppressive effects, via modulation of regulatory cells. Thus, according to at least some embodiments, anti-VSIG3 or anti-VISTA antibodies or VSIG3 or VISTA fusion proteins disclosed herein for cancer immunotherapy is used in combination with drugs selected from but not limited to cyclophosphamide, gemcitabine, mitoxantrone, fludarabine, fludarabine, docetaxel, paclitaxel, thalidomide and thalidomide derivatives.

In addition, according to at least some embodiments, anti-VSIG3 or anti-VISTA antibody or VSIG3 or VISTA fusion proteins disclosed herein for cancer immunotherapy is used in combination with novel Treg-specific targeting agents including: 1) depleting or killing antibodies that directly target Tregs through recognition of Treg cell surface receptors such as anti-CD25 mAbs daclizumab, basiliximab or 2) ligand-directed toxins such as denileukin diftitox (Ontak)—a fusion protein of human IL-2 and diphtheria toxin, or LMB-2—a fusion between an scFv against CD25 and *Pseudomonas* exotoxin and 3) antibodies targeting Treg cell surface receptors such as CTLA4, PD-1, OX40 and GITR or 4) antibodies, small molecules or fusion proteins targeting other NK receptors such as previously identified.

According to at least some embodiments, anti-VSIG3 or anti-VISTA antibody or VSIG3 or VISTA fusion proteins disclosed herein for cancer immunotherapy is used in combination with any of the options described below for disrupting Treg induction and/or function, including TLR (toll like receptors) agonists; agents that interfere with the adenosinergic pathway, such as ectonucleotidase inhibitors, or inhibitors of the A2A adenosine receptor; TGF-β inhibitors, such as fresolimumab, lerdelimumab, metelimumab, trabedersen, LY2157299, LY210976; blockade of Tregs recruitment to tumor tissues including chemokine receptor inhibitors, such as the CCR4/CCL2/CCL22 pathway.

According to at least some embodiments, anti-VSIG3 or anti-VISTA antibody or VSIG3 or VISTA fusion proteins disclosed herein for cancer immunotherapy is used in combination with any of the options described below for inhibiting the immunosuppressive tumor microenvironment, including inhibitors of cytokines and enzymes which exert immunosuppressive activities, such as IDO (indoleamine-2, 3-dioxygenase) inhibitors; inhibitors of anti-inflammatory cytokines which promote an immunosuppressive microenvironment, such as IL-10, IL-35, IL-4 and IL-13; Bevacizumab® which reduces Tregs and favors the differentiation of DCs.

According to at least some embodiments, anti-VSIG3 or anti-VISTA antibodies or VSIG3 or VISTA fusion proteins disclosed herein for cancer immunotherapy are used in combination with any of the options described below for targeting MDSCs (myeloid-derived suppressor cells), including promoting their differentiation into mature myeloid cells that do not have suppressive functions by Vitamin D3, or Vitamin A metabolites, such as retinoic acid, all-trans retinoic acid (ATRA); inhibition of MDSCs suppressive activity by COX2 inhibitors, phosphodiesterase 5 inhibitors like sildenafil, ROS inhibitors such as nitroaspirin.

According to at least some embodiments, anti-VSIG3 or anti-VISTA antibodies or VSIG3 or VISTA proteins disclosed herein for cancer immunotherapy are used in combination with immuno stimulatory antibodies or other agents which potentiate anti-tumor immune responses. Immuno stimulatory antibodies promote anti-tumor immunity by directly modulating immune functions, i.e. blocking other inhibitory targets or enhancing immuno stimulatory proteins. According to at least some embodiments, anti-VSIG3 or anti-VISTA antibodies for cancer immunotherapy are used in combination with antagonistic antibodies targeting immune checkpoints including anti-CTLA4 mAbs, such as ipilimumab, tremelimumab; anti-PD-1 such as nivolumab BMS-936558/MDX-1106/ONO-4538, AMP224, CT-011, MK-3475, anti-PDL-1 antagonists such as BMS-936559/MDX-1105, MEDI4736. RG-7446/MPDL3280A; Anti-LAG-3 such as IMP-321), anti-TIM-3, anti-BTLA, anti-B7-H4, anti-B7-H3, Anti-VISTA; Agonistic antibodies targeting immunostimulatory proteins, including anti-CD40 mAbs such as CP-870,893, lucatumumab, dacetuzumab; anti-CD137 mAbs such as BMS-663513 urelumab, PF-05082566; anti-OX40 mAbs, such as anti-OX40; anti-GITR mAbs such as TRX518; anti-CD27 mAbs, such as CDX-1127; and anti-ICOS mAbs.

Cytokines are molecular messengers that allow the cells of the immune system to communicate with one another to generate a coordinated, robust, but self-limited response to a target antigen. Cytokine-based therapies embody a direct attempt to stimulate the patient's own immune system to reject cancer. The growing interest over the past two decades in harnessing the immune system to eradicate cancer has been accompanied by heightened efforts to characterize cytokines and exploit their vast signaling networks to develop cancer treatments. Cytokines directly stimulate immune effector cells and stromal cells at the tumor site and enhance tumor cell recognition by cytotoxic effector cells. Numerous animal tumor model studies have demonstrated that cytokines have broad anti-tumor activity and this has been translated into a number of cytokine-based approaches for cancer therapy. A number of cytokines are in preclinical or clinical development as agents potentiating anti-tumor immune responses for cancer immunotherapy, including among others: IL-2, IL-7, IL-12, IL-15, IL-17, IL-18 and IL-21, IL-23, IL-27, GM-CSF, IFNα (interferon α), IFNβ, and IFN γ.

Several cytokines have been approved for therapy of cancer and many more are under development. However, therapeutic efficacy is often hampered by severe side effects and poor pharmacokinetic properties. Thus, in addition to systemic administration of cytokines, a variety of strategies can be employed for the delivery of therapeutic cytokines and their localization to the tumor site, in order to improve their pharmacokinetics, as well as their efficacy and/or toxicity, including antibody-cytokine fusion molecules (immunocytokines), chemical conjugation to polyethylene glycol (PEGylation), transgenic expression of cytokines in autologous whole tumor cells, incorporation of cytokine genes into DNA vaccines, recombinant viral vectors to deliver cytokine genes, etc. In the case of immunocytokines, fusion of cytokines to tumor-specific antibodies or antibody fragments allows for targeted delivery and therefore improved efficacy and pharmacokinetics, and reduced side effects.

According to at least some embodiments, anti-VSIG3 or anti-VISTA antibody or VSIG3 or VISTA fusion proteins disclosed herein for cancer immunotherapy is used in combination with cytokine therapy, involving the use of cytokines as agents potentiating anti-tumor immune responses, including cytokines such as IL-2, IL-7, IL-12, IL-15, IL-17, IL-18 and IL-21, IL-23, IL-27, GM-CSF, IFNα (interferon α), IFNα-2b, IFNβ, IFN γ, and their different strategies for delivery, as described above.

Cancer vaccines are used to treat existing cancer (therapeutic) or prevent the development of cancer in certain high-risk individuals (prophylactic). Therapeutic cancer vaccines allow for improved priming of T cells and improved antigen presentation, and can be used as therapeutic agents for potentiating anti-tumor immune responses.

Several types of therapeutic cancer vaccines are in preclinical and clinical development. These include for example whole tumor cell vaccines, in which cancer cells removed during surgery are treated to enhance their immunogenicity, and injected into the patient to induce immune responses against antigens in the tumor cells. The tumor cell vaccine can be autologous, i.e. a patient's own tumor, or allogeneic which typically contain two or three established and characterized human tumor cell lines of a given tumor type, such as the GVAX vaccine platforms. Tumor antigen vaccines, in which a tumor antigen (or a combination of a few tumor antigens), usually proteins or peptides, are administered to boost the immune system (possibly with an adjuvant and/or with immune modulators or attractants of dendritic cells such as GM-CSF). The tumor antigens may be specific for a certain type of cancer. Vector-based tumor antigen vaccines and DNA vaccines can be used as a way to provide a steady supply of antigens to stimulate an anti-tumor immune response. Vectors encoding for tumor antigens are injected into the patient (possibly with proinflammatory or other attractants such as GM-CSF), taken up by cells in vivo to make the specific antigens, which would then provoke the desired immune response. Vectors may be used to deliver more than one tumor antigen at a time, to increase the immune response. In addition, recombinant virus, bacteria or yeast vectors should trigger their own immune responses, which may also enhance the overall immune response.

Oncolytic virus vaccines, such as OncoVex/T-VEC, which involves the intratumoral injection of replication-conditional herpes simplex virus which preferentially infects cancer cells. The virus, which is also engineered to express GM-CSF, is able to replicate inside a cancer cell causing its lysis, releasing new viruses and an array of tumor antigens, and secreting GM-CSF in the process. Thus, such oncolytic virus vaccines enhance DCs function in the tumor microenvironment to stimulate anti-tumor immune responses.

Dendritic cell vaccines include dendritic cells (DCs), phagocytose tumor cells and present tumor antigens to tumor specific T cells. In this approach, DCs are isolated from the cancer patient and primed for presenting tumor-specific T cells. To this end, several methods can be used: DCs are loaded with tumor cells or lysates, DCs are loaded with fusion proteins or peptides of tumor antigens, or coupling of tumor antigens to DC-targeting mAbs. The DCs are treated in the presence of a stimulating factor (such as GM-CSF), activated and matured ex vivo, and then re-infused back into the patient in order provoke an immune response to the cancer cells. Dendritic cells can also be primed in vivo by injection of patients with irradiated whole tumor cells engineered to secrete stimulating cytokines (such as GM-CSF). Similar approaches can be carried out with monocytes. Sipuleucel-T (Provenge), a therapeutic cancer vaccine which has been approved for treatment of advanced prostate cancer, is an example of a dendritic cell vaccine.

Thus, according to at least some embodiments, anti-VSIG3 or anti-VISTA antibody or VSIG3 or VISTA fusion proteins disclosed herein for cancer immunotherapy is used in combination with therapeutic cancer vaccines. Non limiting examples of such therapeutic cancer vaccines include whole tumor cell vaccines, tumor antigen vaccines, vector-based vaccines, oncolytic virus vaccines and dendritic-cell vaccines, as described above.

One approach to cancer immunotherapy is based on adoptive T cell therapy or adoptive cell transfer (ACT), which involves the ex vivo identification and expansion of autologous naturally occurring tumor specific T cells, which are then adoptively transferred back into the cancer patient. Cells that are infused back into a patient after ex vivo expansion can traffic to the tumor and mediate its destruction. Prior to this adoptive transfer, hosts can be immunodepleted by irradiation and/or chemotherapy. The combination of lymphodepletion, adoptive cell transfer, and a T cell growth factor (such as IL-2), can lead to prolonged tumor eradication in tumor patients. A more novel approach involves the ex vivo genetic modification of normal peripheral blood T cells to confer specificity for tumor-associated antigens. For example, clones of TCRs of T cells with particularly good anti-tumor responses can be inserted into viral expression vectors and used to infect autologous T cells from the patient to be treated. Another option is the use of chimeric antigen receptors (CARs) which are essentially a chimeric immunoglobulin-TCR molecule, also known as a T-body. CARs have antibody-like specificities and recognize MHC-nonrestricted structures on the surface of target cells (the extracellular target-binding module), grafted onto the TCR intracellular domains capable of activating T cells.

According to at least some embodiments, anti-VSIG3 or anti-VISTA antibodies or VSIG3 or VISTA fusion proteins disclosed herein for cancer immunotherapy are used in combination with adoptive cell transfer to potentiate anti-tumor immune responses, including genetically modified T cells, as described above.

The VSIG3 or VISTA specific antibodies, and/or alternative scaffolds and/or multispecific and bispecific molecules and immunoconjugates, compositions comprising same according to at least some embodiments can be coadministered together with one or more other therapeutic agents, which acts in conjunction with or synergistically with the composition according to at least some embodiments to treat or prevent the cancer. The VSIG3 or VISTA related therapeutic agents and the one or more other therapeutic agents can be administered in either order or simultaneously. The other therapeutic agents are for example, a cytotoxic agent, a radiotoxic agent or an immunosuppressive agent. The composition can be linked to the agent (as an immunocomplex) or can be administered separately from the agent. In the latter case (separate administration), the composition can be administered before, after or concurrently with the agent or can be coadministered with other known therapies, e.g., an anti-cancer therapy, e.g., radiation. Such therapeutic agents include, among others, anti-neoplastic agents such as doxorubicin (Adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/dose once every four weeks and Adriamycin is intravenously administered as a 60-75 mg/ml dose once every 21 days. Co-administration of the human anti-VSIG3 antibodies, or antigen-binding fragments and/or alternative scaffolds thereof, according to at least some embodiments with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody. In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

Target-specific effector cells, e.g., effector cells linked to compositions (e.g., human antibodies, multispecific and bispecific molecules) according to at least some embodiments can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered will vary depending on the therapeutic purpose. In general, the amount will be sufficient to obtain localization at the target cell, e.g., a tumor cell expressing VSIG3 or VISTA proteins, and to effect cell killing e.g., by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) according to at least some embodiments and/or effector cells armed with these compositions can be used in conjunction with chemotherapy.

Additionally, combination immunotherapy may be used to direct two distinct cytotoxic effector populations toward tumor cell rejection. For example, anti-VSIG3 or anti-VISTA antibodies linked to anti-Fc-γ RI or anti-CD3 may be used in conjunction with IgG- or IgA-receptor specific binding agents.

Bispecific and multispecific molecules according to at least some embodiments can also be used to modulate FcγR or FcγR levels on effector cells, such as by capping and elimination of receptors on the cell surface. Mixtures of anti-Fc receptors can also be used for this purpose.

The therapeutic compositions (e.g., human antibodies, alternative scaffolds multispecific and bispecific molecules and immunoconjugates) according to at least some embodiments which have complement binding sites, such as portions from IgG1, -2, or -3 or IgM which bind complement, can also be used in the presence of complement. In one embodiment, ex vivo treatment of a population of cells comprising target cells with a binding agent according to at least some embodiments and appropriate effector cells can be supplemented by the addition of complement or serum containing complement. Phagocytosis of target cells coated with a binding agent according to at least some embodiments can be improved by binding of complement proteins. In another embodiment, target cells coated with the compositions (e.g., human antibodies, multispecific and bispecific molecules) can also be lysed by complement. In yet another embodiment, the compositions do not activate complement.

The therapeutic compositions (e.g., human antibodies, alternative scaffolds multispecific and bispecific molecules and immunoconjugates) can also be administered together with complement. Thus, according to at least some embodiments, there are compositions, comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules and the complement or serum can be administered separately.

A therapeutically effective amount of an anti-VSIG3 or anti-VISTA antibody or VSIG3 or VISTA fusion proteins disclosed herein according to at least some embodiments may result in a decrease in severity of disease symptoms, an increase in frequency and duration of disease symptom-free periods, an increase in lifespan, disease remission, or a prevention or reduction of impairment or disability due to the disease affliction. For example, for the treatment of VSIG3 positive tumors, a therapeutically effective amount can, in some embodiments, preferably inhibit cell growth or tumor growth by at least 20%, more preferably by at least 40%, even more preferably by at least 60%, and still more preferably by at least 80% relative to untreated subjects. The ability of a compound to inhibit tumor growth can be evaluated in an animal model system predictive of efficacy in human tumors.

Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject.

One of ordinary skill in the art would be able to determine a therapeutically effective amount based on such factors as the subject's size, the severity of the subject's symptoms, and the particular composition or route of administration selected.

The anti-VSIG3 or anti-VISTA antibodies, according to at least some embodiments, can be used as neutralizing antibodies. A neutralizing antibody (Nabs), is an antibody that is capable of binding and neutralizing or inhibiting a specific antigen thereby inhibiting its biological effect, for example by blocking the receptors on the cell or the virus, inhibiting the binding of the virus to the host cell. NAbs will partially or completely abrogate the biological action of an agent by either blocking an important surface molecule needed for its activity or by interfering with the binding of the agent to its receptor on a target cell.

As used herein, "therapeutic agent" can include any one of the monoclonal and/or polyclonal antibodies, and/or antigen-binding fragments, and/or conjugates containing same, and/or alternative scaffolds, thereof comprising an antigen-binding site that binds specifically to any one of the VSIG3 or VISTA polypeptides or an epitope thereof, adopted for treatment of cancer, as recited herein.

According to an additional aspect, the therapeutic agents can be used to prevent pathologic inhibition of T cell activity, such as that directed against cancer cells.

According to an additional aspect, the therapeutic agents can be used to inhibit T cell activation, as can be manifested for example by T cell proliferation and cytokine secretion.

Thus, according to an additional aspect, there is provided a method of treating cancer as recited herein, and/or for promoting immune stimulation mediated by the VSIG3 or VISTA polypeptide in a subject by administering to a subject in need thereof an effective amount of any one of the therapeutic agents and/or a pharmaceutical composition comprising any of the therapeutic agents and further comprising a pharmaceutically acceptable diluent or carrier.

A therapeutic agent or pharmaceutical composition according to at least some embodiments may also be administered in conjunction with other compounds or immunotherapies. For example, the combination therapy can include a compound combined with at least one other therapeutic or immune modulatory agent, or immuno stimulatory strategy, including, but not limited to, tumor vaccines, adoptive T cell therapy, Treg depletion, antibodies (e.g. bevacizumab, Erbitux), peptides, peptibodies, small molecules, chemotherapeutic agents such as cytotoxic and cytostatic agents (e.g. paclitaxel, cisplatin, vinorelbine, docetaxel, gemcitabine, temozolomide, irinotecan, SFU, carboplatin), immunological modifiers such as interferons and interleukins, immuno stimulatory antibodies, growth hormones or other cytokines, folic acid, vitamins, minerals, aromatase inhibitors, RNAi, Histone Deacetylase Inhibitors, proteasome inhibitors, and so forth.

According to at least some embodiments, immune cells, preferably T cells, can be contacted in vivo or ex vivo with the therapeutic agents to modulate immune responses. The T cells contacted with the therapeutic agents can be any cell which expresses the T cell receptor, including α/β and γ/Δ T cell receptors. T-cells include all cells which express CD3, including T-cell subsets which also express CD4 and CDS. T-cells include both naive and memory cells and effector cells such as CTL. T-cells also include cells such as Th1, Te1, Th2, Th2, Th3, Th17, Th22, Treg, and Tr1 cells. T-cells also include NKT-cells and similar unique classes of the T-cell lineage.

VSIG3 or VISTA blockade may also be combined with standard cancer treatments. VSIG3 or VISTA blockade may be effectively combined with chemotherapeutic regimes. In these instances, it may be possible to reduce the dose of chemotherapeutic reagent administered. An example of such a combination is an anti-VSIG3 or anti-VISTA antibody or VSIG3 or VISTA fusion proteins disclosed herein in combination with Temsirolimus for the treatment of late stage renal cell cancer. Another example of such a combination is an anti-VSIG3 or anti-VISTA antibody or VSIG3 or VISTA fusion proteins disclosed herein in combination with interleukin-2 (IL-2) for the treatment of late stage renal cell cancer as well as combination with Ipilimumab or BMS-936558. The scientific rationale behind the combined use of VSIG3 or VISTA blockade and chemotherapy is that cell death, that is a consequence of the cytotoxic action of most chemotherapeutic compounds, should result in increased levels of tumor antigen in the antigen presentation pathway. Other combination therapies that may result in synergy with VSIG3 or VISTA blockade through cell death are radiotherapy, cryotherapy, surgery, and hormone deprivation. Other additional combination therapies with additional immunomodulatory molecules will synergistically contribute to the stimulation of the immune system to eradicate the cancer. Each of these protocols creates a source of tumor antigen in the host. Angiogenesis inhibitors may also be combined with VSIG3 or VISTA blockade. Inhibition of angiogenesis leads to tumor cell death which may feed tumor antigen into host antigen presentation pathways.

VSIG3 or VISTA blocking antibodies can also be used in combination with bispecific antibodies that target Fcα or Fcγ receptor-expressing effectors cells to tumor cells. Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by the use of VSIG3 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-β, IL-10, and Fas ligand. Antibodies to each of these entities may be used in combination with anti-VSIG3 or anti-VISTA to counteract the effects of the immunosuppressive agent and favor tumor immune responses by the host.

Other antibodies which may be used to activate host immune responsiveness can be used in combination with anti-VSIG3 or anti-VISTA. These include molecules on the surface of dendritic cells which activate DC function and antigen presentation. Anti-CD40 antibodies are able to substitute effectively for T cell helper activity and can be used in conjunction with VSIG3 or VISTA antibodies. Activating antibodies to T cell costimulatory molecules such as OX-40, and ICOS as well as antibodies which block the activity of negative costimulatory molecules such as CTLA-4 or BTLA, B7-H4 or PD-1 may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. VSIG3/VISTA blockade can be used to increase the effectiveness of the donor engrafted tumor specific T cells. There are also several experimental treatment protocols that involve ex vivo activation and expansion of antigen specific T cells and adoptive transfer of these cells into recipients in order to antigen-specific T cells against tumor. These methods may also be used to activate T cell responses to infectious agents such as CMV. Ex vivo activation in the presence of anti-VSIG3 or anti-VISTA antibodies may be expected to increase the frequency and activity of the adoptively transferred T cells Optionally, antibodies to VSIG3 or VISTA can be combined with an immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of MUC1 for treatment of colon cancer, peptides of MUC-1/CEA/TRICOM for the treatment of ovary cancer, or tumor cells transfected to express the cytokine GM-CSF (discussed further below).

In humans, some tumors have been shown to be immunogenic such as RCC. It is anticipated that by raising the threshold of T cell activation by VSIG3 or VISTA blockade, tumor responses may be activated in the host. VSIG3 or VISTA blockade is likely to be most effective when combined with a vaccination protocol. Many experimental strategies for vaccination against tumors have been devised. In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination.

Treating Immune System Related Conditions

According to at least some embodiments, VSIG3 or VISTA antibodies, fragments, conjugates thereof, or fusion proteins and/or a pharmaceutical composition comprising same, as described herein may optionally be used for treating an immune system related condition. According to at least some embodiments, a VSIG3/VISTA agonist or a VSIG3/VISTA antagonist may be used for treating a subject including, a subject having an immune system related condition. In some embodiments, the VSIG3/VISTA agonist or a VSIG3/VISTA antagonist may be administered in a therapeutically effective amount. In some embodiments, the subject may exhibit overexpression of VSIG3 in a tissue relative to a control or relative to a subject not having a disease. In some embodiments, VSIG3 may be overexpressed in a biological sample obtained from the subject.

Optionally, the immune system related condition includes an immune related condition, autoimmune diseases, transplant rejection, and/or graft versus host disease.

Optionally the immune system related condition is selected from autoimmune disease, transplant rejection, or graft versus host disease. Optionally the treatment is combined with another moiety useful for treating immune system related condition.

Thus, treatment of multiple sclerosis using the agents according to at least some embodiments may be combined with, for example, any known therapeutic agent or method for treating multiple sclerosis, optionally as described herein.

Thus, treatment of rheumatoid arthritis, using the agents according to at least some embodiments may be combined with, for example, any known therapeutic agent or method for treating rheumatoid arthritis, optionally as described herein. Thus, treatment of IBD, using the agents according to at least some embodiments may be combined with, for example, any known therapeutic agent or method for treating IBD, optionally as described herein.

Thus, treatment of psoriasis, using the agents according to at least some embodiments may be combined with, for example, any known therapeutic agent or method for treating psoriasis, optionally as described herein.

Thus, treatment of type 1 diabetes, using the agents according to at least some embodiments may be combined with, for example, any known therapeutic agent or method for treating type I diabetes, optionally as described herein.

Thus, treatment of uveitis, using the agents according to at least some embodiments may be combined with, for example, any known therapeutic agent or method for treating uveitis, optionally as described herein.

Thus, treatment for Sjogren's syndrome, using the agents according to at least some embodiments may be combined with, for example, any known therapeutic agent or method for treating for Sjogren's syndrome, optionally as described herein.

Thus, treatment for systemic lupus erythematosus, using the agents according to at least some embodiments may be combined with, for example, any known therapeutic agent or method for treating for systemic lupus erythematosus, optionally as described herein.

In the above-described therapies preferably a subject with one of the aforementioned autoimmune or inflammatory conditions will be administered an immunoinhibitory anti-VSIG3 or anti-VISTA antibody or VSIG3 or VISTA fusion proteins disclosed herein or antigen-binding fragment, which antibody or VSIG3 or VISTA fusion proteins disclosed herein mimics or agonizes at least one VSIG3 or VISTA mediated effect on immunity, e.g., it suppresses cytotoxic T cells, or NK activity and/or the production of proinflammatory cytokines which are involved in the disease pathology, thereby preventing or ameliorating the disease symptoms and potentially resulting in prolonged disease remission, e.g., because of the induction of Tregs which elicit T cell tolerance or prolonged immunosuppression.

The therapeutic agents and/or a pharmaceutical composition may be administered as the sole active ingredient or together with other drugs in immunomodulating regimens or other anti-inflammatory agents e.g. for the treatment or prevention of alio- or xenograft acute or chronic rejection or inflammatory or autoimmune disorders, or to induce tolerance.

Treating Infectious Disease

According to at least some embodiments, anti-VSIG3 or anti-VISTA antibodies, fragments, conjugates thereof or VSIG3 or VISTA fusion proteins and/or a pharmaceutical compositions as described herein, which function as VSIG3/VISTA blocking therapeutic agents, may optionally be used for treating infectious disease.

Chronic infections are often characterized by varying degrees of functional impairment of virus-specific T-cell responses, and this defect is a principal reason for the inability of the host to eliminate the persisting pathogen. Although functional effector T cells are initially generated during the early stages of infection, they gradually lose function during the course of the chronic infection as a result of persistent exposure to foreign antigen, giving rise to T cell exhaustion. Exhausted T cells express high levels of multiple co-inhibitory receptors such as CTLA-4, PD-1 and LAGS. PD-1 overexpression by exhausted T cells was observed clinically in patients suffering from chronic viral infections including HIV, HCV and HBV. There has been some investigation into this pathway in additional pathogens, including other viruses, bacteria, and parasites. For example, the PD-1 pathway was shown to be involved in controlling bacterial infection using a sepsis model induced by the standard cecal ligation and puncture method. The absence of PD-1 in knockout mice protected from sepsis-induced death in this model.

T cell exhaustion can be reversed by blocking co-inhibitory pathways such as PD-1 or CTLA-4, thus allowing restoration of anti-viral immune function. The therapeutic potential of co-inhibition blockade for treating viral infection was extensively studied by blocking the PD-I/PD-LI pathway, which was shown to be efficacious in several animal models of infection including acute and chronic simian immunodeficiency virus (SrV) infection in rhesus macaques and in mouse models of chronic viral infection, such as lymphocytic choriomeningitis virus (LCMV), and Theiler's murine encephalomyelitis virus (TMEV) model in SJL/J mice. In these models PD-I/PD-LI blockade improved anti-viral responses and promoted clearance of the persisting viruses. In addition, PD-I/PD-LI blockade increased the humoral immunity manifested as elevated production of specific anti-virus antibodies in the plasma, which in combination with the improved cellular responses leads to decrease in plasma viral loads and increased survival.

As used herein the term "infectious disorder and/or disease" and/or "infection", used interchangeably, includes any disorder, disease and/or condition caused by presence and/or growth of pathogenic biological agent in an individual host organism. As used herein the term "infection" comprises the disorder, disease and/or condition as above, exhibiting clinically evident illness (i.e., characteristic medical signs and/or symptoms of disease) and/or which is asymptomatic for much or all of it course. As used herein the term "infection" also comprises disorder, disease and/or condition caused by persistence of foreign antigen that lead to exhaustion T cell phenotype characterized by impaired functionality which is manifested as reduced proliferation and cytokine production. As used herein the term "infectious disorder and/or disease" and/or "infection", further includes any of the below listed infectious disorders, diseases and/or conditions, caused by a bacterial infection, viral infection, fungal infection and/or parasite infection.

According to at least some embodiments, one or more of the therapeutic agents and/or a pharmaceutical composition may be use for treating infection. Such therapeutic agents and/or a pharmaceutical composition may also be used with a known therapeutic agent effective for treating infection.

The therapeutic agents and/or a pharmaceutical composition comprising same, as recited herein, can be administered in combination with one or more additional therapeutic agents used for treatment of bacterial infections, optionally as described herein.

The therapeutic agents and/or a pharmaceutical composition can be administered in combination with one or more additional therapeutic agents used for treatment of viral infections, optionally as described herein. The therapeutic agents and/or a pharmaceutical composition can be administered in combination with one or more additional therapeutic agents used for treatment of fungal infections, optionally as described herein.

In the above-described therapies preferably a subject with one of the aforementioned infectious conditions will be administered an immunostimulatory anti-VSIG3 or anti-VISTA antibody or VSIG3 or VISTA fusion proteins disclosed herein or antigen-binding fragment, which antibody or VSIG3 or VISTA fusion proteins disclosed herein antagonizes at least one VSIG3 or VISTA mediated effect on immunity, e.g., its inhibitory effect on cytotoxic T cells or NK activity and/or its inhibitory effect on the production of proinflammatory cytokines, or inhibits the stimulatory effect of VSIG3 or VISTA on Tregs thereby prompting the depletion or killing of the infected cells or the pathogen, and potentially resulting in disease remission based on enhanced killing of the pathogen or infected cells by the subject's immune cells.

Treating Sepsis

According to at least some embodiments, VSIG3 or VISTA antibodies, fragments, conjugates thereof and/or pharmaceutical compositions as described herein, which function as VSIG3 or VISTA blocking therapeutic agents, may optionally be used for treating sepsis.

Sepsis is a potentially life-threatening complication of an infection. Sepsis represents a complex clinical syndrome that develops when the initial host response against an infection becomes inappropriately amplified and dysregulated, becoming harmful to the host. The initial hyperinflammatory phase ("cytokine storm") in sepsis is followed by a state of immunosuppression. This latter phase of impaired immunity, also referred to as "immunoparalysis", is manifested in failure to clear the primary infection, reactivation of viruses such as HSV and cytomegalovirus, and development of new, secondary infections, often with organisms that are not particularly virulent to the immunocompetent patient. The vast majority of septic patients today survive their initial hyperinflammatory insult only to end up in the intensive care unit with sepsis-induced multi-organ dysfunction over the ensuing days to weeks. Sepsis-induced immunosuppression is increasingly recognized as the overriding immune dysfunction in these vulnerable patients. The impaired pathogen clearance after primary infection and/or susceptibility to secondary infections contribute to the high rates of morbidity and mortality associated with sepsis.

Upregulation of inhibitory proteins has lately emerged as one of the critical mechanisms underlying the immunosuppression in sepsis. The PD-I/PDL-1 pathway, for example, appears to be a determining factor of the outcome of sepsis, regulating the delicate balance between effectiveness and damage by the antimicrobial immune response. During sepsis in an experimental model, peritoneal macrophages and blood monocytes markedly increased PD-1 levels, which was associated with the development of cellular dysfunction. Similarly, in patients with septic shock the expression of PD-1 on peripheral T cells and of PDL-1 on monocytes was dramatically upregulated. Recent animal studies have shown that blockade of the PD-I/PDL-1 pathway by anti-PDI or anti-PDLI antibodies improved survival in sepsis. Similarly, blockade of CTLA-4 with anti-CTLA4 antibodies improved survival in sepsis. Taken together, these findings suggest that blockade of inhibitory proteins, including negative costimulatory molecules, is a potential therapeutic approach to prevent the detrimental effects of sepsis.

According to at least some embodiments, one or more of the therapeutic agents and/or a pharmaceutical composition may be use for treating sepsis. Such therapeutic agents and/or a pharmaceutical composition may also be used with a known therapeutic agent effective for treating sepsis.

The restoration of the delicate balance that normally exists between the active and suppressor arms of the immune system in sepsis patients may depend on the precise nature of the imbalance, i.e. the pathogenic organism responsible for the infection, its location, the amount of time passed since onset of infection, and other individual parameters. Thus, the correct choice of tools may well depend on the specific immune status or deficit of each individual patient, and may require combination of different drugs.

According to at least some embodiments, the therapeutic agents and/or a pharmaceutical composition comprising can be combined with standard of care or novel treatments for sepsis, with therapies that block the cytokine storm in the initial hyperinflammatory phase of sepsis, and/or with therapies that have immunostimulatory effect in order to overcome the sepsis-induced immunosuppression phase.

One or more of an anti-VSIG3 antibody, an anti-VISTA antibody, an VSIG3 fusion protein, or a VISTA fusion protein can be used with other immunomodulatory agents, such as immunostimulatory antibodies, cytokine therapy, immunomodulatory drugs. Such agents bring about increased immune responsiveness, especially in situations in which immune defenses (whether innate and/or adaptive) have been degraded, such as in sepsis-induced hypoinflammatory and immunosuppressive condition. Reversal of sepsis-induced immunoparalysis by therapeutic agents that augments host immunity may reduce the incidence of secondary infections and improve outcome in patients who have documented immune suppression.

Immunostimulatory antibodies promote immune responses by directly modulating immune functions, i.e. blocking other inhibitory proteins or by enhancing costimulatory proteins. Experimental models of sepsis have shown that immuno stimulation by antibody blockade of inhibitory proteins, such as PD-1, PDL-1 or CTLA-4 improved survival in sepsis, pointing to such immunostimulatory agents as potential therapies for preventing the detrimental effects of sepsis-induced immunosuppression Immunostimulatory antibodies include: 1) antagonistic antibodies targeting inhibitory immune checkpoints include anti-CTLA4 mAbs (such as ipilimumab, tremelimumab), anti-PD-1 (such as nivolumab BMS-936558/MDX-1106/ONO-4538, AMP224, CT-011, lambrozilumab MK-3475), anti-PDL-1 antagonists (such as BMS-936559/MDX-1105, MEDI4736, RG-7446/MPDL3280A), anti-LAG-3 such as IMP-321, anti-TIM-3, anti-BTLA, anti-B7-H4, anti-B7-H3 and anti-VISTA. Agonistic antibodies enhancing immunostimulatory proteins include anti-CD40 mAbs (such as CP-870,893, lucatumumab, dacetuzumab), anti-CD137 mAbs (such as BMS-663513 urelumab, PF-05082566), anti-OX40 mAbs (such as anti-OX40), anti-GITR mAbs (such as TRX518), anti-CD27 mAbs (such as CDX-1127), and anti-ICOS mAbs.

Cytokines which directly stimulate immune effector cells and enhance immune responses can be used in combination with anti-GEN antibody for sepsis therapy: IL-2, IL-7, IL-12, IL-15, IL-17, IL-18 and IL-21, IL-23, IL-27, GM-CSF, IFNα (interferon α), IFNβ, IFNγ. Cytokine-based therapies embody a direct attempt to stimulate the patient's own immune system. Experimental models of sepsis have shown administration of cytokines, such as IL-7 and IL-15, promote T cell viability and result in improved survival in sepsis. Interferon-γ (IFN γ) reverses sepsis-induced immunoparalysis of monocytes in vitro. An in vivo study showed that IFN γ partially reverses immunoparalysis in vivo in humans. IFN γ and granulocyte-macrophage colony-stimulating factor (GM-CSF) restore immune competence of ex vivo stimulated leukocytes of patients with sepsis.

Immunomodulatory drugs such as thymosin a 1 can be used. Thymosin a 1 (Ta1) is a naturally occurring thymic peptide which acts as an endogenous regulator of both the innate and adaptive immune systems. It is used worldwide for treating diseases associated with immune dysfunction including viral infections such as hepatitis B and C, certain cancers, and for vaccine enhancement. Notably, recent development in immunomodulatory research has indicated the beneficial effect of Ta1 treatment in septic patients In the above-described sepsis therapies, preferably a subject with sepsis or at risk of developing sepsis because of a virulent infection, e.g., one resistant to antibiotics or other drugs, will be administered an immunostimulatory anti-VSIG3 or anti-VISTA antibody or VSIG3 or VISTA fusion proteins disclosed herein or antigen-binding fragment, which antibody or VSIG3 or VISTA fusion proteins disclosed herein antagonizes at least one VSIG3/VISTA mediated effect on immunity, e.g., its inhibitory effect on cytotoxic T cells or NK activity and/or its inhibitory effect on the production of proinflammatory cytokines, or inhibits the stimulatory effect of VSIG3 on Tregs thereby promoting the depletion or killing of the infected cells or the pathogen, and potentially resulting in disease remission based on enhanced killing of the pathogen or infected cells by the subject's endogenous immune cells. Because sepsis may rapidly result in organ failure, in this embodiment it may be beneficial to administer anti-VSIG3 or anti-VISTA antibody fragments such as Fabs rather than intact antibodies as they may reach the site of sepsis and infection quicker than intact antibodies.

Use with Gene Therapy or Cell Therapy or Transplant

As used herein the term "gene therapy" encompasses any type of gene therapy, vector-mediated gene therapy, gene transfer, virus-mediated gene transfer.

According to at least some embodiments, anti-VSIG3 or anti-VISTA antibodies, a fragment, a conjugate thereof and/or pharmaceutical compositions as described herein, which target VSIG3 or VISTA and have inhibitory activity on immune responses, could be used as therapeutic agents for reducing the undesirable immune activation that follows gene therapy used for treatment of various genetic diseases.

Gene therapy products for the treatment of genetic diseases are currently in clinical trials. Recent studies document therapeutic success for several genetic diseases using gene therapy vectors. Gene therapy strategies are characterized by three elements, the gene to be transferred, the target tissue into which the gene will be introduced, and the vector (gene delivery vehicle) used to facilitate entry of the gene to the target tissue. The vast majority of gene therapy clinical trials have exploited viral vectors as very efficient delivery vehicles, including retroviruses, lentiviruses, adenoviruses, adeno-associated viruses, pseudotype viruses and herpes simplex viruses. However, the interactions between the human immune system and all the components of gene therapy vectors seem to represent one of the major limitations to long-lasting therapeutic efficacy. Human studies have shown that the likelihood of a host immune response to the viral vector is high. Such immune responses to the virus or the transgene product itself, resulting in formation of neutralizing antibodies and/or destruction of transduced cells by cytotoxic cells, can greatly interfere with therapeutic efficacy. Therefore, developing strategies to circumvent immune responses and facilitate long-term expression of transgenic therapeutic proteins is one of the main challenges for the success of gene therapy in the clinic.

Factors influencing the immune response against transgenic proteins encoded by viral vectors include route of administration, vector dose, immunogenicity of the transgenic protein, inflammatory status of the host and capsid serotype. These factors are thought to influence immunogenicity by triggering innate immunity, cytokine production, APC maturation, antigen presentation and, ultimately, priming of naive T lymphocytes to functional effectors. Therefore, the idea to dampen immune activation by interfering with these very mechanisms has logically emerged with the aim to induce a short-term immunosuppression, avoid the early Immune priming that follows vector administration and promote long-term tolerance.

As a strategy to inhibit the undesirable immune activation that follows gene therapy, particularly after multiple injections, immunomodulation treatment by targeting of two non-redundant checkpoints of the immune response at the time of vector delivery was tested in animal models. Studies of vector-mediated immune responses upon adenoviral vector instilled into the lung in mice or monkeys showed that transient treatment with an anti-CD40L antibody lead to suppression of adenovirus-induced immune responses; consequently, the animals could be re-administered with adenovirus vectors. Short treatment with this Ab resulted in long-term effects on immune functions and prolonged inhibition of the adenovirus-specific humoral response well beyond the time when the Ab effects were no longer significant, pointing to the therapeutic potential in blockade of this costimulatory pathway as an immunomodulatory regimen to enable administration of gene transfer vectors. Other studies showed that co-administration of CTLA4-Ig and an anti-CD40L Ab around the time of primary vector administration decreased immune responses to the vector, prolonged long term adenovirus-mediated gene expression and enabled secondary adenovirus-mediated gene transfer even after the immunosuppressive effects of these agents were no longer present, indicating that it may be possible to obtain persistence as well as secondary adenoviral-mediated gene transfer with transient immunosuppressive therapies. In another study, similar administration of CTLA4-Ig and an anti-CD40L Ab abrogated the formation of neutralizing Abs against the vector, and enabled gene transfer expression, provided the treatment was administered during each gene transfer injection. Furthermore, administration of CTLA4-Ig to mice, even as single administration, resulted in suppression of immune responses and prolonged transgene expression at early time points. However, CTLA4-Ig alone was not sufficient to permanently wipe out the immune responses against the transgene product. Combined treatment targeting two immune checkpoints with CTLA4-Ig and PD-LI or PDL-2 resulted in synergistic improvement of transgene tolerance at later time points, by probably targeting two non-redundant mechanisms of immunomodulation, resulting in long term transgene persistence and expression.

According to at least some embodiments, nucleic acid sequences encoding soluble VSIG3 or VISTA proteins and/or a fusion protein as described herein; alone or in combination with another immunomodulatory agent or in combination with any of the strategies and approaches tested to overcome the limitation of immune responses to gene therapy, could be used for reducing the undesirable immune activation that follows gene therapy.

Current approaches include exclusion of patients with antibodies to the delivery vector, administration of high vector doses, use of empty capsids to adsorb anti-vector antibodies allowing for subsequent vector transduction, repeated plasma exchange (plasmapheresis) cycles to adsorb immunoglobulins and reduce the anti-vector antibody titer.

Novel approaches attempting to overcome these limitations can be divided into two broad categories: selective modification of the Ad vector itself and pre-emptive immune modulation of the host. The first category comprises several innovative strategies including: (1) Ad-capsid-display of specific inhibitors or ligands; (2) covalent modifications of the entire Ad vector capsid moiety; (3) the use of tissue specific promoters and local administration routes; (4) the use of genome modified Ads; and (5) the development of chimeric or alternative serotype Ads.

The second category of methods includes the use of immunosuppressive drugs or specific compounds to block important immune pathways, which are known to be induced by viral vectors. Immunosuppressive agents have been tested in preclinical studies and shown efficacy in prevention or eradication of immune responses to the transfer vector and transgene product. These include general immunosuppressive agents such as cyclosporine A; cyclophosphamide; FK506; glucocorticoids or steroids such as dexamethasone; TLR9 blockade such as the TLR9 antagonist oligonucleotide ODN-2088; TNF-a blockade with anti-TNF-a antibodies or TNFR-Ig antibody, Erk and other signaling inhibitors such as U0126. In the clinical setting, administration of glucocorticoids has been successfully used to blunt T cell responses directed against the viral capsid upon liver gene transfer of adenovirus-associated virus (AAV) vector expressing human factor IX transgene to severe hemophilia B patients.

In contrast to the previous approaches that utilize drugs that tend to "globally" and non-specifically immunosuppress the host, more selective immunosuppressive approaches have been developed. These include the use of agents which provide blockade of positive co-stimulatory interactions, such as between CD40 and CD 154, ICOS and ICOSL, CD28 and CD80 or CD86 (including CTLA4-Ig), NKG2D and NKG2D ligands, LFA-1 and ICAM, LFA-3 and CD2, 4-IBB and 4-1BBL, OX40 and OX40L, GITR and GITRL and agents that stimulate negative costimulatory receptors such as CTLA-4, PD-1, BTLA, LAG-3, TIM-1, TEVI-3, KIRs, and the receptors for B7-H4 and B7-H3. Some of these have been utilized in preclinical or clinical transplantation studies.

In the above-described gene or cell therapies or in treating transplant indications preferably a subject who has or is to receive cell or gene therapy or a transplanted tissue or organ will be administered an immunoinhibitory anti-VSIG3 or anti-VISTA antibody or VSIG3 or VISTA fusion proteins disclosed herein or antigen-binding fragment, which antibody or VSIG3 fusion proteins disclosed herein enhances, agonizes or mimics at least one VSIG3 or VISTA mediated effect on immunity, e.g., its inhibitory effect on cytotoxic T cells or NK activity and/or its inhibitory effect on the production of proinflammatory cytokines, or its stimulatory effect on Tregs thereby preventing or reducing host immune responses against the cell or gene used in therapy or an undesired immune response against the transplanted cells, organ or tissue. Preferably the treatment will elicit prolonged immune tolerance against the transplanted or infused cells, tissue or organ. In some instances, e.g., in the case of transplanted cells, tissues or organs containing immune cells, the immunoinhibitory anti-VSIG3 or anti-VISTA antibody or VSIG3 or VISTA fusion proteins disclosed herein or antigen-binding fragment may be contacted with the cells, tissue or organ prior to infusion or transplant, and/or potentially immune cells of the transplant recipient in order to tolerize the immune cells and potentially prevent an undesired immune response or GVHD immune reaction.

Compositions Including Pharmaceutical Compositions

Other embodiments provide a composition, e.g., a pharmaceutical composition, containing one or a combination of the therapeutic agent, according to at least some embodiments. Thus, the present disclosure features a pharmaceutical composition comprising a therapeutically effective amount of a therapeutic agent according to at least some embodiments.

The pharmaceutical composition according to at least some embodiments is further preferably used for the treatment of cancer, for treatment of an immune related disorder, for treatment of an infectious disorder, and/or for treatment of sepsis. In some embodiments, the cancer is non-metastatic, invasive, or metastatic.

The therapeutic agents can be provided to the subject alone or as part of a pharmaceutical composition where they are mixed with a pharmaceutically acceptable carrier.

A composition is said to be a "pharmaceutically acceptable carrier" if its administration can be tolerated by a recipient patient. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

Such compositions include sterile water, buffered saline (e.g., Tris-HCl, acetate, phosphate), pH and ionic strength and optionally additives such as detergents and solubilizing agents (e.g., Polysorbate 20, Polysorbate 80), antioxidants (e.g., ascorbic acid, sodium metabisulfite), preservatives (e.g., Thimersol, benzyl alcohol) and bulking substances (e.g., lactose, mannitol). Non-aqueous solvents or vehicles may also be used as detailed below.

Examples of suitable aqueous and nonaqueous carriers that may be employed in the pharmaceutical compositions according to at least some embodiments include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Depending on the route of administration, the active compound, i.e., monoclonal or polyclonal antibodies and antigen-binding fragments and conjugates containing same, and/or alternative scaffolds, that specifically bind any one of VSIG3 or VISTA proteins, or bispecific molecule, may be coated in a material to protect the compound from the action of acids and other natural conditions that may inactivate the compound. The pharmaceutical compounds according to at least some embodiments may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydriodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, a-tocopherol, and the like; and (3) metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A composition can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intraspinal) or parenteral (including subcutaneous, intramuscular, intravenous and intradermal), transmucosal (e.g., sublingual administration), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In a specific embodiment, a protein, a therapeutic agent or a pharmaceutical composition according to at least some embodiments can be administered intraperitoneally or intravenously.

Alternatively, a VSIG3 or VISTA specific antibody or VSIG3 or VISTA fusion protein disclosed herein or can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

Therapeutic compositions can be administered with medical devices known in the art. For example, in a preferred embodiment, a therapeutic composition according to at least some embodiments can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules that may be useful include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-VSIG3 or anti-VISTA antibodies can be formulated to ensure proper distribution in vivo. For example, the blood-brain barrier (BBB) excludes many highly hydrophilic compounds. To ensure that the therapeutic compounds according to at least some embodiments cross the BBB (if desired), they can be formulated, for example, in liposomes. The liposomes may comprise one or more moieties which are selectively transported into specific cells or organs, thus enhance targeted drug delivery. Exemplary targeting moieties include folate or biotin, mannosides, antibodies, and surfactant protein A receptor.

In yet another embodiment, immunoconjugates can be used to target compounds (e.g., therapeutic agents, labels, cytotoxins, radiotoxins immunosuppressants, etc.) to cells which have VSIG3 or VISTA cell surface receptors by linking such compounds to the antibody or VSIG3 or VISTA fusion proteins disclosed herein. Thus, the invention also provides methods for localizing ex vivo or in vivo cells expressing VSIG3 or VISTA (e.g., with a detectable label, such as a radioisotope, a fluorescent compound, an enzyme, or an enzyme co-factor). Alternatively, the immunoconjugates can be used to kill cells which have VSIG3 cell surface receptors by targeting cytotoxins or radiotoxins to VSIG3 or VISTA antigen.

Depending on the route of administration, the active compound, i.e., soluble polypeptide conjugate containing the ectodomain of the VSIG3 or VISTA antigen, antibody, immunoconjugate, alternative scaffolds, and/or bispecific molecule, may be coated in a material to protect the compound from the action of acids and other natural conditions that may inactivate the compound. The pharmaceutical compounds according to at least some embodiments may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, a-tocopherol, and the like; and (3) metal chelating agents, such as citric acid, ethylenediamine tetraacetic acid (EDTA), sorbitol, tartaric acid, phosphoric acid, and the like. Examples of suitable aqueous and non-aqueous carriers that may be employed in the pharmaceutical compositions according to at least some embodiments include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from 0.01 percent to 99 percent of active ingredient, preferably from 0.1 percent to 70 percent, most preferably from 1 percent to 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody or VSIG3 or VISTA fusion proteins disclosed herein, the dosage ranges from 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody or VSIG3 or VISTA fusion proteins disclosed herein according to at least some embodiments include 1 mg/kg body weight or 3 mg/kg body weight via intravenous administration, with the antibody or VSIG3 or VISTA fusion proteins disclosed herein may be given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered sequentially or simultaneously, in which case the dosage of each antibody or VSIG3 or VISTA fusion proteins disclosed herein administered falls within the ranges indicated. Antibody or VSIG3 or VISTA fusion proteins disclosed herein is usually administered on multiple occasions. Intervals between single dosages can be, for example, daily, weekly, monthly, every three months or yearly. Intervals can also be irregular as indicated by measuring blood levels of antibody to the target antigen in the patient. In some methods, dosage is adjusted to achieve a plasma antibody concentration of 1-1000 µg/ml and in some methods 25-300 µg/ml.

Alternatively, therapeutic agent can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions may be varied to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

EXAMPLES

Example 1

Recombinant human VSIG3 Fc Chimera ("rhVSIG3"—encoded by SEQ ID NO:3; see Table 1) specifically binds to a recombinant human VISTA Fc Chimera ("rhVISTA"—encoded by SEQ ID NO:6; see Table 1) on a functional ELISA binding assay. rhVISTA was coated on the wells of a ELISA microtiter plate at 2 µg/ml in a 100 µL volume. Following blocking of the wells with 1% BSA, varying amounts of rhVSIG3 labeled with biotin was added. Biotin label associated with the plate due to the rhVSIG3—rhVISTA interaction was detected with streptavidin-HRP. As shown in FIG. 1A, when rhVISTA is immobilized on wells of a microtiter plate at 2 µg/mL in a 100 µL volume per well, the concentration of rhVSIG3 that produces 50% of the optimal binding response is approximately 0.25 µg/mL. The non-specific binding is subtracted and in all cases was less than 5% of the total signal.

Figure 1B:
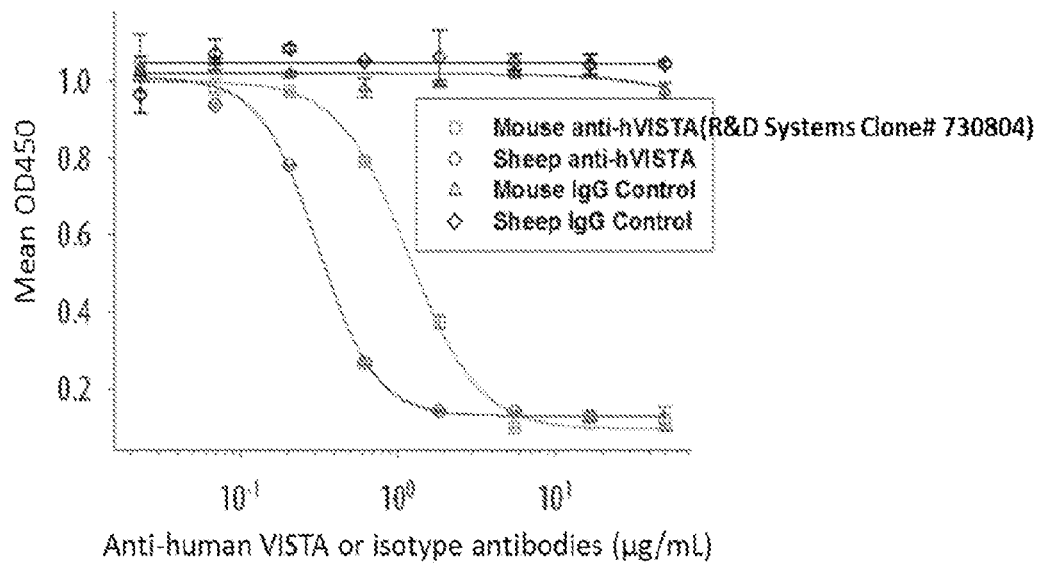
FIG. 1B shows that anti-VISTA antibodies (polyclonal Sheep anti-hVISTA and a monoclonal antibody (clone #730804)) can block the binding of VSIG3 and VISTA in an exemplary ELISA binding assay.

As shown in FIG. 1B shows, anti-VISTA antibodies can block the binding of VSIG3 and VISTA. The specificity of the interaction between rhVSIG3 and rhVISTA was confirmed by carrying out the ELISA assay in the presence of antibodies specific for VISTA. Two monoclonal and one polyclonal antibodies were tested. One of the monoclonal antibodies (clone #730804, Catalog No. MAB71261, R&D Systems, Minneapolis, Minn.) and a polyclonal antibody (Sh x hVISTA, Catalog No. AF7126, R&D Systems, Minneapolis, Minn.) blocked the interaction between rhVSIG3 and rhVISTA (FIG. 1B), indicating that the binding interaction shown in FIG. 1A is not non-specific.

Figure 1C:
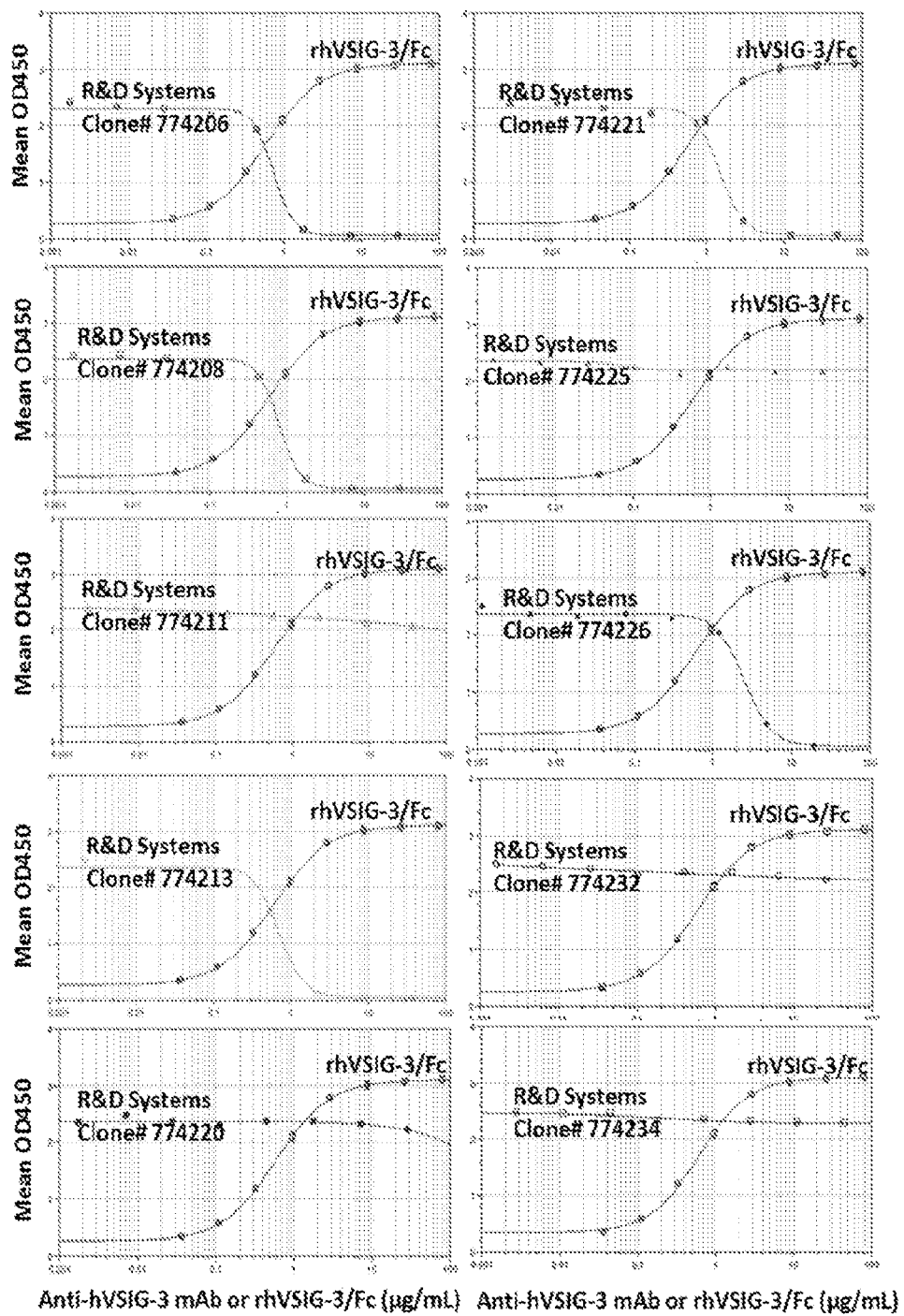
FIG. 1C shows anti-VSIG-3 antibodies block the interaction of VSIG3 and VISTA in a functional ELISA binding assay.
Figure 1D:
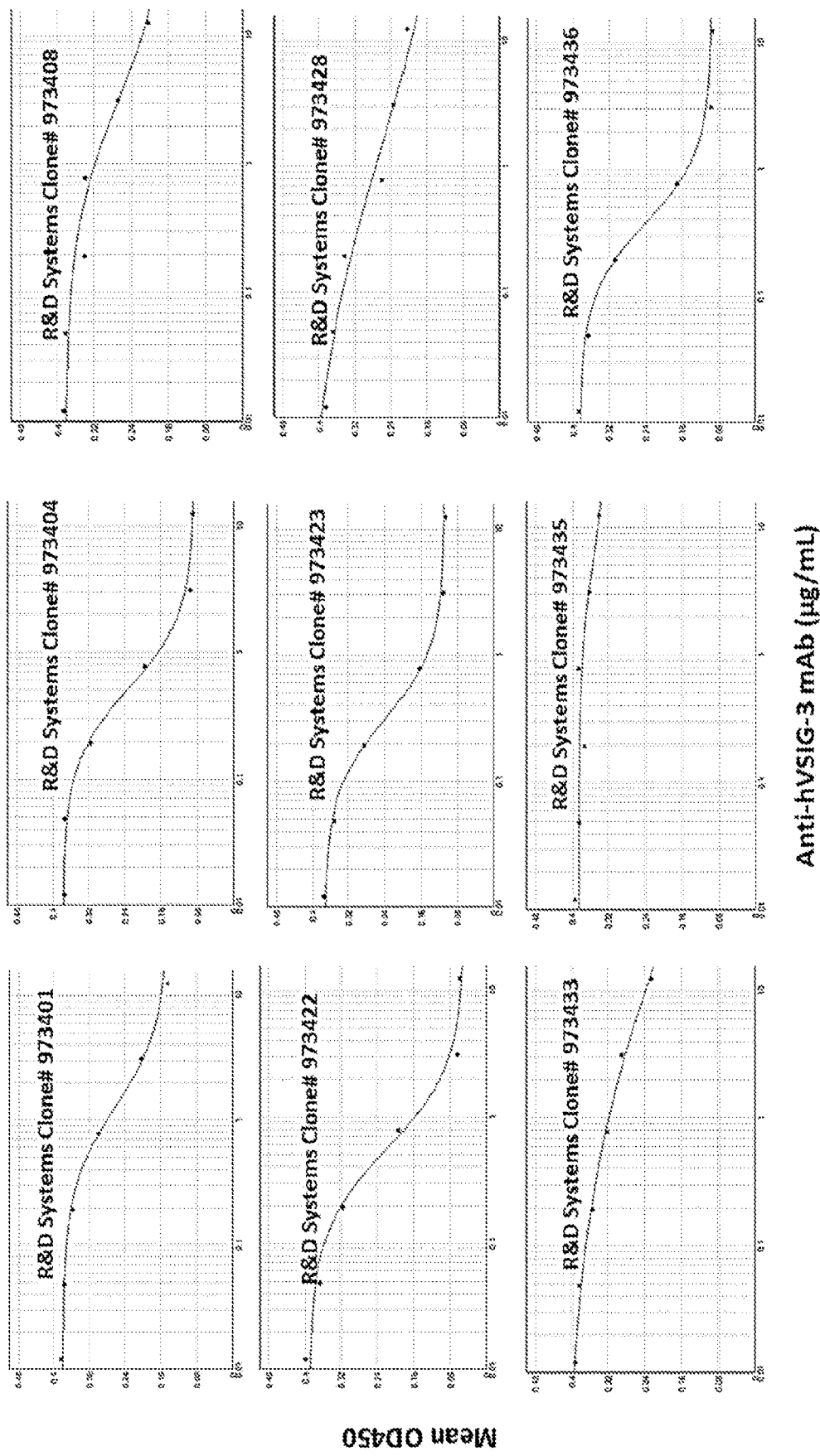
FIG. 1D shows anti-VSIG-3 antibodies block the interaction of VSIG3 and VISTA in a functional ELISA binding assay.

The specificity of the interaction between rhVSIG3 and rhVISTA was further confirmed by carrying out the functional ELISA binding assay in the presence of antibodies specific for human VSIG-3. rhVSIG-3 was coated on the wells of a ELISA microtiter plate at 2 µg/ml in a 100 µL volume. Following blocking of the wells with 1% BSA, varying amounts of mouse anti-human VSIG3 (MsxhVSIG-3) monoclonal antibodies (antibodies from clones #774206, #774208, #774211, #774213, #774220, #774221, #774225, #774226, #774232, and #774234 (FIG. 1C) or from clones #973401, #973404, #973408, #973422, #973423, #973428, #973433, #973435, and #973436 (FIG. 1D)) were added and incubated at room temperature for 1 hour. Then biotinylated rhVISTA 2 µg/ml in a 100 µL volume was added into each well. Biotin label associated with the plate due to the rhVSIG3— rhVISTA interaction was detected with streptavidin-HRP. As shown in FIG. 1C and FIG. 1D, five of the monoclonal antibodies from each panel (antibodies from clones #774206, #774208, #774213, #774221, and #774226 (FIG. 1C) or antibodies from clones #973401, #973404, #973422, #973423, and #973436 (FIG. 1D)) were observed to block the interaction between rhVSIG3 and rhVISTA, suggesting that VSIG-3-VISTA binding is a specific interaction.

Figure 2:
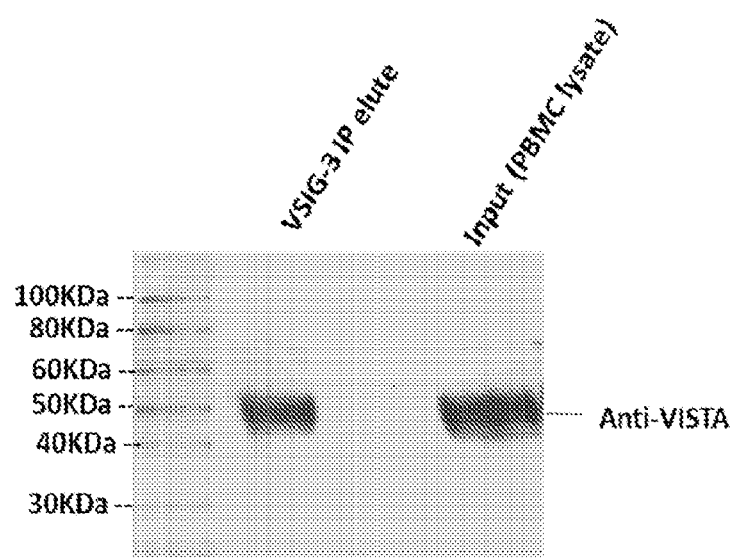
FIG. 2 shows VSIG3 immunoprecipitation of VISTA.

Further evidence of the specificity of VSIG3 and VISTA interaction on a biological level was provided by coimmunoprecipitation of VSIG-3 and VISTA in PBMCs (FIG. 2). Cytoplasmic extracts of PBMCs were prepared by lysis in ice cold Pierce IP Lysis Buffer (Thermo Fisher Scientific, Waltham, Mass.) with Halt proteinase inhibitor (Thermo Fisher Scientific, Waltham, Mass.) at $100 \times 10^6$ PBMC/100 µL buffer. Nuclei and insoluble cell debris were removed by centrifugation at 14,000 g for 10 min at 2-8° C. Immunoprecipitation was performed using DYNABEADS M-280 Streptavidin kit (Thermo Fisher Scientific, Waltham, Mass.) according to the manufacturer's instructions. Briefly, biotinylated VSIG-3 with a polyhistidine tag was incubated with DYNABEADS M-280 Streptavidin magnetic beads for 30 minutes at room temperature on a rotary mixer. After removing unbound proteins from the supernatant, the DYNABEADS-VSIG-3 protein complex was added into PBMC lysates and incubated at room temperature for 30 minutes. Next, the VSIG-3 protein-binding partner protein complex was collected by eluting the DYNABEADS M-280 Streptavidin magnetic beads with elution buffer. Co-immunoprecipitated proteins were subjected to 4-20% SDS-PAGE and transferred to a PVDF membrane (Millipore, Bilerica, Mass.). Immunoblotting was performed with anti-human VISTA or isotype control mAbs (R&D Systems, Minneapolis, Minn.). Proteins were visualized by enhanced chemiluminescence using HRP-conjugated goat anti-mouse IgG (R&D Systems, Minneapolis, Minn.) and Pierce ECL Western Blotting Substrate (Thermo Fisher Scientific, Waltham, Mass.). The results shown in FIG. 2 suggest that rhVSIG3 recognizes and interacts with membrane bound human VISTA.

Figure 3A:
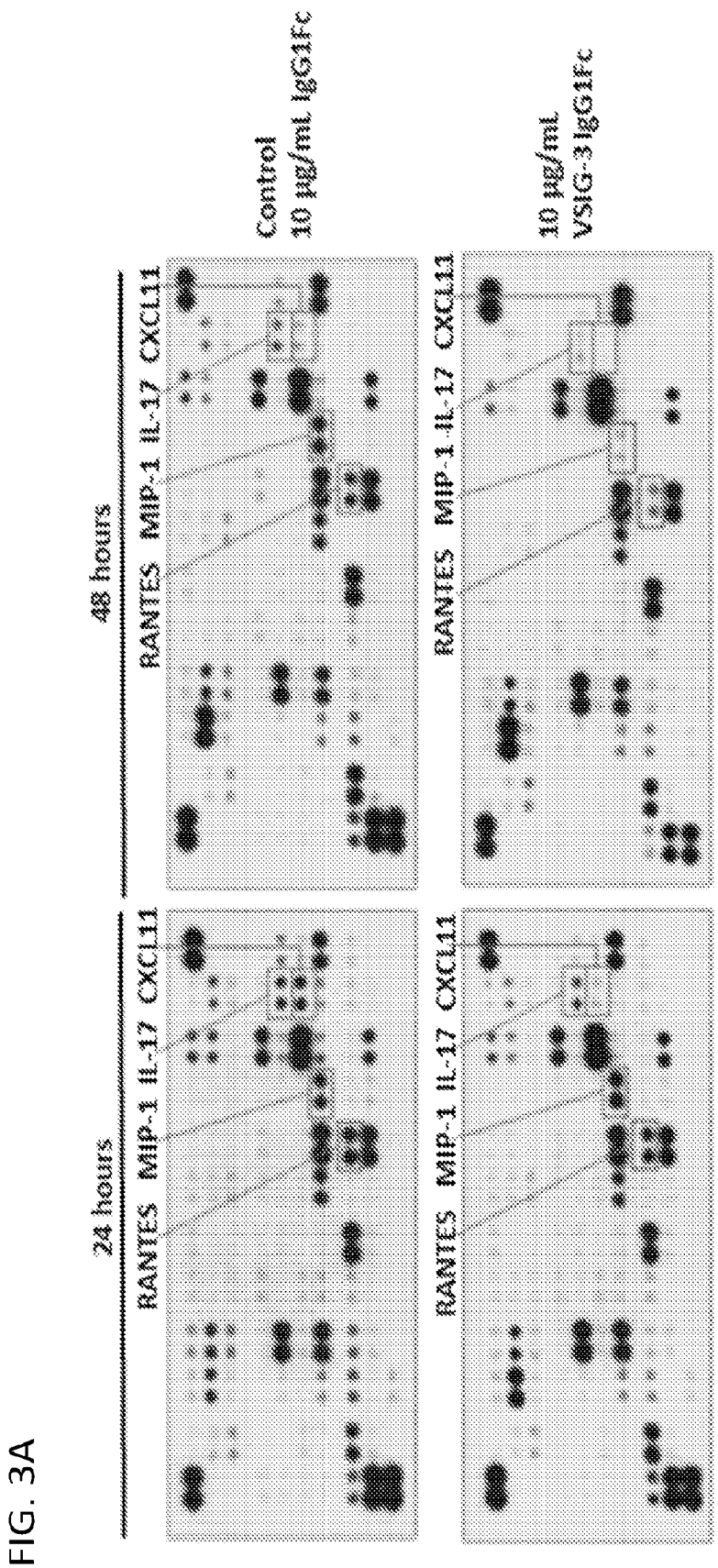
FIG. 3A shows cytokine levels measured using a PROTEOME PROFILER Human Cytokine Array Kit (R&D Systems, Minneapolis, Minn.).
Figure 3B:
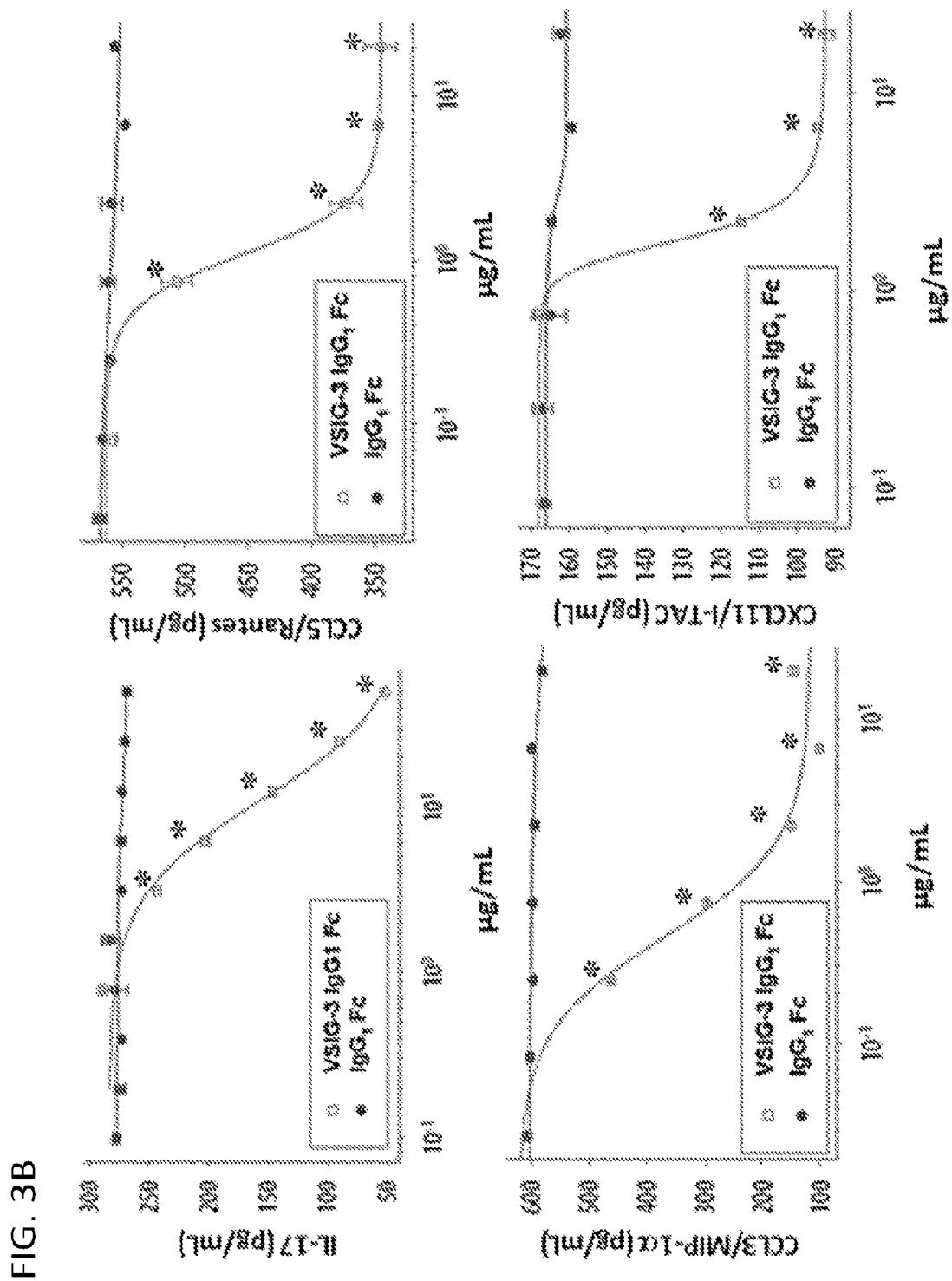
FIG. 3B shows cytokine levels measured using QUANTIKINE ELISA Kits (R&D Systems, Minneapolis, Minn.).

VISIG3 inhibits anti-CD3 induced RANTES, MIP-1 alpha, IL-17, and CXCL11 production on anti-CD3 activated human PBMCs in a dose-dependent manner (FIG. 3). To gain insight in the immune functions of VSIG3, the effects of rhVSIG3 on the cytokine secretion profile of PBMCs were investigated. Human PBMCs were treated with immobilized mouse anti-human CD3-epsilon monoclonal antibody (1 µg/mL) (R&D Systems, Minneapolis, Minn.) and either plate-bound rhVSIG3 (10 µg/mL) or a control (recombinant human Fc) (10 µg/mL) for 24 hours and 48 hours. Cytokine levels of the cell culture supernatants were measured using the Proteome Profiler™ Human Cytokine Array Kit (R&D Systems, Minneapolis, Minn.) (FIG. 3A). rhVSIG3 was observed to significantly decrease secretion of the T cell-derived cytokines Rantes, MIP-1 alpha, IL-17 and CXCL11. These results were confirmed by measuring individually the levels of Rantes, MIP-1 alpha, IL-17A and CXCL11 with QUANTIKINE ELISA Kits (R&D Systems, Minneapolis, Minn.) while varying the concentration of rhVSIG3 (FIG. 3B). rhVSIG3 inhibited secretion of Rantes and MIP-1 alpha from activated T cells in human PBMCs with an ED50 of 0.5 ug/mL, while its inhibitory effect on secretion of CXCL11 and IL-17 occurred at 2 ug/mL and 10 ug/mL, respectively. This inhibitory effect of rhVSIG3 is in a low nM concentration range, and is, therefore, expected to be physiologically significant.

The data presented in FIG. 1 and FIG. 2 provide evidence for the molecular association between VSIG3 and VISTA, and the data in FIG. 3 suggests that VSIG3 modulates the cytokine secretion profile of activated T cells.

Figure 4:
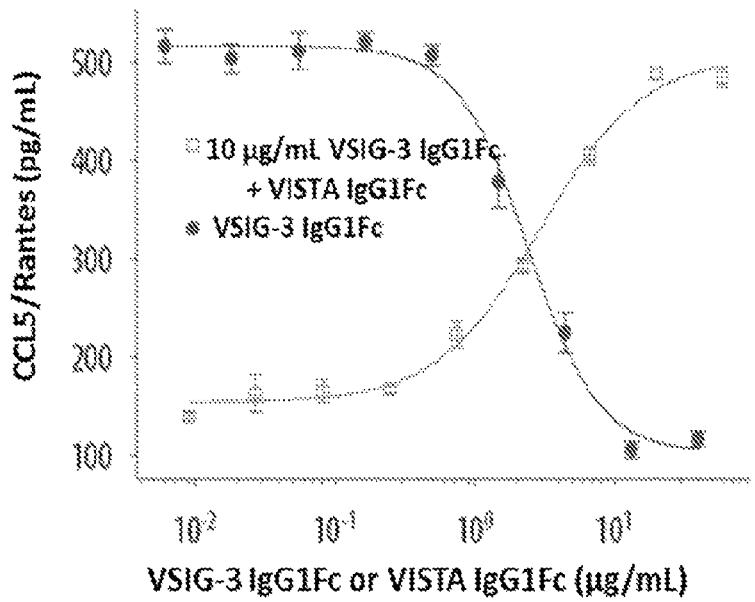
FIG. 4 shows that the soluble extracellular domain of VISTA protein attenuated the inhibitory effect of VSIG3 on anti-CD3-induced Rantes secretion in PBMCs.
Figure 5:
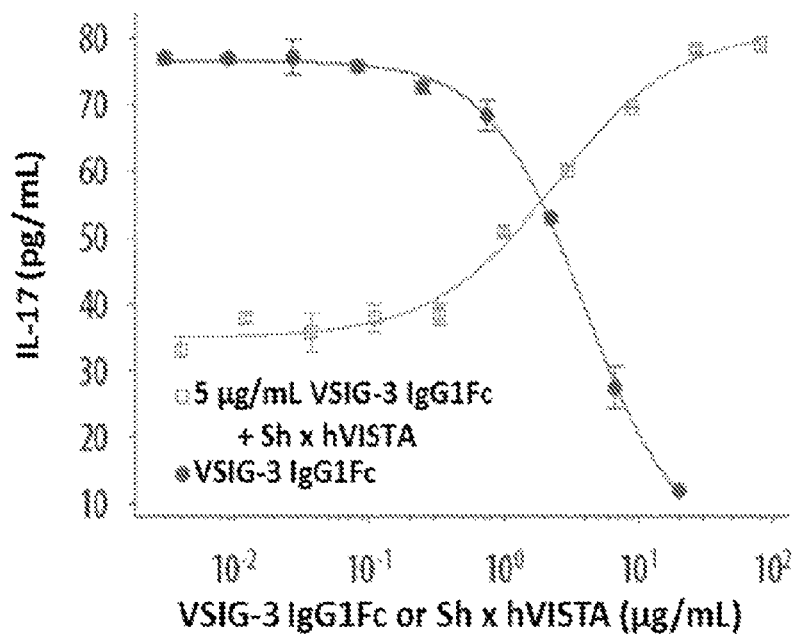
FIG. 5 shows that a polyclonal sheep anti-human VISTA antibody attenuated rhVSIG3-induced IL-17 inhibition of anti-CD3-activated PBMCs.

A VSIG-3/VISTA interaction can exhibit a co-inhibitory function, and VSIG3 can modulate T cell activation through VISTA. As shown in FIG. 4, the soluble extracellular domain of VISTA protein attenuated Rantes secretion inhibition induced by VSIG3 in T cells. Anti-human CD3 (1 μg/mL, R&D Systems, Minneapolis, Minn.) was pre-coated in the 96-well plates overnight at 2-8° C. rhVSIG3 (10 μg/mL) were immobilized for 3 hours at 37° C. in the wells. Immobilized rhVSIG3 (10 μg/mL) was treated with the indicated concentrations of rhVISTA for 1 hour at 37° C.; then PBMCs were added into the wells and cultured at 37° C. in 5% $CO_2$ for 24 hours. rhVISTA significantly attenuated the ability of VSIG3 to inhibit Rantes secretion from activated T cells. As shown in FIG. 5, a polyclonal sheep anti-human VISTA antibody (Sh x hVISTA, Catalog No. AF7126, R&D Systems, Minneapolis, Minn.) blocked VSIG3-induced IL-17 inhibition on anti-CD3 activated PBMCs. Anti-human CD3 (1 μg/mL, R&D Systems, Minneapolis, Minn.) was pre-coated in the 96-well plates overnight at 2° C.-8° C. rhVSIG3 (5 μg/mL) was immobilized for 3 hours at 37° C. in the wells. The concentrations of sheep anti-human VISTA antibodies indicated in FIG. 5 were added into the wells, then PBMCs were added into the wells and cultured at 37° C. in 5% $CO_2$ for 24 hours. rhVSIG3 significantly inhibited anti-CD3 induced IL-17 production in a dose dependent manner. Sheep anti human VISTA antibodies (Sh x hVISTA) attenuated the ability of VSIG3 to inhibit IL-17 secretion in activated T cells. Measured ND50 was approximately 1.5 μg/mL.

Figure 7:
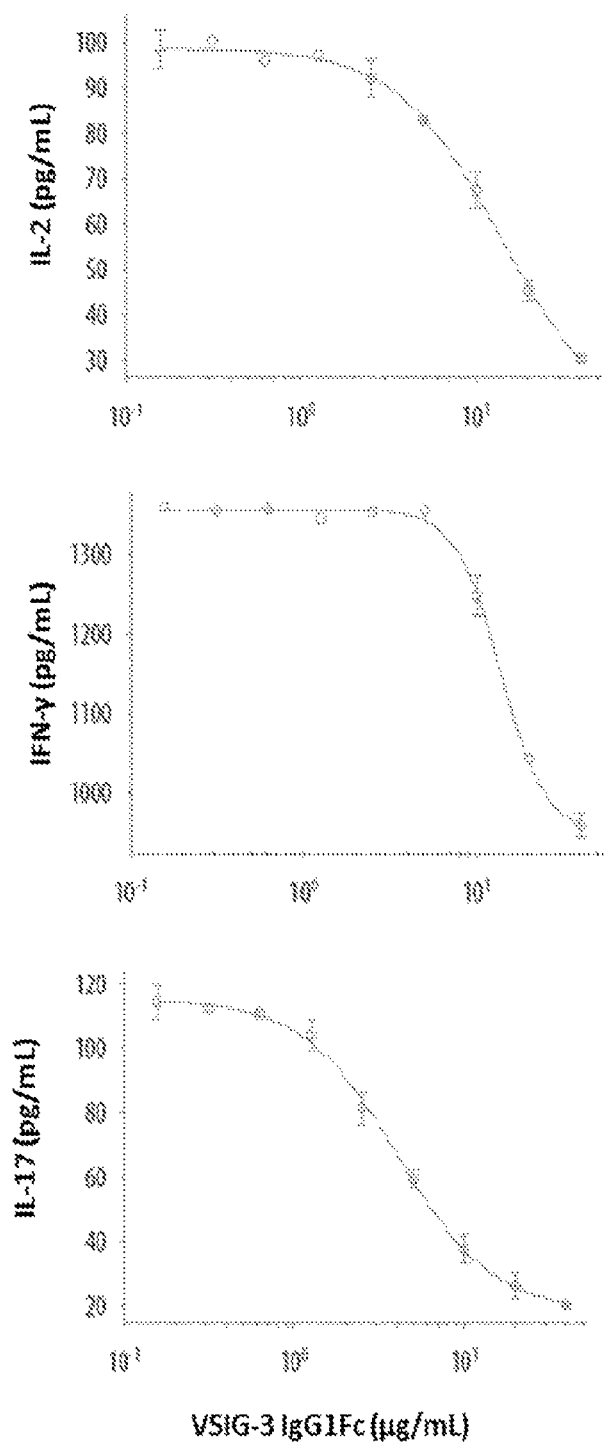
FIG. 7 shows that rhVSIG3 inhibits anti-CD3 induced IL-2, IFN-γ, and IL-17 production in human T cells in a dose dependent manner.

VSIG3 inhibits anti-CD3 induced IL-2, IFN-γ, and IL-17 production on human CD3+ T cells in a dose dependent manner (FIG. 7). Human CD3+ T cells were isolated from PBMCs using a MagCellect Human CD3+ T Cell Isolation Kit (R&D Systems, Minneapolis, Minn.). Then, human T cells were incubated with immobilized mouse anti-human CD3 epsilon monoclonal antibody (1 μg/mL, R&D Systems, Minneapolis, Minn.) and with the indicated concentrations of rhVSIG3 for 24 hours. IL-2, IFN-γ, and IL-17 secretion into the cell culture supernatant was measured using the human IL-2, IFN-γ, and IL-17 QUANTIKINE ELISA kits (R&D Systems, Minneapolis, Minn.).

Figure 8A:
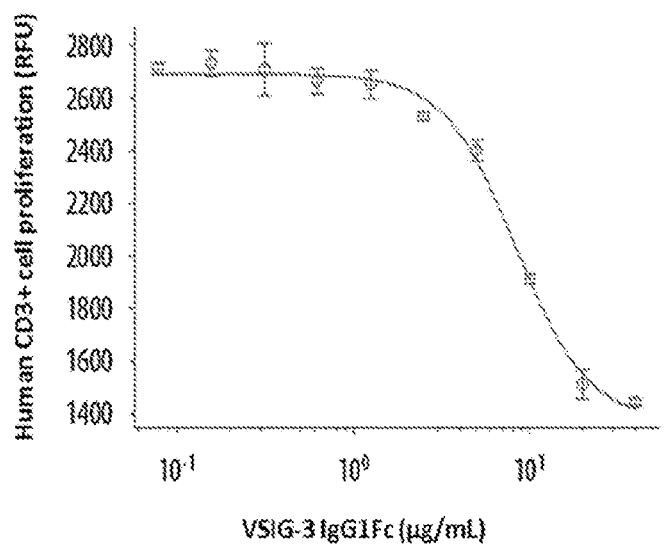
FIG. 8A. Human CD3+ T cells were incubated with immobilized mouse anti-human CD3 epsilon monoclonal antibody (1 μg/mL) and with the indicated concentrations of rhVSIG3 for 72 hours. Cell proliferation was assessed by a fluorometric assay using the redox-sensitive dye Alamar Blue (resazurin).
Figure 8B:
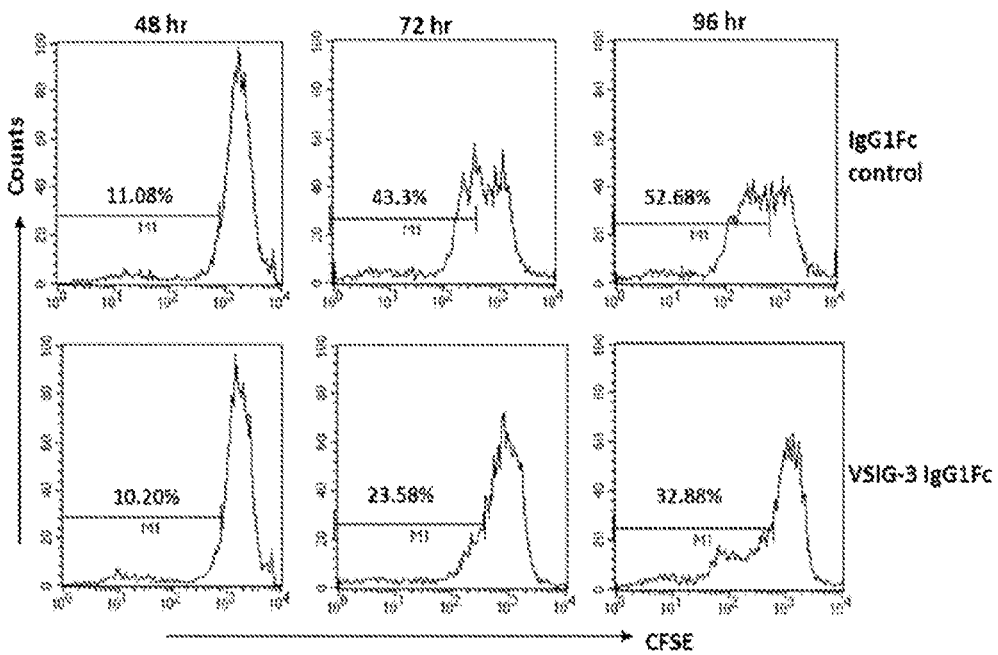
FIG. 8B. CSFE-labeled T cells were incubated with plate-bound anti-human CD3 (1 μg/mL) and rhVSIG3 (10 μg/mL) or control rhIgG1Fc for 48 hours, 72 hours, or 96 hours. Cell proliferation was determined by flow cytometry analysis.

VSIG3 inhibits anti-CD3 induced human CD3+ T cell proliferation (FIG. 8). Human CD3+ T cells were isolated from PBMCs using a MagCellect Human CD3+ T Cell Isolation Kit (R&D Systems, Minneapolis, Minn.), and T cells were incubated with immobilized mouse anti-human CD3 epsilon monoclonal antibody (1 μg/mL) and with the indicated concentrations of rhVSIG3 for 72 hours. Cell proliferation was assessed by a fluorometric assay using the redox-sensitive dye Alamar Blue (resazurin). As shown in FIG. 8A, VSIG3 inhibited anti-CD3 induced human CD3+ T cell proliferation in a dose dependent manner. T cell division was also monitored using a Carboxyfluorescein Diacetate Succinimidyl Ester (CFSE, Thermo Fisher Scientific, Waltham, Mass.)-labeled T cell proliferation assay. CSFE-labeled T cells were incubated with plate-bound anti-human CD3 (1 μg/mL) and rhVSIG-3 (10 μg/mL) or control rhIgG1Fc for 48 hours, 72 hours, or 96 hours and then stained with anti-human CD3 for flow cytometry analysis. Cell division was measured by flow cytometry (BD Bisciences) in CD3+ cells. CD3+ T cells proliferated strongly in the presence of plate-bound anti-CD3 and control rhIgG1Fc, with more than 40% (72 hours) or 50% (96 hours) of CD3+ T cells dividing. In contrast, T cells proliferated weakly in the presence of plate-bound anti-CD3 and rhVSIG-3, with less than 25% (72 hours) or 35% (96 hours) CD3+ T cells dividing (FIG. 8B). The results suggest that VSIG-3 acts as an inhibitory ligand, and can inhibit human T cell activation.

Figure 9A:
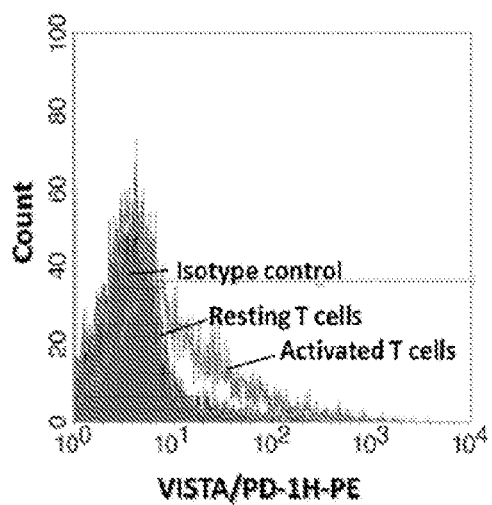
FIG. 9A. The CD3-activated or resting cells were stained with phycoerythrin (PE)-conjugated anti-human VISTA antibody or an isotype control antibody.
Figure 9B:
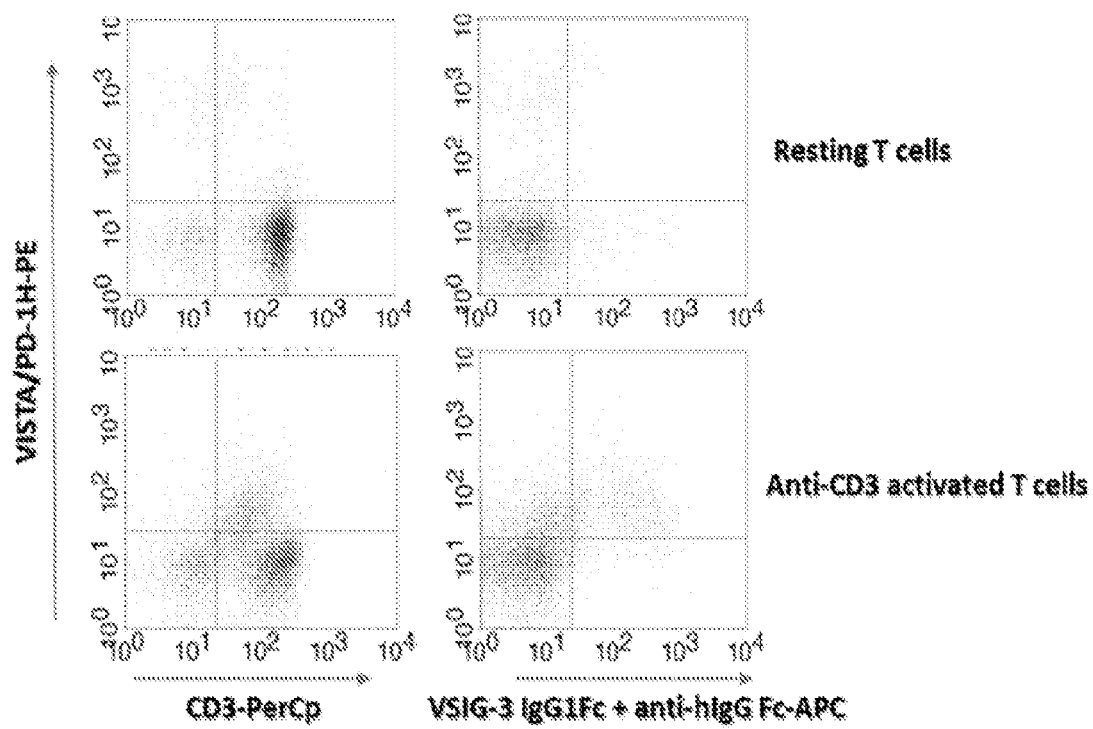
FIG. 9B. rhVSIG-3Fc protein was incubated with the resting or CD3-activated T cells, and rhVSIG-3 protein binding to T cells was detected using anti-human IgG1 Fc-APC antibody.

Activated T cells express VISTA, and VSIG-3 protein binds to anti-CD3 activated human T cells (FIG. 9). Human CD3+ T cells were isolated from PMBCs using a MagCellect Human CD3+ Isolation Kit (R&D Systems, Minneapolis, Minn.) and then incubated with immobilized mouse anti-human CD3 epsilon monoclonal antibody (1 μg/mL) or media only for 24 hours to provide activated or resting T cells, respectively. As shown in FIG. 9A, when the cells were stained with human VISTA PE-conjugated antibody or an isotype control antibody, VISTA expression was detected on anti-CD3 activated T cells, but not on resting T cells (FIG. 9A). As shown in FIG. 9B, when the cells were stained with human VISTA PE-conjugated and human CD3-PerCP conjugated antibodies, VISTA expression was detected on anti-CD3 activated T cells. When rhVSIG-3 protein was incubated with resting or anti-CD3 activated T cells, rhVSIG-3 binding to activated T cells but not resting T cells was detected using anti-human IgG1 Fc-APC antibody (FIG. 9B). Taken together, these results suggest that VISTA is only expressed on activated T cells and VSIG-3 protein binds to anti-CD3 activated human T cells.

Figure 11A:
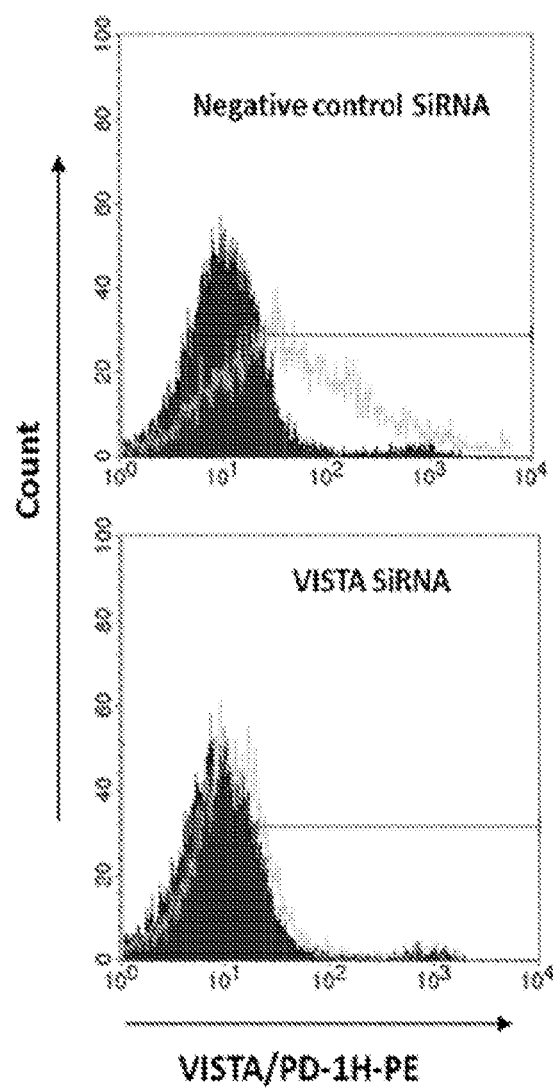
FIG. 11A. After 24 hours of treatment, VISTA expression was measured by anti-human VISTA staining and flow cytometry analysis. VISTA was expressed on negative control siRNA transfected T cells (gray line, upper panel) but not on VISTA siRNA transfected T cells (gray line, lower panel).
Figure 11B:
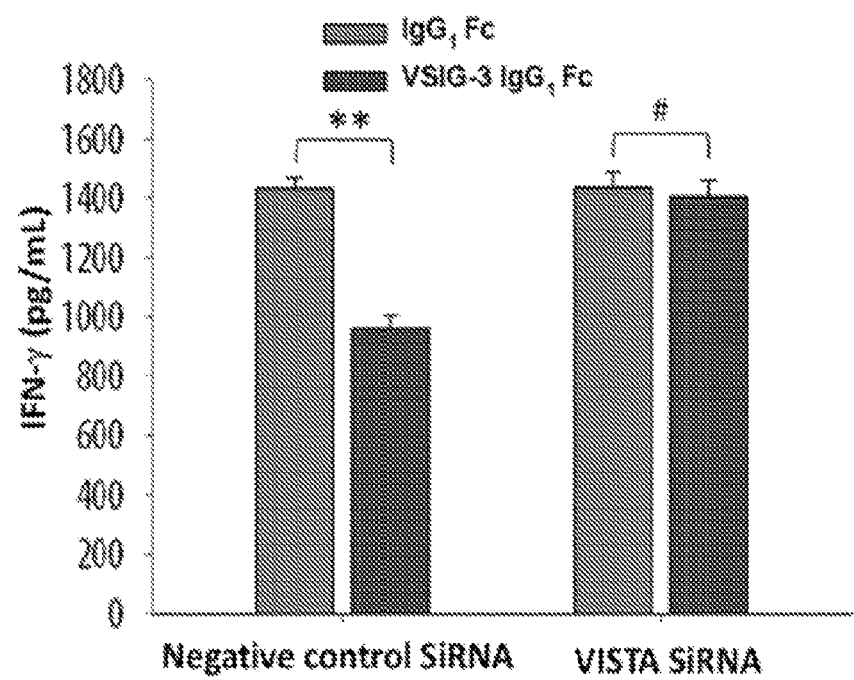
FIG. 11B. After 24 hours of treatment, cell free culture supernatants were collected to measure cytokine production. IFN-γ secretion was measured using a Quantikine ELISA kit. VSIG-3 significantly inhibited IFN-γ secretion on negative control siRNA-transfected T cells but not on VISTA siRNA-transfected T cells.

A VSIG-3/VISTA interaction can deliver a negative coinhibitory signal to T cells (FIG. 11). To further investigate whether a VSIG-3/VISTA interaction is involved in T cell activation, VISTA expression in T cells was knocked down using VISTA siRNA. Human CD3+ T cells were transfected with human VISTA siRNA (Catalog #4392420 Thermo Fisher Scientific Waltham, Mass.) or negative control siRNA (5 μg siRNA per $1×10^6$T cells, Thermo Fisher Scientific, Waltham, Mass.) using the Amaxa Lonza nucleofector system and NUCLEOFECTOR Kits for Human T Cells (Lonza, Inc., Allendale, N.J.). After nucleofection, T cells were transferred to media in a 24-well plate and cultured overnight. Nucleofected cells were used for the cytokine secretion assay. VISTA siRNA and negative control siRNA transfected T cells were treated with 1 μg/mL platebound anti-human CD3 and 10 μg/mL rhVSIG-3 or control rhIgG1Fc proteins. After 24 hours of treatment, cells were harvested for testing VISTA expression to verify VISTA siRNA transfection and cell free culture supernatants were collected to measure cytokine production. VISTA was expressed on negative control siRNA transfected T cells but not on VISTA siRNA transfected T cells. (FIG. 11A). The expression of VISTA on T cells correlated with the inhibitory effect of VSIG-3 on IFN-γ secretion from T cells, since VSIG-3 significantly inhibited IFN-γ secretion on negative control siRNA transfected T cells but not on VISTA siRNA transfected T cells (FIG. 11B). Silencing of VISTA expression on T cells abolished the VSIG-3 inhibitory effect, suggesting that VISTA may act as a receptor for VSIG-3 to deliver a negative signal to inhibit T cell activation VSIG3 is highly expressed in colon cancer (FIG. 6). VSIG-3 transcript levels were detected using RNAscope 2.0 HD red detection kit (Advanced Cell Diagnostics, Newark, Calif.). A custom-designed human VSIG-3 RNAscope probe was used to stain following RNAscope 2.0 HD red detection kit instruction. As shown in FIG. 6, no VSIG3 expression was seen in normal human colon tissue. However, VSIG3 was detected at high levels in human colon tumor adenocarcinoma tissue. These results suggest that VSIG3 expression may have a high prevalence in certain malignancies such as human gastric cancers, suggesting that the VSIG3/VISTA pathway may be applicable for gastric cancer immunotherapy, as well as for the development of novel therapeutic strategies to a wide range of human cancers.

In summary, as illustrated in an exemplary schematic model shown in FIG. 10, VSIG-3 is a novel ligand for VISTA, and that the engagement of VSIG-3 with VISTA on activated T cells can inhibit T cell proliferation and/or cytokine and chemokine production. The coinhibitory functions of VSIG-3 on activated T cells, combined with the highly elevated expression of VSIG-3 in colorectal cancers, hepatocellular carcinomas, and intestinal-type gastric cancers suggest that the blockage of the VSIG-3/VISTA pathway may provide a new cancer immunotherapeutic strategy.

The ectodomains of VSIG3, VISTA, and other immunoregulatory receptors were cloned into a construct containing the rat cartilage oligomeric matrix protein (COMP), which forms a covalent, pentameric coiled-coil helix oligomer (Malashkevich et al. Science. 274 (1996) 761-5), followed by an alkaline phosphatase enzyme for detection. To screen for pairwise interactions between the ectodomains, purified recombinant Fc-fusion proteins (i.e. bait proteins) were captured individually on protein A-coated plates (Thermo Fisher Scientific, Waltham, Mass.) and subsequently blocked with 1% BSA blocking buffer. Conditioned media containing the oligomeric prey protein fused to the COMP

TABLE 1

```
Full length sequence for      mtsqrsplap llllslhgva aslevsespg siqvargqpa vlpctfttsa alinlnviwm   60
human (homo sapiens)          vtplsnanqp eqvilyqggq mfdgaprfhg rvgftgtmpa tnvsifinnt qlsdtgtyqc  120
VSIG 3                        lvnnlpdigg rnigvtgltv lvppsaphcq iqgsqdigsd villcsseeg iprptylwek  180
(SEQ ID NO: 1)                ldntlklppt atqdqvqgtv tirnisalss glyqcvasna igtstclldl qvispqprni  240
                              gliagaigtg aviiifcial ilgaffywrs knkeeeeeei pneireddlp pkcssakafh  300
                              teisssdnnt ltssnaynsr ywsnnpkvhr ntesvshfsd lgqsfsfhsg nanipsiyan  360
                              gthlvpgqhk tlvvtanrgs spqvmsrsng svsrkprpph thsytishat lerigavpvm  420
                              vpaqsragsl v                                                       431

Extracellular domain          mtsqrsplap llllslhgva aslevsespg siqvargqta vlpctfttsa alinlnviwm   60
sequence listing for human    vtplsnanqp eqvilyqggq mfdgaprfhg rvgftgtmpa tnvsifinnt qlsdtgtyqc  120
(homo sapiens) VSIG3          lvnnlpdigg rnigvtgltv lvppsaphcq iqgsqdigsd villcsseeg iprptylwek  180
(SEQ ID NO: 2)                ldntlklppt atqdqvqgtv tirnisalss glyqcvasna igtstclldl qvispqprni  240
                              gliag                                                              245

Extracellular domain          levsespgsi qvargqtavl pctfttsaal inlnviwmvt plsnanqpeq vilyqggqmf   60
sequence for human            dgaprfhgrv gftgtmpatn vsifinntql sdtgtyqclv nnlpdiggrn igvtgltvlv  120
(homo sapiens) VISG3/FC       ppsaphcqiq gsqdigsdvi llcsseegip rptylwekld ntlklpptat qdqvqgtvti  180
fusion protein                rnisalssgl yqcvasnaig tstclldlqv ispqprnigl iagiegrmdp kscdkthtcp  240
(SEQ ID NO: 3)                pcpapeaega psvflfppkp kdtlmisrtp evtcvvvdvs hedpevkfnw yvdgvevhna  300
                              ktkpreeqyn styrvvsvlt vlhqdwlngk eykckvsnka lpapiektis kakgqprepq  360
                              vytlppsrde ltknqvsltc lvkgfypsdi avewesngqp ennykatppv ldsdgsffly  420
                              skltvdksrw qqgnvfscsv mhealhnhyt qkslslspgk                        460

Full length sequence for      mgvptaleag swrwgsllfa lflaaslgpv aafkvatpys lyvcpegqnv tltcrllgpv   60
human (homo                   dkghdvtfyk twyrssrgev qtcserrpir nltfqdlhlh hgghqaants hdlaqrhgle  120
sapiens) VISTA                sasdhhgnfs itmrnltlld sglycclvve irhhhsehrv hgamelqvqt gkdapsncvv  180
(SEQ ID NO: 4)                ypsssqdsen itaaalatga civgilclpl illlvykqrq aasnrraqel vrmdsniqgi  240
                              enpgfeaspp aqgipeakvr hplsyvaqrq psesgrhlls epstplsppg pgdvffpsld  300
                              pvpdspnfev i                                                       311

Extracellular domain          mgvptaleag swrwgsllfa lflaaslgpv aafkvatpys lyvcpegqnv tltcrllgpv   60
sequence for human            dkghdvtfyk twyrssrgev qtcserrpir nltfqdlhlh hgghqaants hdlaqrhgle  120
(homo sapiens) VISTA          sasdhhgnfs itmrnltlld sglycclvve irhhhsehrv hgamelqvqt gkdapsncvv  180
(SEQ ID NO: 5)                ypsssqesen itaaiegr                                                198

Extracellular domain          fkvatpysly vcpegqnvtl tcrllgpvdk ghdvtfyktw yrssrgevqt cserrpirnl   60
sequence for human            tfqdlhlhhg ghqaantshd laqrhglesa sdhhgnfsit mrnltlldsg lycclvveir  120
(homo sapiens) VISTA/         hhhsehrvhg amelqvqtgk dapsncvvyp sssqesenit aaiegrmdpk scdkthtcpp  180
IgG Fc fusion protein         cpapeaegap svflfppkpk dtlmisrtpe vtcvvvdvsh edpevkfnwy vdgvevhnak  240
(SEQ ID NO: 6)                tkpreeqyns tyrvvsvltv lhqdwlngke ykckvsnkal papiektisk akgqprepqv  300
                              ytlppsrdel tknqvsltcl vkgfypsdia vewesngqpe nnykatppvl dsdgsfflys  360
                              kltvdksrwq qgnvfscsvm healhnhytq kslslspgk                         399
```

Example 2

The interaction between VSIG3 and VISTA, as well as other known immunoregulatory receptor pairs was assessed using a modified version of the avidity-based extracellular interaction screen (AVEXIS) as previously described (Bushell et al., Genome Res. 18 (2008) 622-630. doi:10.1101/gr.7187808; Özkan et al. Cell. 154 (2013) 228-239. doi: 10.1016/j.cell.2013.06.006). AVEXIS is a high-throughput, high-sensitivity technique to detect low-affinity interactions by increasing the avidity. The increase in interaction avidity results in a ~250-fold higher sensitivity over monomeric interactions, enabling detection of low-affinity (e.g. micromolar) interactions such as CD200-CD200R (Bushell et al., Genome Res. 18 (2008) 622-630. doi:10.1101/gr.7187808)

helical oligomer and alkaline phosphatase was incubated and washed, and the interaction was quantitatively measured by detection of alkaline phosphatase activity using the BLUEPHOS reagent (KPL/Sera Care, Milford, Mass.). FIG. 12A provides a schematic of the interaction screen setup.

Figure 12B:
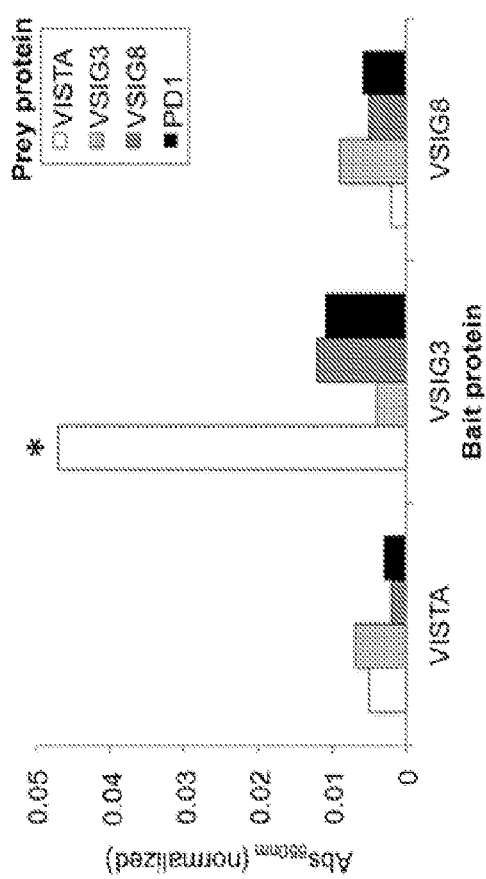
FIG. 12B AVEXIS was used to screen interactions between VISTA and VSIG3, VSIG8, and PD1, and results were quantified by measuring absorbance at 650 nm using the alkaline phosphatase reagent BluePhos. An interaction between VSIG3 and VISTA was observed when VSIG3 was used as bait and VISTA was used as prey (asterisk), but not vice versa. No other interactions were observed between VISTA, VSIG3, VSIG8, and PD1.
Figure 12A:
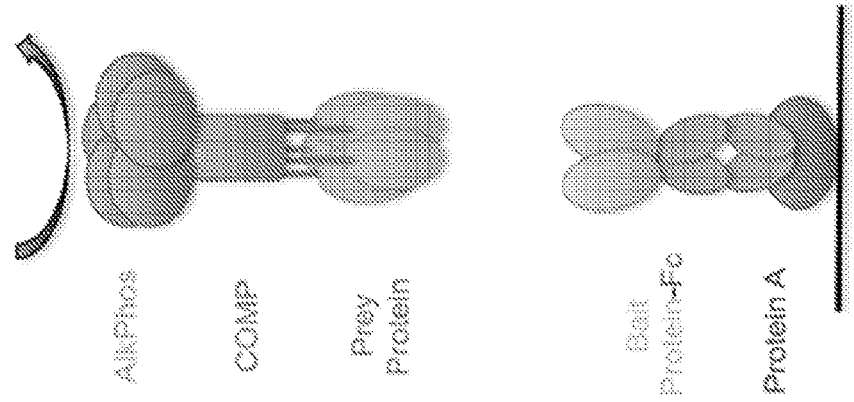
FIG. 12A shows a schematic of an exemplary avidity-based extracellular interaction screen (AVEXIS).
Figure 12C:
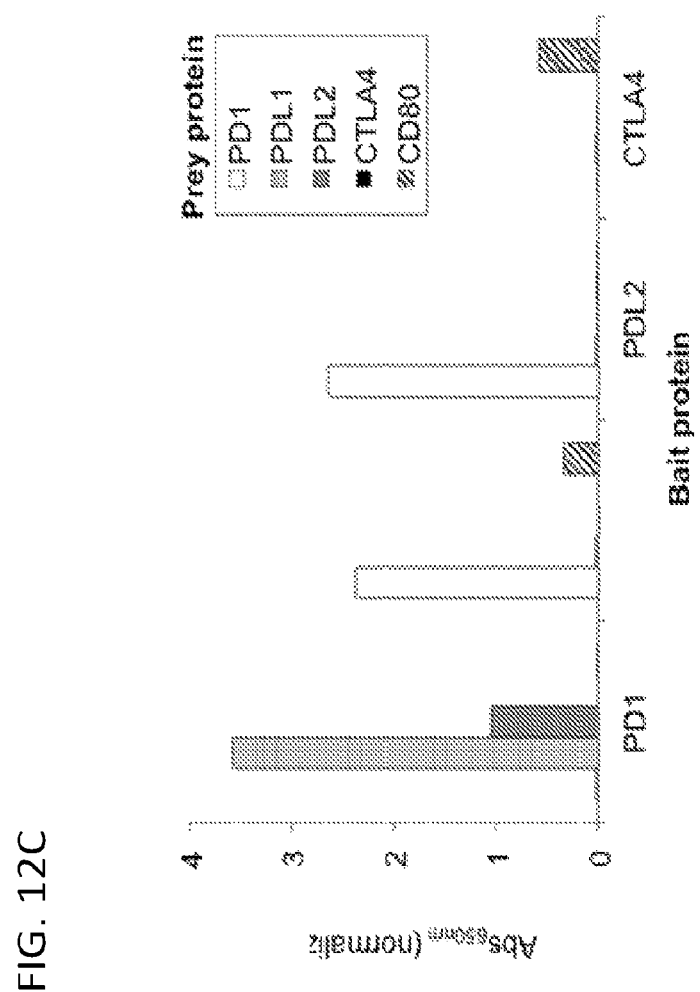
FIG. 12C. Positive control tests using PD1, PDL1, PDL2, CTLA4, and CD80 immunoregulatory receptors demonstrated only known interactions. Based on the magnitude of the absorbance at 650 nm, the observed VSIG3-VISTA interaction is of relatively weak affinity compared to the positive controls.

The pairwise interaction screen revealed a positive interaction above the background when VSIG3 is coated as bait and with VISTA as oligomeric prey (FIG. 12B, see asterisk). Interestingly, the reverse orientation of this interacting pair (VISTA as bait and VSIG3 oligomer as prey) showed no signal above the background; however, these results are not controlled for the variable expression of the prey protein in conditioned media from transiently expressing cells. VSIG8, previously reported to be the putative ligand for VISTA (US Patent Application No. 2016/0159927) showed no interaction with VISTA in either orientation. Additionally, interactions among other immunoregulatory receptors were tested and only known interactions were detected, for example PD1-PDL1, PD1-PDL2, CTLA40-CD80, and PDL1-CD80 (FIG. 12C). The magnitude of the signal in these previously characterized interaction pairs in comparison with the low signal in the VSIG3-VISTA interaction suggests that VISTA-VSIG3 interaction may be relatively weak.

Figure 13B:
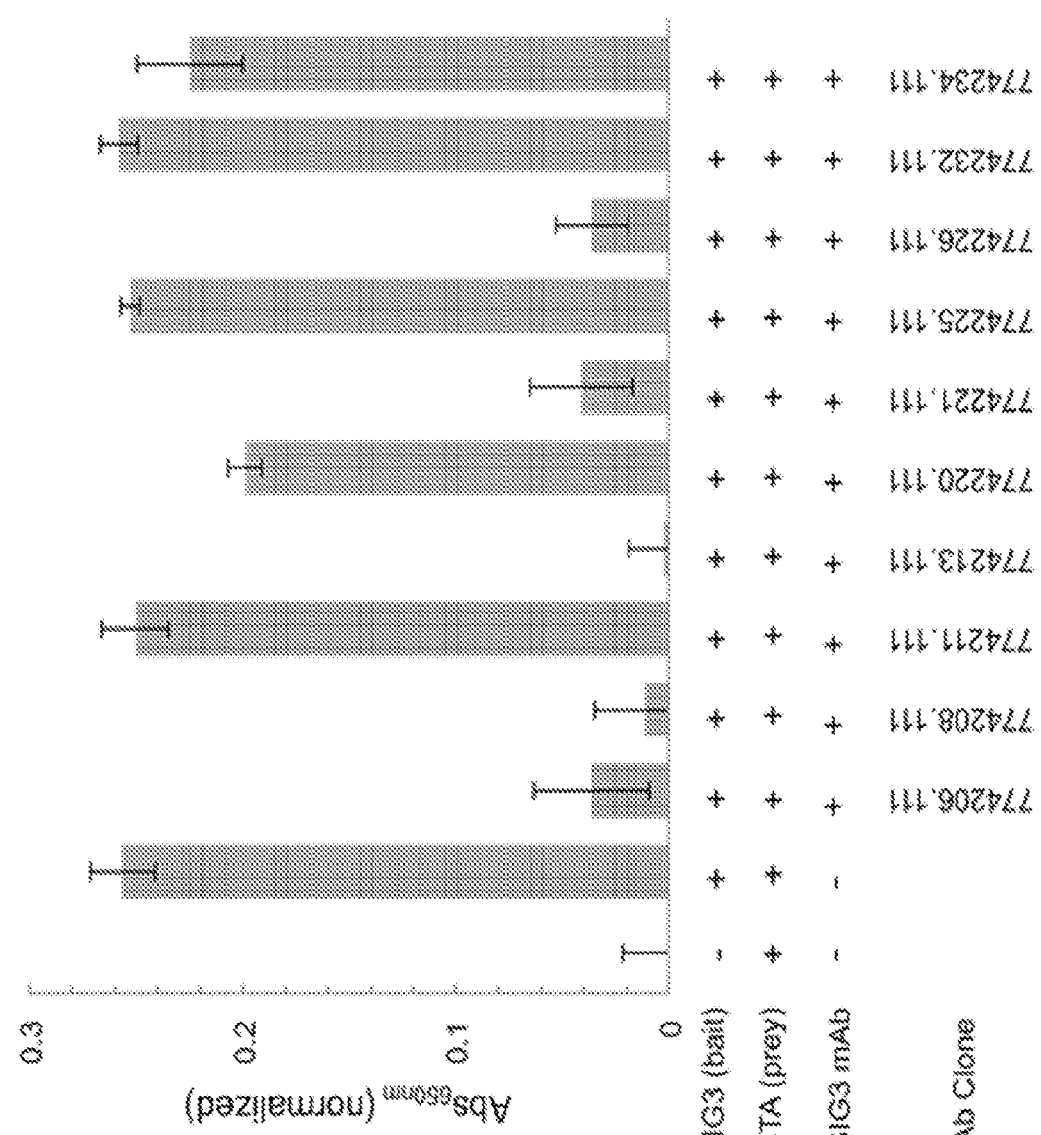
FIG. 13B. Alkaline phosphatase activity was measured by detecting absorbance at 650 nm using BluePhos reagent in the absence and presence of mAbs from a panel of anti-VSIG3 antibodies; each assay was performed in quadruplicate. Shown is the mean±standard deviation of four measurements. Five of the ten antibodies tested were found to block the VSIG3-VISTA interaction to near background levels.
Figure 13A:
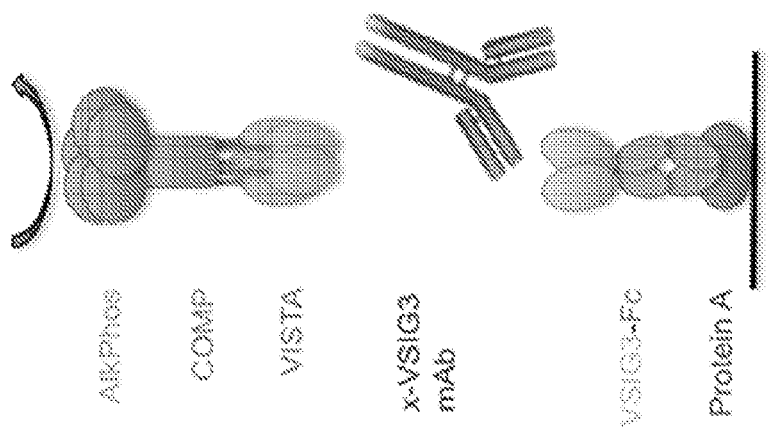
FIG. 13A shows a schematic of the modified AVEXIS screen to test for blocking antibodies. VSIG3-Fc was coated on Protein A plates, blocked, and incubated with individual mAbs from a panel of monoclonal antibodies against VSIG3. The VISTA ectodomain (ECD) coupled to a pentamerizing rat cartilage oligomeric matrix protein (COMP) helix and alkaline phosphatase was added, and the interaction between VSIG3 and VISTA was measured based on alkaline phosphatase activity.
Figure 14A:
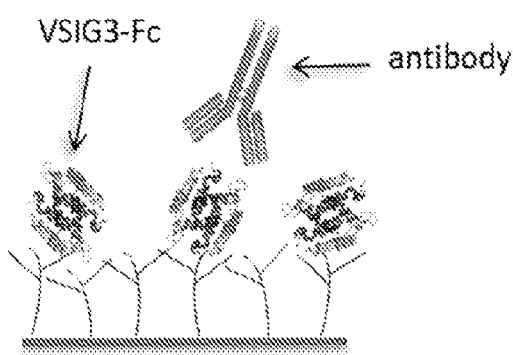
FIG. 14A shows a schematic of the BIACORE analysis. VSIG3-Fc was immobilized to the surface of a CM5 chip and the antibody was used as the analyte.
Figure 14B:
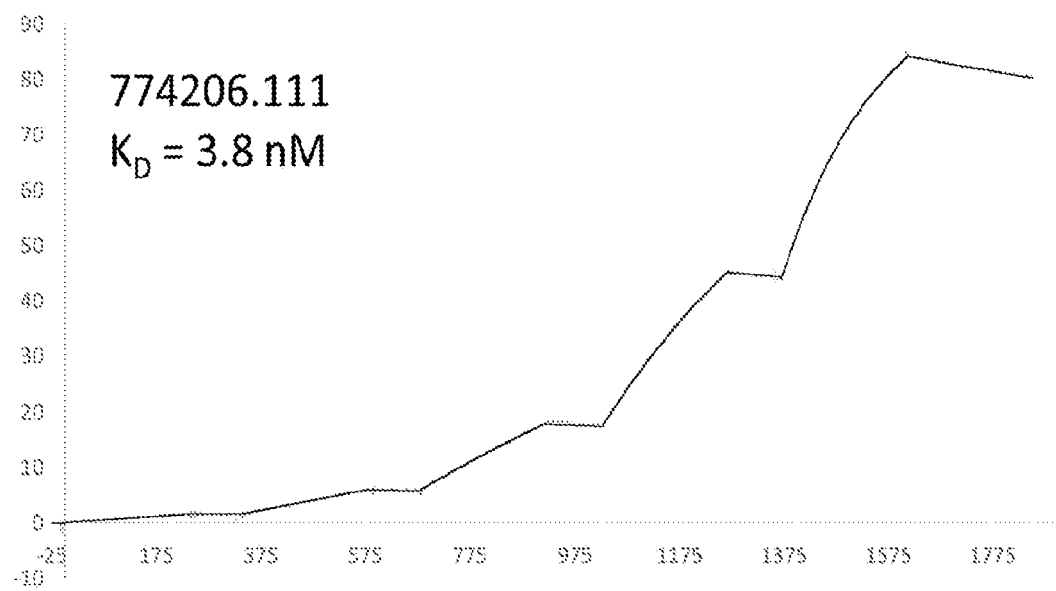
FIG. 14(A-F) shows the affinities of anti-human VSIG3 antibodies determined by an exemplary BIACORE analysis.
Figure 14C:
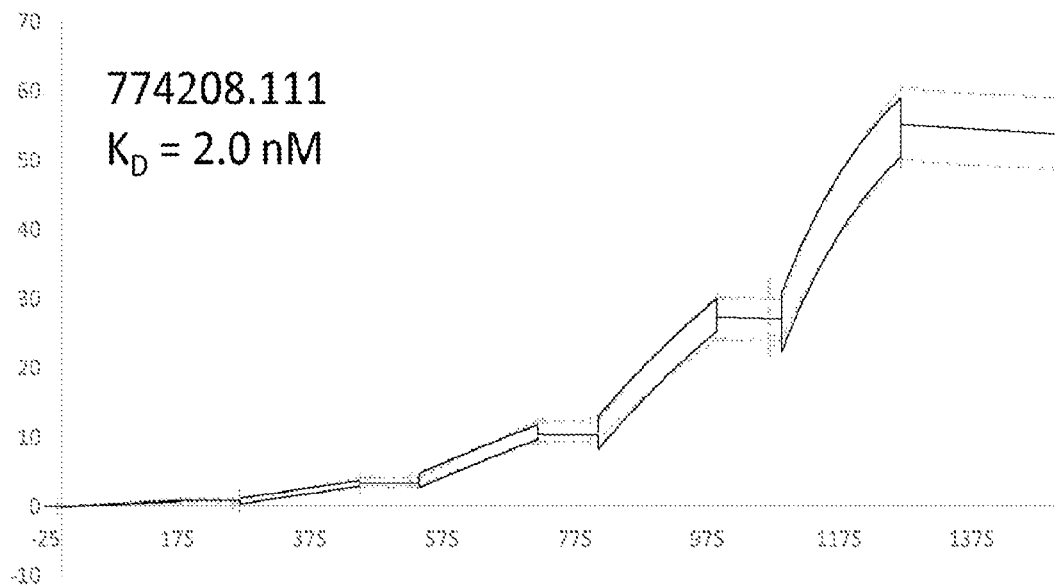
Figure 14D:
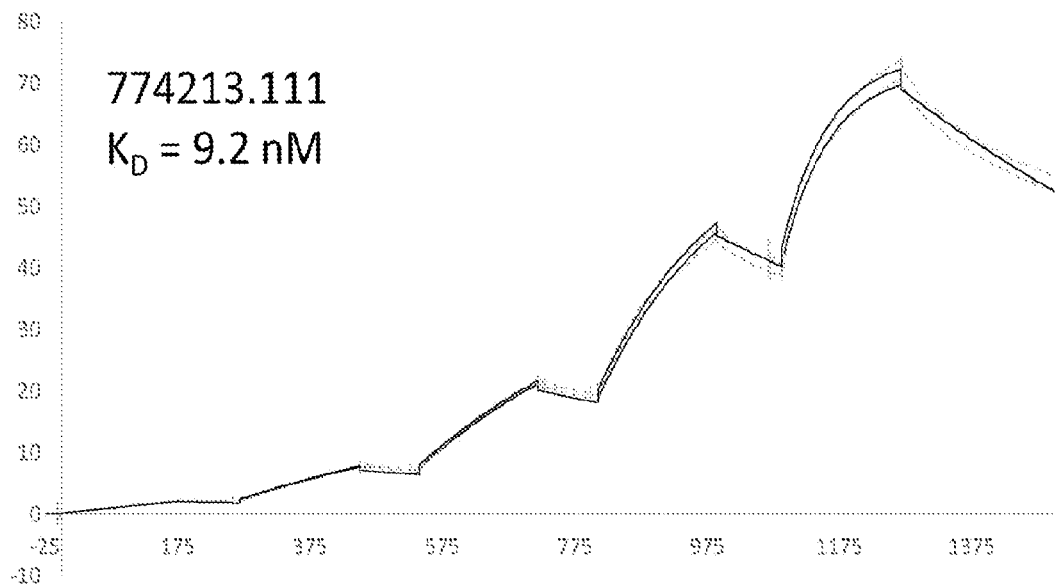
Figure 14E:
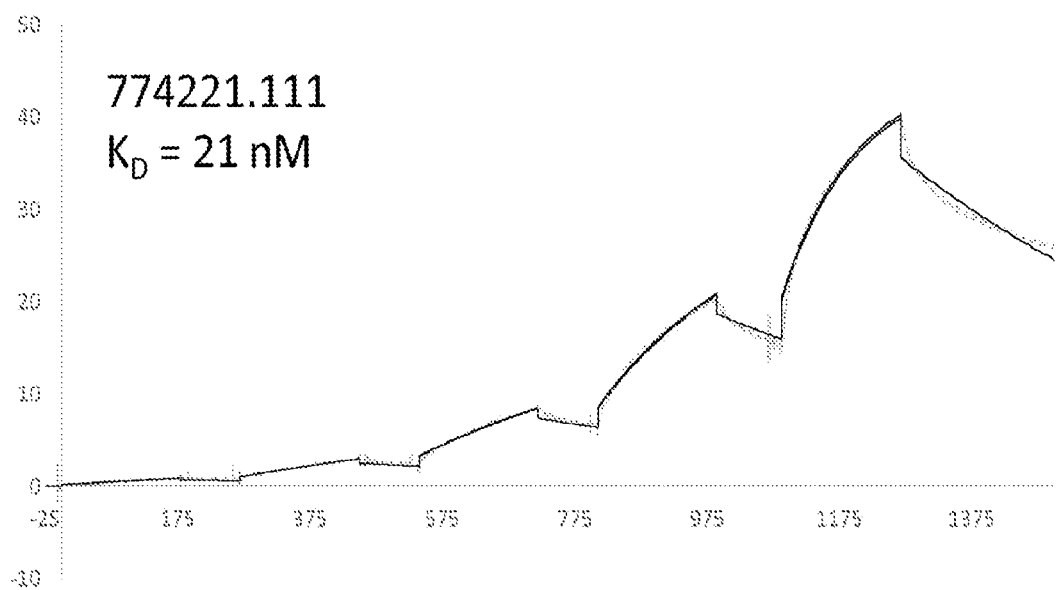
Figure 14F:
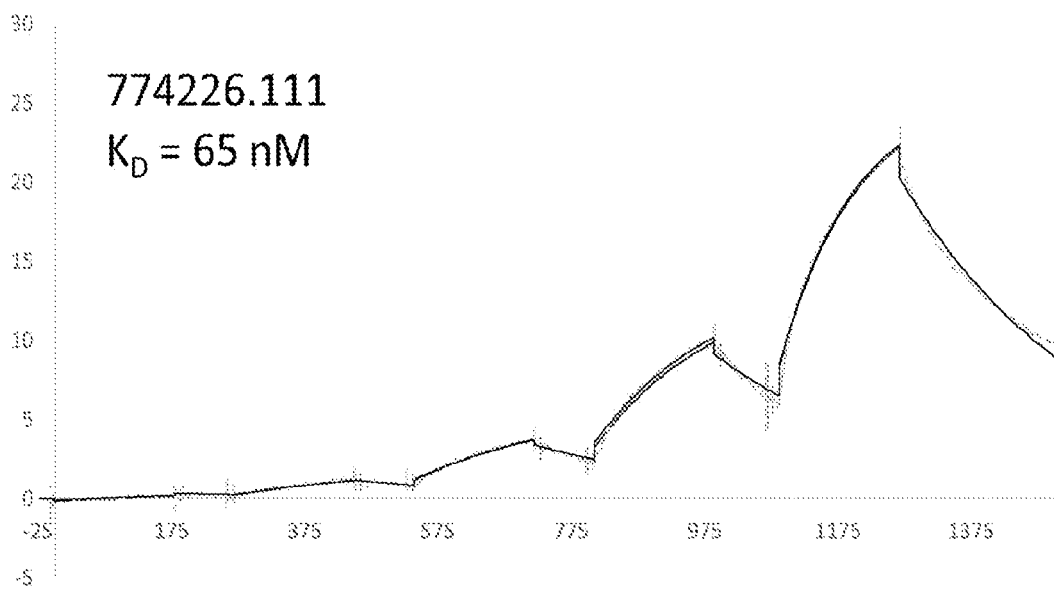
Figure 14G:
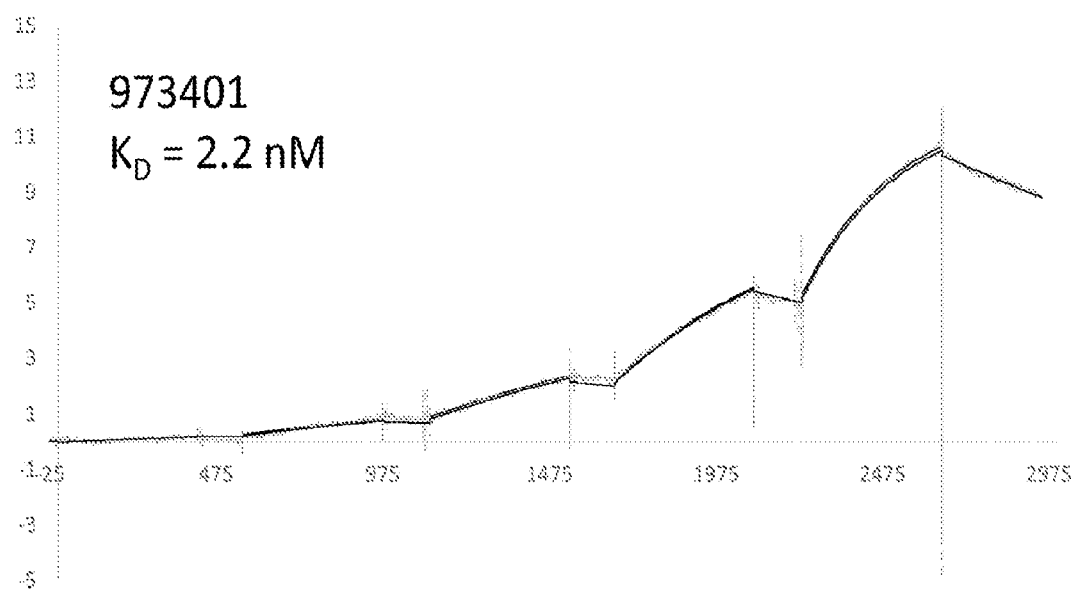
Figure 14H:
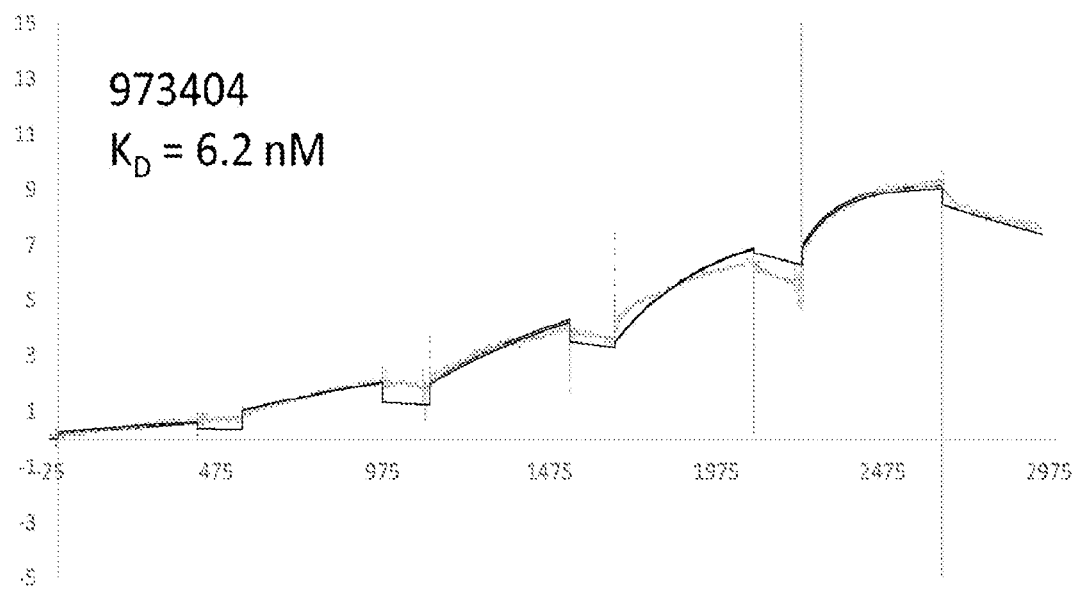
Figure 14I:
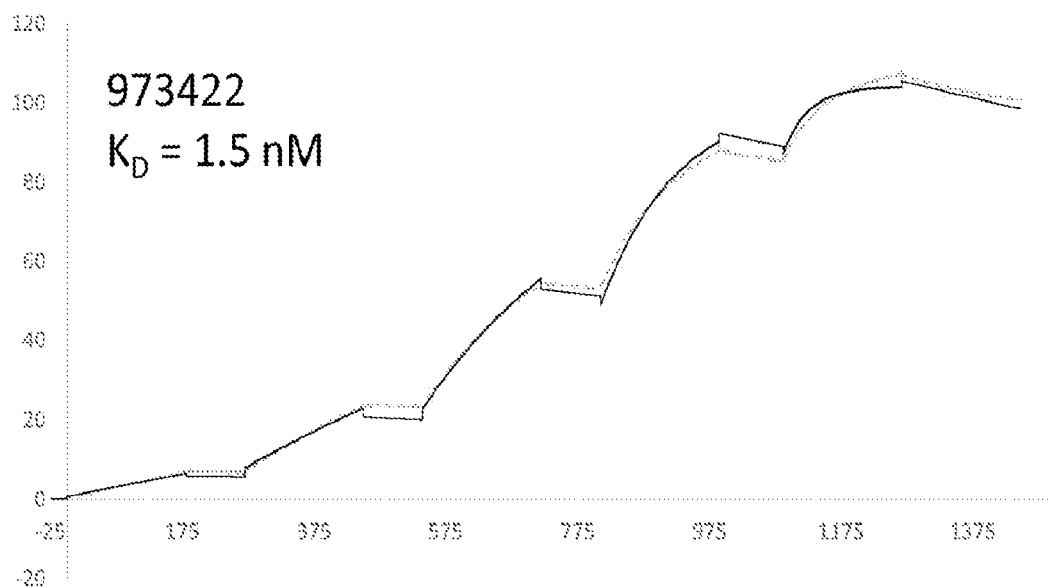
Figure 14J:
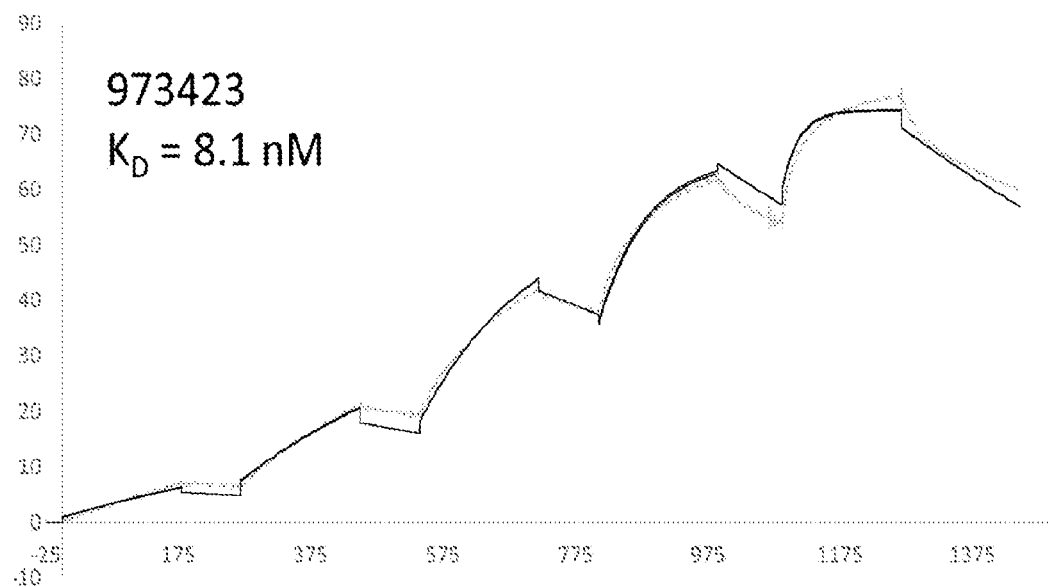
Figure 14K:
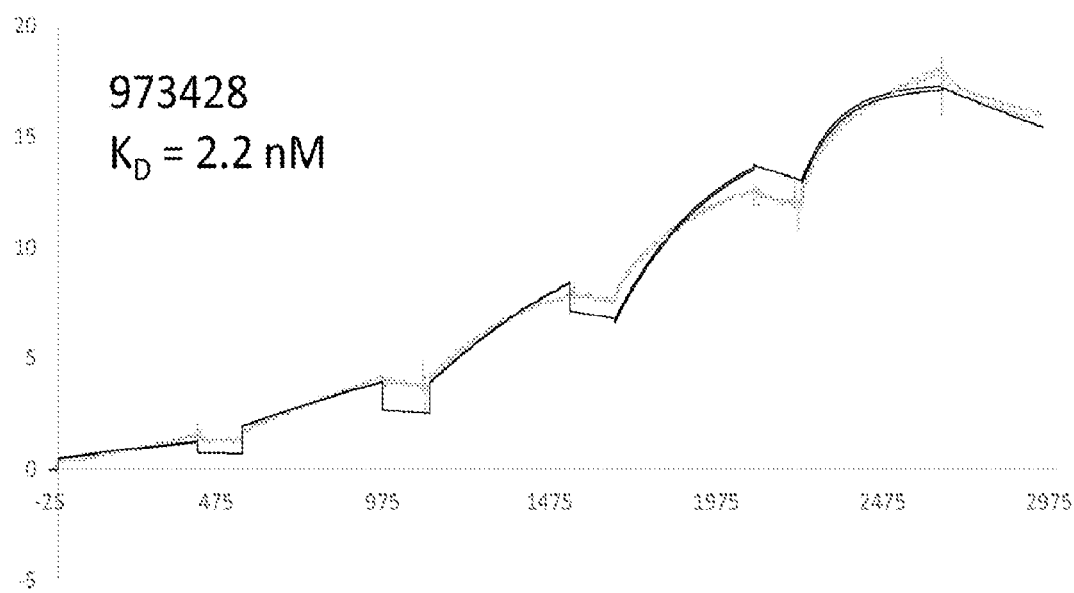
Figure 14L:
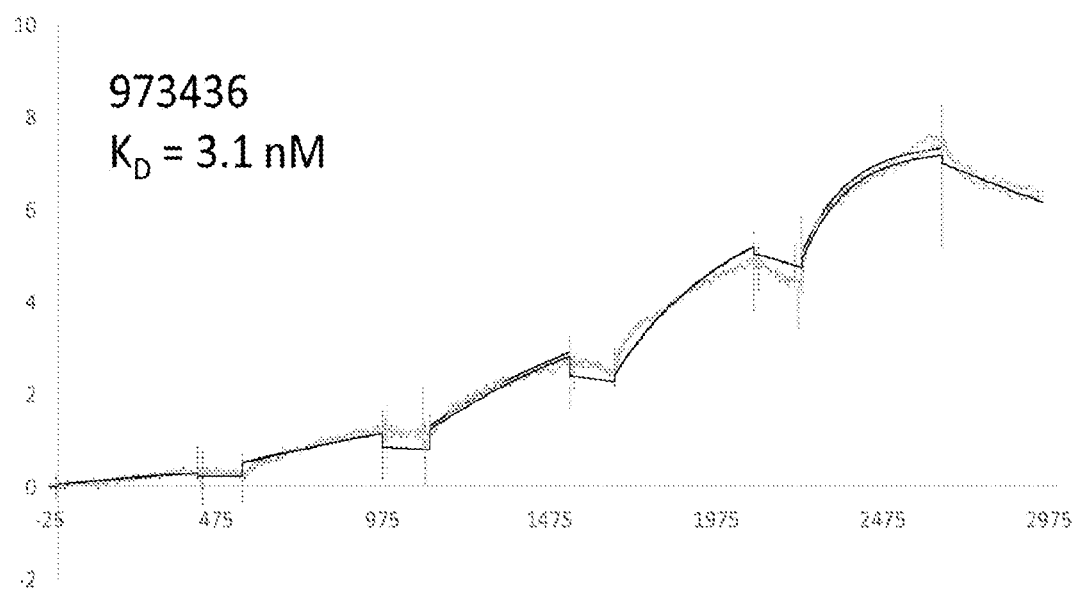
Figure 15A:
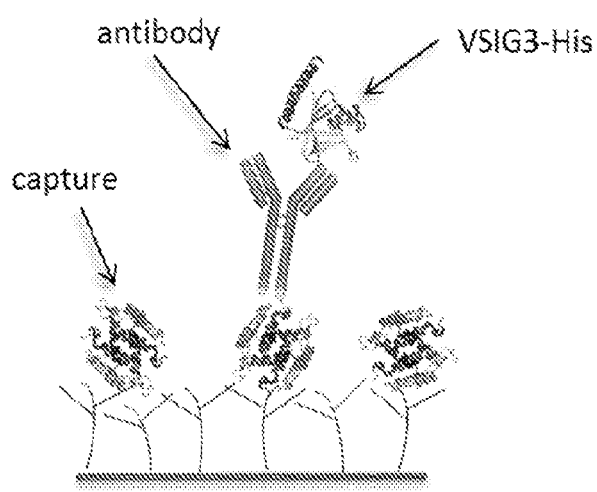
FIG. 15A shows a schematic of the BIACORE analysis. The antibody was captured to a surface containing immobilized protein A/G/L and VSIG3-His was used as the analyte.
Figure 15B:
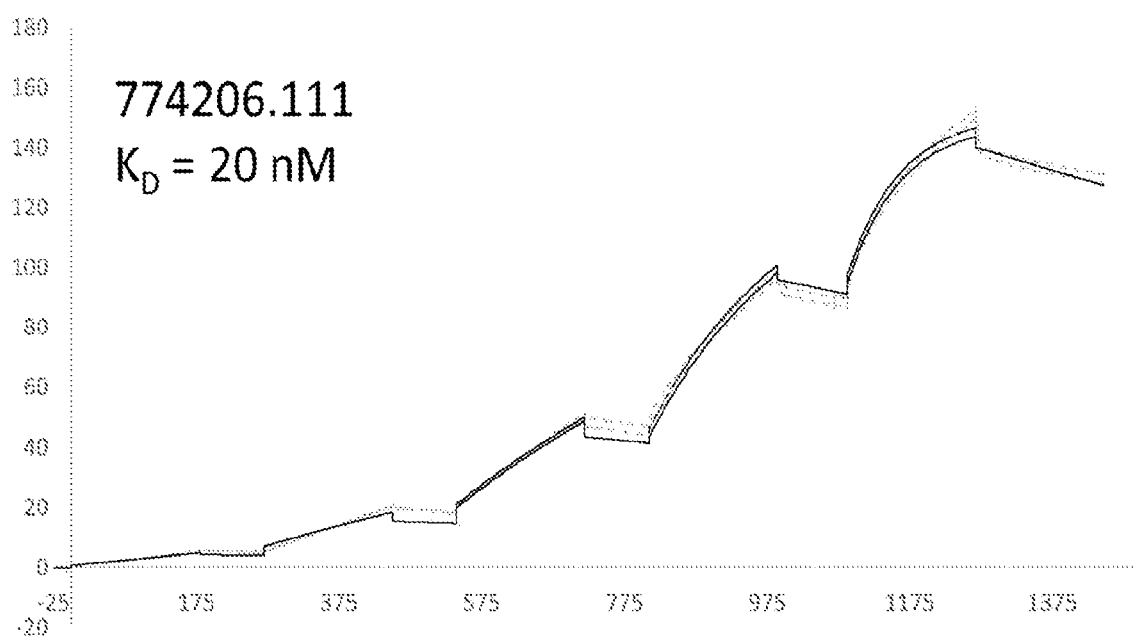
FIG. 15(A-F) shows the affinities of anti-human VSIG3 antibodies determined by BIACORE analysis.
Figure 15C:
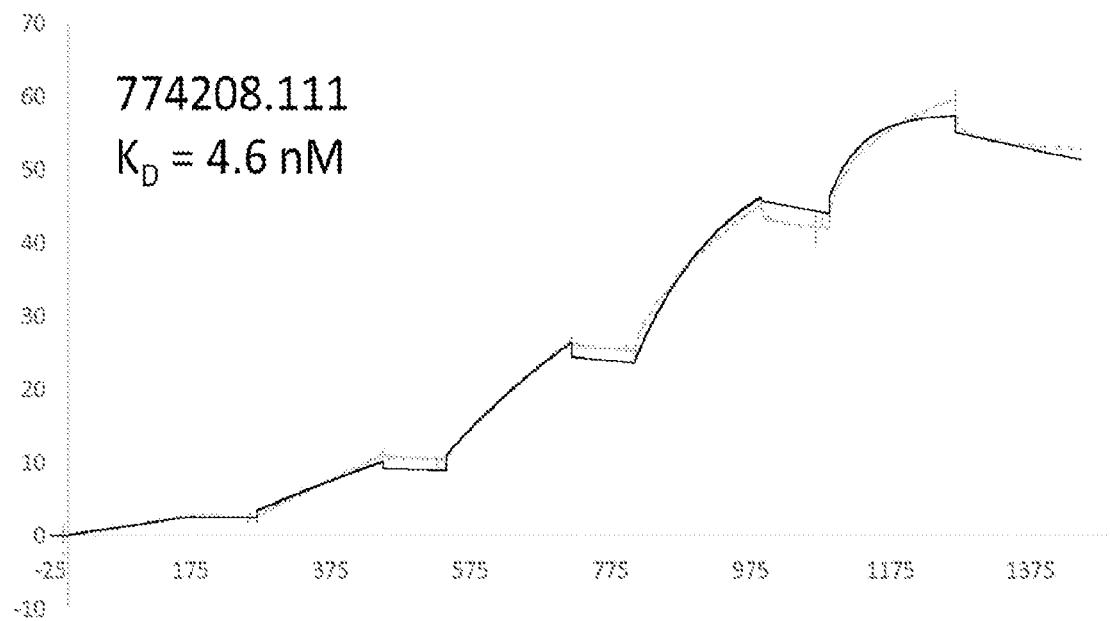
Figure 15D:
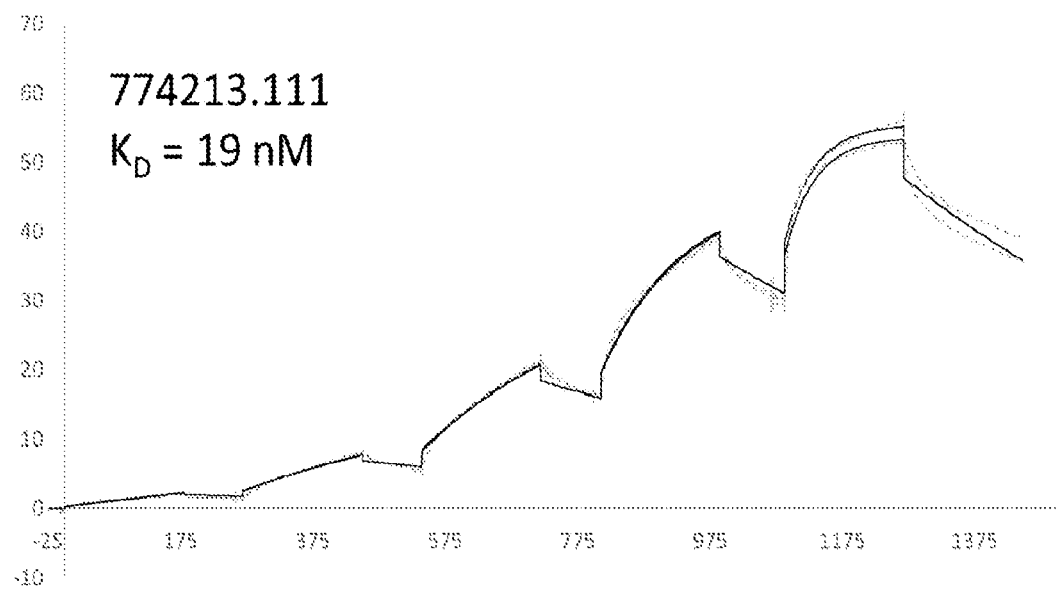
Figure 15E:
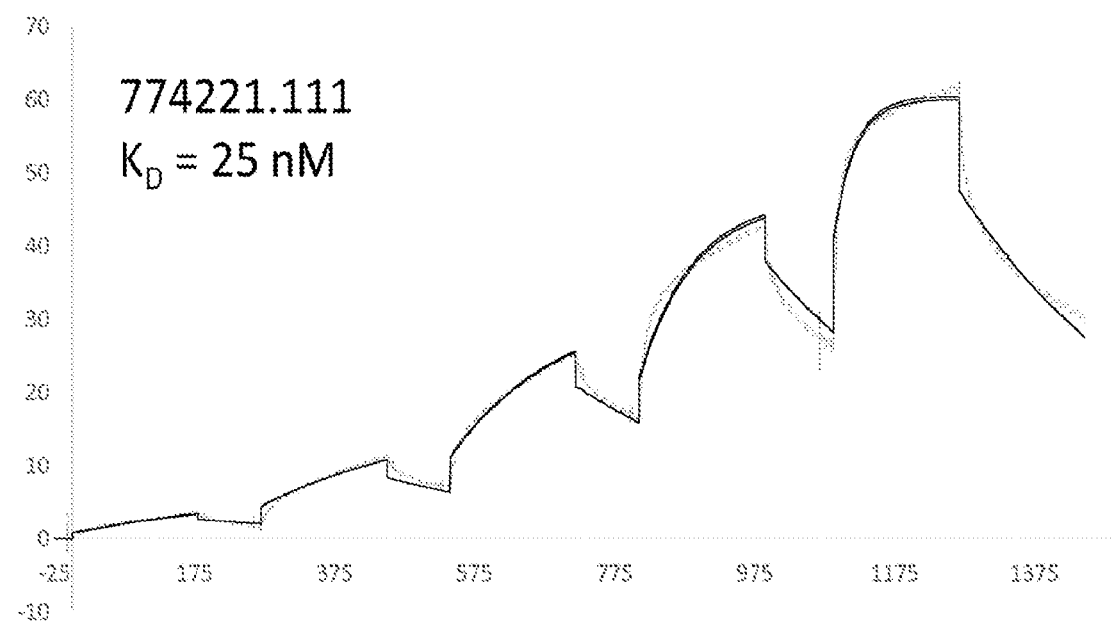
Figure 15F:
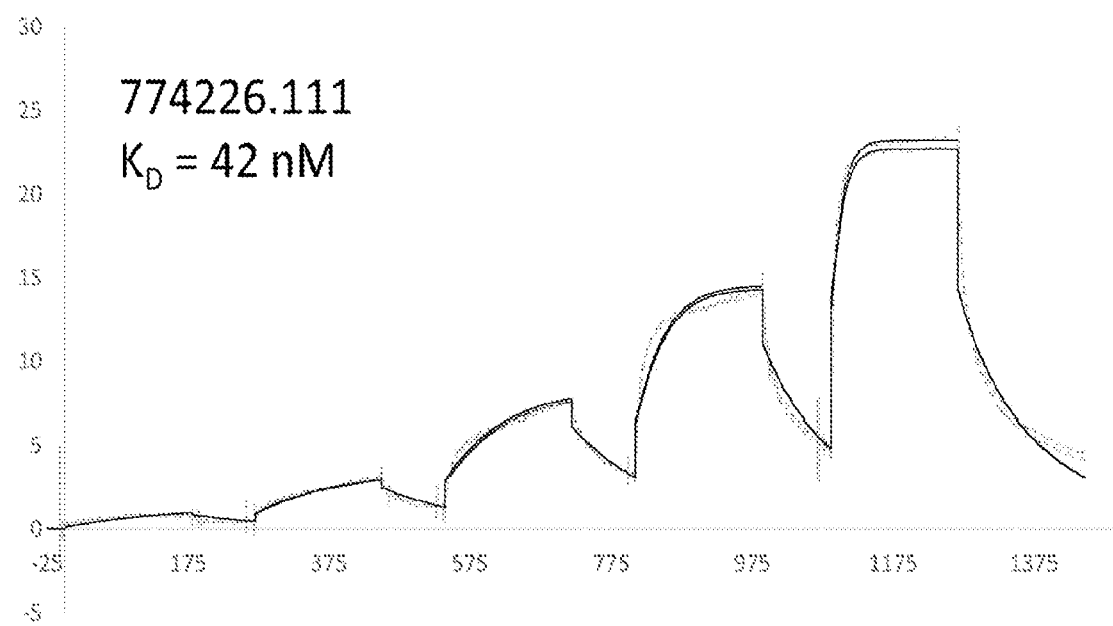

The AVEXIS interaction screen procedure was modified to determine the capacity for antibodies against VSIG3 to block the interaction between VSIG3 and VISTA. After capturing VSIG3-Fc bait on protein A coated plates, wells were incubated individually with each of ten monoclonal antibodies antibodies against VSIG3, and subsequently exposed to the VISTA oligomer (FIG. 13A). The interaction between VSIG3 and VISTA was performed as described above and was quantified using the alkaline phosphatase reagent. Results demonstrate that five of the ten antibodies within the panel block the VSIG3-VISTA interaction to near background levels (FIG. 13B).

The affinity of these blocking antibodies to purified recombinant VSIG3 was measured by surface plasmon resonance (SPR) using a Biacore T200 in two assay orientations. For the first assay design, VSIG3 Fc-fusion was covalently immobilized to the surface of a CM5 chip (GE Healthcare, US) by standard amine coupling chemistry. Dilutions of antibody were then flowed over the surface and the double reference subtracted data fit to a 1:1 Langmuir binding model with Biacore T200 Evaluation Software version 3.1 (FIG. 14). In a separate assay, a fusion protein containing protein A/G/L (Novus Biologicals, Littleton, Colo.) was covalently immobilized to the surface of a CM5 chip by standard amine coupling chemistry. Antibody was captured, followed by dilutions of VSIG3 His-fusion. Double reference subtracted data were fit to a 1:1 Langmuir binding model as described above (FIG. 15).

Example 3

Figures 16A, 16B:
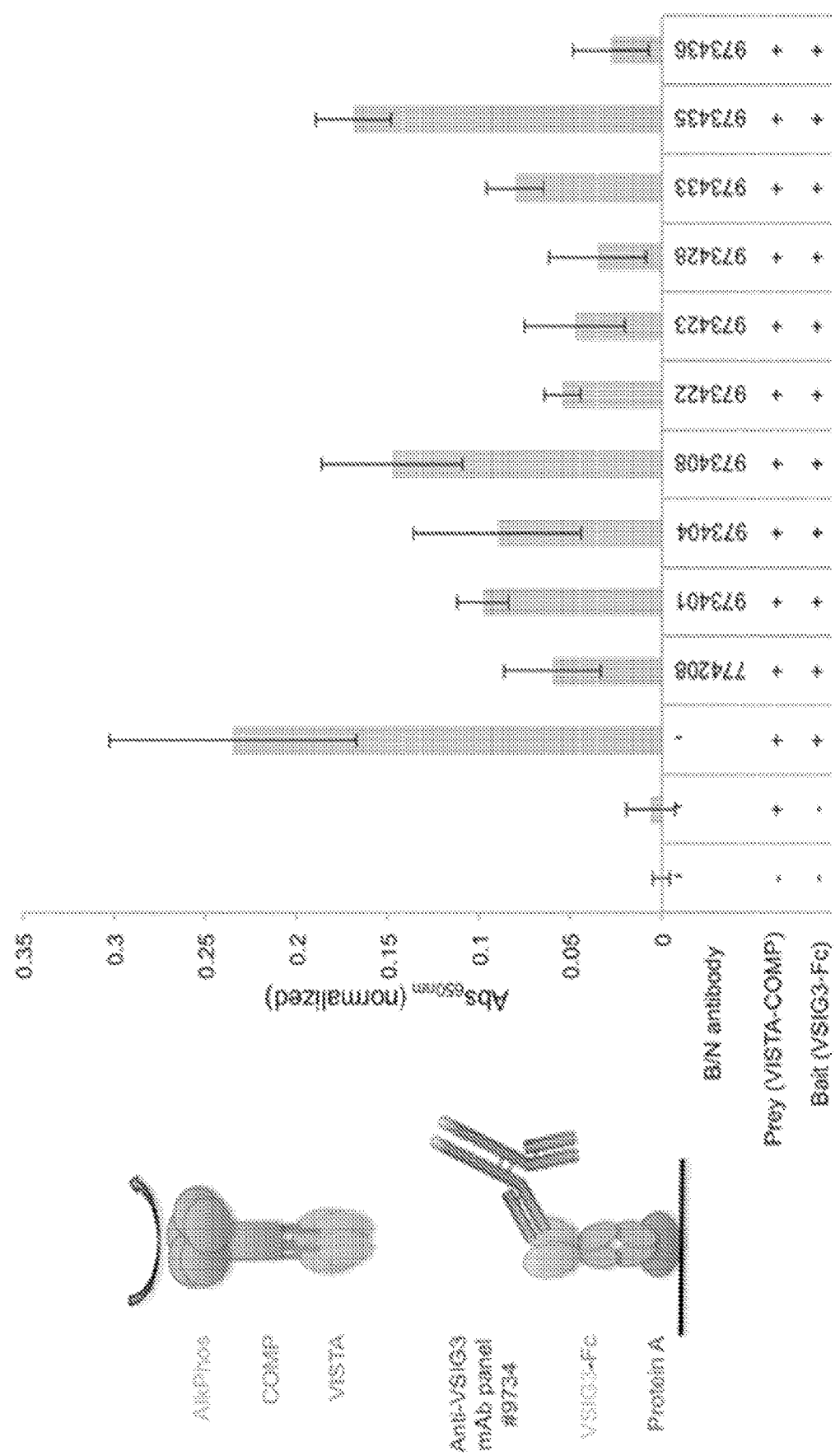
FIG. 16A shows a schematic of the modified AVEXIS screen to test for blocking antibodies. VSIG3-Fc was coated on Protein A plates, blocked, and incubated with individual anti-VSIG3 monoclonal antibodies. The VISTA ECD coupled to a pentamerizing rat cartilage oligomeric matrix protein (COMP) helix and alkaline phosphatase was added, and the interaction between VSIG3 and VISTA was measured based on alkaline phosphatase activity.
FIG. 16B. Alkaline phosphatase activity was measured by detecting absorbance at 650 nm using BluePhos reagent in the absence and presence of mAbs; each assay was performed in quadruplicate. Shown is the mean±standard deviation of four measurements. All antibodies in the panel blocked the VSIG3-VISTA interaction to some extent. Included as a control is clone 774208 (see FIG. 13) which binds VSIG3 with ~2-5 nM affinity and blocks its interaction with VISTA (see FIG. 14 and FIG. 15).

Antibodies recognizing human VSIG3 were generated and tested for their ability to block a VSIG3-VISTA interaction. AVEXIS assay screening for antibody blockade of the VSIG3-VISTA interaction was conducted as described in Example 2. Briefly, VSIG3-Fc was captured on Protein A coated plates and blocked without or with antibodies (antibodies from clones #973401, #973404, #973408, #973422, #973423, #973428, #973433, #973435, and #973436) at 10 μg/mL. As a control, the antibodies from clone #774208 was used at 10 μg/mL, as it was shown in Example 2 (see FIG. 13) to block a VSIG3-VISTA interaction. The bait protein, multimeric VISTA with alkaline phosphatase, was incubated in the presence of anti-VSIG3 antibodies. After washing, the interaction between VSIG3 and VISTA was measured using alkaline phosphatase substrate. At 10 μg/mL, all antibodies tested blocked the interaction between VSIG3 and VISTA to some extent (FIG. 16B).

Example 4

Exemplary antibodies recognizing human VSIG3 were sequenced. Results, including alignments, are shown in FIG. 18, FIG. 19, and FIG. 20. Additional information about these antibodies is provided in Table 2

TABLE 2

Antibody clone summary

| Target | Fusion # | Clone | type | Isotype | Block y/n |
|---|---|---|---|---|---|
| VSIG3 | 2271 | 2271a | rb mono | IgG | y |
| | 7742 | 6 | ms mono | IgG2B | y |
| | | 8 | ms mono | IgG1 | y |
| | | 11 | ms mono | IgG2A | n |
| | | 13 | ms mono | IgG2B | y |
| | | 20 | ms mono | IgG2B | n |
| | | 21 | ms mono | IgG1 | y |
| | | 25 | ms mono | IgG2B | n |
| | | 26 | ms mono | IgG2B | y |
| | | 32 | ms mono | IgG2A | n |
| | | 34 | ms mono | IgG2A | n |
| | 9734 | 1 | ms mono | IgG1 | y |
| | | 4 | ms mono | IgG1 | y |
| | | 8 | ms mono | IgG1 | y |
| | | 22 | ms mono | IgG2B | y |
| | | 23 | ms mono | IgG2B | n |
| | | 28 | ms mono | IgG1 | y |
| | | 33 | ms mono | IgG2B | y |
| | | 35 | ms mono | IgG2B | n |
| | | 36 | ms mono | IgG2B | y |

Exemplary Embodiments

1. A compound which agonizes or antagonizes the interaction of VISTA and VSIG3.
2. The compound of embodiment 1 comprising an agonistic anti-VSIG3 antibody or antibody fragment.
3. The compound of embodiment 1 comprising an agonistic anti-VISTA antibody or antibody fragment.
4. The compound of embodiment 1 comprising an antagonistic anti-VSIG3 antibody or antibody fragment.
5. The compound of embodiment 1 comprising an antagonistic anti-VISTA antibody or antibody fragment.
6. The compound of embodiment 1 comprising at least one copy of a polypeptide comprising the extracellular region of VSIG3, a fragment thereof that elicits a suppressive effect on T cell immunity or a derivative of said VSIG3 polypeptide that possesses at least 80, 90, 95, 96, 97, 98 or 99% sequence identity to the extracellular region of VSIG3 or to SEQ ID NO: 2.
7. The compound of embodiment 6 comprising at least one polypeptide comprising the entire extracellular region of human, non-human primate or murine VSIG3.
8. The compound of embodiment 6 comprising a fusion protein.
9. The compound of embodiment 8 comprising an Ig fusion protein.
10. The compound of embodiment 9 comprising a human IgG1, IgG2, IgG3 or IgG4 constant region or fragment thereof, which optionally is mutagenized to eliminate FcR or complement binding.
11. The compound of embodiment 9 comprising a fusion protein that possesses at least 80, 90, 95, 96, 97, 98 or 99% sequence identity to SEQ ID NO:2 or SEQ ID NO:3.
12. The compound of embodiment 1 comprising recombinant human VSIG3 Fc chimera.
13. The compound of embodiment 1 comprising at least one copy of a polypeptide comprising the extracellular region of VISTA, a fragment thereof that elicits a suppressive effect on T cell immunity or a derivative of said VISTA polypeptide that possesses at least 80, 90, 95, 96, 97, 98 or 99% sequence identity to the extracellular region of VISTA or to SEQ ID NO: 5.

14. The compound of embodiment 13, which comprises at least one polypeptide comprising the entire extracellular region of human, non-human primate or murine VISTA.

15. The compound of embodiment 13 which is a fusion protein.

16. The compound of embodiment 15 which is an Ig fusion protein.

17. The compound of embodiment 16 comprising a human IgG1, IgG2, IgG3 or IgG4 constant region or fragment thereof, which optionally is mutagenized to eliminate FcR or complement binding.

18. The compound of embodiment 15 comprising a fusion protein that possesses at least 80, 90, 95, 96, 97, 98 or 99% sequence identity to SEQ ID NO:5 or SEQ ID NO:6.

19. The compound of embodiment 1 comprising recombinant human VISTA Fc chimera.

20. An isolated complex comprising VISTA and VSIG3.

21. The complex of embodiment 20, wherein said VISTA and/or VSIG3 is oligomeric or multimeric.

22. An antibody or antibody fragment that specifically binds to the VISTA-VSIG3 complex of embodiment 20.

23. A pharmaceutical composition comprising a compound according to any one of embodiments 1-19.

24. A vaccine composition comprising a compound according to any one of embodiments 1-19 and an antigen.

25. A method of treatment and/or diagnosis, or use of a composition containing a compound according to any one of embodiments 1-19 for diagnostic or therapeutic use, which method or use comprises the administration to a subject in need thereof at least one dosage or composition comprising a therapeutically or diagnostically effective amount the compound.

26. A diagnostic method comprising detecting whether an individual has a condition associated with an increase or decrease in VSIG3 and/or VISTA-mediated effects on immunity wherein the method or use includes contacting a tissue sample from the individual with a compound according to any one of embodiments 1-19 and detecting specific binding thereto.

27. A method of treatment and/or diagnosis, which comprises promoting T cell immunity or natural killer (NK) immunity and/or suppressing Tregs or MDSC's in a subject in need thereof, which comprises administering a therapeutically or diagnostically effective amount of a composition containing a compound according to any one of embodiments 1-19.

28. The method of embodiment 27, which administers a VSIG antagonist or VISTA antagonist which suppresses the inhibitory effect of VSIG3 and/or VISTA on T cell immunity.

29. The method or use of embodiment 27, which administers VSIG antagonist or VISTA antagonist which promotes CTL activity.

30. A method of treatment and/or diagnosis and/or diagnosis, which comprises promoting NK or T cell immunity in a subject in need thereof, and which comprises administering a therapeutically or diagnostically effective amount of a compound according to any one of embodiments 1-19.

31. The method of embodiment 30, wherein the treated individual suffers from an infectious disease.

32. The method of embodiment 30, wherein the treated individual suffers from cancer.

33. The method of embodiment 30 which mediates any one or combination of at least one of the following immunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity.

34. A method of treatment and/or diagnosis, which comprises suppressing T cell immunity or natural killer (NK) immunity and/or promoting Tregs or MDSC's in a subject in need thereof, which comprises administering a therapeutically or diagnostically effective amount of at least one compound according to any one of embodiments 1-19 comprising an anti-VSIG3 antibody, antigen-binding fragment or a composition containing, wherein such antibody or antigen-binding fragment agonizes, mimics or promotes at least one effect of a polypeptide (VSIG3) having the amino acid sequence of SEQ ID NO: 1 or SEQ ID NO: 2.

35. A method of treatment and/or diagnosis, which comprises suppressing T cell immunity or natural killer (NK) immunity and/or promoting Tregs or MDSC's in a subject in need thereof, which comprises administering a therapeutically or diagnostically effective amount of at least one compound according to any one of embodiments 1-19 comprising an anti-VISTA antibody, antigen-binding fragment or a composition containing, wherein such antibody or antigen-binding fragment agonizes, mimics or promotes at least one effect of a polypeptide (VSIG3) having the amino acid sequence of SEQ ID NO: 4 or SEQ ID NO: 5.

36. The method of any one of embodiments 34 or 35, which is used in the treatment of allergy, autoimmunity, transplant, gene therapy, inflammatory conditions, or combination thereof.

37. The method of any one of embodiments 34-36, further comprising the administration of an antibody selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD137, OX40, GITR, CD27, CD28 or ICOS.

38. The method of any one of embodiments 34-37, which includes assaying VSIG3 and/or VISTA protein by the individual's cells prior, concurrent and/or after treatment.

39. The method of any one of embodiments 34-38, wherein the method comprises (i) obtaining one or more antibodies that putatively bind to a VSIG3 polypeptide having a sequence selected from an amino acid sequence set forth in any of SEQ ID NOs: 1 or 2 or binding to a polypeptide possessing at least 90% sequence identity therewith or to a non-human VSIG3 ortholog, or a fragment or variant thereof containing at least one VSIG3 epitope, which fragment or variant possesses at least 90% identity thereto, or to a non-human VSIG3 ortholog (ii) determining whether said antibody or antigen-binding fragment specifically binds to said VSIG3 polypeptide, (ii) determining whether said antibody or antigen-binding fragment modulates (agonizes or antagonizes) at least one effect of VSIG3 on immunity, and (iv) if (ii) and (ii) are satisfied selecting said antibody as one potentially useful in a method or use according to any of the foregoing embodiments.

40. The method of embodiment 39, wherein the selected antibody is demonstrated to mediate at least one of the following effects: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) induces direct killing of cancer cells, (xxvii) increases Th1 7 activity and/or (xxviii) induces complement dependent cytotoxicity and/or antibody dependent cell-mediated cytotoxicity, with the proviso that said anti-VSIG3 antibody or antigen-binding fragment may elicit an opposite effect to one or more of (i)-(xxviii).

41. The method of embodiment 39, wherein the selected antibody is demonstrated to mediate at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VSIG3 antibody or antigen-binding fragment may elicit an opposite effect to one or more of (i)-(xxviii).

42. The method of embodiment 39 wherein the selected antibody is demonstrated to compete with binding to human or rodent VSIG3 to VISTA.

43. A diagnostic or therapeutic composition comprising a diagnostically or therapeutically effective amount of a compound according to any one of embodiments 1-19.

44. The method of embodiment 43, which further comprises or includes the administration of an PD-1 or PD-L1 agonist or antagonist or other immune modulator.

45. A method of contacting immune cells with a VSIG3 agonist or antagonist compound according to any one of embodiments 1-19.

46. A screening assay which comprises the use of VSIG3 alone or in association with VISTA to identify VSIG3/VISTA agonists or antagonists according to any one of embodiments 1-19.

47. A VSIG3 agonist according to any one of embodiments 1-19 comprising an isolated polypeptide comprising a fragment of a VSIG3 ECD, wherein said fragment consists essentially of or consists of an amino acid sequence as set forth in any one of SEQ ID NO: 1 or SEQ ID NO: 2 or a variant thereof that possesses at least 80, 85, 90, 95, 96, 97, 98, or 99% sequence identity therewith.

48. The isolated polypeptide of embodiment 47, which comprises 2-10 of said VSIG3 ECD polypeptide fragments.

49. An isolated polypeptide according to embodiments 47, wherein said fragments are intervened by a heterologous linker, wherein said linker is not a fragment of a VSIG3 polypeptide.

50. A VISTA agonist according to any one of embodiments 1-19 comprising an isolated polypeptide comprising a fragment of a VISTA ECD, wherein said fragment consists essentially of or consists of an amino acid sequence as set forth in any one of SEQ ID NO: 4 or SEQ ID NO: 5 or a variant thereof that possesses at least 80, 85, 90, 95, 96, 97, 98, or 99% sequence identity therewith.

51. The isolated polypeptide of embodiment 50, which comprises 2-10 of said VISTA ECD polypeptide fragments.

52. An isolated polypeptide according to embodiment 50, wherein said fragments are intervened by a heterologous linker, wherein said linker is not a fragment of a VISTA polypeptide.

53. A fusion protein comprising the isolated polypeptide of SEQ ID NO 3 or SEQ ID NO 6, joined to a heterologous polypeptide and/or half-life extending moiety.

54. The fusion protein of embodiment 53, comprising a human immunoglobulin heavy chain constant region selected from the group consisting of a human IgG1, IgG2, IgG3, and IgG4.

55. The fusion protein of embodiment 53 or 54, which comprises at least one heterologous polypeptide which is a receptor, hormone, cytokine, antigen, B-cell target, NK cell target, T cell target, TNF receptor superfamily member, Hedgehog family member, a receptor tyrosine kinase, a proteoglycan-related molecule, a TGF-β superfamily member, a Wnt-related molecule, a receptor ligand, a Dendritic cell target, a myeloid cell target, a monocyte/macrophage cell target or an angiogenesis target.

56. The fusion protein of any one of embodiments 53-55, wherein the antigen is a tumor antigen, autoantigen, allergen, or an infectious agent antigen.

57. The fusion protein of any one of embodiments 53-56, which comprises at least one heterologous polypeptide which is an immunomodulatory polypeptide.

58. The fusion protein of any one of embodiments 53-57, which mediates at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-y production by T-cells, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said isolated or recombinant VSIG3 polypeptide or fusion protein may elicit an opposite effect to one or more of (i)-(xxviii).

59. The fusion protein of any one of embodiments 53-58, which agonizes or antagonizes at least one effect of VSIG3 and/or VISTA on T cells, natural killer (NK) cells or the production of one or more proinflammatory cytokines.

60. The fusion protein of any one of embodiments 53-59, which inhibits or promotes one or more of CTL activity, CD4+ T cell activation and/or CD4+ T cell proliferation and/or cell depletion or the secretion of proinflammatory cytokines.

61. A method of immunotherapy or treatment, e.g., of cancer, infection, allergy, autoimmunity, inflammatory conditions, transplant or sepsis which includes the administration of at least one compound according to any one of embodiments 1-19, optionally in combination with another drug or immunomodulator.

62. A diagnostic method for diagnosing or aiding in the diagnosis of a disease in a subject, wherein the disease is selected from the group consisting of cancer, autoimmune disease, or an infectious disease, wherein the diagnostic method is performed in vivo, comprising administering at least one compound according to any one of embodiments 1-19, to a subject and detecting specific binding to tissues.

VSIG3 Clauses

Clause 1. A compound which agonizes or antagonizes the interaction of VISTA and VSIG3.

Clause 2. The compound of Clause 1 which is an antibody or antibody fragment that specifically binds VSIG3.

Clause 3. The compound of Clause 1, which is an agonistic anti-VSIG3 antibody or antibody fragment.

Clause 4. The compound of Clause 1, which is an antagonistic anti-VSIG3 antibody or antibody fragment.

Clause 5. The compound of Clause 2, 3 or 4, which is a humanized, human, primatized, or chimeric anti-VSIG3 antibody or antibody fragment.

Clause 6. The antibody of Clause 5, which comprises a human IgG1, IgG2, IgG3 or IgG4 constant region or fragment thereof, which optionally is mutagenized to eliminate FcR or complement binding.

Clause 7. The antibody of Clause 5, which comprises an IgG1 or IgG3 constant region or portion thereof, which optionally is mutagenized to enhance FcR or complement binding.

Clause 8. The compound of any of the foregoing Clauses which is a Fab, Fab', scFv or Fab2.

Clause 9. The compound of Clause 1 comprising at least one copy of a polypeptide comprising the extracellular region of VSIG3, a fragment thereof that elicits a suppressive effect on T cell immunity or a derivative of said VSIG3 polypeptide that possesses at least 80, 90, 95, 96, 97, 98 or 99% sequence identity to the extracellular region of VSIG3 or to SEQ ID NO:1.

Clause 10. The compound of Clause 9, which comprises at least one polypeptide comprising the entire extracellular region of human, non-human primate or murine VSIG3.

Clause 11. The compound of Clause 9 or 10 which is a fusion protein.

Clause 12. The compound of Clause 11, which is an Ig fusion protein.

Clause 13. The compound of Clause 12, which comprises a human IgG1, IgG2, IgG3 or IgG4 constant region or fragment thereof, which optionally is mutagenized to eliminate FcR or complement binding.

Clause 14. The compound of Clause 12, which comprises an IgG1 or IgG3 constant region or portion thereof, which optionally is mutagenized to enhance FcR or complement binding.

Clause 15. A compound according to any one of Clauses 1-14, which is attached to a water soluble polymer to increase serum half-life.

Clause 16. The compound of Clause 15 which is Pegylated.

Clause 17. An Isolated complex comprising VISTA and VSIG3.

Clause 18. The complex of Clause 17, wherein said VISTA and/or VSIG3 is oligomeric or multimeric.

Clause 19. The complex of Clause 17 or 18 which is comprised on a recombinant cell that expresses VISTA or VSIG3.

Clause 20. An isolated cell membrane that comprises a complex according to Clause 17, 18 or 19.

Clause 21. An antibody or antibody fragment that specifically binds to the VISTA-VSIG3 complex of Clause 17, 18 or 19.

Clause 22. The antibody or antibody fragment of Clause 21 which is human, humanized, primatized or chimeric.

Clause 23. The antibody fragment of Clause 21 or 22 which is a Fab, Fab', scFv or Fab2.

Clause 24. The VSIG3 agonist or antagonist compound of Clause 1, which is a small molecule.

Clause 25. An antibody or an antigen-binding fragment according to any of the foregoing Clauses which comprises a human constant region, e.g., a human IgG1, IgG2, IgG3 or IgG4 constant region or variant thereof, which optionally contains one or more domains deleted.

Clause 26. An antibody or an antigen-binding fragment thereof according to any of the foregoing Clauses which comprises a human constant region which contains at least one mutation that increases or decreases an Fc effector function and/or glycosylation and/or a mutation which modulates or abrogates IgG4 Fab arm exchange.

Clause 27. An antibody or an antigen-binding fragment thereof according to Clause 26, wherein said effector functions include FcR binding, ADCC activity, CDC activity, degranulation, phagocytosis, and cytokine release.

Clause 28. An antibody or an antigen-binding fragment thereof to any of the foregoing Clauses, which is selected from the group consisting of a Fab, Fab', F(ab')2, F(ab'), F(ab), Fv or scFv fragment and a minimal recognition unit which optionally has an in vivo half-life of at least one week, 2 weeks, 3 weeks or a month.

Clause 29. An antibody or an antigen-binding fragment thereof according to any of the above Clauses, which is coupled to another moiety, e.g., a therapeutic moiety, detectable moiety, or a moiety that alters (increases or decreases) in vivo half-life.

Clause 30. An antibody or an antigen-binding fragment thereof according to any of the above Clauses, which is coupled to a therapeutic agent selected from a drug, a radionuclide, a fluorophore, an enzyme, a toxin, or a chemotherapeutic agent; and/or a detectable marker selected from a radioisotope, a metal chelator, an enzyme, a fluorescent compound, a bioluminescent compound or a chemiluminescent compound.

Clause 31. An antibody or an antigen-binding fragment thereof or VSIG3 fusion protein according to any of the above Clauses, which is not coupled to any other moiety.

Clause 32. An antibody or an antigen-binding fragment thereof or VSIG3 fusion protein according to any of the above Clauses, wherein the antibody or antigen-binding fragment is coupled to another antibody or antigen-binding fragment or fusion protein, e.g., an NK and/or T cell receptor, e.g., an NK cell receptor that agonizes or antagonizes NK cell activity or inhibits NK cell mediated cell depletion or is one that promotes or activates NK cell mediated cell depletion.

Clause 33. An antibody or an antigen-binding fragment thereof or VSIG3 fusion protein according to 32, wherein the inhibitory NK cell receptor is selected from the group consisting of KIR2DL1, KIR2DL2/3, KIR2DL4, KIR2DL5A, KIR2DL5B, KIR3DL1, KIR3DL2, KIR3DL3, LILRB 1, NKG2A, NKG2C, NKG2E and LILRB5. And the NK activating receptor is selected from the group consisting of NKp30, NKp44, NKp46, NKp46, NKG2D, KIR2DS4 CD2, CD16, CD69, DNAX accessory molecule-1 (DNAM-1), 2B4, NK1.1; a killer immunoglobulin (Ig)-like activating receptors (KAR); ILTs/LIRs; NKRP-1, CD69; CD94/NKG2C and CD94/NKG2E heterodimers, NKG2D homodimer KIR2DS and KIR3DS.

Clause 34. An antibody or an antigen-binding fragment according to any one of the foregoing Clauses which binds human, primate or murine VSIG3 with a binding affinity ($K_D$) no more than 500 nM as determined by any of the binding affinity methods disclosed herein, e.g., a binding affinity ($K_D$) of $10^{-5}$, $10^{-6}$, $10^{-7}$, $10^{-8}$, $10^{-9}$, $10^{-10}$, $10^{-11}$, $10^{-12}$ M or less as determined by any of the binding affinity methods disclosed herein.

Clause 35. An antibody or an antigen-binding fragment or VSIG3 fusion protein according to any one of the foregoing Clauses wherein such antibody or antigen-binding fragment either (1) enhances, agonizes or mimics, or (2) inhibits, antagonizes or blocks at least one effect elicited by the interaction of VSIG3 and VISTA on immunity or on one or more types of immune cells.

Clause 36. An antagonistic antibody or the antigen-binding fragment or VSIG3 fusion protein of any of the above Clauses, which mediates any combination of at least one of the following immunostimulatory effects on immunity: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) induces direct killing of cancer cells, (xxvii) increases Th17 activity and/or (xxviii) induces complement dependent cytotoxicity and/or antibody dependent cell-mediated cytotoxicity, with the proviso that said antibody or antigen-binding fragment may elicit an opposite effect to one or more of (i)-(xxviii).

Clause 37. An agonistic antibody or the antigen-binding fragment or VSIG3 fusion protein of any of the foregoing Clauses, which mediates any combination of at least one of the following immunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VSIG3 antibody or the antigen-binding fragment may elicit an opposite effect to one or more of (i)-(xxviii).

Clause 38. An immunomodulatory antibody or an antigen-binding fragment thereof of any of the foregoing Clauses which increases the inhibitory effect of VSIG3 and/or VISTA on T cell immunity and/or which inhibits CTL activity and/or wherein inhibited CTL activity includes reduced secretion of one or more proinflammatory cytokines and/or reduced CTL mediated killing of target cells and/or inhibition of CD4+ T cell activation and/or CD4+ T cell proliferation and/or CD4+ T cell mediated cell depletion.

Clause 39. An immunomodulatory antibody or an immunomodulatory antigen-binding fragment thereof or VSIG3 fusion protein, of any of the foregoing Clauses which inhibit NK cell activity, and/or NK cell proliferation and/or NK cell mediated cell depletion.

Clause 40. An immunomodulatory antibody or an immunomodulatory antigen-binding fragment thereof or VSIG3 fusion protein of any of the foregoing Clauses which promotes antigen-specific tolerance or prolonged suppression of an antigen-specific immune responses e.g., against transplanted cells, tissue or organ by enhancing one or more of the effects of VSIG3 and/or VISTA on immunity.

Clause 41. An immunomodulatory antibody or an immunomodulatory antigen-binding fragment thereof or VSIG3 fusion protein of any of the foregoing Clauses which promotes which inhibits an immune response against an autoantigen, allergen, or inflammatory agent by promoting one or more of the effects of VSIG3 and/or VISTA on immunity.

Clause 42. An immunomodulatory antibody or an immunomodulatory antigen-binding fragment thereof or VSIG3 fusion protein of any of the foregoing Clauses, for use in inhibiting an immune response against an autoantigen, allergen, or inflammatory agent, and/or for treating an inflammatory disease or response and/or for treating an autoimmune disease and/or for reducing or prevent transplant rejection and/or graft vs host disease.

Clause 43. A pharmaceutical composition comprising at least one compound according to any of the above Clauses.

Clause 44. A vaccine composition comprising at least one compound according to any of the above Clauses and an antigen.

Clause 45. An immunosuppressive vaccine composition comprising at least one antibody or antigen-binding fragment thereof or VSIG3 fusion protein according to any of the above Clauses, wherein said antibody or antigen-binding fragment thereof in said composition suppresses antigen-specific T and/or B cell immunity or induces tolerance.

Clause 46. The vaccine composition of Clause 45 wherein the antigen to which immunity is suppressed is a human antigen, tumor antigen, infectious agent antigen, autoantigen, or an allergen, e.g., a human antigen, cell or antigen of a cell, tissue, or organ to be transplanted into a subject, autoantigen, inflammatory agent or an allergen.

Clause 47. The composition of any one of Clauses 43-46 which is suitable for administration by a route selected from intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, wherein "parenteral administration" refers to modes of administration other than enteral and topical administration.

Clause 48. The composition of any one of Clauses 43-47, which comprises at least one other active agent, e.g., a therapeutic or diagnostic agent, e.g., another immunomodulatory compound, a chemo therapeutic, a drug, a cytokine, a radionuclide, and an enzyme.

Clause 49. The composition of any one of Clauses 43-47, which comprises an antigen that is expressed by a target cell (e.g., a tumor or infected cell).

Clause 50. The composition of any one of Clauses 43-49, which comprises or is used with another composition containing at least one immunomodulatory agent selected from PD-1 agonists and antagonists, PD-L1 and PD-L2 antibodies and antibody fragments, TLR agonists, CD40 agonists or antagonists, CTLA-4 fusion proteins, CD28 agonists or antagonists, 4-IBB agonists or antagonists, CD27 or CD70 agonists or antagonists, LAG3 agonists or antagonists, TIM3 agonists or antagonists, TIGIT agonists or antagonists, ICOS agonists or antagonists, ICOS ligand agonists or antagonists.

Clause 51. A method of treatment and/or diagnosis, or use of a composition containing a VSIG3 agonist or antagonist according to any of the foregoing Clauses for diagnostic or therapeutic use, which method or use comprises the administration to a subject in need thereof at least one dosage or composition comprising a therapeutically or diagnostically effective amount of at least one VSIG3 agonist or antagonist according to any of the foregoing Clauses or composition containing according to any of the above Clauses.

Clause 52. A diagnostic method or use of an antibody or antigen-binding fragment or VSIG3 fusion protein or composition containing in detecting whether an individual has a condition associated with an increase or decrease in VSIG3 and/or VISTA-mediated effects on immunity wherein the method or use includes contacting a tissue sample from the individual with a compound, e.g., an antibody, or antigen-binding fragment or composition according to any one of the foregoing Clauses and detecting specific binding thereto.

Clause 53. The method or use of Clause 51 or 52, wherein the disease is selected from the group consisting of cancer, autoimmune disease, or infectious disease.

Clause 54. The method or use of any of Clauses 51-53 which detects the upregulation of VSIG3 or expression and/or increased number of VSIG3 expressing cells or the downregulation of VSIG3 and/or VISTA expression and/or the decreased number of VSIG3 and/or VISTA expressing cells.

Clause 55. A diagnostic method or use of an anti-VSIG3 antibody or antigen-binding fragment or composition containing which includes detecting whether an individual has a condition associated with an increase or decrease in VSIG3-mediated effects on immunity comprising contacting a tissue sample from the individual with an antibody, or antigen-binding fragment or composition according to any one of the foregoing Clauses wherein the diagnostic method is performed in vivo, comprising administering to the subject with an immunomodulatory antibody, or antigen-binding fragment or composition according to any one of the foregoing Clauses and detecting specific binding thereto.

Clause 56. The method or use of Clause 55, wherein the disease is selected from the group consisting of cancer, autoimmune disease, inflammatory condition, allergic condition or an infectious disease.

Clause 57. A diagnostic method or use which includes an anti-VSIG3 antibody or antigen-binding fragment or composition containing, and which method or use includes diagnosing a disease in a subject, wherein the disease is selected from the group consisting of cancer, autoimmune disease, or an infectious disease wherein the diagnostic method is performed ex vivo or in vivo, comprising contacting a sample from the individual or administering the individual an antibody, or antigen-binding fragment or composition according to any one of the foregoing Clauses and detecting specific binding of the immune molecule or antibody of any of the above Clauses to a tissue of the subject.

Clause 58. The diagnostic method or use of any of the foregoing Clauses, wherein the diagnostic method or use is performed before administering to the individual a therapeutically effective amount of an antibody, antigen-binding fragment, or immunomodulatory polypeptide or pharmaceutical composition containing according to any one of the foregoing Clauses.

Clause 59. The diagnostic method or use of any of the foregoing Clauses, wherein a therapeutically effective amount of an antibody, antigen-binding fragment, or immunomodulatory polypeptide or a pharmaceutical composition containing according to any one of the foregoing Clauses is only administered if the individual has a condition characterized by increased expression of VSIG3 and/or VISTA by diseased and/or APC cells and/or increased numbers of diseased and/or APC cells which express VSIG3 and/or VISTA, e.g., on is at least 1 on a scale of 0 to 3.

Clause 60. The method or use of any of the foregoing Clauses, wherein VSIG3 expression is detected on one or more of cancer cells, immune infiltrate or stromal cells.

Clause 61. A diagnostic method or use of an anti-VSIG3 antibody or antigen-binding fragment or VSIG3 fusion protein, which method or use includes diagnosing whether a tissue sample taken from a subject exhibits an immune related condition associated with increased or decreased VSIG3 expression, comprising (i) contacting the sample with a compound or composition according to any one of the foregoing Clauses, or with a nucleic acid that detects VSIG3 expression and (ii) conducting a binding or amplification assay that detects VSIG3 expression, and (iii) based thereon diagnosing whether the sample is from an individual with a condition associated with an immune related condition associated with increased or decreased VSIG3 expression.

Clause 62. The method or use of Clause 61, wherein the immune related condition is selected from the group consisting of cancer, autoimmune disease, inflammatory condition, an allergic condition, an infectious disease or sepsis.

Clause 63. The method or use of any of the foregoing Clauses, wherein said anti-VSIG3 antibody or antigen-binding fragment or VSIG3 fusion protein is an immuno stimulatory antibody or compound which mediates any combination of at least one of the following immunostimulatory effects on immunity: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) Induces direct killing of cancer cells, (xxvii) increases Th17 activity and/or (xxviii) induces complement dependent cytotoxicity and/or antibody dependent cell-mediated cytotoxicity, with the proviso that said anti-VSIG3 antibody or antigen-binding fragment may elicit an opposite effect to one or more of (i)-(xxviii).

Clause 64. A method of treatment and/or diagnosis, or use of a composition containing an anti-VSIG3 antibody or antigen-binding fragment or VSIG3 fusion protein for diagnostic or therapeutic use, which comprises promoting T cell immunity or natural killer (NK) immunity and/or suppressing Tregs or MDSC's in a subject in need thereof, which comprises administering a therapeutically or diagnostically effective amount of at least one antibody, antigen-binding fragment or a composition containing according to any of the above Clauses, wherein such antibody or antigen-binding fragment inhibits, antagonizes or blocks at least one effect of a VSIG3 polypeptide having an amino acid sequence at least 90% identical to the polypeptide of SEQ ID NO: 1 on immunity or immune cells.

Clause 65. The method or use of any of the foregoing Clauses, which uses a VSIG3 antagonist which suppresses the inhibitory effect of VSIG3 and/or VISTA on T cell immunity.

Clause 66. The method or use of any of the foregoing Clauses, which uses a VSIG3 antagonist which promotes CTL activity.

Clause 67. The method or use according to Clause 66, wherein CTL activity includes the secretion of one or more proinflammatory cytokines and/or CTL mediated killing of target cells.

Clause 68. The method or use of any of the foregoing Clauses, which uses a VSIG3 antagonist which promotes CD4+ T cell activation and/or CD4+ T cell proliferation and/or CD4+ T cell mediated cell depletion.

Clause 69. The method or use of any of the foregoing Clauses, which uses a VSIG3 antagonist which promotes CD8+ T cell activation and/or CD8+ T cell proliferation and/or CD8+ T cell mediated cell depletion.

Clause 70. The method or use of any of the foregoing Clauses, which uses a VSIG3 antagonist which enhances NK cell activity.

Clause 71. The method or use of Clause 70, wherein enhanced NK cell activity includes increased depletion of target cells and/or proinflammatory cytokine release.

Clause 72. The method or use of any of the foregoing Clauses, which uses a VSIG3 antagonist which suppresses and or decreases the differentiation, proliferation and/or activity of regulatory cells, such as Tregs and/or the differentiation, proliferation, infiltration and/or activity myeloid derived suppressor cells (MDSCs).

Clause 73. The method or use of any of the foregoing Clauses, which uses a VSIG3 antagonist which suppresses and/or decreases the infiltration of infiltration of regulatory cells, such as Tregs and MDSCs into a target site.

Clause 74. The method or use of Clause 73, wherein said target site is a transplanted cell, tissue or organ, or an autoimmune, allergic or inflammatory site or lesion.

Clause 75. The method or use of any of the foregoing Clauses, which uses a VSIG3 antagonist which promotes NK-mediated cell depletion.

Clause 76. The method or use of any of the foregoing Clauses, which uses a VSIG3 antagonist which promotes antitumor immunity by suppressing one or more of the effects of VSIG3 and/or VISTA on immunity.

Clause 77. The method or use of any of the foregoing Clauses, which uses a VSIG3 antagonist, which is used in the treatment of cancer, sepsis or an infectious condition or combination thereof.

Clause 78. A method of treatment and/or diagnosis and/or diagnosis, or use of a composition containing an anti-VSIG3 antibody or antigen-binding fragment or VSIG3 fusion protein for diagnostic or therapeutic use, which comprises promoting NK or T cell immunity in a subject in need thereof, and which comprises administering a therapeutically or diagnostically effective amount of at least one antibody, antigen-binding fragment or a composition containing according to any of the foregoing Clauses, wherein such antibody or antigen-binding fragment inhibits at least one effect of a polypeptide (VSIG3) having the amino acid sequence of SEQ ID NO:1 or a polypeptide having at least 90% sequence identity therewith or to a non-human VSIG3 ortholog on immunity or immune cells or to human VISTA.

Clause 79. The method or use of any of the foregoing Clauses, wherein the treated individual suffers from an infectious disease.

Clause 80. The method or use of Clause 79, wherein the infectious disease is caused by a virus, bacterium, parasite, nematode, yeast, mycoplasm, fungus or prion.

Clause 81. The method or use of Clauses 78 or 79, wherein the infectious disease is caused by a Retroviridae (e.g., human immunodeficiency viruses, such as HIV-1 or HIV-2, acquired immune deficiency (AIDS) also referred to as HTLV-III, LAV or HTLV-III/LAV, or HIV-III; and other isolates, such as HIV-LP; Picomaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxviridae (variola virsues, vaccinia viruses, pox viruses); and Iridoviridae (e.g., African swine fever virus); an unclassified virus (e.g., the etiological agents of Spongiform encephalopathies, the agent of delta hepatitides, the agents of non-A, non-B hepatitis (class 1—internally transmitted; class 2—parenterally transmitted (i.e., Hepatitis C); Norwalk and related viruses, and astroviruses) as well as Severe acute respiratory syndrome virus and respiratory syncytial virus (RSV), West Nile encephalitis, coronavirus infection, rhinovirus infection, Influenza, dengue, hemorrhagic fever; an otological infection; severe acute respiratory syndrome (SARS), acute febrile pharyngitis, pharyngoconjunctival fever, epidemic keratoconjunctivitis, infantile gastroenteritis, infectious mononucleosis, Burkitt lymphoma, acute hepatitis, chronic hepatitis, hepatic cirrhosis, hepatocellular carcinoma, primary HSV-1 infection, (gingivostomatitis in children, tonsillitis & pharyngitis in adults, keratoconjunctivitis), latent HSV-1 infection (herpes labialis, cold sores), aseptic meningitis, Cytomegalovirus infection, Cytomegalic inclusion disease, Kaposi sarcoma, Castleman disease, primary effusion lymphoma, influenza, measles, encephalitis, postinfectious encephalomyelitis, Mumps, hyperplastic epithelial lesions (common, flat, plantar and anogenital warts, laryngeal papillomas, epidermodysplasia verruciformis), croup, pneumonia, bronchiolitis, Poliomyelitis, Rabies, bronchiolitis, pneumonia, German measles, congenital rubella, Hemorrhagic Fever, Chickenpox, Dengue, Ebola infection, Echovirus infection, EBV infection, Fifth Disease, Filovirus, Flavivirus, Hand, foot & mouth disease, Herpes Zoster Virus (Shingles), Human Papilloma Virus Associated Epidermal Lesions, Lassa Fever, Lymphocytic choriomeningitis, Parainfluenza Virus Infection, Paramyxovirus, Parvovirus B19 Infection, Picornavirus, Poxviruses infection, Rotavirus diarrhea, Rubella, Rubeola, Varicella, Variola infection.

Clause 82. The method or use of Clauses 79 or 80, wherein the infectious disease is a parasite infection caused by a parasite selected from a protozoa, such as Amebae, *Flagellates, Plasmodium falciparum, Toxoplasma gondii*, Ciliates, Coccidia, Micro sporidia, Sporozoa; helminthes, Nematodes (Roundworms), Cestodes (Tapeworms), Trematodes (Flukes), Arthropods, and aberrant proteins known as prions.

Clause 83. The method or use of Clauses 79 or 80, wherein the infectious disease is an infectious disorder and/or disease caused by bacteria selected from the group consisting of Sepsis, septic shock, sinusitis, skin infections, pneumonia, bronchitis, meningitis, Bacterial vaginosis, Urinary tract infection (UCI), Bacterial gastroenteritis, Impetigo and erysipelas, Erysipelas, Cellulitis, anthrax, whooping cough, lyme disease, Brucellosis, enteritis, acute enteritis, Tetanus, diphtheria, Pseudomembranous colitis, Gas gangrene, Acute food poisoning, Anaerobic cellulitis, Nosocomial infections, Diarrhea, Meningitis in infants, Traveller's diarrhea, Hemorrhagic colitis, Hemolytic-uremic syndrome, Tularemia, Peptic ulcer, Gastric and Duodenal ulcers, Legionnaire's Disease, Pontiac fever, Leptospirosis, Listeriosis, Leprosy (Hansen's disease), Tuberculosis, Gonorrhea, Ophthalmia neonatorum, Septic arthritis, Meningococcal disease including meningitis, Waterhouse-Friderichsen syndrome, Pseudomonas infection, Rocky mountain spotted fever, Typhoid fever type salmonellosis, Salmonellosis with gastroenteritis and enterocolitis, Bacillary dysentery/Shigellosis, Coagulase-positive staphylococcal infections: Localized skin infections including Diffuse skin infection (Impetigo), Deep localized infections, Acute infective endocarditis, Septicemia, Necrotizing pneumonia, Toxinoses such as Toxic shock syndrome and Staphylococcal food poisoning, Cystitis, Endometritis, Otitis media, Streptococcal pharyngitis, Scarlet fever, Rheumatic fever, Puerperal fever, Necrotizing fasciitis, Cholera, Plague (including Bubonic plague and Pneumonic plague), as well as any infection caused by a bacteria selected from but not limited to *Helicobacter pyloris, Boreliai burgdorferi, Legionella pneumophila, Mycobacteria* sps (e.g., *M. tuberculosis, M. avium, M. intracellulare, M. kansaii, M gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fuso-*

*bacterium nucleatum, Streptobacillus moniliformis, Treponema pallidum, Treponema pertenue, Leptospira,* and *Actinomyces israelii.*

Clause 84. The method or use of Clauses 79 or 80, wherein the infectious disease is an infectious disorder and/or disease caused by fungi selected from Allergic bronchopulmonary aspergillosis, Aspergilloma, Aspergillosis, Basidiobolomycosis, Blastomycosis, Candidiasis, Chronic pulmonary aspergillosis, Chytridiomycosis, Coccidioidomycosis, Conidiobolomycosis, Covered smut (barley), Cryptococcosis, Dermatophyte, Dermatophytid, Dermatophytosis, Endothrix, Entomopathogenic fungus, Epizootic lymphangitis, Epizootic ulcerative syndrome, Esophageal candidiasis, Exothrix, Fungemia, Histoplasmosis, Lobomycosis, Massospora cicadina, Mycosis, *Mycosphaerella* fraganae, Myringomycosis, Paracoccidioidomycosis, Pathogenic fungi, Penicilliosis, Thousand cankers disease, Tinea, Zeaspora, Zygomycosis; a parasite selected from the group consisting of but not limited to *Acanthamoeba*, Amoebiasis, Ascariasis, Ancylostomiasis, Anisakiasis, Babesiosis, Balantidiasis, Baylisascariasis, Blastocystosis, Candiru, Chagas disease, Clonorchiasis, *Cochliomyia*, Coccidia, Chinese Liver Fluke Cryptosporidiosis, Dientamoebiasis, Diphyllobothriasis, *Dioctophyme* renalis infection, Dracunculiasis, Echinococcosis, Elephantiasis, Enterobiasis, Fascioliasis, Fasciolopsiasis, Filariasis, Giardiasis, Gnathostomiasis, Hymenolepiasis, Halzoun Syndrome, Isosporiasis, Katayama fever, Leishmaniasis, lymphatic filariasis, Malaria, Metagonimiasis, Myiasis, Onchocerciasis, Pediculosis, Primary amoebic meningoencephalitis, Parasitic pneumonia, Paragonimiasis, Scabies, Schistosomiasis, Sleeping sickness, Strongyloidiasis, Sparganosis, Rhinosporidiosis, River blindness, Taeniasis (cause of Cysticercosis), Toxocarlasis, Toxoplasmosis, Trichinosis, Trichomoniasis, Trichuriasis, Trypanosomiasis, Tapeworm infection, *Cryptococcus neoformans, Histoplasma capsulatum, Coccidioides immitis, Blastomyces dermatitidis, Chlamydia trachomatis, Candida albicans.*

Clause 85. The method or use of any of Clauses 79-84, wherein the infectious disease is caused by any of hepatitis B, hepatitis C, infectious mononucleosis, EBV, cytomegalovirus, AIDS, HIV-1, HIV-2, tuberculosis, malaria and schistosomiasis.

Clause 86. An anti-VSIG3 antibody or antigen-binding fragment or composition, or method or use according to any of the foregoing Clauses which includes another therapeutic agent useful for treating bacterial infection, viral infection, fungal infection, parasitic infection or sepsis.

Clause 87. The method, composition, antibody or fragment or VSIG3 fusion protein, or use of any of the foregoing Clauses which promotes an immune response against an infectious agent by suppressing one or more of the effects of VSIG3 and/or VISTA on immunity.

Clause 88. The method, composition, antibody or fragment or VSIG3 fusion protein, or use of any of the foregoing Clauses further comprising one or more additional therapeutic agents used for treatment of bacterial infections.

Clause 89. The method, composition, antibody or fragment, or use of Clause 88, wherein said agent is selected from the group consisting of antibiotics including Aminoglycosides, Carbapenems, Cephalosporins, Macrolides, Lincosamides, Nitrofurans, penicillins, Polypeptides, Quinolones, Sulfonamides, Tetracyclines, drugs against mycobacteria including but not limited to Clofazimine, Cycloserine, Cycloserine, Rifabutin, Rifapentine, Streptomycin and other antibacterial drugs such as Chloramphenicol, Fosfomycin, Metronidazole, Mupirocin, and Tinidazole, or a combination thereof.

Clause 90. The method, composition, antibody or fragment or VSIG3 fusion protein, or use of any of the foregoing Clauses further comprising one or more additional therapeutic agents used for treatment of viral infections.

Clause 91. The method, composition, antibody or fragment or VSIG3 fusion protein, or use of Clause 90, wherein said agent is selected from the group consisting of antiviral drugs such as oseltamivir (brand name Tamiflu®) and zanamivir (brand name Relenza®) Arbidol®—adamantane derivatives (Amantadine®, Rimantadine®)—neuraminidase inhibitors (Oseltamivir®, Laninamivir®, Peramivir®, Zanamivir®) nucleotide analog reverse transcriptase inhibitor including Purine analogue guanine (Aciclovir®/Valacyclovir®, Ganciclovir®/Valganciclovir®, Penciclovir®/Famciclovir®) and adenine (Vidarabine®), Pyrimidine analogue, uridine (Idoxuridine®, Trifluridine®, Edoxudine®), thymine (Brivudine®), cytosine (Cytarabine®); Foscarnet; Nucleoside analogues/NARTIs: Entecavir, Lamivudine®, Telbivudine®, Clevudine®; Nucleotide analogues/NtRTIs: Adefovir®, Tenofovir; Nucleic acid inhibitors such as Cidofovir®; Interferoninterferon alfa-2b, Peginterferon a-2a; Ribavirin®/Taribavirin®, antiretroviral drugs including zidovudine, lamivudine, abacavir, lopinavir, ritonavir, tenofovir/emtricitabine, efavirenz each of them alone or a various combinations, gp41 (Enfuvirtide), Raltegravir®, protease inhibitors such as Fosamprenavir®, Lopinavir® and Atazanavir®, Methisazone®, Docosanol®, Fomivirsen®, and Tromantadine®.

Clause 92. The method, composition, antibody or fragment or VSIG3 fusion protein, or use of any of the foregoing Clauses further comprising one or more additional therapeutic agents used for treatment of fungal infections.

Clause 93. The method, composition, antibody or fragment or VSIG3 fusion protein, or use of Clause 92, selected from the group consisting of antifungal drugs of the Polyene antifungals, Imidazole, triazole, and thiazole antifungals, Allylamines, Echinocandins or other anti-fungal drugs.

Clause 94. The method or use of any of the foregoing Clauses, wherein the treated individual suffers from cancer.

Clause 95. The method or use of Clause 94, wherein the cancer is selected from the group consisting of breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous miillerian cancer, malignant ascites, gastrointestinal stromal tumor (GIST), Li-Fraumeni syndrome and Von Hippel-Lindau syndrome (VHL), and cancer of unknown origin either primary or metastatic.

Clause 96. The method or use of Clause 94, wherein the cancer is selected from B-cell lymphoma, Burkitt's lymphoma, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma cancer, keratoacanthomas, anaplastic large-cell lymphoma, esophageal squamous cells carcinoma, hepatocellular carcinoma cancer, follicular dendritic cell carcinoma, muscle-invasive cancer, seminal vesicle tumor, epidermal carcinoma, cancer of the retina, biliary cancer, small bowel cancer, salivary gland cancer, cancer of connective tissue, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, esophagogastric, fallopian tube cancer, peritoneal cancer, papillary serous mullerian cancer, malignant ascites, gastrointestinal stromal tumor (GIST), Li-Fraumeni syndrome and Von Hippel-Lindau syndrome (VHL); endometrial cancer, Breast carcinoma, preferably any of ductal-carcinoma, infiltrating ductal carcinoma, lobular carcinoma, mucinous adenocarcinoma, intra duct and invasive ductal carcinoma, and Scirrhous adenocarcinoma, Colorectal adenocarcinoma, preferably any of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, Moderately Differentiated Mucinous adenocarcinoma of the rectum; Lung cancer, preferably any of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, Small cell lung cancer, preferably Small cell lung carcinoma, more preferably undifferentiated Small cell lung carcinoma; Prostate adenocarcinoma, preferably any of Adenocarcinoma Gleason Grade 6 to 9, Infiltrating adenocarcinoma, High grade prostatic intraepithelial neoplasia, undifferentiated carcinoma; Stomach adenocarcinoma, preferably moderately differentiated gastric adenocarcinoma; Ovary carcinoma, preferably any of cystadenocarcinoma, serous papillary cystic carcinoma, Serous papillary cystic carcinoma, Invasive serous papillary carcinoma; Brain cancer, preferably any of Astrocytoma and Glioblastoma multiforme; Kidney carcinoma, preferably Clear cell renal cell carcinoma; Liver cancer, preferably any of Hepatocellular carcinoma, preferably Low Grade hepatocellular carcinoma, Fibrolamellar Hepatocellular Carcinoma; and Lymphoma, preferably any of, Hodgkin's Lymphoma and High to low grade Non-Hodgkin's Lymphoma.

Clause 97. The method or use of any of the foregoing Clauses wherein the levels of VSIG3 and/or VISTA protein are elevated compared to normal cell samples.

Clause 98. The method or use of Clause any one the foregoing Clauses, wherein the treated individual suffers from a cancer wherein the cancer or other cells contained at the tumor sites do not express VSIG3 and/or VISTA protein or do not express VSIG3 and/or protein at levels higher than normal.

Clause 99. The method or use of any one of the foregoing Clauses, wherein the treated subject suffers from a cancer wherein the diseased cells, APC's, hematopoietic cells, NK cells, monocytes, dendritic cells, neutrophils, monocytes, or other immune cells at the disease site, e.g., myeloid suppressor cells express VSIG3 and/or VISTA protein.

Clause 100. An anti-VSIG3 antibody or antigen-binding fragment or VSIG3 fusion protein or composition, or method or use according to any of the foregoing Clauses which includes treatment with an anti-VSIG3 antibody or antigen-binding fragment or composition containing and the therapy comprises one or more of radiotherapy, cryotherapy, antibody therapy, chemotherapy, photodynamic therapy, surgery, hormonal deprivation or combination therapy with conventional drugs.

Clause 101. An anti-VSIG3 antibody or antigen-binding fragment or composition, or method or use according to any of the foregoing Clauses which includes treatment with an anti-VSIG3 antibody or antigen-binding fragment or VSIG3 fusion protein or composition containing and another therapeutic agent selected from the group consisting of cytotoxic drugs, tumor vaccines, antibodies, peptides, pepti-bodies, small molecules, chemotherapeutic agents, cytotoxic and cytostatic agents, immunological modifiers, interferons, interleukins, immuno stimulatory growth hormones, cytokines, vitamins, minerals, aromatase inhibitors, RNAi, Histone Deacetylase Inhibitors, and proteasome inhibitors.

Clause 102. An anti-VSIG3 antibody or antigen-binding fragment or VSIG3 fusion protein or composition, or method or use according to any of the foregoing Clauses which includes treatment with an anti-VSIG3 antibody or antigen-binding fragment or composition containing and another therapeutic or an imaging agent administered to a subject simultaneously or sequentially in combination with one or more potentiating agents to obtain a therapeutic effect, wherein said one or more potentiating agents is selected from the group consisting of radiotherapy, conventional/classical anti-cancer therapy potentiating anti-tumor immune responses, Targeted therapy potentiating anti-tumor immune responses, Therapeutic agents targeting immunosuppressive cells Tregs and/or MDSCs, Immuno stimulatory antibodies, Cytokine therapy, Adoptive cell transfer.

Clause 103. An anti-VSIG3 antibody or antigen-binding fragment or VSIG3 fusion protein or composition, or method or use according to any of the foregoing Clauses, wherein the conventional/classical anti-cancer agent is selected from platinum based compounds, antibiotics with anti-cancer activity, Anthracyclines, Anthracenediones, alkylating agents, antimetabolites, Antimitotic agents, Taxanes, Taxoids, microtubule inhibitors, *Vinca* alkaloids, Folate antagonists, Topoisomerase inhibitors, Antiestrogens, Antiandrogens, Aromatase inhibitors, GnRh analogs, inhibitors of 5a-reductase, biphosphonates.

Clause 104. An anti-VSIG3 antibody or antigen-binding fragment or composition, or method or use according to any of the foregoing Clauses or VSIG3 fusion protein further comprising Platinum based compounds such as oxaliplatin, cisplatin, carboplatin; Antibiotics with anti-cancer activity, such as dactinomycin, bleomycin, mitomycin-C, mithramycin and Anthracyclines, such as doxorubicin, daunorubicin, epirubicin, idarubicin; Anthracenediones, such as mitoxantrone; Alkylating agents, such as dacarbazine, melphalan, cyclophosphamide, temozolomide, chlorambucil, busulphan, nitrogen mustard, nitrosoureas; Antimetabolites, such as fluorouracil, raltitrexed, gemcitabine, cytosine arabinoside, hydroxyurea and Folate antagonists, such as methotrexate, trimethoprim, pyrimethamine, pemetrexed; Antimitotic agents such as polokinase inhibitors and Microtubule inhibitors, such as Taxanes and Taxoids, such as paclitaxel, docetaxel; *Vinca* alkaloids such as vincristine, vinblastine, vindesine, vinorelbine; Topoisomerase inhibitors, such as etoposide, teniposide, amsacrine, topotecan, irinotecan, camptothecin; Cytostatic agents including Antiestrogens such as tamoxifen, fulvestrant, toremifene, raloxifene, droloxifene, iodoxyfene, Antiandrogens such as bicalutamide, flutamide, nilutamide and cyproterone acetate, Progestogens such as megestrol acetate, Aromatase inhibitors such as anastrozole, letrozole, vorozole, exemestane; GnRH analogs, such as leuprorelin, goserelin, buserelin, degarelix; inhibitors of 5a-reductase such as finasteride.

Clause 105. An anti-VSIG3 antibody or antigen-binding fragment or VSIG3 fusion protein or composition, or method or use according to any of the foregoing Clauses, further comprising a Platinum based compound.

Clause 106. An anti-VSIG3 antibody or antigen-binding fragment or VSIG3 fusion protein or composition, or method or use according to any of the foregoing Clauses, further comprising a targeted therapy selected from the group consisting of but not limited to: histone deacetylase (HDAC) inhibitors, such as vorinostat, romidepsin, panobinostat, belinostat, mocetinostat, abexinostat, entinostat, resminostat, givinostat, quisinostat, sodium butyrate; Proteasome inhibitors, such as bortezomib, carfilzomib, disulfiram; mTOR pathway inhibitors, such as temsirolimus, rapamycin, everolimus; PI3K inhibitors, such as perifosine, CAL101, PX-866, IPI-145, BAY 80-6946; B-raf inhibitors such as vemurafenib, sorafenib; JAK2 Inhibitors, such as lestaurtinib, pacritinib; Tyrosine kinase inhibitors (TKIs), such as erlotinib, imatinib, sunitinib, lapatinib, gefitinib, sorafenib, nilotinib, toceranib, bosutinib, neratinib, vatalanib, regorafenib, cabozantinib; other Protein kinase inhibitors, such as crizotinib; Inhibitors of serine/threonine kinases for example Ras/Raf signaling inhibitors such as farnesyl transferase inhibitors; Inhibitors of serine proteases for example matriptase, hepsin, urokinase; Inhibitors of intracellular signaling such as tipifarnib, perifosine; Inhibitors of cell signaling through MEK and/or AKT kinases; aurora kinase inhibitors such as AZD1152, PH739358, VX-680, MLN8054, R763, MP235, MP529, VX-528, AX39459; Cyclin dependent kinase inhibitors such as CDK2 and/or CDK4 inhibitors; Inhibitors of survival signaling proteins including Bcl-2, Bcl-XL, such as ABT-737; HSP90 inhibitors; Therapeutic monoclonal antibodies, such as anti-EGFR mAbs cetuximab, panitumumab, nimotuzumab, anti-ERBB2 mAbs trastuzumab, pertuzumab, anti-CD20 mAbs such as rituximab, ofatumumab, veltuzumab and mAbs targeting other tumor antigens such as alemtuzumab, labetuzumab, adecatumumab, oregovomab, onartuzumab; TRAIL pathway agonists, such as dulanermin (soluble rhTRAIL), apomab, mapatumumab, lexatumumab, conatumumab, tigatuzumab; Antibody fragments, bi-specific antibodies and bi-specific T-cell engagers (BiTEs), such as catumaxomab, blinatumomab; Antibody drug conjugates (ADC) and other immunoconjugates, such as ibritumomab triuxetan, tositumomab, brentuximab vedotin, gemtuzumab ozogamicin, clivatuzumab tetraxetan, pemtumomab, trastuzumab emtansine; Anti-angiogenic therapy such as bevacizumab, etaracizumab, volociximab, ramucirumab, aflibercept, sorafenib, sunitinib, regorafenib, axitinib, nintedanib, motesanib, pazopanib, cediranib; Metalloproteinase inhibitors such as marimastat; Inhibitors of urokinase plasminogen activator receptor function; Inhibitors of cathepsin activity.

Clause 107. An anti-VSIG3 antibody or antigen-binding fragment or VSIG3 fusion protein or composition, or method or use according to Clause 106, the another therapeutic agent is another antibody selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Clause 108. An anti-VSIG3 antibody or antigen-binding fragment or VSIG3 fusion protein or composition, or method or use according to any of the foregoing Clauses, further comprising a Therapeutic cancer vaccine selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cell-based vaccines, whole tumor cell vaccines, gene modified tumor cells expressing GM-CSF, ICOS and/or Flt3-ligand, oncolytic virus vaccines.

Clause 109. An anti-VSIG3 antibody or antigen-binding fragment or VSIG3 fusion protein or composition, or method or use according to any of the foregoing Clauses, further comprising a Cytokine therapy selected from one or more of the following cytokines such as IL-2, IL-7, IL-12, IL-15, IL-17, IL-18 and IL-21, IL-23, IL-27, GM-CSF, IFNa (interferon α), IFNa-2b, IFN β, IFN γ, and their different strategies for delivery.

Clause 110. An anti-VSIG3 antibody or antigen-binding fragment or VSIG3 fusion protein or composition, or method or use according to any of the foregoing Clauses, further comprising adoptive cell transfer therapy which is carried out following ex vivo treatment selected from expansion of the patient autologous naturally occurring tumor specific T cells or genetic modification of T cells to confer specificity for tumor antigens.

Clause 111. The method or use of any of the foregoing Clauses, wherein said anti-VSIG3 antibody or antigen-binding fragment comprises an immunoinhibitory antibody or an antigen-binding fragment which mediates any combination of at least one of the following immunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VSIG3 antibody or antigen-binding fragment may elicit an opposite effect to one or more of (i)-(xxviii).

Clause 112. A method of treatment and/or diagnosis, or use of a composition containing an anti-VSIG3 antibody or antigen-binding fragment f or VSIG3 fusion protein or diagnostic or therapeutic use, which comprises suppressing T cell immunity or natural killer (NK) immunity and/or promoting Tregs or MDSC's in a subject in need thereof, which comprises administering a therapeutically or diagnostically effective amount of at least one antibody, antigen-binding fragment or a composition containing according to any one of the above Clauses, wherein such antibody or antigen-binding fragment agonizes, mimics or promotes at least one effect of a polypeptide (VSIG3) having the amino acid sequence of SEQ ID NO: 1 or an ortholog on immunity or immune cells.

Clause 113. The method or use of Clauses 111 or 112, which is used in the treatment of allergy, autoimmunity, transplant, gene therapy, inflammatory conditions, or combination thereof.

Clause 114. A method or use according to any one of the foregoing Clauses wherein the treated individual has or is to receive cell therapy, gene therapy or a transplanted tissue or organ, and the treatment reduces or inhibits the undesirable immune activation that is associated with such cell therapy, gene therapy or a transplanted tissue or organ.

Clause 115. The method or use of any one of the foregoing Clauses, wherein the antibody, or antigen-binding fragment thereof or VSIG3 fusion protein is an immunoinhibitory antibody or fragment which effects one or more of the following: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) Increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VSIG3 antibody or antigen-binding fragment may elicit an opposite effect to one or more of (i)-(xxviii).

Clause 116. The method or use of any one of the foregoing Clauses, which enhances, agonizes or mimics at least one effect of VSIG3 and/or VISTA on T or natural killer (NK) cell immunity.

Clause 117. The method or use of any one of the foregoing Clauses which increases the inhibitory effect of VSIG3 and/or VISTA on T cell immunity.

Clause 118. The method or use of any one of the foregoing Clauses which inhibits CTL activity.

Clause 119. The method or use of Clause 118, wherein inhibited CTL activity includes reduced secretion of one or more proinflammatory cytokines and/or reduced CTL mediated killing of target cells.

Clause 120. The method or use of any one of the foregoing Clauses which inhibits CD4+ T cell activation and/or CD4+ T cell proliferation and/or CD4+ T cell mediated cell depletion.

Clause 121. The method or use of any one of the foregoing Clauses which inhibits CD8+ T cell activation and/or CD8+ T cell proliferation and/or CD8+ T cell mediated cell depletion.

Clause 122. The method or use of any one of the foregoing Clauses which inhibits NK cell activity.

Clause 123. The method or use of Clause 122, wherein inhibited NK cell activity includes reduced depletion of target cells and/or proinflammatory cytokine release.

Clause 124. The method or use of any one of the foregoing Clauses which promotes and/or increases the differentiation, proliferation and/or activity of regulatory cells, such as T cells (Tregs) and/or the differentiation, proliferation, infiltration and/or activity of myeloid derived suppressor cells (MDSC's).

Clause 125. The method or use of any one the foregoing Clauses which promotes and/or increases the infiltration of regulatory cells, such as Tregs or MDSCs into a disease site.

Clause 126. The method or use of any one of the foregoing Clauses which inhibits an allergic, autoimmune or inflammatory immune response by promoting one or more of the effects of VSIG3 and/or VISTA on immunity.

Clause 127. The method or use of any one of the foregoing Clauses which promotes antigen-specific tolerance or prolonged suppression of an antigen-specific immune response by enhancing one or more of the effects of VSIG3 and/or VISTA on immunity.

Clause 128. The method or use of any one of the foregoing Clauses which elicits tolerance or prolonged suppression of antigen-specific immunity against transplanted cells, tissue or organ.

Clause 129. The method or use of any one of the foregoing Clauses which inhibits an immune response against an autoantigen, allergen, or inflammatory agent by promoting one or more of the effects of VSIG3 and/or VISTA on immunity.

Clause 130. The method or use of any one the foregoing Clauses wherein the treated individual has or is to receive cell therapy, gene therapy or a transplanted tissue or organ, and the treatment reduces or inhibits the undesirable immune activation that is associated with such cell therapy, gene therapy or a transplanted tissue or organ.

Clause 131. The method or use of any one of the foregoing Clauses which is used to treat an inflammatory condition or autoimmune disorder selected from Acid Reflux/Heartburn, Acne, Acne Vulgaris, Allergies and Sensitivities, Alzheimer's Disease, Asthma, Atherosclerosis and Vascular Occlusive Disease, optionally Atherosclerosis, Ischemic Heart Disease, Myocardial Infarction, Stroke, Peripheral Vascular Disease, or Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases, optionally Systemic Lupus Erythematosus, Systemic Sclerosis, Polymyositis, Dermatomyositis, or Sjogren's Syndrome and related conditions such as Sjogren's syndrome" herein includes one or more of Sjogren's syndrome, Primary Sjogren's syndrome and Secondary Sjogren's syndrome, as well as conditions or complications relating to Sjogren's syndrome including connective tissue disease, such as rheumatoid arthritis, systemic lupus erythematosus, or scleroderma, pneumonia, pulmonary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, Inflammation in the esophagus, stomach, pancreas, and liver (including hepatitis), Polymyositis, Raynaud's phenomenon, Vasculitis, Autoimmune thyroid problems, lymphoma, Corneal Disease, Crohn's Disease, Crystal Arthropathies, optionally Gout, Pseudogout, Calcium Pyrophosphate Deposition Disease, Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain, Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases, Rheumatoid Arthritis, Osteoarthritis, or Psoriatic Arthritis, Rheumatoid Arthritis, Sarcoidosis, Scleroderma, Sinusitis, "Sjogren's syndrome" and related conditions or complications associated therewith such as one or more of Sjogren's syndrome, Primary Sjogren's syndrome and Secondary Sjogren's syndrome, conditions relating to Sjogren's syndrome including connective tissue disease, such as rheumatoid arthritis, systemic lupus erythematosus, or scleroderma, and complications relating to Sjogren's syndrome such as pneumonia, pulmonary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, inflammation in the esophagus, stomach, pancreas, and liver (including hepatitis), Polymyositis, Raynaud's phenomenon, Vasculitis, Autoimmune thyroid problems, lymphoma, Sjogren's Syndrome, Spastic Colon, Spondyloarthropathies, optionally Ankylosing Spondylitis, Reactive Arthritis, or Reiter's Syndrome, Systemic Candidiasis, Tendonitis, Transplant Rejection, UTI's, Vaginitis, Vascular Diseases including Atherosclerotic Vascular Disease, Vasculitides, Polyarteritis Nodosa, Wegener's Granulomatosis, Churg-Strauss Syndrome, or vasculitis.

Clause 132. The method or use of any of the foregoing Clauses which is used to treat an autoimmune or allergic disease selected from acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, optionally, large vessel vasculitis, optionally, polymyalgia rheumatica and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia greata, alopecia totalis, Alport's syndrome, alveolitis, optionally allergic alveolitis or fibrosing alveolitis, Alzheimer's disease, amyloidosis, amylotrophic lateral sclerosis (ALS; Lou Gehrig's disease), an eosinophil-related disorder, optionally eosinophilia, anaphylaxis, ankylosing spondylitis, angiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis, optionally rheumatoid arthritis such as acute arthritis, or chronic rheumatoid arthritis, arthritis chronica progrediente, arthritis deformans, ascariasis, aspergilloma, granulomas containing eosinophils, aspergillosis, aspermiogenese, asthma, optionally asthma bronchiale, bronchial asthma, or auto-immune asthma, ataxia telanglectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease, optionally autoimmune inner ear disease (AGED), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies, optionally epilepsy, channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy, optionally IgM polyneuropathies or IgM-mediated neuropathy, chronic obstructive airway disease, chronic pulmonary inflammatory disease, Chronic recurrent multifocal osteomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogan's syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, optionally chronic cyclitis, heterochronic cyclitis, iridocyclitis, or Fuch's cyclitis, cystic fibrosis, cytokine-induced toxicity, deafness, degenerative arthritis, demyelinating diseases, optionally autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis, optionally allergic encephalomyelitis or encephalomyelitis allergica and experimental allergic encephalomyelitis (EAE), endarterial hyperplasia, endocarditis, endocrine ophthalmopathy, endometriosis, endomyocardial fibrosis, endophthalmia phacoanaphylactica, endophthalmitis, enteritis allergica, eosinophilia-myalgia syndrome, eosinophilic fascitis, epidemic keratoconjunctivitis, epidermolysis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, filariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, hemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) Infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases, optionally anaphylaxis and allergic or atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type I), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with Streptococcus), paraneoplastic cerebellar degeneration, paraneoplastic syndrome, paraneoplastic syndromes, including neurologic paraneoplastic syndromes, optionally Lambert-Eaton myasthenic syndrome or Eaton-Lambert syndrome, parasitic diseases such as *Leishmania*, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, poly endocrine failure, polyglandular syndromes, optionally autoimmune polyglandular syndromes (or polyglandular endocrinopathy syndromes), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis, optionally benign monoclonal gammopathy and monoclonal gammopathy of undetermined significance, MGUS, primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyroiditis, Raynaud's phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma, optionally systemic scleroderma, sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiffman (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes, cutaneous SLE, systemic necrotizing vasculitis, ANCA-associated vasculitis, optionally Churg-Strauss vasculitis or syndrome (CSS), tabes dorsalis, Takayasu's arteritis, telangiectasia, temporal arteritis/Giant cell arteritis, thromboangiitis ubiterans, thrombocytopenia, including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria, optionally chronic allergic urticaria and chronic idiopathic urticaria, including chronic autoimmune urticaria, uveitis, anterior uveitis, uveoretinitis, valvulitis, vascular dysfunction, vasculitis, vertebral arthritis, vesiculobullous dermatosis, vitiligo, Wegener's granulomatosis (Granulomatosis with Polyangiitis (GPA)), Wiskott-Aldrich syndrome, or x-linked hyper IgM syndrome.

Clause 133. The method or use of any of the foregoing Clauses which is used to treat an autoimmune disease selected from the group consisting of multiple sclerosis, psoriasis; rheumatoid arthritis; psoriatic arthritis, systemic lupus erythematosus (SLE); discoid lupus erythematosus, inflammatory bowel disease, ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune haemolytica anemia, Guillain-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anemia, pemphigus, pemphigus vulgaris, cirrhosis, primary biliary cirrhosis, dermatomyositis, polymyositis, fibromyositis, myogelosis, celiac disease, immunoglobulin A nephropathy, Henoch-Schonlein purpura, Evans syndrome, dermatitis, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis nodosa, chondrocalcinosis, Wegener's granulomatosis, microscopic polyangiitis, chronic urticaria, bullous skin disorders, pemphigoid, atopic eczema, childhood autoimmune hemolytic anemia, idiopathic autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, idiopathic pericarditis, myocarditis, vasculitis, gastritis, gout, gouty arthritis, and inflammatory skin disorders, normocomplementemic urticarial vasculitis, pericarditis, myositis, anti-synthetase syndrome, scleritis, macrophage activation syndrome, Behcet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, a rheumatic disease, polymyalgia rheumatica, mixed connective tissue disease, inflammatory rheumatism, degenerative rheumatism, extraarticular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, temporal arteritis, giant cell arteritis, Takayasu arteritis, Behcet's disease, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, fibromyalgia, chronic fatigue and immune dysfunction syndrome (CFIDS), autoimmune inner ear disease, Hyper IgD syndrome, Schnitzler's syndrome, autoimmune retinopathy, age-related macular degeneration, atherosclerosis, chronic prostatitis, alopecia, alopecia areata, alopecia universalis, alopecia totalis, autoimmune thrombocytopenic purpura, idiopathic thrombocytopenic purpura, pure red cell aplasia, and TNF receptor-associated periodic syndrome (TRAPS).

Clause 134. The method or use of any of the foregoing Clauses, wherein the diagnosis and/or treatment is combined with another moiety useful for treating immune related condition.

Clause 135. The method or use of Clause 134, wherein said other moiety useful for treating immune related condition is selected from immunosuppressants such as corticosteroids, cyclosporin, cyclophosphamide, prednisone, azathioprine, methotrexate, rapamycin, tacrolimus, lef unomide or an analog thereof; mizoribine; mycophenolic acid; mycophenolate mofetil; 15-deoxyspergualine or an analog thereof; biological agents such as TNF-a blockers or antagonists, or any other biological agent targeting any inflammatory cytokine, nonsteroidal antiinflammatory drugs/Cox-2 inhibitors, hydroxychloroquine, sulphasalazopryine, gold salts, etanercept, infliximab, mycophenolate mofetil, basiliximab, atacicept, rituximab, Cytoxan, interferon β-Ia, interferon β-Ib, glatiramer acetate, mitoxantrone hydrochloride, anakinra and/or other biologies and/or intravenous immunoglobulin (IVIG), interferons such as IFN-p-Ia (REBIF®. AVONEX® and CINNOVEX®) and IFN-p-Ib (BETASERON®); EXTAVIA®, BETAFERON®, ZIFERON®); glatiramer acetate (COPAXONE®), a polypeptide; natalizumab (TYSABRI®), mitoxantrone (NOVANTRONE®), a cytotoxic agent, a calcineurin inhibitor, e.g. cyclosporin A or FK506; an immunosuppressive macrolide, e.g. rapamycine or a derivative thereof; e.g. 40-O-(2-hydroxy)ethyl-rapamycin, a lymphocyte homing agent, e.g. FTY720 or an analog thereof, corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CDI Ia/CD18, CD7, CD25, CD27, B7, CD40, CD45, CD58, CD137, ICOS, CD150 (SLAM), OX40, 4-1BB or their ligands; or other immunomodulatory compounds, e.g. CTLA4-Ig (abatacept, ORENCIA®, belatacept), CD28-g, B7-H4-Ig, or other costimulatory agents, or adhesion molecule inhibitors, e.g. mAbs or low molecular weight inhibitors including LFA-1 antagonists, Selectin antagonists and VLA-4 antagonists, or another immunomodulatory agent.

Clause 136. An anti-VSIG3 antibody or antigen-binding fragment or VSIG3 fusion protein or composition, or method or use according to any of the foregoing Clauses which includes another moiety is useful for reducing the undesirable immune activation that follows gene therapy.

Clause 137. An anti-VSIG3 antibody or antigen-binding fragment or VSIG3 fusion protein or composition, or method or use according to any of the foregoing Clauses which includes treatment with an anti-VSIG3 antibody or antigen-binding fragment or composition containing combined with another therapeutic agent or therapy.

Clause 138. An anti-VSIG3 antibody or antigen-binding fragment or VSIG3 fusion protein or composition, or method or use according to any of the foregoing Clauses, further comprising a Therapeutic agent targeting immunosuppressive cells Tregs and/or MDSCs is selected from antimitotic drugs, cyclophosphamide, gemcitabine, mitoxantrone, fludarabine, thalidomide, thalidomide derivatives, COX-2 Inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors, sildenafil, ROS inhibitors and nitroaspirin.

Clause 139. An anti-VSIG3 antibody or antigen-binding fragment or VSIG3 fusion protein or composition, or method or use according to any of the foregoing Clauses, further comprising another antibody is selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD137, OX40, GITR, CD27, CD28 or ICOS.

Clause 140. The method or use of any of the foregoing Clauses, which includes assaying VSIG3 and/or VISTA protein by the individual's cells prior, concurrent and/or after treatment.

Clause 141. The method or use of Clause 140, wherein the method detects the expression of VSIG3 and/or VISTA protein by diseased and/or normal cells prior to treatment, optionally by the use of an antibody or nucleic acid that detects VSIG3 and/or VISTA expression.

Clause 142. The method or use of any one of the foregoing Clauses, which further includes the administration or use of another diagnostic or therapeutic agent, which may be administered prior, concurrent or after the administration of the anti-VSIG3 antibody, or antigen-binding fragment or composition containing according to any one of the foregoing Clauses.

Clause 143. The method or use of Clause 142, which includes the administration of another therapeutic agent.

Clause 144. The method or use of Clause 143, wherein the other therapeutic agent is selected from a drug, another immunomodulatory compound, a radionuclide, a fluorophore, an enzyme, a toxin, or a chemotherapeutic agent; and the detectable agent is selected from a radioisotope, a metal chelator, an enzyme, a fluorescent compound, a bioluminescent compound or a chemiluminescent compound.

Clause 145. The method or use of any one of the foregoing Clauses, which further includes the administration of an antibody or antigen-binding fragment thereof which specifically binds to a NK cell receptor.

Clause 146. The method or use of Clause 145, wherein the antibody or antigen-binding fragment thereof which specifically binds to an NK cell receptor agonizes the effect of said NK cell receptor.

Clause 147. The method or use of Clause 146, wherein the antibody or antigen-binding fragment thereof which specifically binds to an NK cell receptor antagonizes the effect of said NK cell receptor or one that inhibits NK cell activity.

Clause 148. The method or use of Clause 147, wherein the inhibitory NK cell receptor is selected from the group consisting of KIR2DL1, KIR2DL2/3, KIR2DL4, KIR2DL5A, KIR2DL5B, KIR3DL1, KIR3DL2, KIR3DL3, LILRB 1, NKG2A, NKG2C, NKG2E and LILRB5.

Clause 149. The method or use of Clause 145, wherein the NK cell receptor is one that promotes NK cell activity.

Clause 150. The method or use of Clause 149, wherein the NK cell activating receptor is selected from the group consisting of NKp30, NKp44, NKp46, NKp46, NKG2D, KIR2DS4 CD2, CD 16, CD69, DNAX accessory molecule-1 (DNAM-1), 2B4, NK1.1; a killer immunoglobulin (Ig)-like activating receptors (KAR); ILTs/LIRs; NKRP-1, CD69; CD94/NKG2C and CD94/NKG2E heterodimers, NKG2D homodimer KIR2DS and KIR3DS.

Clause 151. An assay method for selecting an anti-VSIG3 antibody or antigen-fragment or VSIG3 fusion protein according to any of the foregoing Clauses, or an anti-VSIG3 antibody or antigen-fragment suitable for use in a method or use according to any of the foregoing Clauses, wherein the method comprises (i) obtaining one or more antibodies or VSIG3 fusion protein that putatively bind to a VSIG3 polypeptide having a sequence selected from an amino acid sequence set forth in any of SEQ ID NOs: 1, or binding to a polypeptide possessing at least 90% sequence identity therewith or to a non-human VSIG3 ortholog, or a fragment or variant thereof containing at least one VSIG3 epitope, which fragment or variant possesses at least 90% identity thereto, or to a non-human VSIG3 ortholog (ii) determining whether said antibody or antigen-binding fragment specifically binds to said VSIG3 polypeptide, (iii) determining whether said antibody or antigen-binding fragment modulates (agonizes or antagonizes) at least one effect of VSIG3 on immunity, and (iv) if (ii) and (iii) are satisfied selecting said antibody as one potentially useful in a method or use according to any of the foregoing Clauses.

Clause 152. The method of Clause 151 which further includes humanization, primatization or chimerization if the antibody or antigen-binding fragment is not a human or non-human primate antibody or a fragment thereof.

Clause 153. The method of Clauses 151 or 152 wherein the immunogen used to derive said antibody or antigen-binding fragment comprises a VSIG3 polypeptide having a sequence selected from an amino acid sequence set forth in any of SEQ ID NO: 1, or binding to a polypeptide possessing at least 90% sequence identity therewith or to a non-human VSIG3 ortholog or the same region of a nn-human VSIG3 ortholog, or a fragment or variant thereof containing at least one VSIG3 epitope.

Clause 154. The method of any of Clauses 151-153 wherein the immunogen used to derive said antibody or antigen-binding fragment comprises a VSIG3 polypeptide having a sequence selected from an amino acid sequence set forth in any of SEQ ID NO: for binding to a polypeptide possessing at least 90% sequence identity therewith or to the same region of a non-human ortholog of hVSIG3.

Clause 155. The method of any of Clauses 151-154, wherein the immunogen used to derive said antibody or antigen-binding fragment thereof consists of a polypeptide having an amino acid sequence set forth in any of SEQ ID NO: 1, or binding to a polypeptide possessing at least 90% sequence identity therewith or to the same region of a non-human VSIG3 ortholog, or a conjugate thereof not containing another portion of any of the VSIG3 polypeptide.

Clause 156. The method of any of Clauses 151-155, wherein step (iii) detects whether the anti-VSIG3 antibody or antigen binding fragment antagonizes at least one effect of VSIG3 and/or VISTA on immunity.

Clause 157. The method of any of Clauses 151-156, wherein step (iii) detects whether the anti-VSIG3 antibody or antigen binding fragment agonizes at least one effect of VSIG3 and/or VISTA on immunity.

Clause 158. The method of any of Clauses 151-157, wherein the selected antibody or VSIG3 fusion protein is demonstrated to mediate at least one of the following effects: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) induces direct killing of cancer cells, (xxvii) increases Th1 7 activity and/or (xxviii) induces complement dependent cytotoxicity and/or antibody dependent cell-mediated cytotoxicity, with the proviso that said anti-VSIG3 antibody or antigen-binding fragment may elicit an opposite effect to one or more of (i)-(xxviii).

Clause 159. The method of any of the foregoing Clauses, wherein the selected antibody or VSIG3 fusion protein is demonstrated to mediate at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv)

decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VSIG3 antibody or antigen-binding fragment may elicit an opposite effect to one or more of (i)-(xxviii).

Clause 160. The method of any of Clauses 149-159 wherein the selected antibody or VSIG3 fusion protein agonizes or antagonizes the effects of VSIG3 and/or VISTA on T cell activity, NK cell activity, and/or the production of one or more proinflammatory cytokines.

Clause 161. The method of any of Clauses 149-160 wherein the selected antibody or VSIG3 fusion protein is demonstrated to compete with binding to human or rodent VSIG3 to VISTA.

Clause 162. An immunomodulatory antibody or antigen-binding fragment or VSIG3 fusion protein according to any one of the foregoing Clauses or a pharmaceutical or diagnostic composition containing same.

Clause 163. Use of immunomodulatory antibody or antigen-binding fragment or VSIG3 fusion protein according to any one of the foregoing Clauses or a pharmaceutical or diagnostic composition containing same for treating or diagnosing a disease selected from cancer, infection, sepsis, autoimmunity, inflammatory conditions, allergic or other immune related condition or to suppress an undesired immune reaction to a cell or gene therapy therapeutic or a transplanted cell, tissue or organ.

Clause 164. A transplant therapy which includes the transplant of cells, tissue or organ into a recipient, wherein the cells, tissue or organ or treated ex vivo using a composition containing an anti-VSIG3 antibody or antigen-binding fragment or VSIG3 fusion protein or composition according to any one of the foregoing Clauses prior to infusion or transplant of said cells, tissue or organ into the recipient.

Clause 165. The method of Clause 164, wherein the composition comprises immune cells of the donor and/or transplant recipient.

Clause 166. The method of Clauses 164 or 165 wherein the transplanted cells, tissue or organ comprises bone marrow, other lymphoid cells or tissue or stem cells.

Clause 167. A nucleic acid encoding the variable heavy and/or light region polypeptide of an anti-VSIG3 antibody or antibody fragment according to any one of the foregoing Clauses or a vector or virus containing.

Clause 168. An isolated or recombinant cell which comprises at least one nucleic acid or vector or virus according to Clause 167.

Clause 169. The cell of Clause 168 which is selected from a hybridoma and a recombinant bacterial, yeast or fungal, mammalian, insect, amphibian, reptilian, plant, and avian cell or egg.

Clause 170. A method of producing an anti-VSIG3 antibody or antibody fragment by culturing an isolated or recombinant cell according to Clause 169.

Clause 171. The method of Clause 170 wherein the cell is a bacterial, yeast, fungal, insect, plant, reptilian, mammalian cell or an avian egg.

Clause 172. An in vitro or in vivo method of using an antagonist compound according to any one of the foregoing Clauses to inhibit the interaction of VISTA and VSIG3.

Clause 173. An in vitro or in vivo method of using an antagonist compound according to any one of the foregoing Clauses to inhibit the suppressive effects of VISTA and/or VSIG3 on immune cells or immunity.

Clause 174. The method of Clause 172 or 173, which inhibits or blocks the suppressive effect of VISTA and/or VSIG3 on T cell activation, T cell proliferation or cytokine production or on myeloid dendritic cells.

Clause 175. The method of Clause 172 or 173, which inhibit or block the promoting effect of VISTA on T suppressor (Tsup) cells.

Clause 176. The method of any of Clause 172-175 which is used to treat a cancer or infectious disease.

Clause 177. The method of Clause 176, wherein the cancer is a solid tumor, e.g., a sarcoma, carcinoma or lymphoma or a blood cancer.

Clause 178. The method of Clause 176, wherein the infectious disease is a viral, bacterial, protozoan, yeast, fungal, or parasitic disease.

Clause 179. A method of using a VSIG3 agonist compound according to any one of the foregoing Clauses to enhance the interaction of VISTA and VSIG3.

Clause 180. The method of Clause 179, which enhances or promotes the suppressive effect of VISTA on T cell activation, proliferation or cytokine production.

Clause 181. The method of Clause 178 or 179, which is used to treat an autoimmune, allergic or inflammatory condition.

Clause 182. A compound according to any one of the foregoing Clauses, which is attached to a detectable label.

Clause 183. A diagnostic or therapeutic composition comprising a diagnostically or therapeutically effective amount of a compound according to any one of the foregoing Clauses.

Clause 184. The composition of Clause 183, which is suitable for use in human therapy.

Clause 185. The composition of Clause 184 which is an intravenous, subcutaneous or intramuscularly administrable composition.

Clause 186. A method according to any one of the foregoing Clauses, which further comprises the administration of a PD-1 or PD-L1 agonist or antagonist.

Clause 187. The method of Clause 186, wherein said PD-1 or PD-L1 agonist or antagonist is selected from an anti-PD-1 antibody or antibody fragment, an anti-PD-L1 antibody or antibody fragment, a PD-L1 polypeptide or fragment thereof which may be monovalent or multimeric, a PD-1 polypeptide or fragment thereof which may be monovalent or multimeric, or a complex or fusion protein comprising any of the foregoing.

Clause 188. A method of contacting immune cells with a VSIG3 agonist or antagonist compound according to any one of the foregoing Clauses.

Clause 189. The method of Clause 188, wherein said contacted cells are infused into a human subject.

Clause 190. The method of Clause 188 or 189, wherein the subject has cancer or an infectious disease.

Clause 191. The method of Clause 188 or 189, wherein the subject has an inflammatory, allergic or autoimmune condition.

Clause 192. A screening assay which comprises the use of VSIG3 alone or in association with VSIG3 to identify VSIG3/VISTA agonists or antagonists.

Clause 193. The assay of Clause 192 which is a binding assay that identifies compounds that bind VSIG3 and inhibit the VSIG3/VISTA interaction.

Clause 194. The assay of Clause 192 which is a binding assay that identifies compounds that bind VSIG3 and enhance the VSIG3/VISTA interaction.

Clause 195. The assay of Clause 192 which is a functional assay that screens for compounds that inhibit the effects the VISTA/VSIG3 interaction on T cell immunity or cytokine production.

Clause 196. The assay of Clause 192-195 which is a functional assay that screens for compounds that enhance the effects the VISTA/VSIG3 interaction on T cell immunity or cytokine production.

Clause 197. The assay of any one of Clauses 192-196 which uses human or rodent immune cells.

Clause 198. The assay of any one of Clauses 192-196 which uses a transgenic animal that expresses human VISTA and/or human VSIG3.

Clause 199. The assay of Clause 192-198 which is a high throughput screening assay.

Clause 200. The compound or method of any of the foregoing Clauses wherein said VSIG3 is a human, murine, or non-human primate VSIG3 protein.

Clause 201. An isolated polypeptide comprising a fragment of a VSIG3 ECD, wherein said fragment consists essentially of or consists of an amino acid sequence as set forth in any one of SEQ ID NO: 1 or a variant thereof that possesses at least 80, 85, 90, 95, 96, 97, 98, or 99% sequence identity therewith.

Clause 202. The isolated polypeptide of Clause 201, which comprises 2-10 of said VSIG3 ECD polypeptide fragments.

Clause 203. An isolated polypeptide according to Clauses 201 or 202, wherein said fragments are intervened by a heterologous linker, wherein said linker is not a fragment of a VSIG3 polypeptide.

Clause 204. The isolated peptide of Clause 203, wherein said linker is directly or indirectly conjugated to said fragments.

Clause 205. The isolated polypeptide of Clauses 202, 203 or 204, wherein said linker is an amino acid spacer.

Clause 206. The isolated peptide of Clause 205, wherein said amino acid spacer is of sufficient length of amino acid residues so that the different fragments can successfully bind to their individual targets.

Clause 207. The isolated polypeptide of Clauses 205 or 206, wherein said linker is a peptide comprising 5-50 amino acid residues, more preferably 5-25 amino acid residues.

Clause 208. The isolated peptide of Clause 207, wherein said linker is a peptide comprising 5-15 amino acid residues.

Clause 209. The isolated polypeptide of any of Clauses 205-208, wherein said linker comprises or consists essentially of glycine, serine, and/or alanine residues or predominantly (at least 50, 60, 70 or 80% of the residues) consists of glycine, serine, and/or alanine residues.

Clause 210. The isolated peptide of any of Clauses 205-209, wherein said linker comprises at least 4-40, 4-30, 4-20, or 4-12 glycine, serine, and/or alanine residues.

Clause 211. A fusion protein comprising the isolated polypeptide of any of the preceding Clauses, or SEQ ID NO. 1, joined to a heterologous polypeptide and/or half-life extending moiety, with the proviso that said heterologous polypeptide or said half-life extending moiety is not a fragment of a VSIG3 polypeptide.

Clause 212. The fusion protein according to Clause 211, wherein said isolated polypeptide and said heterologous molecule are intervened by a heterologous linker, with the proviso that said linker does not comprise a polypeptide that is a fragment of a VSIG3 polypeptide.

Clause 213. The fusion protein of Clause 212, wherein said linker is directly or indirectly conjugated to said fragments.

Clause 214. The fusion protein of Clauses 212 or 213, wherein said linker is an amino acid spacer.

Clause 215. The fusion protein of Clause 214, wherein said amino acid spacer is of sufficient length of amino acid residues so that the different fragments can successfully bind to their individual targets.

Clause 216. The fusion protein of Clauses 214 or 215, wherein said linker is a peptide comprising 5-50 amino acid residues, more preferably 5-25 amino acid residues.

Clause 217. The fusion protein of Clause 216, wherein said linker is a peptide comprising 5-15 amino acid residues.

Clause 218. The fusion protein of any of Clauses 214-217, wherein said linker comprises or consists essentially of glycine, serine, and/or alanine residues or predominantly (at least 50, 60, 70 or 80% of the residues) consists of glycine, serine, and/or alanine residues.

Clause 219. The fusion protein of any of Clauses 214-218, wherein said linker comprises at least 4-40, 4-30, 4-20, or 4-12 glycine, serine, and/or alanine residues.

Clause 220. The fusion protein of any of the above Clauses, comprising or further comprising a half-life extending moiety.

Clause 221. The fusion protein according to any of Clauses 214-220, wherein the half-life extending moiety comprises polyethylene glycol (PEG), monomethoxy PEG (mPEG), an XTEN molecule, an rPEG molecule, an adnectin, a serum albumin, human serum albumin, immunoglobulin constant region or fragment thereof, or acyl group.

Clause 222. The fusion protein according to any one of Clauses 214-221, wherein the addition of said heterologous polypeptide, half-life extending moiety, or other heterologous molecule increases the in vivo half-life of said fusion protein by at least 2-fold, at least 3-fold, at least 4-fold, at least 5-fold, at least 10-fold, or more, as compared to the identical molecule without such said heterologous polypeptide, half-life extending moiety, or other heterologous molecule.

Clause 223. The fusion protein according to any of the foregoing Clauses which comprises an immunoglobulin molecule or a fragment thereof.

Clause 224. The fusion protein according to Clause 214 wherein at least one of the heterologous polypeptides is a human or non-human immunoglobulin Fc polypeptide or fragment that comprises heavy and/or light chain Cm and Cm domains.

Clause 225. The fusion protein of Clauses 214 or 215, wherein at least one of the heterologous polypeptides is a human or non-human immunoglobulin Fc polypeptide or fragment that comprises heavy chain Cm and Cm domains.

Clause 226. The fusion protein according to any of Clauses 214-216 that comprises heavy and/or light chain $C_{H1}$ domains.

Clause 227. The fusion protein according to any of Clauses 214-216 that lacks heavy and/or light chain $C_{H1}$ domains.

Clause 228. The fusion protein according to any of Clauses 214-218 that lacks heavy chain $C_{H1}$ domains.

Clause 229. The fusion protein of any of the above Clauses, wherein said immunoglobulin molecule or a fragment thereof comprises a hinge region.

Clause 230. The fusion protein of Clause 229, wherein said hinge region is an intact hinge region.

Clause 231. The fusion protein of any of the above Clauses, wherein said immunoglobulin molecule or a fragment thereof does not feature a hinge region.

Clause 232. The fusion protein according to any of the foregoing Clauses which comprises a human immunoglobulin molecule or a fragment thereof.

Clause 233. The fusion protein of any of the foregoing Clauses, wherein said heterologous polypeptide comprises or consists of an Fc fragment of the immunoglobulin heavy chain constant region.

Clause 234. The fusion protein of any of the foregoing Clauses, wherein said heterologous polypeptide comprises or consists of an Fc fragment and hinge region of a human immunoglobulin heavy chain constant region.

Clause 235. The fusion protein of any of the foregoing Clauses comprising an immunoglobulin heavy chain constant region derived from an immunoglobulin isotype selected from the group consisting of an IgG1, IgG2, IgG3, IgG4, IgM, IgE, IgA and IgD.

Clause 236. The fusion protein of any of the foregoing Clauses comprising a human immunoglobulin heavy chain constant region selected from the group consisting of a human IgG1, IgG2, IgG3, and IgG4.

Clause 237. The fusion protein of any of the foregoing Clauses comprising a mouse IgG1, IgG2a or IgG2b immunoglobulin heavy chain constant region or fragment thereof.

Clause 238. The fusion protein of any of the foregoing Clauses, which comprises an immunoglobulin Fc region that contains at least one mutation that alters effector function and/or glycosylation.

Clause 239. The fusion protein of Clause 238 wherein said effector function is selected from FcR binding, complement binding, ADCC activity, CDC activity, degranulation, phagocytosis, and/or cytokine release.

Clause 240. The fusion protein according to any of the above Clauses, wherein the heterologous sequence comprises at least a portion of an immunoglobulin molecule that specifically binds to a target cell or comprises another moiety that specifically binds to a target cell.

Clause 241. The fusion protein according to Clause 41 wherein the target cell is a cancerous, immune, infectious agent cell, an infected cell, an immune cell, an inflammatory cell, a disease site or a cell which is to be transplanted into a human recipient.

Clause 242. The fusion protein of Clause 241, wherein said infectious agent cell is selected from the group consisting of a virus, bacterium, mycoplasm, fungus, yeast or parasite.

Clause 243. The fusion protein of Clauses 240 or 241, wherein said infected cell is infected with an infectious agent selected from the group consisting of a virus, bacterium, mycoplasm, fungus, yeast or parasite.

Clause 244. The fusion protein of any of the above Clauses, wherein at least one of the heterologous polypeptides is a receptor, hormone, cytokine, antigen, B-cell target, NK cell target, T cell target, TNF receptor superfamily member, Hedgehog family member, a receptor tyrosine kinase, a proteoglycan-related molecule, a TGF-β superfamily member, a Wnt-related molecule, a receptor ligand, a Dendritic cell target, a myeloid cell target, a monocyte/macrophage cell target or an angiogenesis target.

Clause 245. The fusion protein of Clause 244, wherein the antigen is a tumor antigen, autoantigen, allergen, or an infectious agent antigen.

Clause 246. The fusion protein of any of the above Clauses, wherein the at least one heterologous polypeptide includes an immunomodulatory polypeptide.

Clause 247. The fusion protein of any of Clauses 244-246, wherein the T cell target is selected from the group consisting of 2B4/SLAMF4, IL-2 Ra, 4-1BB/TNFRSF9, IL-2R, ALCAM, B7-1/CD80, IL-4R, B7-H3, BLAME/SLAMF8, BTLA, IL-6R, CCR3, IL-7 Ra, CCR4, CXCRI/IL-8 RA, CCR5, CCR6, IL-10 R a, CCR7, IL-10 Rβ, CCR8, IL-12 R131, CCR9, IL-12 Rβ2, CD2, IL-13Ra1, IL-13, CD3, CD4, ILT2/CD85j, ILT3/CD85k, ILT4/CD85d, ILT5/CD85a, Integrin a 4/CD49d, CD5, Integrin aE/CD103, CD6, Integrin a M/CD1 Ib, CD8, Integrin a X/CD1 Ic, Integrin 2/CD18, KIR/CD158, CD27/TNFRSF7, KIR2DL1, CD28, KIR2DL3, CD30/TNFRSF8, KIR2DL4/CD158d, CD31/PECAM-1, KIR2DS4, CD40 Ligand/TNFSF5, LAG-3, CD43, LAIR1, CD45, LAIR2, CD83, Leukotriene B4 RI, CD84/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 Ry, Osteopontin, CRACC/SLAMF7, PD-1, CRTAM, PSGL-1, CTLA-4, RANK/TNFRSF11 A, CX3CR1, CX3CL1, L-Selectin, CXCR3, SIRP βi, CXCR4, SLAM, CXCR6, TCCRAVSX-1, DNAM-1, Thymopoietin, EMMPRIN/CD 147, TIM-1, EphB6, TIM-2, Fas/TNFRSF6, TIM-3, Fas Ligand/TNFSF6, TIM-4, Fey RIII/CD16, TIM-6, GITR/TNFRSF18, TNF RI/TNFRSFIA, Granulysin, TNF R11/TNFRSF1B, HVEM/TNFRSF14, TRAIL RI/TNFRSFIOA, ICAM-1/CD54, TRAIL R2/TNFRSF10B, ICAM-2/CD102, TRAIL R3/TNFRSF10C, IFN-yRI, TRAIL R4/TNFRSF10D, IFN-yR2, TSLP, IL-1 RI and TSLP R.

Clause 248. The fusion protein of any of Clauses 244-246, wherein the monocyte/macrophage cell target is selected from the group consisting of B7-1/CD80, ILT4/CD85d, B7-H1, ILT5/CD85a, Common (3 Chain, Integrin a 4/CD49d, BLAME/SLAMF8, Integrin a X/CDI Ic, CCL6/C10, Integrin β2/CD18, CD155/PVR, Integrin β3/CD61, CD31/PECAM-1, Latexin, CD36/SR-B3, Leukotriene B4 RI, CD40/TNFRSF5, LIMPII/SR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc yRI/CD64, Osteopontin, Fc γ RIIB/CD32b, PD-L2, Fc yRIIC/CD32c, Siglec-3/CD33, Fey RIIA/CD32a, SIGNR1/CD209, Fey RIII/CD16, SLAM, GM-CSF R a, TCCR/WSX-1, ICAM-2/CD102, TLR3, IFN-y RI, TLR4, IFN-y R2, TREM-1, IL-1 RII, TREM-2, ILT2/CD85j, TREM-3, ILT3/CD85k, TREMLI/TLT-1, 2B4/SLAMF4, IL-10 R a, ALCAM, IL-10 R (3, Aminopeptidase N/ANPEP, ILT2/CD85j, Common β Chain, ILT3/CD85k, Clq R1/CD93, ILT4/CD85d, CCR1, ILT5/CD85a, CCR2, Integrin a 4/CD49d, CCR5, Integrin a M/CDI Ib, CCR8, Integrin a X/CDI Ic, CD155/PVR, Integrin β2/CD18, CD14, Integrin β3/CD61, CD36/SR-B3, LAIR1, CD43, LAIR2, CD45, Leukotriene B4 RI, CD68, LIMPII/SR-B2, CD84/SLAMF5, LMIR1/CD300A, CD97, LMIR2/CD300c, CD 163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD 147, MMR, Endoglin/CD105, NCAM-L1, Fc y R1/CD64, PSGL-1, Fc y RIII/CD16, RP105, G-CSF R, L-Selectin, GM-CSF R a, Siglec-3/CD33, HVEM/TNFRSF14, SLAM, ICAM-1/CD54, TCCR/WSX-1, ICAM-2/CD102, TREM-1, IL-6 R, TREM-2, CXCRI/IL-8 RA, TREM-3 and TREMLI/TLT-1.

Clause 249. The fusion protein of any of Clauses 244-246, wherein the Dendritic cell target is selected from the group consisting of CD36/SR-B3, LOX-1/SR-E1, CD68, MARCO, CD163, SR-AI/MSR, CD5L, SREC-I, CL-P1/COLEC12, SREC-II, LIMPII/SR-B2, RP105, TLR4, TLR1, TLR5, TLR2, TLR6, TLR3, TLR9, 4-1BB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, Integrin a 4/CD49d, Aag, Integrin β2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB, CCR7, LMIR6/CD300LE, CD40/TNFRSF5, MAG/Siglec-4a, CD43, MCAM, CD45, MD-1, CD68, MD-2, CD83, MDL-1/CLEC5A, CD84/SLAMF5, MMR, CD97, NCAM-L1, CD2F-10/SL AMF9, Osteoactivin/GPNMB, Chem 23, PD-L2, CLEC-1, RP105, CLEC-2, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD 148, SIGNR4, DLEC, SLAM, EMMPRIN/CD 147, TCCR/WSX-1, Fc γ R1/CD64, TLR3, Fc γ RIIB/CD32b, TREM-1, Fc Y RIIC/CD32C, TREM-2, Fc γ RIIA/CD32a, TREM-3, Fc γ RIII/CD16, TREMLI/TLT-1, ICAM-2/CD102 and Vanilloid RI.

Clause 250. The fusion protein of any of Clauses 244-246, wherein the TNF receptor superfamily member is selected from the group consisting of 4-1BB/TNFRSF9, NGF R/TNFRSF16, BAFF R/TNFRSF13C, Osteoprotegerin/TNFRSFIIB, B CMA/TNFRSF 17, OX40/TNFRSF4, CD27/TNFRSF7, RANK/TNFRSF11 A, CD30/TNFRSF8, RELT/TNFRSF19L, CD40/TNFRSF5, TACI/TNFRSF13B, DcR3/TNFRSF6B, TNF RI/TNFRSF1A, DcTRAIL R1/TNFRSF23, TNF RII/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF 10D, Fas/TNFRSF6, TROY/TNFRSF19, GITR/TNFRSF 18, TWEAK R/TNFRSF12, HVEM/TNFRSF14, XEDAR, Lymphotoxin (3 R/TNFRSF3, 4-1BB Ligand/TNFSF9, Lymphotoxin, APRIL/TNFSF 13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF-/TNFSFIB, EDA-A2, TRAIL/TNFSF10, Fas Ligand/TNFSF6, TR ANCE/TNF SF 11, GITR Ligand/TNFSF18, TWEAK/TNF SF12 and LIGHT/TNFSF14.

Clause 251. The fusion protein of any of Clauses 244-246, wherein the Hedgehog family member is selected from the group consisting of Patched and Smoothened.

Clause 252. The fusion protein of any of Clauses 244-246, wherein the receptor tyrosine kinase is selected from the group consisting of Axl, FGF R4, Clq R1/CD93, FGF R5, DDR1, Flt-3, DDR2, HGF R, Dtk, IGF-I R, EGF R, IGF-II R, Eph, INSRR, EphAI, Insulin R/CD220, EphA2, M-CSF R, Eph A3, Mer, EphA4, MSP R/Ron, EphA5, MuSK, EphA6, PDGF R a, EphA7, PDGF R (3, EphA8, Ret, EphB I, ROR1, EphB2, ROR2, EphB3, SCF R/c-kit, EphB4, Tie-1, EphB6, Tie-2, ErbB2, TrkA, ErbB3, TrkB, ErbB4, TrkC, FGF RI, VEGF RI/Flt-1, FGF R2, VEGF R2/Flk-1, FGF R3 and VEGF R3/Flt-4.

Clause 253. The fusion protein of any of Clauses 244-246, wherein the Transforming Growth Factor (TGF)-superfamily member is selected from the group consisting of Activin RIA/ALK-2, GFR a-1, Activin RIB/ALK-4, GFR a2, Activin RHA, GFR a-3, Activin RUB, GFR a-4, ALK-1, MIS RII, ALK-7, Ret, B MPR-I A/ALK-3, TGF-beta RI/ALK-5, BMPR-IB/ALK-6, TGF-β RII, BMPR-II, TGF-β RIIb, Endoglin/CD 105 and TGF-β RIII.

Clause 254. The fusion protein of any of Clauses 244-246, wherein the Wnt-related molecule selected from the group consisting of Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP, LRP 5, LRP 6, Wnt-1, Wnt-8a, Wnt-3a, Wnt-10b, Wnt-4, Wnt-11, Wnt-5a, Wnt-9a and Wnt-7a.

Clause 255. The fusion protein of any of Clauses 244-246, wherein the receptor ligand is selected from the group consisting of 4-IBB Ligand/TNFSF9, Lymphotoxin, APRIL/TNFSF13, Lymphotoxin/TNF SF3, BAFF/TNFSF13C, OX40 Ligand/TNF SF4, CD27 Ligand/TNF SF7, TL1A/TNFSF15, CD30 Ligand/TNFSF8, TNF-a/TNFSFIA, CD40 Ligand/TNFSF5, TNF/TNFSFIB, EDA-A2, TRAIL/TNFSF10, Fas Ligand/TNFSF6, TRANCE/TNFSF11, GITR Ligand/TNFSF18, TWEAK/TNFSF12, LIGHT/TNFSF 14, Amphiregulin, NRG1 isoform GGF2, Betacellulin, NRG1 Isoform SMDF, EGF, NRGI-a/HRGI-a, Epigen, NRGI-β I/HRGI-β 1, Epiregulin, TGF-a, HB-EGF, TMEFFI/Tomoregulin-1, Neuregulin-3, TMEFF2, IGF-I, IGF-II, Insulin, Activin A, Activin B, Activin AB, Activin C, BMP-2, BMP-7, BMP-3, BMP-8, BMP-3b/GDF-10, BMP-9, BMP-4, BMP-15, BMP-5, Decapentaplegic, BMP-6, GDF-1, GDF-8, GDF-3, GDF-9, GDF-5, GDF-11, GDF-6, GDF-15, GDF-7, Arternin, Neurturin, GDNF, Persephin, TGF-β, TGF-β 2, TGF-β 1, TGF-β3, LAP (TGF-β1), TGF-β 5, Latent TGF-β 1, Latent TGF-β bpl, TGF-β 1.2, Lefty, Nodal, MIS/AMH, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, Neuropilin-1, P1GF, Neuropilin-2, P1GF-2, PDGF, PDGF-A, VEGF, PDGF-B, VEGF-B, PDGF-C, VEGF-C, PDGF-D, VEGF-D and PDGF-AB.

Clause 256. The fusion protein of any of Clauses 244-246, wherein the tumor antigen is selected from the group consisting of Squamous Cell Carcinoma Antigen 1 (SCCA-1), (PROTEIN T4-A), Squamous Cell Carcinoma Antigen 2 (SCCA-2), Ovarian carcinoma antigen CA125 (1A1-3B; KIAA0049), MUCIN 1 (TUMOR-ASSOCIATED MUCIN; Carcinoma-Associated Mucin; Polymorphic Epithelial Mucin; PEM; PEMT; EPISIALIN; Tumor-Associated Epithelial Membrane Antigen; EMA; H23AG; Peanut-Reactive Urinary Mucin; PUM; and Breast Carcinoma-Associated Antigen DF3), CTCL tumor antigen sel-1, CTCL tumor antigen se14-3, CTCL tumor antigen se20-4, CTCL tumor antigen se20-9, CTCL tumor antigen se33-I, CTCL tumor antigen se37-2, CTCL tumor antigen se57-I, CTCL tumor antigen se89-I, Prostate-specific membrane antigen, 5T4 oncofetal trophoblast glycoprotein, Orf73 Kaposi's sarcoma-associated herpesvirus, MAGE-CI (cancer/testis antigen CT7), MAGE-B 1 ANTIGEN (MAGE-XP Antigen; DAM 10), MAGE-B2 Antigen (DAME), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, Tumor-Associated Antigen CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195 and L6.

Clause 257. The fusion protein of any of Clauses 244-246, wherein the B cell target is selected from the group consisting of CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138 and CDw150.

Clause 258. The fusion protein of any of Clauses 244-246, wherein the angiogenesis target is selected from the group consisting of Angiopoietin-1, Angiopoietin-like 2, Angiopoietin-2, Angiopoietin-like 3, Angiopoietin-3, Angiopoietin-like 7/CDT6, Angiopoietin-4, Tie-1, Angiopoietin-like 1, Tie-2, Angiogenin, iNOS, Coagulation Factor III/Tissue Factor, nNOS, CTGF/CCN2, NOV/CCN3, DANCE, OSM, EDG-1, Plfr, EG-VEGF/PK1, Proliferin, Endostatin, ROB04, Erythropoietin, Thrombospondin-1, Kininostatin, Thrombospondin-2, MFG-E8, Thrombospondin-4, Nitric Oxide, VGSQ, eNOS, EphAI, EphA5, EphA2, EphA6, EphA3, EphA7, EphA4, EphA8, EphBI, EphB4, EphB2, EphB6, EphB3, Ephrin-AI, Ephrin-A4, Ephrin-A2, Ephrin-A5, Ephrin-A3, Ephrin-B I, Ephrin-B3, Ephrin-B2, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, FGF RI, FGF R4, FGF R2, FGF R5, FGF R3, Neuropilin-1, Neuropilin-2, Semaphorin 3 A, Semaphorin 6B, Semaphorin 3C, Semaphorin 6C, Semaphorin 3E, Semaphorin 6D, Semaphorin 6A, Semaphorin 7A, MMP, MMP-11, MMP-1, MMP-12, MMP-2, MMP-13, MMP-3, MMP-14, MMP-7, MMP-15, MMP-8, MMP-16/MT3-MMP, MMP-9, MMP-24/MT5-MMP, MMP-10, MMP-25/MT6-MMP, TIMP-1, TIMP-3, TIMP-2, TIMP-4, ACE, IL-13 R a 1, IL-13, Clq R1/CD93, Integrin a 4/CD49d, VE-Cadherin, Integrin β 2/CD18, CD31/PECAM-1, KLF4, CD36/SR-B3, LYVE-1, CD151, MCAM, CL-P1/COLEC12, Nectin-2/CD112, Coagulation Factor III/Tissue Factor, E-Selectin, D6, P-Selectin, DC-SIGNR/CD299, SLAM, EMMPRIN/CD 147, Tie-2, Endoglin/CD105, TNF RI/TNFRSF1A, EPCR, TNF RII/TNFRSF1B, Erythropoietin R, TRAIL RI/TNFRSFIOA, ESAM, TRAIL R2/TNFRSF10B, FABP5, VCAM-1, ICAM-1/CD54, VEGF R2/Flk-1, ICAM-2/CD102, VEGF R3/Flt-4, IL-1 RI and VGSQ.

Clause 259. An isolated polypeptide or the fusion protein according to any of the foregoing Clauses which agonizes at least one immune inhibitory effect of VSIG3 and/or VISTA.

Clause 260. An isolated polypeptide or fusion protein according to Clause 259 which mediates at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-y production by T-cells, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases Inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said isolated or recombinant VSIG3 polypeptide or fusion protein may elicit an opposite effect to one or more of (i)-(xxviii).

Clause 261. An isolated polypeptide or fusion protein according to any of the foregoing Clauses which antagonizes at least one immune inhibitory effect of VSIG3 and/or VISTA.

Clause 262. An isolated polypeptide or fusion protein according to Clause 261 which mediates at least one of the following effects (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-y production by T-cells, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxiv) induces direct killing of cancer cells, (xxvi) increases Th17 activity and/or (xxvii) induces complement dependent cytotoxicity and/or antibody dependent cell-mediated cytotoxicity, with the proviso that said isolated or recombinant VSIG3 polypeptide or fusion protein may elicit an opposite effect to one or more of (i)-(xxvii).

Clause 263. An isolated polypeptide or fusion protein according to any of the above Clauses which agonizes or antagonizes at least one effect of VSIG3 and/or VISTA on T cells, natural killer (NK) cells or the production of one or more proinflammatory cytokines.

Clause 264. An isolated polypeptide or fusion protein according to any of the above Clauses which inhibits or promotes one or more of CTL activity, CD4+ T cell activation and/or CD4+ T cell proliferation and/or cell depletion or the secretion of proinflammatory cytokines.

Clause 265. An isolated polypeptide or fusion protein according to any of the above Clauses which inhibits or promotes NK cell activity.

Clause 266. An Isolated polypeptide or fusion protein according to any of the above Clauses which inhibits or promotes the differentiation, proliferation and/or activity of Tregs, MDSCs, iMCs, mesenchymal stromal cells, TIE2-expressing monocytes, and/or the infiltration of Tregs (Tregs), MDSCs iMCs, mesenchymal stromal cells, TIE2-expressing monocytes.

Clause 267. The polypeptide or fusion protein of Clause 266, wherein said Tregs are inducible Tregs.

Clause 268. An isolated polypeptide or fusion protein according to any of the foregoing Clauses which specifically binds to a receptor expressed by NK cells.

Clause 269. An isolated polypeptide or fusion protein according to any of the foregoing Clauses which specifically binds to a receptor expressed by activated T cells or dendritic or myeloid suppressor or monocyte or neutrophil cells.

Clause 270. A polynucleotide encoding an isolated polypeptide or fusion protein according to any of the foregoing Clauses.

Clause 271. An expression vector or a virus, comprising at least one polynucleotide according to Clause 270.

Clause 272. A recombinant cell comprising an expression vector according to Clause 270 or a virus containing a polynucleotide according to Clause 271, wherein the cell constitutively or inducibly expresses the polypeptide encoded by the DNA segment.

Clause 273. A method of producing an isolated polypeptide or fusion protein according to any of Clauses 200-269, comprising culturing the recombinant cell according to Clause 272, under conditions whereby the cell expresses the polypeptide encoded by the DNA segment or nucleic acid and recovering said polypeptide.

Clause 274. A pharmaceutical composition comprising the isolated protein or fusion protein of any of Clauses 200-269 or comprising a VSIG3 ECD protein set forth in any of SEQ ID NO:1 the polynucleotide of Clause 270, the expression vector or virus of Clause 271, or the recombinant cell of Clause 272.

Clause 275. A pharmaceutical composition according to Clause 274, the isolated polypeptide or fusion protein of any of Clauses 200-269, the polynucleotide of Clause 270, the expression vector or virus of Clause 271, the recombinant cell of Clause 272, for use in treatment in a subject suffering from cancer.

Clause 276. The pharmaceutical composition, cancer immunotherapy, the isolated polypeptide or fusion protein, the polynucleotide, the expression vector or virus, the recombinant cell or the use of Clause 275, for use in immunotherapy treatment of cancer.

Clause 277. The pharmaceutical composition, cancer immunotherapy, the isolated polypeptide or fusion protein, the polynucleotide, the expression vector or virus, the recombinant cell or the use of Clauses 275 or 276, wherein the cancer does not express sufficient levels of VSIG3 protein at diagnosis or prior to the treatment.

Clause 278. The pharmaceutical composition, cancer immunotherapy, the isolated polypeptide or fusion protein, the polynucleotide, the expression vector or virus, the recombinant cell or the use of Clauses 275 or 276, wherein the cancer does express sufficient levels of VSIG3 protein at diagnosis or prior to the treatment.

Clause 279. The pharmaceutical composition, cancer immunotherapy, the isolated polypeptide or fusion protein, the polynucleotide, the expression vector or virus, the recombinant cell or the use of any of Clauses 275-278, wherein said pharmaceutical composition, isolated polypeptide, fusion protein, polynucleotide, expression vector, virus or cell is administered to the subject in need thereof in combination with a therapeutic agent useful for treatment of cancer.

Clause 280. The pharmaceutical composition, cancer immunotherapy, the Isolated polypeptide or fusion protein, the polynucleotide, the expression vector or virus, the recombinant cell or the use of any of Clauses 275-279, for performing at least one of the following: (i) increasing immune response, (ii) increasing T cell activation, (iii) increasing cytotoxic T cell activity, (iv) increasing NK cell activity, (v) increasing Th17 activity, (vi) alleviating T-cell suppression, (vii) increasing pro-inflammatory cytokine secretion, (viii) increasing IL-2 secretion; (ix) increasing interferon-y production by T-cells, (x) increasing Th1 response, (xi) decreasing Th2 response, (xii) decreasing or eliminating at least one of regulatory T cells (Tregs), myeloid derived suppressor cells (MDSCs), iMCs, mesenchymal stromal cells, TIE2-expressing monocytes, (xiii) reducing regulatory cell activity and/or the activity of one or more of myeloid derived suppressor cells (MDSCs), iMCs, mesenchymal stromal cells, TIE2-expressing monocytes, (xiv) decreasing or eliminating M2 macrophages, (xv) reducing M2 macrophage pro-tumorigenic activity, (xvi) decreases or eliminates N2 neutrophils, (xvii) reduces N2 neutrophils pro-tumorigenic activity, (xviii) reducing inhibition of T cell activation, (xix) reducing inhibition of CTL activation, (xx) reducing inhibition of NK cell activation, (xxi) reversing T cell exhaustion, (xxii) increasing T cell response, (xxiii) increasing activity of cytotoxic cells, (xxiv) stimulating antigen-specific memory responses, (xxv) eliciting apoptosis or lysis of cancer cells, (xxvi) stimulating cytotoxic or cytostatic effect on cancer cells, (xxvii) inducing direct killing of cancer cells, and/or (xxviii) inducing complement dependent cytotoxicity and/or (xxix) inducing antibody dependent cell-mediated cytotoxicity.

Clause 281. The pharmaceutical composition, cancer immunotherapy, the isolated polypeptide or fusion protein, the polynucleotide, the expression vector or virus, the recombinant cell or the use of any of Clauses 275-280, further comprising administering an additional therapy comprising one or more of radiotherapy, cryotherapy, antibody therapy, chemotherapy, photodynamic therapy, surgery, hormonal deprivation, targeted therapy agent, a cancer vaccine or combination therapy with conventional drugs.

Clause 282. The pharmaceutical composition, cancer immunotherapy, the isolated polypeptide or fusion protein, the polynucleotide, the expression vector or virus, the recombinant cell or the use of any of Clauses 275-281, wherein the therapeutic agent or additional therapy is selected from the group consisting of cytotoxic drugs, tumor vaccines, antibodies, peptides, pepti-bodies, small molecules, chemotherapeutic agents, cytotoxic and cytostatic agents, immunological modifiers, interferons, interleukins, immunostimulatory growth hormones, cytokines, vitamins, minerals, aromatase inhibitors, RNAi, Histone Deacetylase Inhibitors, and proteasome inhibitors.

Clause 283. The pharmaceutical composition, cancer immunotherapy, the isolated polypeptide or fusion protein, the polynucleotide, the expression vector or virus, the recombinant cell or the use of any of Clauses 275-282, administered to a subject simultaneously or sequentially in combination with one or more therapeutic agents, additional therapy or potentiating agents to obtain a therapeutic effect, wherein said one or more potentiating agents is selected from the group consisting of radiotherapy, conventional/classical anti-cancer therapy potentiating anti-tumor immune responses, Targeted therapy potentiating anti-tumor immune responses, Therapeutic agents targeting immunosuppressive cells Tregs and/or MDSCs, Immunostimulatory antibodies, Cytokine therapy, and Adoptive cell transfer.

Clause 284. The pharmaceutical composition, cancer immunotherapy, the isolated polypeptide or fusion protein, the polynucleotide, the expression vector or virus, the recombinant cell or the use of any of Clauses 275-283, wherein the conventional/classical anti-cancer agent is selected from the group consisting of platinum based compounds, antibiotics with anti-cancer activity, Anthracyclines, Anthracenediones, alkylating agents, antimetabolites, Antimitotic agents, Taxanes, Taxoids, microtubule inhibitors, *Vinca* alkaloids, Folate antagonists, Topoisomerase inhibitors, Antiestrogens, Antiandrogens, Aromatase inhibitors, GnRh analogs, inhibitors of 5a-reductase, bisphosphonates and antibodies.

Clause 285. The pharmaceutical composition, cancer immunotherapy, the isolated polypeptide or fusion protein, the polynucleotide, the expression vector or virus, the recombinant cell or the use of any of Clauses 275-284, wherein the Targeted therapy agent is selected from the group consisting of histone deacetylase (HDAC) inhibitors, proteasome inhibitors, mTOR pathway inhibitors, JAK2 inhibitors, tyrosine kinase inhibitors (TKIs), PI3K inhibitors, Protein kinase inhibitors, Inhibitors of serine/threonine kinases, inhibitors of intracellular signaling, inhibitors of Ras/Raf signaling, MEK inhibitors, AKT inhibitors, inhibitors of survival signaling proteins, cyclin dependent kinase inhibitors, therapeutic monoclonal antibodies, TRAIL pathway agonists, anti-angiogenic agents, metalloproteinase inhibitors, cathepsin inhibitors, inhibitors of urokinase plasminogen activator receptor function, immunoconjugates, antibody drug conjugates, antibody fragments, bispecific antibodies, bispecific T cell engagers (BiTEs).

Clause 286. The pharmaceutical composition, cancer immunotherapy, the isolated polypeptide or fusion protein, the polynucleotide, the expression vector or virus, the recombinant cell or the use of any of Clauses 275-285, wherein the antibody is selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Clause 287. The pharmaceutical composition, cancer immunotherapy, the isolated polypeptide or fusion protein, the polynucleotide, the expression vector or virus, the recombinant cell or the use of any of Clauses 275-286, wherein the Therapeutic agent targeting immunosuppressive cells Tregs and/or MDSCs is selected from antimitotic drugs, cyclophosphamide, gemcitabine, mitoxantrone, fludarabine, thalidomide, thalidomide derivatives, COX-2 inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors, sildenafil, ROS inhibitors and nitroaspirin.

Clause 288. The pharmaceutical composition, cancer immunotherapy, the isolated polypeptide or fusion protein, the polynucleotide, the expression vector or virus, the recombinant cell or the use of any of Clauses 275-287, wherein the Immunostimulatory antibody is selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD 137, OX40, GITR, CD27, CD28 or ICOS.

Clause 289. The pharmaceutical composition, cancer immunotherapy, the isolated polypeptide or fusion protein, the polynucleotide, the expression vector or virus, the recombinant cell or the use of any of Clauses 275-288, wherein the therapeutic cancer vaccine is selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cell-based vaccines, whole tumor cell vaccines, gene modified tumor cells expressing GM-CSF, ICOS and/or Flt3-ligand, oncolytic virus vaccines.

Clause 290. The pharmaceutical composition, cancer immunotherapy, the isolated polypeptide or fusion protein, the polynucleotide, the expression vector or virus, the recombinant cell or the use of any of Clauses 275-289, wherein the cytokine therapy is selected from one or more of the cytokines IL-2, IL-7, IL-12, IL-15, IL-17, IL-18 and IL-21, IL23, IL-27, GM-CSF, IFNa (interferon alpha), IFNa-2b, IFNβ, IFNγ, and their different strategies for delivery.

Clause 291. The pharmaceutical composition, cancer immunotherapy, the isolated polypeptide or fusion protein, the polynucleotide, the expression vector or virus, the recombinant cell or the use of any of Clauses 275-290, wherein the adoptive cell transfer therapy is carried out following ex vivo treatment selected from expansion of the patient autologous naturally occurring tumor specific T cells or genetic modification of T cells to confer specificity for tumor antigens.

Clause 292. An assay for diagnosing or aiding in the diagnosis of a disease in a subject, wherein the disease is selected from the group consisting of cancer, autoimmune disease, or an infectious disease, comprising the isolated polypeptide or fusion protein of any of the above Clauses and/or with VSIG3 ECD protein set forth in any of SEQ ID NO. 1, and a detector for detecting specific binding of the isolated protein or fusion protein to a tissue sample taken from the subject.

Clause 293. A diagnostic method for diagnosing or aiding in the diagnosis of a disease in a subject, wherein the disease is selected from the group consisting of cancer, autoimmune disease, or infectious disease, comprising using the assay of Clause 292 for performing the method.

Clause 294. A diagnostic method for diagnosing or aiding in the diagnosis of a disease in a subject, wherein the disease is selected from the group consisting of cancer, autoimmune disease, or infectious disease, wherein the diagnostic method is performed ex vivo, and comprises contacting a tissue sample from the subject with the isolated polypeptide or fusion protein of any of the above Clauses and/or with VSIG3 ECD protein set forth in any of SEQ ID NO: 1 and detecting specific binding to the tissue sample.

Clause 295. A diagnostic method for diagnosing or aiding in the diagnosis of a disease in a subject, wherein the disease is selected from the group consisting of cancer, autoimmune disease, or an infectious disease, wherein the diagnostic method is performed in vivo, comprising administering the isolated polypeptide or fusion protein of any of the above Clauses, and/or with VSIG3 ECD protein set forth in any of SEQ ID NO. 1 to a subject and detecting specific binding to tissues.

Clause 296. The method of any of Clauses 293-295, or use of the assay of Clause 292 wherein the diagnostic method is performed before therapy or treatment comprising administering the isolated polypeptide or fusion protein of any of Clauses 200-269, the polynucleotide of Clause 270, the expression vector or virus of Clause 271, the recombinant cell of Clause 272, the pharmaceutical composition of Clause 274, the use of Clause 275, or the protein, the polynucleotide, the expression vector or virus, the recombinant cell, the pharmaceutical composition, or the use of any of Clauses 276-291, to the subject.

Clause 297. The method of any of Clauses 293-296, for screening for a disease, screening for VSIG3-mediated immunosuppression, detecting a presence or a severity of a disease, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations.

Clause 298. The isolated polypeptide or fusion protein of any of Clauses 200-269, the polynucleotide of Clause 270, the expression vector or virus of Clause 271, the recombinant cell of Clause 272, the pharmaceutical composition of Clause 274, the use of Clause 275, or the protein, the polynucleotide, the expression vector or virus, the recombinant cell, the pharmaceutical composition, the use of any of Clauses 276-291, the assay of Clause 292 or the method of any of Clauses 94-98, wherein said cancer is selected from the group consisting of breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous millierian cancer, malignant ascites, gastrointestinal stromal tumor (GIST), Li-Fraumeni syndrome and Von Hippel-Lindau syndrome (VHL), and cancer of unknown origin either primary or metastatic.

Clause 299. The isolated protein, the fusion protein, the polynucleotide, the expression vector or virus, the recombinant cell, the pharmaceutical composition, the assay or the method of Clause 298, wherein said breast cancer is breast carcinoma, and is selected from the group consisting of ductal-carcinoma, infiltrating ductal carcinoma, lobular carcinoma, mucinous adenocarcinoma, intra duct and invasive ductal carcinoma, and Scirrhous adenocarcinoma.

Clause 300. The isolated protein, the fusion protein, the polynucleotide, the expression vector or virus, the recombinant cell, the pharmaceutical composition, the assay or the method of Clause 298, wherein said colon cancer is selected from the group consisting of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, and Moderately Differentiated Mucinous adenocarcinoma of the rectum.

Clause 301. The isolated protein, the fusion protein, the polynucleotide, the expression vector or virus, the recombinant cell, the pharmaceutical composition, the assay or the method of Clause 298, wherein said lung cancer is selected from the group consisting of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, and Small cell lung cancer, preferably Small cell lung carcinoma, more preferably undifferentiated Small cell lung carcinoma.

Clause 302. The isolated protein, the fusion protein, the polynucleotide, the expression vector or virus, the recombinant cell, the pharmaceutical composition, the assay or the method of Clause 298, wherein said prostate cancer is prostate adenocarcinoma and is selected from the group consisting of Adenocarcinoma Gleason Grade 6 to 9, Infiltrating adenocarcinoma, High grade prostatic intraepithelial neoplasia, undifferentiated carcinoma.

Clause 303. The isolated protein, the fusion protein, the polynucleotide, the expression vector or virus, the recombinant cell, the pharmaceutical composition, the assay or the method of Clause 298, wherein said stomach cancer is moderately differentiated gastric adenocarcinoma.

Clause 304. The isolated protein, the fusion protein, the polynucleotide, the expression vector or virus, the recombinant cell, the pharmaceutical composition, the assay or the method of Clause 298, wherein said ovarian cancer is selected from the group consisting of cystadenocarcinoma, serous papillary cystic carcinoma, Serous papillary cystic carcinoma, and Invasive serous papillary carcinoma.

Clause 305. The isolated protein, the fusion protein, the polynucleotide, the expression vector or virus, the recombinant cell, the pharmaceutical composition, the assay or the method of Clause 298, wherein said brain cancer is selected from the group consisting of Astrocytoma and Glioblastoma multiforme.

Clause 306. The isolated protein, the fusion protein, the polynucleotide, the expression vector or virus, the recombinant cell, the pharmaceutical composition, the assay or the method of Clause 298, wherein said brain cancer is astrocytoma.

Clause 307. The isolated protein, the fusion protein, the polynucleotide, the expression vector or virus, the recombinant cell, the pharmaceutical composition, the assay or the method of Clause 298, wherein said kidney cancer is clear cell renal cell carcinoma.

Clause 308. The isolated protein, the fusion protein, the polynucleotide, the expression vector or virus, the recombinant cell, the pharmaceutical composition, the assay or the method of Clause 298, wherein liver cancer is Hepatocellular carcinoma.

Clause 309. The isolated protein, the fusion protein, the polynucleotide, the expression vector or virus, the recombinant cell, the pharmaceutical composition, the assay or the method of Clause 308, wherein said Hepatocellular carcinoma is Low Grade hepatocellular carcinoma or Fibrolamellar Hepatocellular Carcinoma.

Clause 310. The isolated protein, the fusion protein, the polynucleotide, the expression vector or virus, the recombinant cell, the pharmaceutical composition, the assay or the method of Clause 298, wherein said lymphoma is selected from the group consisting of Hodgkin's Lymphoma and High to low grade Non-Hodgkin's Lymphoma.

Clause 311. The isolated protein, the fusion protein, the polynucleotide, the expression vector or virus, the recombinant cell, the pharmaceutical composition, the assay or the method of Clause 298, for treating a subject suffering from a disease selected from the group consisting of B-cell lymphoma, Burkitt's lymphoma, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma cancer, keratoacanthomas, anaplastic large-cell lymphoma, esophageal squamous cells carcinoma, hepatocellular carcinoma cancer, follicular dendritic cell carcinoma, muscle-invasive cancer, seminal vesicle tumor, epidermal carcinoma, cancer of the retina, biliary cancer, small bowel cancer, salivary gland cancer, cancer of connective tissue, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, esophagogastric, fallopian tube cancer, peritoneal cancer, papillary serous miillerian cancer, malignant ascites, gastrointestinal stromal tumor (GIST), Li-Fraumeni syndrome and Von Hippel-Lindau syndrome (VHL); endometrial cancer, Breast carcinoma, preferably any of ductal-carcinoma, infiltrating ductal carcinoma, lobular carcinoma, mucinous adenocarcinoma, intra duct and invasive ductal carcinoma, and Scirrhous adenocarcinoma, Colorectal adenocarcinoma, preferably any of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, Moderately Differentiated Mucinous adenocarcinoma of the rectum; Lung cancer, preferably any of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, Small cell lung cancer, preferably Small cell lung carcinoma, more preferably undifferentiated Small cell lung carcinoma; Prostate adenocarcinoma, preferably any of Adenocarcinoma Gleason Grade 6 to 9, Infiltrating adenocarcinoma, High grade prostatic intraepithelial neoplasia, undifferentiated carcinoma; Stomach adenocarcinoma, preferably moderately differentiated gastric adenocarcinoma; Ovary carcinoma, preferably any of cystadenocarcinoma, serous papillary cystic carcinoma, Serous papillary cystic carcinoma, Invasive serous papillary carcinoma; Brain cancer, preferably any of Astrocytoma, with the proviso that it is not a grade 2 astrocytoma, preferably grade 4 Astrocytoma, Glioblastoma multiforme; Kidney carcinoma, preferably Clear cell renal cell carcinoma; Liver cancer, preferably any of Hepatocellular carcinoma, preferably Low Grade hepatocellular carcinoma, Fibrolamellar Hepatocellular Carcinoma; Lymphoma, preferably any of, Hodgkin's Lymphoma and High to low grade Non-Hodgkin's Lymphoma.

Clause 312. A pharmaceutical composition according to Clause 274, the isolated polypeptide or fusion protein of any of Clauses 200-269, the polynucleotide of Clause 270, the expression vector or virus of Clause 271, or the recombinant cell of Clause 272, for use in the treatment of an immune related condition in a subject suffering from same.

Clause 313. The pharmaceutical composition, the isolated polypeptide or fusion protein, the polynucleotide, the expression vector or virus, the recombinant cell or the use of Clause 312, wherein said pharmaceutical composition, isolated polypeptide, fusion protein, polynucleotide, expression vector, virus or cell is administered to the subject in need thereof in combination with a therapeutic agent useful for treatment of an immune related condition.

Clause 314. The pharmaceutical composition, the isolated polypeptide or fusion protein, the polynucleotide, the expression vector or virus, the recombinant cell or the use of Clauses 312 or 313, for treating an immune related condition, in a subject in need thereof.

Clause 315. The pharmaceutical composition, the isolated polypeptide or fusion protein, the polynucleotide, the expression vector or virus, the recombinant cell or the use of any of Clauses 312-314, wherein said protein, said polynucleotide, said expression vector or virus, said recombinant cell, or said pharmaceutical composition is used for treatment of treatment of immune related diseases and/or for reducing the undesirable immune activation that follows gene or cell therapy, or transplantation of cells, tissues, and/or organs into a subject, and is capable of at least one of: inhibiting immune response, reducing T cell activity, reducing NK cell activity, enhancing regulatory cell activity, enhancing T-cell suppression, enhancing immune regulatory cell activity, inducing establishment of immune tolerance, reducing pro-inflammatory cytokine secretion, re-establishing Th1-Th2 immune balance, reducing immune memory responses to self-antigens, decreasing or eliminating pro-inflammatory immune cells, decreasing or eliminating autoreactive immune cells.

Clause 316. The pharmaceutical composition, the isolated polypeptide or fusion protein, the polynucleotide, the expression vector or virus, the recombinant cell or the use of any of Clauses 312-315, for performing at least one of the following: (i) decreasing immune response, (ii) decreasing T cell activation, (iii) decreasing cytotoxic T cell activity, (iv) decreasing natural killer (NK) cell activity, (v) decreasing T-cell activity, (vi) decreasing Th17 activity, (vii) decreasing pro-inflammatory cytokine secretion, (viii) decreasing IL-2 secretion; (ix) decreasing interferon-y production by T-cells, (x) decreasing Th1 response, (xi) decreasing Th2 response, (xii) increasing regulatory T cells and/or one or more of myeloid derived suppressor cells (MDSCs), iMCs, mesenchymal stromal cells, TIE2-expressing monocytes, (xiii) increasing regulatory cell activity and/or the activity of one or more of myeloid derived suppressor cells (MDSCs), iMCs, mesenchymal stromal cells, TIE2-expressing monocytes, (xiv) increasing M2 macrophages, (xv) increasing M2 macrophage activity, (xvi) increasing N2 neutrophils, (xvii) increasing N2 neutrophils activity, (xviii) increasing inhibition of T cell activation, (xix) increasing inhibition of CTL activation, (xx) increasing inhibition of NK cell activation, (xxi) increasing T cell exhaustion, (xxii) decreasing T cell response, (xxiii) decreasing activity of cytotoxic cells, (xxiv) reducing antigen-specific memory responses, (xxv) inhibiting apoptosis or lysis of cells, (xxvi) decreasing cytotoxic or cytostatic effect on cells, (xxvii) reducing direct killing of cells, and/or (xxviii) reducing complement dependent cytotoxicity and/or (xxix) reducing antibody dependent cell-mediated cytotoxicity.

Clause 317. The pharmaceutical composition, the isolated polypeptide or fusion protein, the polynucleotide, the expression vector or virus, the recombinant cell or the use of any of Clauses 312-316, wherein said immune related condition is selected from the group consisting of autoimmune disease, transplant rejection, and graft versus host disease.

Clause 318. The pharmaceutical composition, the isolated polypeptide or fusion protein, the polynucleotide, the expression vector or virus, the recombinant cell or the use of any of Clauses 312-316, wherein said autoimmune disease is selected from the group consisting of multiple sclerosis, psoriasis; rheumatoid arthritis; psoriatic arthritis, systemic lupus erythematosus (SLE); discoid lupus erythematosus, inflammatory bowel disease, ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune hemolytic anaemia, Guillain-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anaemia, pemphigus, pemphigus vulgaris, cirrhosis, primary biliary cirrhosis, dermatomyositis, polymyositis, fibromyositis, myogelosis, celiac disease, immunoglobulin A nephropathy, Henoch-Schonlein purpura, Evans syndrome, Dermatitis, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis *nodosa*, chondrocalcinosis, Wegener's granulomatosis, microscopic polyangiitis, chronic urticaria, bullous skin disorders, pemphigoid, atopic eczema, bullous pemphigoid, cicatricial pemphigoid, vitiligo, atopic eczema, eczema, chronic urticaria, autoimmune urticaria, normocomplementemic urticarial vasculitis, hypocomplementemic urticarial vasculitis, autoimmune lymphoproliferative syndrome, Devic's disease, sarcoidosis, pernicious anemia, childhood autoimmune hemolytic anemia, idiopathic autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, myocarditis, vasculitis, gastritis, gout, gouty arthritis, and inflammatory skin disorders, normocomplementemic urticarial vasculitis, pericarditis, idiopathic pericarditis, myositis, antisynthetase syndrome, scleritis, macrophage activation syndrome, Behcet's Syndrome, PAPA Syndrome, Blau's Syndrome, gout, adult and juvenile Still's disease, cryopyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, a rheumatic disease, polymyalgia rheumatica, mixed connective tissue disease, inflammatory rheumatism, degenerative rheumatism, extra-articular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, temporal arteritis, giant cell arteritis, Takayasu arteritis, Behcet's disease, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anaemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, fibromyalgia, chronic fatigue and immune dysfunction syndrome (CFIDS), autoimmune inner ear disease, Hyper IgD syndrome, Schnitzler's syndrome, autoimmune retinopathy, age-related macular degeneration, atherosclerosis, chronic prostatitis, alopecia, alopecia areata, alopecia universalis, alopecia totalis, utoimmune thrombocytopenic purpura, idiopathic thrombocytopenic purpura, pure red cell aplasia, and TNF receptor-associated periodic syndrome (TRAPS).

Clause 319. The pharmaceutical composition, the isolated polypeptide or fusion protein, the polynucleotide, the expression vector or virus, the recombinant cell or the use of any of Clauses 312-317, for treating an autoimmune disease selected from relapsing-remitting multiple sclerosis, primary progressive multiple sclerosis, secondary progressive multiple sclerosis; progressive relapsing multiple sclerosis, chronic progressive multiple sclerosis, transitional/progressive multiple sclerosis, rapidly worsening multiple sclerosis, clinically-definite multiple sclerosis, malignant multiple sclerosis, also known as Marburg's Variant, acute multiple sclerosis, conditions relating to multiple sclerosis, psoriatic arthritis, gout and pseudo-gout, juvenile idiopathic arthritis, Still's disease, rheumatoid vasculitis, conditions relating to rheumatoid arthritis, discoid lupus, lupus arthritis, lupus pneumonitis, lupus nephritis, conditions relating to systemic lupus erythematosus include osteoarticular tuberculosis, antiphospholipid antibody syndrome, inflammation of various parts of the heart, such as pericarditis, myocarditis, and endocarditis, Lung and pleura inflammation, pleuritis, pleural effusion, chronic diffuse interstitial lung disease, pulmonary hypertension, pulmonary emboli, pulmonary hemorrhage, and shrinking lung syndrome, lupus headache, Guillain-Barre syndrome, aseptic meningitis, demyelinating syndrome, mononeuropathy, mononeuritis multiplex, myelopathy, cranial neuropathy, polyneuropathy, vasculitis, Collagenous colitis, Lymphocytic colitis, Ischaemic colitis, Diversion colitis, Behcet's disease, Indeterminate colitis, thrombocytopenic purpura, idiopathic autoimmune hemolytic anemia, pure red cell aplasia, cryoglobulinemic vasculitis, ANCA-associated vasculitis, antiphospholipid syndrome, autoimmune hemolytic anaemia, Guillain-Barre syndrome, chronic immune polyneuropathy, autoimmune thyroiditis, idiopathic diabetes, juvenile type I diabetes, maturity onset diabetes of the young, latent autoimmune diabetes in adults, gestational diabetes, conditions relating to type 1 diabetes, membranous glomerulonephropathy, autoimmune gastritis, pemphigus vulgaris, cirrhosis, fibromyositis, celiac disease, immunoglobulin A nephropathy, Henoch-Schonlein purpura, Evans syndrome, atopic dermatitis, psoriasis, Graves' ophthalmopathy, systemic scleroderma, asthma, allergy, anterior uveitis (or iridocyclitis), intermediate uveitis (pars planitis), posterior uveitis (or chorioretinitis), panuveitic form, hepatitis, Wegener's granulomatosis, microscopic polyangiitis, chronic urticaria, bullous skin disorders, pemphigoid, atopic eczema, Devic's disease, childhood autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, perodontitis, pancreatitis, myocarditis, vasculitis, gastritis, gout, gouty arthritis, and inflammatory skin disorders, selected from the group consisting of psoriasis, Nonpustular Psoriasis including Psoriasis vulgaris and Psoriatic erythroderma (erythrodermic psoriasis), Pustular psoriasis including Generalized pustular psoriasis (pustular psoriasis of von Zumbusch), Pustulosis palmaris et plantaris (persistent palmoplanar pustulosis, pustular psoriasis of the Barber type, pustular psoriasis of the extremities), Annular pustular psoriasis, Acrodermatitis continua, Impetigo herpetiformis, drug-induced psoriasis, Inverse psoriasis, Napkin psoriasis, Seborrheic-like psoriasis, Guttate psoriasis, Nail psoriasis, Psoriatic arthritis, atopic dermatitis, eczema, rosacea, urticaria, and acne, normocomplementemic urticarial vasculitis, pericarditis, anti-synthetase syndrome, scleritis, macrophage activation syndrome, Behcet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, autoimmune retinopathy, age-related macular degeneration, atherosclerosis, chronic prostatitis and TNF receptor-associated periodic syndrome (TRAPS).

Clause 320. The pharmaceutical composition, the isolated polypeptide or fusion protein, the polynucleotide, the expression vector or virus, the recombinant cell or the use of any of Clauses 312-319, wherein the treatment is combined with another moiety useful for treating said condition.

Clause 321. The pharmaceutical composition, the isolated polypeptide or fusion protein, the polynucleotide, the expression vector or virus, the recombinant cell or the use of any of Clauses 312-320, wherein said other moiety useful for treating immune related condition is selected from immunosuppressants such as corticosteroids, cyclosporin, cyclophosphamide, prednisone, azathioprine, methotrexate, rapamycin, tacrolimus, leflunomide or an analog thereof; mizoribine; mycophenolic acid; mycophenolate mofetil; 15-deoxyspergualine or an analog thereof; biological agents such as TNF-alpha blockers or antagonists, or any other biological agent targeting any inflammatory cytokine, non-steroidal antiinflammatory drugs/Cox-2 inhibitors, hydroxychloroquine, sulfasalazine, gold salts, etanercept, infliximab, mycophenolate mofetil, basiliximab, atacicept, rituximab, Cytoxan® (cyclophosphamide), interferon beta-Ia, interferon beta-Ib, glatiramer acetate, mitoxantrone hydrochloride, anakinra and/or other biologies and/or intravenous immunoglobulin (IVIG), interferons such as IFN-beta-Ia (REBIF®. AVONEX® and CINNOVEX®) and IFN-beta-Ib (BETASERON®); EXTAVIA®, BETASERON®, ZIFERON®); glatiramer acetate (COPAXONE®), a polypeptide; natalizumab (TYSABRI®), mitoxantrone (NOVANTRONE®), a cytotoxic agent, a calcineurin inhibitor; cyclosporin A; FK506; an immunosuppressive macrolide; rapamycin; a rapamycin derivative; 40-O-(2-hydroxy)ethyl-rapamycin, a lymphocyte homing agent, FTY720; an analog of FTY720; corticosteroids; cyclophosphamide; azathioprine; methotrexate; leflunomide or an analog thereof; mizoribine; mycophenolic acid; mycophenolate mofetil; 15-deoxyspergualine or an analog thereof; immunosuppressive monoclonal antibodies, monoclonal antibodies to leukocyte receptors, monoclonal antibodies to MHC, CD2, CD3, CD4, CDI Ia/CD18, CD7, CD25, CD27, B7, CD40, CD45, CD58, CD137, ICOS, CD150 (SLAM), OX40, 4-1BB or their ligands; or other immunomodulatory compounds, CTLA4-Ig (abatacept, ORENCIA®, belatacept), CD28-Ig, B7-H4-Ig, or other costimulatory agents, or adhesion molecule inhibitors, mAbs or low molecular weight inhibitors, LFA-1 antagonists, Selectin antagonists and VLA-4 antagonists, or another immunomodulatory agent.

Clause 322. A pharmaceutical composition according to Clause 274, the isolated polypeptide or fusion protein of any of Clauses 200-269, the polynucleotide of Clause 270, the expression vector or virus of Clause 271, or the recombinant cell of Clause 272, for use in treatment of Infectious disease in a subject suffering from same.

Clause 323. The pharmaceutical composition, the isolated polypeptide or fusion protein, the polynucleotide, the expression vector or virus, the recombinant cell or the use of Clause 322, wherein said protein, said polynucleotide, said expression vector or virus, said recombinant cell, said pharmaceutical composition or said use is used for treatment of infectious disease and is capable of at least one of the following: (i) increasing immune response, (ii) increasing T cell activation, (iii) increasing cytotoxic T cell activity, (iv) increasing NK cell activity, (v) increasing Th17 activity, (vi) alleviating T-cell suppression, (vii) increasing pro-inflammatory cytokine secretion, (viii) increasing IL-2 secretion; (ix) increasing interferon-y production by T-cells, (x) increasing Th1 response, (xi) decreasing Th2 response, (xii) decreasing or eliminating at least one of regulatory T cells (Tregs), myeloid derived suppressor cells (MDSCs), iMCs, mesenchymal stromal cells, TIE2-expressing monocytes, (xiii) reducing regulatory cell activity and/or the activity of one or more of myeloid derived suppressor cells (MDSCs), iMCs, mesenchymal stromal cells, TIE2-expressing monocytes, (xiv) decreasing or eliminating M2 macrophages, (xv) reducing M2 macrophage pro-tumorigenic activity, (xvi) decreasing N2 neutrophils, (xvii) decreasing N2 neutrophils activity, (xviii) reducing inhibition of T cell activation, (xix) reducing inhibition of CTL activation, (xx) reducing inhibition of NK cell activation, (xxi) reversing T cell exhaustion, (xxii) increasing T cell response, (xxiii) increasing activity of cytotoxic cells, (xxiv) stimulating antigen-specific memory responses, (xxv) eliciting apoptosis or lysis of cancer cells, (xxvi) stimulating cytotoxic or cytostatic effect on cancer cells, (xxvii) Inducing direct killing of cancer cells, and/or (xxviii) inducing complement dependent cytotoxicity and/or (xxix) inducing antibody dependent cell-mediated cytotoxicity.

Clause 324. The pharmaceutical composition, the isolated polypeptide or fusion protein, the polynucleotide, the expression vector or virus, the recombinant cell or the use of any of Clauses 321-323, wherein said infectious disease is chronic infectious disease and is selected from the disease caused by bacterial infection, viral infection, fungal infection and/or other parasite infection.

Clause 325. The pharmaceutical composition, the isolated polypeptide or fusion protein, the polynucleotide, the expression vector or virus, the recombinant cell or the use of any of Clauses 321-324, wherein said infectious disease results in sepsis.

Clause 326. The pharmaceutical composition, the isolated polypeptide or fusion protein, the polynucleotide, the expression vector or virus, the recombinant cell or the use of any of Clauses 321-324, wherein the infectious disease is selected from hepatitis B, hepatitis C, infectious mononucleosis, AIDS, tuberculosis, malaria and schistosomiasis.

Clause 327. The pharmaceutical composition, the isolated polypeptide or fusion protein, the polynucleotide, the expression vector or virus, the recombinant cell or the use of any of Clauses 321-326, wherein the treatment is combined with another moiety useful for treating infectious disease, or with another moiety useful for reducing the undesirable immune activation that follows gene therapy, in a subject in need thereof.

Clause 328. The pharmaceutical composition, the isolated polypeptide or fusion protein, the polynucleotide, the expression vector or virus, the recombinant cell or the use of any of Clauses 321-327, wherein said other moiety is a therapeutic agent useful for treating bacterial infection, viral infection, fungal infection, parasitic infection or sepsis.

Clause 329. A compound, composition, method or use according to any of the foregoing Clauses which further includes a VISTA agonist or antagonist compound which is separate or is conjugated to a VSIG3 agonist or antagonist compound.

Clause 330. A fusion protein, pharmaceutical composition, isolated polypeptide, polynucleotide, expression vector or virus, recombinant cell or method or use according to any of the foregoing Clauses which further includes a VISTA agonist or antagonist which is separate or conjugated to a VSIG3 agonist or antagonist compound which preferably comprises an anti-VSIG3 antibody, VSIG3 protein or VSIG3 fusion protein.

VISTA Clauses

Clause 1A. A compound which agonizes or antagonizes the interaction of VISTA and VSIG3.

Clause 2A. The compound of Clause 1A which is an antibody or antibody fragment that specifically binds VISTA.

Clause 3A. The compound of Clause 1A, which is an agonistic anti-VISTA antibody or antibody fragment.

Clause 4A. The compound of Clause 1A, which is an antagonistic anti-VISTA antibody or antibody fragment.

Clause 5A. The compound of Clause 2A, 3A or 4A, which is a humanized, human, primatized, or chimeric anti-VISTA antibody or antibody fragment.

Clause 6A. The antibody of Clause 5A, which comprises a human IgG1, IgG2, IgG3 or IgG4 constant region or fragment thereof, which optionally is mutagenized to eliminate FcR or complement binding.

Clause 7A. The antibody of Clause 5, which comprises an IgG1 or IgG3 constant region or portion thereof, which optionally is mutagenized to enhance FcR or complement binding.

Clause 8A. The compound of any of the foregoing Clauses which is a Fab, Fab', scFv or Fab2.

Clause 9A. The compound of Clause 1 comprising at least one copy of a polypeptide comprising the extracellular region of VISTA, a fragment thereof that elicits a suppressive effect on T cell immunity or a derivative of said VISTA polypeptide that possesses at least 80, 90, 95, 96, 97, 98 or 99% sequence identity to the extracellular region of VISTA or to SEQ ID NO: 3 or to SEQ ID NO. 4.

Clause 10A. The compound of Clause 9, which comprises at least one polypeptide comprising the entire extracellular region of human, non-human primate or murine VISTA.

Clause 11A. The compound of Clause 9 or 10 which is a fusion protein.

Clause 12A. The compound of Clause 11, which is an Ig fusion protein.

Clause 13A. The compound of Clause 12, which comprises a human IgG1, IgG2, IgG3 or IgG4 constant region or fragment thereof, which optionally is mutagenized to eliminate FcR or complement binding.

Clause 14A. The compound of Clause 12, which comprises an IgG1 or IgG3 constant region or portion thereof, which optionally is mutagenized to enhance FcR or complement binding.

Clause 15A. A compound according to any one of Clauses 1-14, which is attached to a water soluble polymer to increase serum half-life.

Clause 16A. The compound of Clause 15 which is Pegylated.

Clause 17A. An Isolated complex comprising VISTA and VSIG3.

Clause 18A. The complex of Clause 17, wherein said VISTA and/or VSIG3 is oligomeric or multimeric.

Clause 19A. The complex of Clause 17 or 18 which is comprised on a recombinant cell that expresses VISTA or VSIG3.

Clause 20A. An isolated cell membrane that comprises a complex according to Clause 17, 18 or 19.

Clause 21A. An antibody or antibody fragment that specifically binds to the VISTA-VSIG3 complex of Clause 17, 18 or 19.

Clause 22A. The antibody or antibody fragment of Clause 21 which is human, humanized, primatized or chimeric.

Clause 23A. The antibody fragment of Clause 21 or 22 which is a Fab, Fab', scFv or Fab2.

Clause 24A. The VISTA agonist or antagonist compound of Clause 1, which is a small molecule.

Clause 25A. An antibody or an antigen-binding fragment according to any of the foregoing Clauses which comprises a human constant region, e.g., a human IgG1, IgG2, IgG3 or IgG4 constant region or variant thereof, which optionally contains one or more domains deleted.

Clause 26A. An antibody or an antigen-binding fragment thereof according to any of the foregoing Clauses which comprises a human constant region which contains at least one mutation that increases or decreases an Fc effector function and/or glycosylation and/or a mutation which modulates or abrogates IgG4 Fab arm exchange.

Clause 27A. An antibody or an antigen-binding fragment thereof according to Clause 26, wherein said effector functions include FcR binding, ADCC activity, CDC activity, degranulation, phagocytosis, and cytokine release.

Clause 28A. An antibody or an antigen-binding fragment thereof to any of the foregoing Clauses, which is selected from the group consisting of a Fab, Fab', F(ab')2, F(ab'), F(ab), FIT or scFv fragment and a minimal recognition unit which optionally has an in vivo half-life of at least one week, 2 weeks, 3 weeks or a month.

Clause 29A. An antibody or an antigen-binding fragment thereof according to any of the above Clauses, which is coupled to another moiety, e.g., a therapeutic moiety, detectable moiety, or a moiety that alters (increases or decreases) in vivo half-life.

Clause 30A. An antibody or an antigen-binding fragment thereof according to any of the above Clauses, which is coupled to a therapeutic agent selected from a drug, a radionuclide, a fluorophore, an enzyme, a toxin, or a chemotherapeutic agent; and/or a detectable marker selected from a radioisotope, a metal chelator, an enzyme, a fluorescent compound, a bioluminescent compound or a chemiluminescent compound.

Clause 31A. An antibody or an antigen-binding fragment thereof or VISTA fusion protein according to any of the above Clauses, which is not coupled to any other moiety.

Clause 32A. An antibody or an antigen-binding fragment thereof or VISTA fusion protein according to any of the above Clauses, wherein the antibody or antigen-binding fragment is coupled to another antibody or antigen-binding fragment or fusion protein, e.g., an NK and/or T cell receptor, e.g., an NK cell receptor that agonizes or antagonizes NK cell activity or inhibits NK cell mediated cell depletion or is one that promotes or activates NK cell mediated cell depletion.

Clause 33A. An antibody or an antigen-binding fragment thereof or VISTA fusion protein according to 32, wherein the inhibitory NK cell receptor is selected from the group consisting of KIR2DL1, KIR2DL2/3, KIR2DL4, KIR2DL5A, KIR2DL5B, KIR3DL1, KIR3DL2, KIR3DL3, LILRB 1, NKG2A, NKG2C, NKG2E and LILRB5. And the NK activating receptor is selected from the group consisting of NKp30, NKp44, NKp46, NKp46, NKG2D, KIR2DS4 CD2, CD16, CD69, DNAX accessory molecule-1 (DNAM-1), 2B4, NK1.1; a killer immunoglobulin (Ig)-like activating receptors (KAR); ILTs/LIRs; NKRP-1, CD69; CD94/NKG2C and CD94/NKG2E heterodimers, NKG2D homodimer KIR2DS and KIR3DS.

Clause 34A. An antibody or an antigen-binding fragment according to any one of the foregoing Clauses which binds human, primate or murine VISTA with a binding affinity ($K_D$) no more than 500 nM as determined by any of the binding affinity methods disclosed herein, e.g., a binding affinity ($K_D$) of $10^{-5}$, $10^{-6}$, $10^{-7}$, $10^{-8}$, $10^{-9}$, $10^{-10}$, $10^{-11}$, $10^{-12}$ M or less as determined by any of the binding affinity methods disclosed herein.

Clause 35A. An antibody or an antigen-binding fragment or VISTA fusion protein according to any one of the foregoing Clauses wherein such antibody or antigen-binding fragment either (1) enhances, agonizes or mimics, or (2) inhibits, antagonizes or blocks at least one effect elicited by the interaction of VSIG3 and VISTA on immunity or on one or more types of immune cells.

Clause 36A. An antagonistic antibody or the antigen-binding fragment or VISTA fusion protein of any of the above Clauses, which mediates any combination of at least one of the following immunostimulatory effects on immunity: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) induces direct killing of cancer cells, (xxvii) increases Th17 activity and/or (xxviii) induces complement dependent cytotoxicity and/or antibody dependent cell-mediated cytotoxicity, with the proviso that said antibody or antigen-binding fragment may elicit an opposite effect to one or more of (i)-(xxviii).

Clause 37A. An agonistic antibody or the antigen-binding fragment or VISTA fusion protein of any of the foregoing Clauses, which mediates any combination of at least one of the following immunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VISTA antibody or the antigen-binding fragment may elicit an opposite effect to one or more of (i)-(xxviii).

Clause 38A. An immunomodulatory antibody or an antigen-binding fragment thereof of any of the foregoing Clauses which increases the inhibitory effect of VSIG3 and/or VISTA on T cell immunity and/or which inhibits CTL activity and/or wherein inhibited CTL activity includes reduced secretion of one or more proinflammatory cytokines and/or reduced CTL mediated killing of target cells and/or inhibition of CD4+ T cell activation and/or CD4+ T cell proliferation and/or CD4+ T cell mediated cell depletion.

Clause 39A. An immunomodulatory antibody or an immunomodulatory antigen-binding fragment thereof or VISTA fusion protein, of any of the foregoing Clauses which inhibit NK cell activity, and/or NK cell proliferation and/or NK cell mediated cell depletion.

Clause 40A. An immunomodulatory antibody or an immunomodulatory antigen-binding fragment thereof or VISTA fusion protein of any of the foregoing Clauses which promotes antigen-specific tolerance or prolonged suppression of an antigen-specific immune responses e.g., against transplanted cells, tissue or organ by enhancing one or more of the effects of VSIG3 and/or VISTA on immunity.

Clause 41A. An immunomodulatory antibody or an immunomodulatory antigen-binding fragment thereof or VISTA fusion protein of any of the foregoing Clauses which promotes which inhibits an immune response against an autoantigen, allergen, or inflammatory agent by promoting one or more of the effects of VSIG3 and/or VISTA on immunity.

Clause 42A. An immunomodulatory antibody or an immunomodulatory antigen-binding fragment thereof or VISTA fusion protein of any of the foregoing Clauses, for use in inhibiting an immune response against an autoantigen, allergen, or inflammatory agent, and/or for treating an inflammatory disease or response and/or for treating an autoimmune disease and/or for reducing or prevent transplant rejection and/or graft vs host disease.

Clause 43A. A pharmaceutical composition comprising at least one compound according to any of the above Clauses.

Clause 44A. A vaccine composition comprising at least one compound according to any of the above Clauses and an antigen.

Clause 45A. An immunosuppressive vaccine composition comprising at least one antibody or antigen-binding fragment thereof or VISTA fusion protein according to any of the above Clauses, wherein said antibody or antigen-binding fragment thereof in said composition suppresses antigen-specific T and/or B cell immunity or induces tolerance.

Clause 46A. The vaccine composition of Clause 45 wherein the antigen to which immunity is suppressed is a human antigen, tumor antigen, infectious agent antigen, autoantigen, or an allergen, e.g., a human antigen, cell or antigen of a cell, tissue, or organ to be transplanted into a subject, autoantigen, inflammatory agent or an allergen.

Clause 47A. The composition of any one of Clauses 43-46 which is suitable for administration by a route selected from intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, wherein "parenteral administration" refers to modes of administration other than enteral and topical administration.

Clause 48A. The composition of any one of Clauses 43-47, which comprises at least one other active agent, e.g., a therapeutic or diagnostic agent, e.g., another immunomodulatory compound, a chemo therapeutic, a drug, a cytokine, a radionuclide, and an enzyme.

Clause 49A. The composition of any one of Clauses 43-47, which comprises an antigen that is expressed by a target cell (e.g., a tumor or infected cell).

Clause 50A. The composition of any one of Clauses 43-49, which comprises or is used with another composition containing at least one immunomodulatory agent selected from PD-1 agonists and antagonists, PD-L1 and PD-L2 antibodies and antibody fragments, TLR agonists, CD40 agonists or antagonists, CTLA-4 fusion proteins, CD28 agonists or antagonists, 4-IBB agonists or antagonists, CD27 or CD70 agonists or antagonists, LAG3 agonists or antagonists, TIM3 agonists or antagonists, TIGIT agonists or antagonists, ICOS agonists or antagonists, ICOS ligand agonists or antagonists.

Clause 51A. A method of treatment and/or diagnosis, or use of a composition containing a VISTA agonist or antagonist according to any of the foregoing Clauses for diagnostic or therapeutic use, which method or use comprises the administration to a subject in need thereof at least one dosage or composition comprising a therapeutically or diagnostically effective amount of at least one VISTA agonist or antagonist according to any of the foregoing Clauses or composition containing according to any of the above Clauses.

Clause 52A. A diagnostic method or use of an antibody or antigen-binding fragment or VISTA fusion protein or composition containing in detecting whether an individual has a condition associated with an increase or decrease in VSIG3 and/or VISTA-mediated effects on immunity wherein the method or use includes contacting a tissue sample from the individual with a compound, e.g., an antibody, or antigen-binding fragment or composition according to any one of the foregoing Clauses and detecting specific binding thereto.

Clause 53A. The method or use of Clause 51 or 52, wherein the disease is selected from the group consisting of cancer, autoimmune disease, or infectious disease.

Clause 54A. The method or use of any of Clauses 51-53 which detects the upregulation of VSIG3 or expression and/or increased number of VSIG3 expressing cells or the downregulation of VSIG3 and/or VISTA expression and/or the decreased number of VSIG3 and/or VISTA expressing cells.

Clause 55A. A diagnostic method or use of an anti-VISTA antibody or antigen-binding fragment or composition containing which includes detecting whether an individual has a condition associated with an increase or decrease in VSIG3-mediated effects on immunity comprising contacting a tissue sample from the individual with an antibody, or antigen-binding fragment or composition according to any one of the foregoing Clauses wherein the diagnostic method is performed in vivo, comprising administering to the subject with an immunomodulatory antibody, or antigen-binding fragment or composition according to any one of the foregoing Clauses and detecting specific binding thereto.

Clause 56A. The method or use of Clause 55, wherein the disease is selected from the group consisting of cancer, autoimmune disease, inflammatory condition, allergic condition or an infectious disease.

Clause 57A. A diagnostic method or use which includes an anti-VISTA antibody or antigen-binding fragment or composition containing, and which method or use includes diagnosing a disease in a subject, wherein the disease is selected from the group consisting of cancer, autoimmune disease, or an infectious disease wherein the diagnostic method is performed ex vivo or in vivo, comprising contacting a sample from the individual or administering the individual an antibody, or antigen-binding fragment or composition according to any one of the foregoing Clauses and detecting specific binding of the immune molecule or antibody of any of the above Clauses to a tissue of the subject.

Clause 58A. The diagnostic method or use of any of the foregoing Clauses, wherein the diagnostic method or use is performed before administering to the individual a therapeutically effective amount of an antibody, antigen-binding fragment, or immunomodulatory polypeptide or pharmaceutical composition containing according to any one of the foregoing Clauses.

Clause 59A. The diagnostic method or use of any one of the foregoing Clauses, wherein a therapeutically effective amount of an antibody, antigen-binding fragment, or immunomodulatory polypeptide or a pharmaceutical composition containing according to any one of the foregoing Clauses is only administered if the individual has a condition characterized by increased expression of VSIG3 and/or VISTA by diseased and/or APC cells and/or increased numbers of diseased and/or APC cells which express VSIG3 and/or VISTA, e.g., on is at least 1 on a scale of 0 to 3.

Clause 60A. The method or use of any of the foregoing Clauses, wherein VSIG3 expression is detected on one or more of cancer cells, immune infiltrate or stromal cells.

Clause 61A. A diagnostic method or use of an anti-VISTA antibody or antigen-binding fragment or VISTA fusion protein, which method or use includes diagnosing whether a tissue sample taken from a subject exhibits an immune related condition associated with increased or decreased VSIG3 expression, comprising (i) contacting the sample with a compound or composition according to any one of the foregoing Clauses, or with a nucleic acid that detects VSIG3 expression and (ii) conducting a binding or amplification assay that detects VSIG3 expression, and (iii) based thereon diagnosing whether the sample is from an individual with a condition associated with an immune related condition associated with increased or decreased VSIG3 expression.

Clause 62A. The method or use of Clause 61, wherein the immune related condition is selected from the group consisting of cancer, autoimmune disease, inflammatory condition, an allergic condition, an infectious disease or sepsis.

Clause 63A. The method or use of any of the foregoing Clauses, wherein said anti-VISTA antibody or antigen-binding fragment or VISTA fusion protein is an immuno stimulatory antibody or compound which mediates any combination of at least one of the following immunostimulatory effects on immunity: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) Induces direct killing of cancer cells, (xxvii) increases Th17 activity and/or (xxviii) induces complement dependent cytotoxicity and/or antibody dependent cell-mediated cytotoxicity, with the proviso that said anti-VISTA antibody or antigen-binding fragment may elicit an opposite effect to one or more of (i)-(xxviii).

Clause 64A. A method of treatment and/or diagnosis, or use of a composition containing an anti-VISTA antibody or antigen-binding fragment or VISTA fusion protein for diagnostic or therapeutic use, which comprises promoting T cell immunity or natural killer (NK) immunity and/or suppressing Tregs or MDSC's in a subject in need thereof, which comprises administering a therapeutically or diagnostically effective amount of at least one antibody, antigen-binding fragment or a composition containing according to any of the above Clauses, wherein such antibody or antigen-binding fragment inhibits, antagonizes or blocks at least one effect of a VISTA polypeptide having an amino acid sequence at least 90% identical to the polypeptide of SEQ ID NO: 3 on immunity or immune cells.

Clause 65A. The method or use of any of the foregoing Clauses, which uses a VISTA antagonist which suppresses the inhibitory effect of VSIG3 and/or VISTA on T cell immunity.

Clause 66A. The method or use of any of the foregoing Clauses, which uses a VISTA antagonist which promotes CTL activity.

Clause 67A. The method or use according to Clause 66, wherein CTL activity includes the secretion of one or more proinflammatory cytokines and/or CTL mediated killing of target cells.

Clause 68A. The method or use of any of the foregoing Clauses, which uses a VISTA antagonist which promotes CD4+ T cell activation and/or CD4+ T cell proliferation and/or CD4+ T cell mediated cell depletion.

Clause 69A. The method or use of any of the foregoing Clauses, which uses a VISTA antagonist which promotes CD8+ T cell activation and/or CD8+ T cell proliferation and/or CD8+ T cell mediated cell depletion.

Clause 70A. The method or use of any of the foregoing Clauses, which uses a VISTA antagonist which enhances NK cell activity.

Clause 71A. The method or use of Clause 70, wherein enhanced NK cell activity includes increased depletion of target cells and/or proinflammatory cytokine release.

Clause 72A. The method or use of any of the foregoing Clauses, which uses a VISTA antagonist which suppresses and or decreases the differentiation, proliferation and/or activity of regulatory cells, such as Tregs and/or the differentiation, proliferation, infiltration and/or activity myeloid derived suppressor cells (MDSCs).

Clause 73A. The method or use of any of the foregoing Clauses, which uses a VISTA antagonist which suppresses and/or decreases the infiltration of infiltration of regulatory cells, such as Tregs and MDSCs into a target site.

Clause 74A. The method or use of Clause 73, wherein said target site is a transplanted cell, tissue or organ, or an autoimmune, allergic or inflammatory site or lesion.

Clause 75A. The method or use of any of the foregoing Clauses, which uses a VISTA antagonist which promotes NK-mediated cell depletion.

Clause 76A. The method or use of any of the foregoing Clauses, which uses a VISTA antagonist which promotes antitumor immunity by suppressing one or more of the effects of VSIG3 and/or VISTA on immunity.

Clause 77A. The method or use of any of the foregoing Clauses, which uses a VISTA antagonist, which is used in the treatment of cancer, sepsis or an infectious condition or combination thereof.

Clause 78A. A method of treatment and/or diagnosis and/or diagnosis, or use of a composition containing an anti-VISTA antibody or antigen-binding fragment or VISTA fusion protein for diagnostic or therapeutic use, which comprises promoting NK or T cell immunity in a subject in need thereof, and which comprises administering a therapeutically or diagnostically effective amount of at least one antibody, antigen-binding fragment or a composition containing according to any of the foregoing Clauses, wherein such antibody or antigen-binding fragment inhibits at least one effect of a polypeptide (VISTA) having the amino acid sequence of SEQ ID NO:3 or a polypeptide having at least 90% sequence identity therewith or to a non-human VISTA ortholog on immunity or immune cells or to human VISTA.

Clause 79A. The method or use of any of the foregoing Clauses, wherein the treated individual suffers from an infectious disease.

Clause 80A. The method or use of Clause 79, wherein the infectious disease is caused by a virus, bacterium, parasite, nematode, yeast, mycoplasm, fungus or prion.

Clause 81A. The method or use of Clauses 78 or 79, wherein the infectious disease is caused by a Retroviridae (e.g., human immunodeficiency viruses, such as HIV-1 or HIV-2, acquired immune deficiency (AIDS) also referred to as HTLV-III, LAV or HTLV-III/LAV, or HIV-III; and other isolates, such as HIV-LP; Picomaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever virus); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herperviridae (herpes simplex virus (HSV) 1 and 2, varicella zoster virus, cytomegalovirus (CMV), herpes viruses); Poxviridae (variola virsues, vaccinia viruses, pox viruses); and Iridoviridae (e.g., African swine fever virus); an unclassified virus (e.g., the etiological agents of Spongiform encephalopathies, the agent of delta hepatitides, the agents of non-A, non-B hepatitis (class 1—internally transmitted; class 2—parenterally transmitted (i.e., Hepatitis C); Norwalk and related viruses, and astroviruses) as well as Severe acute respiratory syndrome virus and respiratory syncytial virus (RSV), West Nile encephalitis, coronavirus infection, rhinovirus infection, Influenza, dengue, hemorrhagic fever; an otological infection; severe acute respiratory syndrome (SARS), acute febrile pharyngitis, pharyngoconjunctival fever, epidemic keratoconjunctivitis, infantile gastroenteritis, infectious mononucleosis, Burkitt lymphoma, acute hepatitis, chronic hepatitis, hepatic cirrhosis, hepatocellular carcinoma, primary HSV-1 infection, (gingivostomatitis in children, tonsillitis & pharyngitis in adults, keratoconjunctivitis), latent HSV-1 infection (herpes labialis, cold sores), aseptic meningitis, Cytomegalovirus infection, Cytomegalic inclusion disease, Kaposi sarcoma, Castleman disease, primary effusion lymphoma, influenza, measles, encephalitis, postinfectious encephalomyelitis, Mumps, hyperplastic epithelial lesions (common, flat, plantar and anogenital warts, laryngeal papillomas, epidermodysplasia verruciformis), croup, pneumonia, bronchiolitis, Poliomyelitis, Rabies, bronchiolitis, pneumonia, German measles, congenital rubella, Hemorrhagic Fever, Chickenpox, Dengue, Ebola infection, Echovirus infection, EBV infection, Fifth Disease, Filovirus, Flavivirus, Hand, foot & mouth disease, Herpes Zoster Virus (Shingles), Human Papilloma Virus Associated Epidermal Lesions, Lassa Fever, Lymphocytic choriomeningitis, Parainfluenza Virus Infection, Paramyxovirus, Parvovirus B19 Infection, Picornavirus, Poxviruses infection, Rotavirus diarrhea, Rubella, Rubeola, Varicella, Variola infection.

Clause 82A. The method or use of Clauses 79 or 80, wherein the infectious disease is a parasite infection caused by a parasite selected from a protozoa, such as Amebae, *Flagellates, Plasmodium falciparum, Toxoplasma gondii,* Ciliates, Coccidia, Micro sporidia, Sporozoa; helminthes, Nematodes (Roundworms), Cestodes (Tapeworms), Trematodes (Flukes), Arthropods, and aberrant proteins known as prions.

Clause 83A. The method or use of Clauses 79 or 80, wherein the infectious disease is an infectious disorder and/or disease caused by bacteria selected from the group consisting of Sepsis, septic shock, sinusitis, skin infections, pneumonia, bronchitis, meningitis, Bacterial vaginosis, Urinary tract infection (UCI), Bacterial gastroenteritis, Impetigo and erysipelas, Erysipelas, Cellulitis, anthrax, whooping cough, lyme disease, Brucellosis, enteritis, acute enteritis, Tetanus, diphtheria, Pseudomembranous colitis, Gas gangrene, Acute food poisoning, Anaerobic cellulitis, Nosocomial infections, Diarrhea, Meningitis in infants, Traveller's diarrhea, Hemorrhagic colitis, Hemolytic-uremic syndrome, Tularemia, Peptic ulcer, Gastric and Duodenal ulcers, Legionnaire's Disease, Pontiac fever, Leptospirosis, Listeriosis, Leprosy (Hansen's disease), Tuberculosis, Gonorrhea, Ophthalmia neonatorum, Septic arthritis, Meningococcal disease including meningitis, Waterhouse-Friderichsen syndrome, *Pseudomonas* infection, Rocky mountain spotted fever, Typhoid fever type *salmonellosis, Salmonellosis* with gastroenteritis and enterocolitis, Bacillary dysentery/Shigellosis, Coagulase-positive staphylococcal infections: Localized skin infections including Diffuse skin infection (Impetigo), Deep localized infections, Acute infective endocarditis, Septicemia, Necrotizing pneumonia, Toxinoses such as Toxic shock syndrome and Staphylococcal food poisoning, Cystitis, Endometritis, Otitis media, Streptococcal pharyngitis, Scarlet fever, Rheumatic fever, Puerperal fever, Necrotizing fasciitis, Cholera, Plague (including Bubonic plague and Pneumonic plague), as well as any infection caused by a bacteria selected from but not limited to *Helicobacter* pyloris, *Boreliai burgdorferi, Legionella pneumophila,* Mycobacteria sps (e.g., *M. tuberculosis, M. avium, M. intracellulare, M. kansaii, M gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus (viridans* group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus anthracis, Corynebacterium diphtheriae, Corynebacterium* sp., Erysipelothrix rhusiopathiae, *Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira,* and *Actinomyces israelii.*

Clause 84A. The method or use of Clauses 79 or 80, wherein the infectious disease is an infectious disorder and/or disease caused by fungi selected from Allergic bronchopulmonary aspergillosis, Aspergilloma, Aspergillosis, Basidiobolomycosis, Blastomycosis, Candidiasis, Chronic pulmonary aspergillosis, Chytridiomycosis, Coccidioidomycosis, Conidiobolomycosis, Covered smut (barley), Cryptococcosis, Dermatophyte, Dermatophytid, Dermatophytosis, Endothrix, Entomopathogenic fungus, Epizootic lymphangitis, Epizootic ulcerative syndrome, Esophageal candidiasis, Exothrix, Fungemia, Histoplasmosis, Lobomycosis, Massospora cicadina, Mycosis, *Mycosphaerella* fraganae, Myringomycosis, Paracoccidioidomycosis, Pathogenic fungi, Penicilliosis, Thousand cankers disease, Tinea, Zeaspora, Zygomycosis; a parasite selected from the group consisting of but not limited to *Acanthamoeba*, Amoebiasis, Ascariasis, Ancylostomiasis, Anisakiasis, Babesiosis, Balantidiasis, Baylisascariasis, Blastocystosis, Candiru, Chagas disease, Clonorchiasis, *Cochliomyia*, Coccidia, Chinese Liver Fluke Cryptosporidiosis, Dientamoebiasis, Diphyllobothriasis, *Dioctophyme* renalis infection, Dracunculiasis, Echinococcosis, Elephantiasis, Enterobiasis, Fascioliasis, Fasciolpsiasis, Filariasis, Giardiasis, Gnathostomiasis, Hymenolepiasis, Halzoun Syndrome, Isosporiasis, Katayama fever, Leishmaniasis, lymphatic filariasis, Malaria, Metagonimiasis, Myiasis, Onchocerciasis, Pediculosis, Primary amoebic meningoencephalitis, Parasitic pneumonia, Paragonimiasis, Scabies, Schistosomiasis, Sleeping sickness, Strongyloidiasis, Sparganosis, Rhinosporidiosis, River blindness, Taeniasis (cause of Cysticercosis), Toxocarlasis, Toxoplasmosis, Trichinosis, Trichomoniasis, Trichuriasis, Trypanosomiasis, Tapeworm infection, *Cryptococcus neoformans, Histoplasma capsulatum, Coccidioides immitis, Blastomyces dermatitidis, Chlamydia trachomatis, Candida albicans*.

Clause 85A. The method or use of any of Clauses 79-84, wherein the infectious disease is caused by any of hepatitis B, hepatitis C, infectious mononucleosis, EBV, cytomegalovirus, AIDS, HIV-1, HIV-2, tuberculosis, malaria and schistosomiasis.

Clause 86A. An anti-VISTA antibody or antigen-binding fragment or composition, or method or use according to any of the foregoing Clauses which includes another therapeutic agent useful for treating bacterial infection, viral infection, fungal infection, parasitic infection or sepsis.

Clause 87A. The method, composition, antibody or fragment or VISTA fusion protein, or use of any of the foregoing Clauses which promotes an immune response against an infectious agent by suppressing one or more of the effects of VSIG3 and/or VISTA on immunity.

Clause 88A. The method, composition, antibody or fragment or VISTA fusion protein, or use of any of the foregoing Clauses further comprising one or more additional therapeutic agents used for treatment of bacterial infections.

Clause 89A. The method, composition, antibody or fragment, or use of Clause 88, wherein said agent is selected from the group consisting of antibiotics including Aminoglycosides, Carbapenems, Cephalosporins, Macrolides, Lincosamides, Nitrofurans, penicillins, Polypeptides, Quinolones, Sulfonamides, Tetracyclines, drugs against mycobacteria including but not limited to Clofazimine, Cycloserine, Cycloserine, Rifabutin, Rifapentine, Streptomycin and other antibacterial drugs such as Chloramphenicol, Fosfomycin, Metronidazole, Mupirocin, and Tinidazole, or a combination thereof.

Clause 90A. The method, composition, antibody or fragment or VISTA fusion protein, or use of any of the foregoing Clauses further comprising one or more additional therapeutic agents used for treatment of viral infections.

Clause 91A. The method, composition, antibody or fragment or VISTA fusion protein, or use of Clause 90, wherein said agent is selected from the group consisting of antiviral drugs such as oseltamivir (brand name Tamiflu®) and zanamivir (brand name Relenza®) Arbidol®—adamantane derivatives (Amantadine®, Rimantadine®)—neuraminidase inhibitors (Oseltamivir®, Laninamivir®, Peramivir®, Zanamivir®) nucleotide analog reverse transcriptase inhibitor including Purine analogue guanine (Aciclovir®/Valacyclovir®, Ganciclovir®/Nalganciclovir®, Penciclovir®/Famciclovir®) and adenine (Vidarabine®), Pyrimidine analogue, uridine (Idoxuridine®, Trifluridine®, Edoxudine®), thymine (Brivudine®), cytosine (Cytarabine®); Foscarnet; Nucleoside analogues/NARTIs: Entecavir, Lamivudine®, Telbivudine®, Clevudine®; Nucleotide analogues/NtRTIs: Adefovir®, Tenofovir; Nucleic acid inhibitors such as Cidofovir®; Interferoninterferon alfa-2b, Peginterferon a-2a; Ribavirin®/Taribavirin®; antiretroviral drugs including zidovudine, lamivudine, abacavir, lopinavir, ritonavir, tenofovir/emtricitabine, efavirenz each of them alone or a various combinations, gp41 (Enfuvirtide), Raltegravir®, protease inhibitors such as Fosamprenavir®, Lopinavir® and Atazanavir®, Methisazone®, Docosanol®, Fomivirsen®, and Tromantadine®.

Clause 92A. The method, composition, antibody or fragment or VISTA fusion protein, or use of any of the foregoing Clauses further comprising one or more additional therapeutic agents used for treatment of fungal infections.

Clause 93A. The method, composition, antibody or fragment or VISTA fusion protein, or use of Clause 92, selected from the group consisting of antifungal drugs of the Polyene antifungals, Imidazole, triazole, and thiazole antifungals, Allylamines, Echinocandins or other anti-fungal drugs.

Clause 94A. The method or use of any of the foregoing Clauses, wherein the treated individual suffers from cancer.

Clause 95A. The method or use of Clause 94, wherein the cancer is selected from the group consisting of breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous miillerian cancer, malignant ascites, gastrointestinal stromal tumor (GIST), Li-Fraumeni syndrome and Von Hippel-Lindau syndrome (VHL), and cancer of unknown origin either primary or metastatic.

Clause 96A. The method or use of Clause 94, wherein the cancer is selected from B-cell lymphoma, Burkitt's lymphoma, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma cancer, keratoacanthomas, anaplastic large-cell lymphoma, esophageal squamous cells carcinoma, hepatocellular carcinoma cancer, follicular dendritic cell carcinoma, muscle-invasive cancer, seminal vesicle tumor, epidermal carcinoma, cancer of the retina, biliary cancer, small bowel cancer, salivary gland cancer, cancer of connective tissue, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, esophagogastric, fallopian tube cancer, peritoneal cancer, papillary serous mullerian cancer, malignant ascites, gastrointestinal stromal tumor (GIST), Li-Fraumeni syndrome and Von Hippel-Lindau syndrome (VHL); endometrial cancer, Breast carcinoma, preferably any of ductal-carcinoma, infiltrating ductal carcinoma, lobular carcinoma, mucinous adenocarcinoma, intra duct and invasive ductal carcinoma, and Scirrhous adenocarcinoma, Colorectal adenocarcinoma, preferably any of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, Moderately Differentiated Mucinous adenocarcinoma of the rectum; Lung cancer, preferably any of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, Small cell lung cancer, preferably Small cell lung carcinoma, more preferably undifferentiated Small cell lung carcinoma; Prostate adenocarcinoma, preferably any of Adenocarcinoma Gleason Grade 6 to 9, Infiltrating adenocarcinoma, High grade prostatic intraepithelial neoplasia, undifferentiated carcinoma; Stomach adenocarcinoma, preferably moderately differentiated gastric adenocarcinoma; Ovary carcinoma, preferably any of cystadenocarcinoma, serous papillary cystic carcinoma, Serous papillary cystic carcinoma, Invasive serous papillary carcinoma; Brain cancer, preferably any of Astrocytoma and Glioblastoma multiforme; Kidney carcinoma, preferably Clear cell renal cell carcinoma; Liver cancer, preferably any of Hepatocellular carcinoma, preferably Low Grade hepatocellular carcinoma, Fibrolamellar Hepatocellular Carcinoma; and Lymphoma, preferably any of, Hodgkin's Lymphoma and High to low grade Non-Hodgkin's Lymphoma.

Clause 97A. The method or use of any of the foregoing Clauses wherein the levels of VSIG3 and/or VISTA protein are elevated compared to normal cell samples.

Clause 98A. The method or use of Clause any one the foregoing Clauses, wherein the treated individual suffers from a cancer wherein the cancer or other cells contained at the tumor sites do not express VSIG3 and/or VISTA protein or do not express VSIG3 and/or protein at levels higher than normal.

Clause 99A. The method or use of any one of the foregoing Clauses, wherein the treated subject suffers from a cancer wherein the diseased cells, APC's, hematopoietic cells, NK cells, monocytes, dendritic cells, neutrophils, monocytes, or other immune cells at the disease site, e.g., myeloid suppressor cells express VSIG3 and/or VISTA protein.

Clause 100A. An anti-VISTA antibody or antigen-binding fragment or VISTA fusion protein or composition, or method or use according to any of the foregoing Clauses which includes treatment with an anti-VISTA antibody or antigen-binding fragment or composition containing and the therapy comprises one or more of radiotherapy, cryotherapy, antibody therapy, chemotherapy, photodynamic therapy, surgery, hormonal deprivation or combination therapy with conventional drugs.

Clause 101A. An anti-VISTA antibody or antigen-binding fragment or composition, or method or use according to any of the foregoing Clauses which includes treatment with an anti-VISTA antibody or antigen-binding fragment or VISTA fusion protein or composition containing and another therapeutic agent selected from the group consisting of cytotoxic drugs, tumor vaccines, antibodies, peptides, pepti-bodies, small molecules, chemotherapeutic agents, cytotoxic and cytostatic agents, immunological modifiers, interferons, interleukins, immuno stimulatory growth hormones, cytokines, vitamins, minerals, aromatase inhibitors, RNAi, Histone Deacetylase Inhibitors, and proteasome inhibitors.

Clause 102A. An anti-VISTA antibody or antigen-binding fragment or VISTA fusion protein or composition, or method or use according to any of the foregoing Clauses which includes treatment with an anti-VISTA antibody or antigen-binding fragment or composition containing and another therapeutic or an imaging agent administered to a subject simultaneously or sequentially in combination with one or more potentiating agents to obtain a therapeutic effect, wherein said one or more potentiating agents is selected from the group consisting of radiotherapy, conventional/classical anti-cancer therapy potentiating anti-tumor immune responses, Targeted therapy potentiating anti-tumor immune responses, Therapeutic agents targeting immunosuppressive cells Tregs and/or MDSCs, Immuno stimulatory antibodies, Cytokine therapy, Adoptive cell transfer.

Clause 103A. An anti-VISTA antibody or antigen-binding fragment or VISTA fusion protein or composition, or method or use according to any of the foregoing Clauses, wherein the conventional/classical anti-cancer agent is selected from platinum based compounds, antibiotics with anti-cancer activity, Anthracyclines, Anthracenediones, alkylating agents, antimetabolites, Antimitotic agents, Taxanes, Taxoids, microtubule inhibitors, *Vinca* alkaloids, Folate antagonists, Topoisomerase inhibitors, Antiestrogens, Antiandrogens, Aromatase inhibitors, GnRh analogs, inhibitors of 5a-reductase, biphosphonates.

Clause 104A. An anti-VISTA antibody or antigen-binding fragment or composition, or method or use according to any of the foregoing Clauses or VISTA fusion protein further comprising Platinum based compounds such as oxaliplatin, cisplatin, carboplatin; Antibiotics with anti-cancer activity, such as dactinomycin, bleomycin, mitomycin-C, mithramycin and Anthracyclines, such as doxorubicin, daunorubicin, epirubicin, idarubicin; Anthracenediones, such as mitoxantrone; Alkylating agents, such as dacarbazine, melphalan, cyclophosphamide, temozolomide, chlorambucil, busulphan, nitrogen mustard, nitrosoureas; Antimetabolites, such as fluorouracil, raltitrexed, gemcitabine, cytosine arabinoside, hydroxyurea and Folate antagonists, such as methotrexate, trimethoprim, pyrimethamine, pemetrexed; Antimitotic agents such as polokinase inhibitors and Microtubule inhibitors, such as Taxanes and Taxoids, such as paclitaxel, docetaxel; *Vinca* alkaloids such as vincristine, vinblastine, vindesine, vinorelbine; Topoisomerase inhibitors, such as etoposide, teniposide, amsacrine, topotecan, irinotecan, camptothecin; Cytostatic agents including Antiestrogens such as tamoxifen, fulvestrant, toremifene, raloxifene, droloxifene, iodoxyfene, Antiandrogens such as bicalutamide, flutamide, nilutamide and cyproterone acetate, Progestogens such as megestrol acetate, Aromatase inhibitors such as anastrozole, letrozole, vorozole, exemestane; GnRH analogs, such as leuprorelin, goserelin, buserelin, degarelix; inhibitors of 5a-reductase such as finasteride.

Clause 105A. An anti-VISTA antibody or antigen-binding fragment or VISTA fusion protein or composition, or method or use according to any of the foregoing Clauses, further comprising a Platinum based compound.

Clause 106A. An anti-VISTA antibody or antigen-binding fragment or VISTA fusion protein or composition, or method or use according to any of the foregoing Clauses, further comprising a targeted therapy selected from the group consisting of but not limited to: histone deacetylase (HDAC) inhibitors, such as vorinostat, romidepsin, panobinostat, belinostat, mocetinostat, abexinostat, entinostat, resminostat, givinostat, quisinostat, sodium butyrate; Proteasome inhibitors, such as bortezomib, carfilzomib, disulfiram; mTOR pathway inhibitors, such as temsirolimus, rapamycin, everolimus; PI3K inhibitors, such as perifosine, CAL101, PX-866, IPI-145, BAY 80-6946; B-raf inhibitors such as vemurafenib, sorafenib; JAK2 Inhibitors, such as lestaurtinib, pacritinib; Tyrosine kinase inhibitors (TKIs), such as erlotinib, imatinib, sunitinib, lapatinib, gefitinib, sorafenib, nilotinib, toceranib, bosutinib, neratinib, vatalanib, regorafenib, cabozantinib; other Protein kinase inhibitors, such as crizotinib; Inhibitors of serine/threonine kinases for example Ras/Raf signaling inhibitors such as farnesyl transferase inhibitors; Inhibitors of serine proteases for example matriptase, hepsin, urokinase; Inhibitors of intracellular signaling such as tipifarnib, perifosine; Inhibitors of cell signaling through MEK and/or AKT kinases; aurora kinase inhibitors such as AZD1152, PH739358, VX-680, MLN8054, R763, MP235, MP529, VX-528, AX39459; Cyclin dependent kinase inhibitors such as CDK2 and/or CDK4 inhibitors; Inhibitors of survival signaling proteins including Bcl-2, Bcl-XL, such as ABT-737; HSP90 inhibitors; Therapeutic monoclonal antibodies, such as anti-EGFR mAbs cetuximab, panitumumab, nimotuzumab, anti-ERBB2 mAbs trastuzumab, pertuzumab, anti-CD20 mAbs such as rituximab, ofatumumab, veltuzumab and mAbs targeting other tumor antigens such as alemtuzumab, labetuzumab, adecatumumab, oregovomab, onartuzumab; TRAIL pathway agonists, such as dulanermin (soluble rhTRAIL), apomab, mapatumumab, lexatumumab, conatumumab, tigatuzumab; Antibody fragments, bi-specific antibodies and bi-specific T-cell engagers (BiTEs), such as catumaxomab, blinatumomab; Antibody drug conjugates (ADC) and other immunoconjugates, such as ibritumomab triuxetan, tositumomab, brentuximab vedotin, gemtuzumab ozogamicin, clivatuzumab tetraxetan, pemtumomab, trastuzumab emtansine; Anti-angiogenic therapy such as bevacizumab, etaracizumab, volociximab, ramucirumab, aflibercept, sorafenib, sunitinib, regorafenib, axitinib, nintedanib, motesanib, pazopanib, cediranib; Metalloproteinase inhibitors such as marimastat; Inhibitors of urokinase plasminogen activator receptor function; Inhibitors of cathepsin activity.

Clause 107A. An anti-VISTA antibody or antigen-binding fragment or VISTA fusion protein or composition, or method or use according to Clause 106, the another therapeutic agent is another antibody selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Clause 108A. An anti-VISTA antibody or antigen-binding fragment or VISTA fusion protein or composition, or method or use according to any of the foregoing Clauses, further comprising a Therapeutic cancer vaccine selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cell-based vaccines, whole tumor cell vaccines, gene modified tumor cells expressing GM-CSF, ICOS and/or Flt3-ligand, oncolytic virus vaccines.

Clause 109A. An anti-VISTA antibody or antigen-binding fragment or VISTA fusion protein or composition, or method or use according to any of the foregoing Clauses, further comprising a Cytokine therapy selected from one or more of the following cytokines such as IL-2, IL-7, IL-12, IL-15, IL-17, IL-18 and IL-21, IL-23, IL-27, GM-CSF, IFNa (interferon α), IFNa-2b, IFN (3, IFN γ, and their different strategies for delivery.

Clause 110A. An anti-VISTA antibody or antigen-binding fragment or VISTA fusion protein or composition, or method or use according to any of the foregoing Clauses, further comprising adoptive cell transfer therapy which is carried out following ex vivo treatment selected from expansion of the patient autologous naturally occurring tumor specific T cells or genetic modification of T cells to confer specificity for tumor antigens.

Clause 111A. The method or use of any of the foregoing Clauses, wherein said anti-VISTA antibody or antigen-binding fragment comprises an immunoinhibitory antibody or an antigen-binding fragment which mediates any combination of at least one of the following immunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VISTA antibody or antigen-binding fragment may elicit an opposite effect to one or more of (i)-(xxviii).

Clause 112A. A method of treatment and/or diagnosis, or use of a composition containing an anti-VISTA antibody or antigen-binding fragment f or VISTA fusion protein or diagnostic or therapeutic use, which comprises suppressing T cell immunity or natural killer (NK) immunity and/or promoting Tregs or MDSC's in a subject in need thereof, which comprises administering a therapeutically or diagnostically effective amount of at least one antibody, antigen-binding fragment or a composition containing according to any one of the above Clauses, wherein such antibody or antigen-binding fragment agonizes, mimics or promotes at least one effect of a polypeptide (VISTA) having the amino acid sequence of SEQ ID NO: 1 or an ortholog on immunity or immune cells.

Clause 113A. The method or use of Clauses 111 or 112, which is used in the treatment of allergy, autoimmunity, transplant, gene therapy, inflammatory conditions, or combination thereof.

Clause 114A. A method or use according to any one of the foregoing Clauses wherein the treated individual has or is to receive cell therapy, gene therapy or a transplanted tissue or organ, and the treatment reduces or inhibits the undesirable immune activation that is associated with such cell therapy, gene therapy or a transplanted tissue or organ.

Clause 115A. The method or use of any one of the foregoing Clauses, wherein the antibody, or antigen-binding fragment thereof or VISTA fusion protein is an immunoinhibitory antibody or fragment which effects one or more of the following: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) Increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VISTA antibody or antigen-binding fragment may elicit an opposite effect to one or more of (i)-(xxviii).

Clause 116A. The method or use of any one of the foregoing Clauses, which enhances, agonizes or mimics at least one effect of VSIG3 and/or VISTA on T or natural killer (NK) cell immunity.

Clause 117A. The method or use of any one of the foregoing Clauses which increases the inhibitory effect of VSIG3 and/or VISTA on T cell immunity.

Clause 118A. The method or use of any one of the foregoing Clauses which inhibits CTL activity.

Clause 119A. The method or use of Clause 118, wherein inhibited CTL activity includes reduced secretion of one or more proinflammatory cytokines and/or reduced CTL mediated killing of target cells.

Clause 120A. The method or use of any one of the foregoing Clauses which inhibits CD4+ T cell activation and/or CD4+ T cell proliferation and/or CD4+ T cell mediated cell depletion.

Clause 121A. The method or use of any one of the foregoing Clauses which inhibits CD8+ T cell activation and/or CD8+ T cell proliferation and/or CD8+ T cell mediated cell depletion.

Clause 122A. The method or use of any one of the foregoing Clauses which inhibits NK cell activity.

Clause 123A. The method or use of Clause 122, wherein inhibited NK cell activity includes reduced depletion of target cells and/or proinflammatory cytokine release.

Clause 124A. The method or use of any one of the foregoing Clauses which promotes and/or increases the differentiation, proliferation and/or activity of regulatory cells, such as T cells (Tregs) and/or the differentiation, proliferation, infiltration and/or activity of myeloid derived suppressor cells (MDSC's).

Clause 125A. The method or use of any one the foregoing Clauses which promotes and/or increases the infiltration of regulatory cells, such as Tregs or MDSCs into a disease site.

Clause 126A. The method or use of any one of the foregoing Clauses which inhibits an allergic, autoimmune or inflammatory immune response by promoting one or more of the effects of VSIG3 and/or VISTA on immunity.

Clause 127A. The method or use of any one of the foregoing Clauses which promotes antigen-specific tolerance or prolonged suppression of an antigen-specific immune response by enhancing one or more of the effects of VSIG3 and/or VISTA on immunity.

Clause 128A. The method or use of any one of the foregoing Clauses which elicits tolerance or prolonged suppression of antigen-specific immunity against transplanted cells, tissue or organ.

Clause 129A. The method or use of any one of the foregoing Clauses which inhibits an immune response against an autoantigen, allergen, or inflammatory agent by promoting one or more of the effects of VSIG3 and/or VISTA on immunity.

Clause 130A. The method or use of any one the foregoing Clauses wherein the treated individual has or is to receive cell therapy, gene therapy or a transplanted tissue or organ, and the treatment reduces or inhibits the undesirable immune activation that is associated with such cell therapy, gene therapy or a transplanted tissue or organ.

Clause 131A. The method or use of any one of the foregoing Clauses which is used to treat an inflammatory conditions or autoimmune disorder selected from Acid Reflux/Heartburn, Acne, Acne Vulgaris, Allergies and Sensitivities, Alzheimer's Disease, Asthma, Atherosclerosis and Vascular Occlusive Disease, optionally Atherosclerosis, Ischemic Heart Disease, Myocardial Infarction, Stroke, Peripheral Vascular Disease, or Vascular Stent Restenosis, Autoimmune Diseases, Bronchitis, Cancer, Carditis, Cataracts, Celiac Disease, Chronic Pain, Chronic Prostatitis, Cirrhosis, Colitis, Connective Tissue Diseases, optionally Systemic Lupus Erythematosus, Systemic Sclerosis, Polymyositis, Dermatomyositis, or Sjogren's Syndrome and related conditions such as Sjogren's syndrome" herein includes one or more of Sjogren's syndrome, Primary Sjogren's syndrome and Secondary Sjogren's syndrome, as well as conditions or complications relating to Sjogren's syndrome including connective tissue disease, such as rheumatoid arthritis, systemic lupus erythematosus, or scleroderma, pneumonia, pulmonary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, Inflammation in the esophagus, stomach, pancreas, and liver (including hepatitis), Polymyositis, Raynaud's phenomenon, Vasculitis, Autoimmune thyroid problems, lymphoma, Corneal Disease, Crohn's Disease, Crystal Arthropathies, optionally Gout, Pseudogout, Calcium Pyrophosphate Deposition Disease, Dementia, Dermatitis, Diabetes, Dry Eyes, Eczema, Edema, Emphysema, Fibromyalgia, Gastroenteritis, Gingivitis, Glomerulonephritis, Heart Disease, Hepatitis, High Blood Pressure, Hypersensitivities, Inflammatory Bowel Diseases, Inflammatory Conditions including Consequences of Trauma or Ischaemia, Insulin Resistance, Interstitial Cystitis, Iridocyclitis, Iritis, Joint Pain, Arthritis, Lyme Disease, Metabolic Syndrome (Syndrome X), Multiple Sclerosis, Myositis, Nephritis, Obesity, Ocular Diseases including Uveitis, Osteopenia, Osteoporosis, Parkinson's Disease, Pelvic Inflammatory Disease, Periodontal Disease, Polyarteritis, Polychondritis, Polymyalgia Rheumatica, Psoriasis, Reperfusion Injury, Rheumatic Arthritis, Rheumatic Diseases, Rheumatoid Arthritis, Osteoarthritis, or Psoriatic Arthritis, Rheumatoid Arthritis, Sarcoidosis, Scleroderma, Sinusitis, "Sjogren's syndrome" and related conditions or complications associated therewith such as one or more of Sjogren's syndrome, Primary Sjogren's syndrome and Secondary Sjogren's syndrome, conditions relating to Sjogren's syndrome including connective tissue disease, such as rheumatoid arthritis, systemic lupus erythematosus, or scleroderma, and complications relating to Sjogren's syndrome such as pneumonia, pulmonary fibrosis, interstitial nephritis, inflammation of the tissue around the kidney's filters, glomerulonephritis, renal tubular acidosis, carpal tunnel syndrome, peripheral neuropathy, cranial neuropathy, primary biliary cirrhosis (PBC), cirrhosis, inflammation in the esophagus, stomach, pancreas, and liver (including hepatitis), Polymyositis, Raynaud's phenomenon, Vasculitis, Autoimmune thyroid problems, lymphoma, Sjogren's Syndrome, Spastic Colon, Spondyloarthropathies, optionally Ankylosing Spondylitis, Reactive Arthritis, or Reiter's Syndrome, Systemic Candidiasis, Tendonitis, Transplant Rejection, UTI's, Vaginitis, Vascular Diseases including Atherosclerotic Vascular Disease, Vasculitides, Polyarteritis *Nodosa*, Wegener's Granulomatosis, Churg-Strauss Syndrome, or vasculitis.

Clause 132A. The method or use of any of the foregoing Clauses which is used to treat an autoimmune or allergic disease selected from acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, optionally, large vessel vasculitis, optionally, polymyalgia rheumatica and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia greata, alopecia totalis, Alport's syndrome, alveolitis, optionally allergic alveolitis or fibrosing alveolitis, Alzheimer's disease, amyloidosis, amylotrophic lateral sclerosis (ALS; Lou Gehrig's disease), an eosinophil-related disorder, optionally eosinophilia, anaphylaxis, ankylosing spondylitis, angiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis, optionally rheumatoid arthritis such as acute arthritis, or chronic rheumatoid arthritis, arthritis chronica progrediente, arthritis deformans, ascariasis, aspergilloma, granulomas containing eosinophils, aspergillosis, aspermiogenese, asthma, optionally asthma bronchiale, bronchial asthma, or auto-immune asthma, ataxia telanglectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease, optionally autoimmune inner ear disease (AGED), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies, optionally epilepsy, channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy, optionally IgM polyneuropathies or IgM-mediated neuropathy, chronic obstructive airway disease, chronic pulmonary inflammatory disease, Chronic recurrent multifocal osteomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogan's syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, optionally chronic cyclitis, heterochronic cyclitis, iridocyclitis, or Fuch's cyclitis, cystic fibrosis, cytokine-induced toxicity, deafness, degenerative arthritis, demyelinating diseases, optionally autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis, optionally allergic encephalomyelitis or encephalomyelitis allergica and experimental allergic encephalomyelitis (EAE), endarterial hyperplasia, endocarditis, endocrine ophthalmopathy, endometriosis, endomyocardial fibrosis, endophthalmia phacoanaphylactica, endophthalmitis, enteritis allergica, eosinophilia-myalgia syndrome, eosinophilic fascitis, epidemic keratoconjunctivitis, epidermolysis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, filariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, hemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schonlein purpura, Herpes gestationis, human immunodeficiency virus (HIV) Infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases, optionally anaphylaxis and allergic or atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type I), insulitis, Interstitial cystitis, interstitial lung disease, interstitial lung fibrosis, iritis, ischemic re-perfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis *nodosa*), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes, optionally Lambert-Eaton myasthenic syndrome or Eaton-Lambert syndrome, parasitic diseases such as *Leishmania*, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus *foliaceus*, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis *nodosa*, Type I, II, & III, polyarthritis chronica primaria, polychondritis (e.g., refractory or relapsed polychondritis), polyendocrine autoimmune disease, poly endocrine failure, polyglandular syndromes, optionally autoimmune polyglandular syndromes (or polyglandular endocrinopathy syndromes), polymyalgia rheumatica, polymyositis, polymyositis/dermatomyositis, polyneuropathies, polyradiculitis *acuta*, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis, optionally benign monoclonal gammopathy and monoclonal gammopathy of undetermined significance, MGUS, primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyroiditis, Raynaud's phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma, optionally systemic scleroderma, sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjogren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes, cutaneous SLE, systemic necrotizing vasculitis, ANCA-associated vasculitis, optionally Churg-Strauss vasculitis or syndrome (CSS), tabes dorsalis, Takayasu's arteritis, telangiectasia, temporal arteritis/Giant cell arteritis, thromboangiitis ubiterans, thrombocytopenia, including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria, optionally chronic allergic urticaria and chronic idiopathic urticaria, including chronic autoimmune urticaria, uveitis, anterior uveitis, uveoretinitis, valvulitis, vascular dysfunction, vasculitis, vertebral arthritis, vesiculobullous dermatosis, vitiligo, Wegener's granulomatosis (Granulomatosis with Polyangiitis (GPA)), Wiskott-Aldrich syndrome, or x-linked hyper IgM syndrome.

Clause 133A. The method or use of any of the foregoing Clauses which is used to treat an autoimmune disease selected from the group consisting of multiple sclerosis, psoriasis; rheumatoid arthritis; psoriatic arthritis, systemic lupus erythematosus (SLE); discoid lupus erythematosus, inflammatory bowel disease, ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune haemolytica anemia, Guillain-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anemia, pemphigus, pemphigus vulgaris, cirrhosis, primary biliary cirrhosis, dermatomyositis, polymyositis, fibromyositis, myogelosis, celiac disease, immunoglobulin A nephropathy, Henoch-Schonlein purpura, Evans syndrome, dermatitis, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis nodosa, chondrocalcinosis, Wegener's granulomatosis, microscopic polyangiitis, chronic urticaria, bullous skin disorders, pemphigoid, atopic eczema, childhood autoimmune hemolytic anemia, idiopathic autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, idiopathic pericarditis, myocarditis, vasculitis, gastritis, gout, gouty arthritis, and inflammatory skin disorders, normocomplementemic urticarial vasculitis, pericarditis, myositis, anti-synthetase syndrome, scleritis, macrophage activation syndrome, Behcet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, a rheumatic disease, polymyalgia rheumatica, mixed connective tissue disease, inflammatory rheumatism, degenerative rheumatism, extraarticular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, temporal arteritis, giant cell arteritis, Takayasu arteritis, Behcet's disease, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, fibromyalgia, chronic fatigue and immune dysfunction syndrome (CFIDS), autoimmune inner ear disease, Hyper IgD syndrome, Schnitzler's syndrome, autoimmune retinopathy, age-related macular degeneration, atherosclerosis, chronic prostatitis, alopecia, alopecia areata, alopecia universalis, alopecia totalis, autoimmune thrombocytopenic purpura, idiopathic thrombocytopenic purpura, pure red cell aplasia, and TNF receptor-associated periodic syndrome (TRAPS).

Clause 134A. The method or use of any of the foregoing Clauses, wherein the diagnosis and/or treatment is combined with another moiety useful for treating immune related condition.

Clause 135A. The method or use of Clause 134, wherein said other moiety useful for treating immune related condition is selected from immunosuppressants such as corticosteroids, cyclosporin, cyclophosphamide, prednisone, azathioprine, methotrexate, rapamycin, tacrolimus, lef unomide or an analog thereof; mizoribine; mycophenolic acid; mycophenolate mofetil; 15-deoxyspergualine or an analog thereof; biological agents such as TNF-a blockers or antagonists, or any other biological agent targeting any inflammatory cytokine, nonsteroidal antiinflammatory drugs/Cox-2 inhibitors, hydroxychloroquine, sulphasalazopryine, gold salts, etanercept, infliximab, mycophenolate mofetil, basiliximab, atacicept, rituximab, Cytoxan, interferon β-Ia, interferon β-Ib, glatiramer acetate, mitoxantrone hydrochloride, anakinra and/or other biologies and/or intravenous immunoglobulin (IVIG), interferons such as IFN-p-Ia (REBIF®. AVONEX® and CINNOVEX®) and IFN-p-Ib (BETASERON®); EXTAVIA®, BETAFERON®, ZIFERON®); glatiramer acetate (COPAXONE®), a polypeptide; natalizumab (TYSABRI®), mitoxantrone (NOVANTRONE®), a cytotoxic agent, a calcineurin inhibitor, e.g. cyclosporin A or FK506; an immunosuppressive macrolide, e.g. rapamycine or a derivative thereof; e.g. 40-O-(2-hydroxy)ethyl-rapamycin, a lymphocyte homing agent, e.g. FTY720 or an analog thereof, corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MEW, CD2, CD3, CD4, CDI Ia/CD18, CD7, CD25, CD27, B7, CD40, CD45, CD58, CD137, ICOS, CD150 (SLAM), OX40, 4-1BB or their ligands; or other immunomodulatory compounds, e.g. CTLA4-Ig (abatacept, ORENCIA®, belatacept), CD28-g, B7-H4-Ig, or other costimulatory agents, or adhesion molecule inhibitors, e.g. mAbs or low molecular weight inhibitors including LFA-1 antagonists, Selectin antagonists and VLA-4 antagonists, or another immunomodulatory agent.

Clause 136A. An anti-VISTA antibody or antigen-binding fragment or VISTA fusion protein or composition, or method or use according to any of the foregoing Clauses which includes another moiety is useful for reducing the undesirable immune activation that follows gene therapy.

Clause 137A. An anti-VISTA antibody or antigen-binding fragment or VISTA fusion protein or composition, or method or use according to any of the foregoing Clauses which includes treatment with an anti-VISTA antibody or antigen-binding fragment or composition containing combined with another therapeutic agent or therapy.

Clause 138A. An anti-VISTA antibody or antigen-binding fragment or VISTA fusion protein or composition, or method or use according to any of the foregoing Clauses, further comprising a Therapeutic agent targeting immunosuppressive cells Tregs and/or MDSCs is selected from antimitotic drugs, cyclophosphamide, gemcitabine, mitoxantrone, fludarabine, thalidomide, thalidomide derivatives, COX-2 Inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the *pseudomonas* exotoxin, antibodies targeting Treg cell surface receptors, TLR modulators, agents that interfere with the adenosinergic pathway, ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors, sildenafil, ROS inhibitors and nitroaspirin.

Clause 139A. An anti-VISTA antibody or antigen-binding fragment or VISTA fusion protein or composition, or method or use according to any of the foregoing Clauses, further comprising another antibody is selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD137, OX40, GITR, CD27, CD28 or ICOS.

Clause 140A. The method or use of any of the foregoing Clauses, which includes assaying VISTA and/or VISTA protein by the individual's cells prior, concurrent and/or after treatment.

Clause 141A. The method or use of Clause 140, wherein the method detects the expression of VSIG3 and/or VISTA protein by diseased and/or normal cells prior to treatment, optionally by the use of an antibody or nucleic acid that detects VSIG3 and/or VISTA expression.

Clause 142A. The method or use of any one of the foregoing Clauses, which further includes the administration or use of another diagnostic or therapeutic agent, which may be administered prior, concurrent or after the administration of the anti-VISTA antibody, or antigen-binding fragment or composition containing according to any one of the foregoing Clauses.

Clause 143A. The method or use of Clause 142, which includes the administration of another therapeutic agent.

Clause 144A. The method or use of Clause 143, wherein the other therapeutic agent is selected from a drug, another immunomodulatory compound, a radionuclide, a fluorophore, an enzyme, a toxin, or a chemotherapeutic agent; and the detectable agent is selected from a radioisotope, a metal chelator, an enzyme, a fluorescent compound, a bioluminescent compound or a chemiluminescent compound.

Clause 145A. The method or use of any one of the foregoing Clauses, which further includes the administration of an antibody or antigen-binding fragment thereof which specifically binds to a NK cell receptor.

Clause 146A. The method or use of Clause 145, wherein the antibody or antigen-binding fragment thereof which specifically binds to an NK cell receptor agonizes the effect of said NK cell receptor.

Clause 147A. The method or use of Clause 146, wherein the antibody or antigen-binding fragment thereof which specifically binds to an NK cell receptor antagonizes the effect of said NK cell receptor or one that inhibits NK cell activity.

Clause 148A. The method or use of Clause 147, wherein the inhibitory NK cell receptor is selected from the group consisting of KIR2DL1, KIR2DL2/3, KIR2DL4, KIR2DL5A, KIR2DL5B, KIR3DL1, KIR3DL2, KIR3DL3, LILRB 1, NKG2A, NKG2C, NKG2E and LILRB5.

Clause 149A. The method or use of Clause 145, wherein the NK cell receptor is one that promotes NK cell activity.

Clause 150A. The method or use of Clause 149, wherein the NK cell activating receptor is selected from the group consisting of NKp30, NKp44, NKp46, NKp46, NKG2D, KIR2DS4 CD2, CD 16, CD69, DNAX accessory molecule-1 (DNAM-1), 2B4, NK1.1; a killer immunoglobulin (Ig)-like activating receptors (KAR); ILTs/LIRs; NKRP-1, CD69; CD94/NKG2C and CD94/NKG2E heterodimers, NKG2D homodimer KIR2DS and KIR3DS.

Clause 151A. An assay method for selecting an anti-VISTA antibody or antigen-fragment or VISTA fusion protein antibody according to any of the foregoing Clauses, or an anti-VISTA antibody or antigen-fragment suitable for use in a method or use according to any of the foregoing Clauses, wherein the method comprises (i) obtaining one or more antibodies or VISTA fusion protein that putatively bind to a VISTA polypeptide having a sequence selected from an amino acid sequence set forth in SEQ ID NOs: 3, or binding to a polypeptide possessing at least 90% sequence identity therewith or to a non-human VISTA ortholog, or a fragment or variant thereof containing at least one VISTA epitope, which fragment or variant possesses at least 90% identity thereto, or to a non-human VISTA ortholog (ii) determining whether said antibody or antigen-binding fragment specifically binds to said VISTA polypeptide, (iii) determining whether said antibody or antigen-binding fragment modulates (agonizes or antagonizes) at least one effect of VISTA on immunity, and (iv) if (ii) and (iii) are satisfied selecting said antibody as one potentially useful in a method or use according to any of the foregoing Clauses.

Clause 152A. The method of Clause 151 which further includes humanization, primatization or chimerization if the antibody or antigen-binding fragment is not a human or non-human primate antibody or a fragment thereof.

Clause 153A. The method of Clauses 151 or 152 wherein the immunogen used to derive said antibody or antigen-binding fragment comprises a VISTA polypeptide having a sequence selected from an amino acid sequence set forth in any of SEQ ID NO: 3, or binding to a polypeptide possessing at least 90% sequence identity therewith or to a non-human VISTA ortholog or the same region of a nn-human VISTA ortholog, or a fragment or variant thereof containing at least one VISTA epitope.

Clause 154A. The method of any of Clauses 151-153 wherein the immunogen used to derive said antibody or antigen-binding fragment comprises a VISTA polypeptide having a sequence selected from an amino acid sequence set forth in SEQ ID NO: 3 or binding to a polypeptide possessing at least 90% sequence identity therewith or to the same region of a non-human ortholog of hVISTA.

Clause 155A. The method of any of Clauses 151-154, wherein the immunogen used to derive said antibody or antigen-binding fragment thereof consists of a polypeptide having an amino acid sequence set forth in any of SEQ ID NO: 1, or binding to a polypeptide possessing at least 90% sequence identity therewith or to the same region of a non-human VISTA ortholog, or a conjugate thereof not containing another portion of any of the VISTA polypeptide.

Clause 156A. The method of any of Clauses 151-155, wherein step (iii) detects whether the anti-VISTA antibody or antigen binding fragment antagonizes at least one effect of VSIG3 and/or VISTA on immunity.

Clause 157A. The method of any of Clauses 151-156, wherein step (iii) detects whether the anti-VISTA antibody or antigen binding fragment agonizes at least one effect of VSIG3 and/or VISTA on immunity.

Clause 158A. The method of any of Clauses 151-157, wherein the selected antibody or VISTA fusion protein is demonstrated to mediate at least one of the following effects: (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-γ production, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxvi) induces direct killing of cancer cells, (xxvii) increases Th17 activity and/or (xxviii) induces complement dependent cytotoxicity and/or antibody dependent cell-mediated cytotoxicity, with the proviso that said anti-VISTA antibody or antigen-binding fragment may elicit an opposite effect to one or more of (i)-(xxviii).

Clause 159A. The method of any of the foregoing Clauses, wherein the selected antibody or VISTA fusion protein is demonstrated to mediate at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VISTA antibody or antigen-binding fragment may elicit an opposite effect to one or more of (i)-(xxviii).

Clause 160A. The method of any of Clauses 149-159 wherein the selected antibody or VISTA fusion protein agonizes or antagonizes the effects of VSIG3 and/or VISTA on T cell activity, NK cell activity, and/or the production of one or more proinflammatory cytokines.

Clause 161A. The method of any of Clauses 149-160 wherein the selected antibody or VISTA fusion protein is demonstrated to compete with binding to human or rodent VSIG3 to VISTA.

Clause 162A. An immunomodulatory antibody or antigen-binding fragment or VISTA fusion protein according to any one of the foregoing Clauses or a pharmaceutical or diagnostic composition containing same.

Clause 163A. Use of immunomodulatory antibody or antigen-binding fragment or VISTA fusion protein according to any one of the foregoing Clauses or a pharmaceutical or diagnostic composition containing same for treating or diagnosing a disease selected from cancer, infection, sepsis, autoimmunity, inflammation, allergic or other immune related condition or to suppress an undesired immune reaction to a cell or gene therapy therapeutic or a transplanted cell, tissue or organ.

Clause 164A. A transplant therapy which includes the transplant of cells, tissue or organ into a recipient, wherein the cells, tissue or organ or treated ex vivo using a composition containing an anti-VISTA antibody or antigen-binding fragment or VISTA fusion protein or composition according to any one of the foregoing Clauses prior to infusion or transplant of said cells, tissue or organ into the recipient.

Clause 165A. The method of Clause 164, wherein the composition comprises immune cells of the donor and/or transplant recipient.

Clause 166A. The method of Clauses 164 or 165 wherein the transplanted cells, tissue or organ comprises bone marrow, other lymphoid cells or tissue or stem cells.

Clause 167A. A nucleic acid encoding the variable heavy and/or light region polypeptide of an anti-VISTA antibody or antibody fragment according to any one of the foregoing Clauses or a vector or virus containing.

Clause 168A. An isolated or recombinant cell which comprises at least one nucleic acid or vector or virus according to Clause 167.

Clause 169A. The cell of Clause 168 which is selected from a hybridoma and a recombinant bacterial, yeast or fungal, mammalian, insect, amphibian, reptilian, plant, and avian cell or egg.

Clause 170A. A method of producing an anti-VISTA antibody or antibody fragment by culturing an isolated or recombinant cell according to Clause 169.

Clause 171A. The method of Clause 170 wherein the cell is a bacterial, yeast, fungal, insect, plant, reptilian, mammalian cell or an avian egg.

Clause 172A. An in vitro or in vivo method of using an antagonist compound according to any one of the foregoing Clauses to inhibit the interaction of VISTA and VSIG3.

Clause 173A. An in vitro or in vivo method of using an antagonist compound according to any one of the foregoing Clauses to inhibit the suppressive effects of VISTA and/or VSIG3 on immune cells or immunity.

Clause 174A. The method of Clause 172 or 173, which inhibits or blocks the suppressive effect of VISTA and/or VSIG3 on T cell activation, T cell proliferation or cytokine production or on myeloid dendritic cells.

Clause 175A. The method of Clause 172 or 173, which inhibit or block the promoting effect of VISTA on T suppressor (Tsup) cells.

Clause 176A. The method of any of Clause 172-175 which is used to treat a cancer or infectious disease.

Clause 177A. The method of Clause 176, wherein the cancer is a solid tumor, e.g., a sarcoma, carcinoma or lymphoma or a blood cancer.

Clause 178A. The method of Clause 176, wherein the infectious disease is a viral, bacterial, protozoan, yeast, fungal, or parasitic disease.

Clause 179A. A method of using a VISTA agonist compound according to any one of the foregoing Clauses to enhance the interaction of VISTA and VSIG3.

Clause 180A. The method of Clause 179, which enhances or promotes the suppressive effect of VISTA on T cell activation, proliferation or cytokine production.

Clause 181A. The method of Clause 178 or 179, which is used to treat an autoimmune, allergic or inflammatory condition.

Clause 182A. A compound according to any one of the foregoing Clauses, which is attached to a detectable label.

Clause 183A. A diagnostic or therapeutic composition comprising a diagnostically or therapeutically effective amount of a compound according to any one of the foregoing Clauses.

Clause 184A. The composition of Clause 183, which is suitable for use in human therapy.

Clause 185A. The composition of Clause 184 which is an intravenous, subcutaneous or intramuscularly administrable composition.

Clause 186A. A method according to any one of the foregoing Clauses, which further comprises the administration of a PD-1 or PD-L1 agonist or antagonist.

Clause 187A. The method of Clause 186, wherein said PD-1 or PD-L1 agonist or antagonist is selected from an anti-PD-1 antibody or antibody fragment, an anti-PD-L1 antibody or antibody fragment, a PD-L1 polypeptide or fragment thereof which may be monovalent or multimeric, a PD-1 polypeptide or fragment thereof which may be monovalent or multimeric, or a complex or fusion protein comprising any of the foregoing.

Clause 188A. A method of contacting immune cells with a VISTA agonist or antagonist compound according to any one of the foregoing Clauses.

Clause 189A. The method of Clause 188, wherein said contacted cells are infused into a human subject.

Clause 190A. The method of Clause 188 or 189, wherein the subject has cancer or an infectious disease.

Clause 191A. The method of Clause 188 or 189, wherein the subject has an inflammatory, allergic or autoimmune condition.

Clause 192A. A screening assay which comprises the use of VISTA alone or in association with VSIG3 to identify VSIG3/VISTA agonists or antagonists.

Clause 193A. The assay of Clause 192 which is a binding assay that identifies compounds that bind VISTA and inhibit the VSIG3/VISTA interaction.

Clause 194A. The assay of Clause 192 which is a binding assay that identifies compounds that bind VISTA and enhance the VSIG3/VISTA interaction.

Clause 195A. The assay of Clause 192 which is a functional assay that screens for compounds that inhibit the effects the VISTA/VSIG3 interaction on T cell immunity or cytokine production.

Clause 196A. The assay of Clause 192-195 which is a functional assay that screens for compounds that enhance the effects the VISTA/VSIG3 interaction on T cell immunity or cytokine production.

Clause 197A. The assay of any one of Clauses 192-196 which uses human or rodent immune cells.

Clause 198A. The assay of any one of Clauses 192-196 which uses a transgenic animal that expresses human VISTA and/or human VSIG3.

Clause 199A. The assay of Clause 192-198 which is a high throughput screening assay.

Clause 200A. The compound or method of any of the foregoing Clauses wherein said VISTA is a human, murine, or non-human primate VISTA protein.

Clause 201A. An isolated polypeptide comprising a fragment of a VISTA ECD, wherein said fragment consists essentially of or consists of an amino acid sequence as set forth in any one of SEQ ID NO: 3 or a variant thereof that possesses at least 80, 85, 90, 95, 96, 97, 98, or 99% sequence identity therewith.

Clause 202A. The isolated polypeptide of Clause 201, which comprises 2-10 of said VISTA ECD polypeptide fragments.

Clause 203A. An isolated polypeptide according to Clauses 201 or 202, wherein said fragments are intervened by a heterologous linker, wherein said linker is not a fragment of a VISTA polypeptide.

Clause 204A. The isolated peptide of Clause 203, wherein said linker is directly or indirectly conjugated to said fragments.

Clause 205A. The isolated polypeptide of Clauses 202, 203 or 204, wherein said linker is an amino acid spacer.

Clause 206A. The isolated peptide of Clause 205, wherein said amino acid spacer is of sufficient length of amino acid residues so that the different fragments can successfully bind to their individual targets.

Clause 207A. The isolated polypeptide of Clauses 205 or 206, wherein said linker is a peptide comprising 5-50 amino acid residues, more preferably 5-25 amino acid residues.

Clause 208A. The isolated peptide of Clause 207, wherein said linker is a peptide comprising 5-15 amino acid residues.

Clause 209A. The isolated polypeptide of any of Clauses 205-208, wherein said linker comprises or consists essentially of glycine, serine, and/or alanine residues or predominantly (at least 50, 60, 70 or 80% of the residues) consists of glycine, serine, and/or alanine residues.

Clause 210A. The isolated peptide of any of Clauses 205-209, wherein said linker comprises at least 4-40, 4-30, 4-20, or 4-12 glycine, serine, and/or alanine residues.

Clause 211A. A fusion protein comprising the isolated polypeptide of any of the preceding Clauses, or SEQ ID NO. 1, joined to a heterologous polypeptide and/or half-life extending moiety, with the proviso that said heterologous polypeptide or said half-life extending moiety is not a fragment of a VISTA polypeptide.

Clause 212A. The fusion protein according to Clause 211, wherein said isolated polypeptide and said heterologous molecule are intervened by a heterologous linker, with the proviso that said linker does not comprise a polypeptide that is a fragment of a VISTA polypeptide.

Clause 213A. The fusion protein of Clause 212, wherein said linker is directly or indirectly conjugated to said fragments.

Clause 214A. The fusion protein of Clauses 212 or 213, wherein said linker is an amino acid spacer.

Clause 215A. The fusion protein of Clause 214, wherein said amino acid spacer is of sufficient length of amino acid residues so that the different fragments can successfully bind to their individual targets.

Clause 216A. The fusion protein of Clauses 214 or 215, wherein said linker is a peptide comprising 5-50 amino acid residues, more preferably 5-25 amino acid residues.

Clause 217A. The fusion protein of Clause 216, wherein said linker is a peptide comprising 5-15 amino acid residues.

Clause 218A. The fusion protein of any of Clauses 214-217, wherein said linker comprises or consists essentially of glycine, serine, and/or alanine residues or predominantly (at least 50, 60, 70 or 80% of the residues) consists of glycine, serine, and/or alanine residues.

Clause 219A. The fusion protein of any of Clauses 214-218, wherein said linker comprises at least 4-40, 4-30, 4-20, or 4-12 glycine, serine, and/or alanine residues.

Clause 220A. The fusion protein of any of the above Clauses, comprising or further comprising a half-life extending moiety.

Clause 221A. The fusion protein according to any of Clauses 214-220, wherein the half-life extending moiety comprises polyethylene glycol (PEG), monomethoxy PEG (mPEG), an XTEN molecule, an rPEG molecule, an adnectin, a serum albumin, human serum albumin, immunoglobulin constant region or fragment thereof, or acyl group.

Clause 222A. The fusion protein according to any one of Clauses 214-221, wherein the addition of said heterologous polypeptide, half-life extending moiety, or other heterologous molecule increases the in vivo half-life of said fusion protein by at least 2-fold, at least 3-fold, at least 4-fold, at least 5-fold, at least 10-fold, or more, as compared to the identical molecule without such said heterologous polypeptide, half-life extending moiety, or other heterologous molecule.

Clause 223A. The fusion protein according to any of the foregoing Clauses which comprises an immunoglobulin molecule or a fragment thereof.

Clause 224A. The fusion protein according to Clause 214 wherein at least one of the heterologous polypeptides is a human or non-human immunoglobulin Fc polypeptide or fragment that comprises heavy and/or light chain Cm and Cm domains.

Clause 225A. The fusion protein of Clauses 214 or 215, wherein at least one of the heterologous polypeptides is a human or non-human immunoglobulin Fc polypeptide or fragment that comprises heavy chain Cm and Cm domains.

Clause 226A. The fusion protein according to any of Clauses 214-216 that comprises heavy and/or light chain $C_{H1}$ domains.

Clause 227A. The fusion protein according to any of Clauses 214-216 that lacks heavy and/or light chain $C_{H1}$ domains.

Clause 228A. The fusion protein according to any of Clauses 214-218 that lacks heavy chain $C_{H1}$ domains.

Clause 229A. The fusion protein of any of the above Clauses, wherein said immunoglobulin molecule or a fragment thereof comprises a hinge region.

Clause 230A. The fusion protein of Clause 229, wherein said hinge region is an intact hinge region.

Clause 231A. The fusion protein of any of the above Clauses, wherein said immunoglobulin molecule or a fragment thereof does not feature a hinge region.

Clause 232A. The fusion protein according to any of the foregoing Clauses which comprises a human immunoglobulin molecule or a fragment thereof.

Clause 233A. The fusion protein of any of the foregoing Clauses, wherein said heterologous polypeptide comprises or consists of an Fc fragment of the immunoglobulin heavy chain constant region.

Clause 234A. The fusion protein of any of the foregoing Clauses, wherein said heterologous polypeptide comprises or consists of an Fc fragment and hinge region of a human immunoglobulin heavy chain constant region.

Clause 235A. The fusion protein of any of the foregoing Clauses comprising an immunoglobulin heavy chain constant region derived from an immunoglobulin isotype selected from the group consisting of an IgG1, IgG2, IgG3, IgG4, IgM, IgE, IgA and IgD.

Clause 236A. The fusion protein of any of the foregoing Clauses comprising a human immunoglobulin heavy chain constant region selected from the group consisting of a human IgG1, IgG2, IgG3, and IgG4.

Clause 237A. The fusion protein of any of the foregoing Clauses comprising a mouse IgG1, IgG2a or IgG2b immunoglobulin heavy chain constant region or fragment thereof.

Clause 238A. The fusion protein of any of the foregoing Clauses, which comprises an immunoglobulin Fc region that contains at least one mutation that alters effector function and/or glycosylation.

Clause 239A. The fusion protein of Clause 238 wherein said effector function is selected from FcR binding, complement binding, ADCC activity, CDC activity, degranulation, phagocytosis, and/or cytokine release.

Clause 240A. The fusion protein according to any of the above Clauses, wherein the heterologous sequence comprises at least a portion of an immunoglobulin molecule that specifically binds to a target cell or comprises another moiety that specifically binds to a target cell.

Clause 241A. The fusion protein according to Clause 41 wherein the target cell is a cancerous, immune, infectious agent cell, an infected cell, an immune cell, an inflammatory cell, a disease site or a cell which is to be transplanted into a human recipient.

Clause 242A. The fusion protein of Clause 241, wherein said infectious agent cell is selected from the group consisting of a virus, bacterium, mycoplasm, fungus, yeast or parasite.

Clause 243A. The fusion protein of Clauses 240 or 241, wherein said infected cell is infected with an infectious agent selected from the group consisting of a virus, bacterium, mycoplasm, fungus, yeast or parasite.

Clause 244A. The fusion protein of any of the above Clauses, wherein at least one of the heterologous polypeptides is a receptor, hormone, cytokine, antigen, B-cell target, NK cell target, T cell target, TNF receptor superfamily member, Hedgehog family member, a receptor tyrosine kinase, a proteoglycan-related molecule, a TGF-β superfamily member, a Wnt-related molecule, a receptor ligand, a Dendritic cell target, a myeloid cell target, a monocyte/macrophage cell target or an angiogenesis target.

Clause 245A. The fusion protein of Clause 244, wherein the antigen is a tumor antigen, autoantigen, allergen, or an infectious agent antigen.

Clause 246A. The fusion protein of any of the above Clauses, wherein the at least one heterologous polypeptide includes an immunomodulatory polypeptide.

Clause 247A. The fusion protein of any of Clauses 244-246, wherein the T cell target is selected from the group consisting of 2B4/SLAMF4, IL-2 Ra, 4-1BB/TNFRSF9, IL-2R, ALCAM, B7-1/CD80, IL-4R, B7-H3, BLAME/SLAMF8, BTLA, IL-6R, CCR3, IL-7 Ra, CCR4, CXCRI/IL-8 RA, CCR5, CCR6, IL-10 R a, CCR7, IL-10 Rβ, CCR8, IL-12 R131, CCR9, IL-12 Rβ2, CD2, IL-13Ral, IL-13, CD3, CD4, ILT2/CD85j, ILT3/CD85k, ILT4/CD85d, ILT5/CD85a, Integrin a 4/CD49d, CD5, Integrin aE/CD103, CD6, Integrin a M/CD1 Ib, CD8, Integrin a X/CD1 Ic, Integrin 2/CD18, KIR/CD158, CD27/TNFRSF7, KIR2DL1, CD28, KIR2DL3, CD30/TNFRSF8, KIR2DL4/CD158d, CD31/PECAM-1, KIR2DS4, CD40 Ligand/TNFSF5, LAG-3, CD43, LAIR1, CD45, LAIR2, CD83, Leukotriene B4 RI, CD84/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 Ry, Osteopontin, CRACC/SLAMF7, PD-1, CRTAM, PSGL-1, CTLA-4, RANK/TNFRSF11 A, CX3CR1, CX3CL1, L-Selectin, CXCR3, SIRP βi, CXCR4, SLAM, CXCR6, TCCRAVSX-1, DNAM-1, Thymopoietin, EMMPRIN/CD 147, TIM-1, EphB6, TIM-2, Fas/TNFRSF6, TIM-3, Fas Ligand/TNFSF6, TIM-4, Fcγ RIII/CD16, TIM-6, GITR/TNFRSF18, TNF RI/TNFRSFIA, Granulysin, TNF R11/TNFRSF1B, HVEM/TNFRSF14, TRAIL RI/TNFRSFIOA, ICAM-1/CD54, TRAIL R2/TNFRSF10B, ICAM-2/CD102, TRAIL R3/TNFRSF10C, IFN-yRI, TRAIL R4/TNFRSF10D, IFN-yR2, TSLP, IL-1 RI and TSLP R.

Clause 248A. The fusion protein of any of Clauses 244-246, wherein the monocyte/macrophage cell target is selected from the group consisting of B7-1/CD80, ILT4/CD85d, B7-H1, ILT5/CD85a, Common β Chain, Integrin a 4/CD49d, BLAME/SLAMF8, Integrin a X/CDI Ic, CCL6/C10, Integrin β2/CD18, CD155/PVR, Integrin β3/CD61, CD31/PECAM-1, Latexin, CD36/SR-B3, Leukotriene B4 RI, CD40/TNFRSF5, LIMPII/SR-B2, CD43, LMIR1/CD300A, CD45, LMIR2/CD300c, CD68, LMIR3/CD300LF, CD84/SLAMF5, LMIR5/CD300LB, CD97, LMIR6/CD300LE, CD163, LRP-1, CD2F-10/SLAMF9, MARCO, CRACC/SLAMF7, MD-1, ECF-L, MD-2, EMMPRIN/CD147, MGL2, Endoglin/CD105, Osteoactivin/GPNMB, Fc yRI/CD64, Osteopontin, Fc γ RIIB/CD32b, PD-L2, Fc yRIIC/CD32c, Siglec-3/CD33, Fey RIIA/CD32a, SIGNR1/CD209, Fey RIII/CD16, SLAM, GM-CSF R a, TCCR/WSX-1, ICAM-2/CD102, TLR3, IFN-y RI, TLR4, IFN-y R2, TREM-1, IL-1 RII, TREM-2, ILT2/CD85j, TREM-3, ILT3/CD85k, TREMLI/TLT-1, 2B4/SLAMF4, IL-10 R a, ALCAM, IL-10 R (3, Aminopeptidase N/ANPEP, ILT2/CD85j, Common (3 Chain, ILT3/CD85k, Clq R1/CD93, ILT4/CD85d, CCR1, ILT5/CD85a, CCR2, Integrin a 4/CD49d, CCR5, Integrin a M/CDI Ib, CCR8, Integrin a X/CDI Ic, CD155/PVR, Integrin β2/CD18, CD14, Integrin β3/CD61, CD36/SR-B3, LAIR1, CD43, LAIR2, CD45, Leukotriene B4 RI, CD68, LIMPII/SR-B2, CD84/SLAMF5, LMIR1/CD300A, CD97, LMIR2/CD300c, CD 163, LMIR3/CD300LF, Coagulation Factor III/Tissue Factor, LMIR5/CD300LB, CX3CR1, CX3CL1, LMIR6/CD300LE, CXCR4, LRP-1, CXCR6, M-CSF R, DEP-1/CD148, MD-1, DNAM-1, MD-2, EMMPRIN/CD 147, MMR, Endoglin/CD105, NCAM-L1, Fc y R1/CD64, PSGL-1, Fc y RIII/CD16, RP105, G-CSF R, L-Selectin, GM-CSF R a, Siglec-3/CD33, HVEM/TNFRSF14, SLAM, ICAM-1/CD54, TCCR/WSX-1, ICAM-2/CD102, TREM-1, IL-6 R, TREM-2, CXCRI/IL-8 RA, TREM-3 and TREMLI/TLT-1.

Clause 249A. The fusion protein of any of Clauses 244-246, wherein the Dendritic cell target is selected from the group consisting of CD36/SR-B3, LOX-1/SR-E1, CD68, MARCO, CD163, SR-AI/MSR, CD5L, SREC-I, CL-P1/COLEC12, SREC-II, LIMPII/SR-B2, RP105, TLR4, TLR1, TLR5, TLR2, TLR6, TLR3, TLR9, 4-IBB Ligand/TNFSF9, IL-12/IL-23 p40, 4-Amino-1,8-naphthalimide, ILT2/CD85j, CCL21/6Ckine, ILT3/CD85k, 8-oxo-dG, ILT4/CD85d, 8D6A, ILT5/CD85a, A2B5, Integrin a 4/CD49d, Aag, Integrin β2/CD18, AMICA, Langerin, B7-2/CD86, Leukotriene B4 RI, B7-H3, LMIR1/CD300A, BLAME/SLAMF8, LMIR2/CD300c, Clq R1/CD93, LMIR3/CD300LF, CCR6, LMIR5/CD300LB, CCR7, LMIR6/CD300LE, CD40/TNFRSF5, MAG/Siglec-4a, CD43, MCAM, CD45, MD-1, CD68, MD-2, CD83, MDL-1/CLEC5A, CD84/SLAMF5, MMR, CD97, NCAM-L1, CD2F-10/SL AMF9, Osteoactivin/GPNMB, Chem 23, PD-L2, CLEC-1, RP105, CLEC-2, Siglec-2/CD22, CRACC/SLAMF7, Siglec-3/CD33, DC-SIGN, Siglec-5, DC-SIGNR/CD299, Siglec-6, DCAR, Siglec-7, DCIR/CLEC4A, Siglec-9, DEC-205, Siglec-10, Dectin-1/CLEC7A, Siglec-F, Dectin-2/CLEC6A, SIGNR1/CD209, DEP-1/CD 148, SIGNR4, DLEC, SLAM, EMMPRIN/CD 147, TCCR/WSX-1, Fc γ R1/CD64, TLR3, Fc γ RIIB/CD32b, TREM-1, Fc Y RIIC/CD32C, TREM-2, Fc γ RIIA/CD32a, TREM-3, Fc γ RIII/CD16, TREMLI/TLT-1, ICAM-2/CD102 and Vanilloid RI.

Clause 250A. The fusion protein of any of Clauses 244-246, wherein the TNF receptor superfamily member is selected from the group consisting of 4-1BB/TNFRSF9, NGF R/TN-FRSF16, BAFF R/TNFRSF13C, Osteoprotegerin/TNFRSFI IB, B CMA/TNFRSF 17, OX40/TNFRSF4, CD27/TN-FRSF7, RANK/TNFRSF11 A, CD30/TNFRSF8, RELT/TNFRSF19L, CD40/TNFRSF5, TACI/TNFRSF13B, DcR3/TNFRSF6B, TNF RI/TNFRSF1A, DcTRAIL R1/TNFRSF23, TNF RII/TNFRSF1B, DcTRAIL R2/TNFRSF22, TRAIL R1/TNFRSF10A, DR3/TNFRSF25, TRAIL R2/TNFRSF10B, DR6/TNFRSF21, TRAIL R3/TNFRSF10C, EDAR, TRAIL R4/TNFRSF 10D, Fas/TNFRSF6, TROY/TNFRSF19, GITR/TNFRSF 18, TWEAK R/TNFRSF12, HVEM/TNFRSF14, XEDAR, Lymphotoxin (3 R/TNFRSF3, 4-1BB Ligand/TNFSF9, Lymphotoxin, APRIL/TNFSF 13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF-/TNFSFIB, EDA-A2, TRAIL/TNFSF10, Fas Ligand/TNFSF6, TR ANCE/TNF SF 11, GITR Ligand/TNFSF18, TWEAK/TNF SF12 and LIGHT/TNFSF14.

Clause 251A. The fusion protein of any of Clauses 244-246, wherein the Hedgehog family member is selected from the group consisting of Patched and Smoothened.

Clause 252A. The fusion protein of any of Clauses 244-246, wherein the receptor tyrosine kinase is selected from the group consisting of Axl, FGF R4, Clq R1/CD93, FGF R5, DDR1, Flt-3, DDR2, HGF R, Dtk, IGF-I R, EGF R, IGF-II R, Eph, INSRR, EphAI, Insulin R/CD220, EphA2, M-CSF R, Eph A3, Mer, EphA4, MSP R/Ron, EphA5, MuSK, EphA6, PDGF R a, EphA7, PDGF R (3, EphA8, Ret, EphB I, ROR1, EphB2, ROR2, EphB3, SCF R/c-kit, EphB4, Tie-1, EphB6, Tie-2, ErbB2, TrkA, ErbB3, TrkB, ErbB4, TrkC, FGF RI, VEGF RI/Flt-1, FGF R2, VEGF R2/Flk-1, FGF R3 and VEGF R3/Flt-4.

Clause 253A. The fusion protein of any of Clauses 244-246, wherein the Transforming Growth Factor (TGF)-superfamily member is selected from the group consisting of Activin RIA/ALK-2, GFR a-1, Activin RIB/ALK-4, GFR a2, Activin RHA, GFR a-3, Activin RUB, GFR a-4, ALK-1, MIS RII, ALK-7, Ret, B MPR-I A/ALK-3, TGF-beta RI/ALK-5, BMPR-IB/ALK-6, TGF-β RII, BMPR-II, TGF-β RIIb, Endoglin/CD 105 and TGF-β RIII Clause 254A. The fusion protein of any of Clauses 244-246, wherein the Wnt-related molecule selected from the group consisting of Frizzled-1, Frizzled-8, Frizzled-2, Frizzled-9, Frizzled-3, sFRP-1, Frizzled-4, sFRP-2, Frizzled-5, sFRP-3, Frizzled-6, sFRP-4, Frizzled-7, MFRP, LRP 5, LRP 6, Wnt-1, Wnt-8a, Wnt-3a, Wnt-10b, Wnt-4, Wnt-11, Wnt-5a, Wnt-9a and Wnt-7a.

Clause 255A. The fusion protein of any of Clauses 244-246, wherein the receptor ligand is selected from the group consisting of 4-IBB Ligand/TNSF9, Lymphotoxin, APRIL/TNFSF13, Lymphotoxin/TNFSF3, BAFF/TNFSF13C, OX40 Ligand/TNFSF4, CD27 Ligand/TNFSF7, TL1A/TNFSF15, CD30 Ligand/TNFSF8, TNF-a/TNFSFIA, CD40 Ligand/TNFSF5, TNF/TNFSFIB, EDA-A2, TRAIL/TNFSF10, Fas Ligand/TNFSF6, TRANCE/TNFSF11, GITR Ligand/TNFSF18, TWEAK/TNFSF12, LIGHT/TNFSF 14, Amphiregulin, NRG1 isoform GGF2, Betacellulin, NRG1 Isoform SMDF, EGF, NRGI-a/HRGI-a, Epigen, NRGI-β I/HRGI-β 1, Epiregulin, TGF-a, HB-EGF, TMEFFI/Tomoregulin-1, Neuregulin-3, TMEFF2, IGF-I, IGF-II, Insulin, Activin A, Activin B, Activin AB, Activin C, BMP-2, BMP-7, BMP-3, BMP-8, BMP-3b/GDF-10, BMP-9, BMP-4, BMP-15, BMP-5, Decapentaplegic, BMP-6, GDF-1, GDF-8, GDF-3, GDF-9, GDF-5, GDF-11, GDF-6, GDF-15, GDF-7, Arternin, Neurturin, GDNF, Persephin, TGF-β, TGF-β 2, TGF-β 1, TGF-β 3, LAP (TGF-β1), TGF-β 5, Latent TGF-β 1, Latent TGF-β bpl, TGF-β 1.2, Lefty, Nodal, MIS/AMH, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, Neuropilin-1, P1GF, Neuropilin-2, P1GF-2, PDGF, PDGF-A, VEGF, PDGF-B, VEGF-B, PDGF-C, VEGF-C, PDGF-D, VEGF-D and PDGF-AB.

Clause 256A. The fusion protein of any of Clauses 244-246, wherein the tumor antigen is selected from the group consisting of Squamous Cell Carcinoma Antigen 1 (SCCA-1), (PROTEIN T4-A), Squamous Cell Carcinoma Antigen 2 (SCCA-2), Ovarian carcinoma antigen CA125 (1A1-3B; KIAA0049), MUCIN 1 (TUMOR-ASSOCIATED MUCIN; Carcinoma-Associated Mucin; Polymorphic Epithelial Mucin; PEM; PEMT; EPISIALIN; Tumor-Associated Epithelial Membrane Antigen; EMA; H23AG; Peanut-Reactive Urinary Mucin; PUM; and Breast Carcinoma-Associated Antigen DF3), CTCL tumor antigen sel-1, CTCL tumor antigen se14-3, CTCL tumor antigen se20-4, CTCL tumor antigen se20-9, CTCL tumor antigen se33-I, CTCL tumor antigen se37-2, CTCL tumor antigen se57-I, CTCL tumor antigen se89-I, Prostate-specific membrane antigen, 5T4 oncofetal trophoblast glycoprotein, Orf73 Kaposi's sarcoma-associated herpesvirus, MAGE-CI (cancer/testis antigen CT7), MAGE-B 1 ANTIGEN (MAGE-XP Antigen; DAM 10), MAGE-B2 Antigen (DAME), MAGE-2 ANTIGEN, MAGE-4a antigen, MAGE-4b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, Tumor-Associated Antigen CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A, parathyroid secretory protein 1, DUPAN-2, CA 19-9, CA 72-4, CA 195 and L6.

Clause 257A. The fusion protein of any of Clauses 244-246, wherein the B cell target is selected from the group consisting of CD10, CD19, CD20, CD21, CD22, CD23, CD24, CD37, CD38, CD39, CD40, CD72, CD73, CD74, CDw75, CDw76, CD77, CD78, CD79a/b, CD80, CD81, CD82, CD83, CD84, CD85, CD86, CD89, CD98, CD126, CD127, CDw130, CD138 and CDw150.

Clause 258A. The fusion protein of any of Clauses 244-246, wherein the angiogenesis target is selected from the group consisting of Angiopoietin-1, Angiopoietin-like 2, Angiopoietin-2, Angiopoietin-like 3, Angiopoietin-3, Angiopoietin-like 7/CDT6, Angiopoietin-4, Tie-1, Angiopoietin-like 1, Tie-2, Angiogenin, iNOS, Coagulation Factor III/Tissue Factor, nNOS, CTGF/CCN2, NOV/CCN3, DANCE, OSM, EDG-1, Plfr, EG-VEGF/PK1, Proliferin, Endostatin, ROB04, Erythropoietin, Thrombospondin-1, Kininostatin, Thrombospondin-2, MFG-E8, Thrombospondin-4, Nitric Oxide, VG5Q, eNOS, EphAI, EphA5, EphA2, EphA6, EphA3, EphA7, EphA4, EphA8, EphBI, EphB4, EphB2, EphB6, EphB3, Ephrin-AI, Ephrin-A4, Ephrin-A2, Ephrin-A5, Ephrin-A3, Ephrin-B I, Ephrin-B3, Ephrin-B2, FGF acidic, FGF-12, FGF basic, FGF-13, FGF-3, FGF-16, FGF-4, FGF-17, FGF-5, FGF-19, FGF-6, FGF-20, FGF-8, FGF-21, FGF-9, FGF-23, FGF-10, KGF/FGF-7, FGF-11, FGF RI, FGF R4, FGF R2, FGF R5, FGF R3, Neuropilin-1, Neuropilin-2, Semaphorin 3A, Semaphorin 6B, Semaphorin 3C, Semaphorin 6C, Semaphorin 3E, Semaphorin 6D, Semaphorin 6A, Semaphorin 7A, MMP, MMP-11, MMP-1, MMP-12, MMP-2, MMP-13, MMP-3, MMP-14, MMP-7, MMP-15, MMP-8, MMP-16/MT3-MMP, MMP-9, MMP-24/MT5-MMP, MMP-10, MMP-25/MT6-MMP, TIMP-1, TIMP-3, TIMP-2, TIMP-4, ACE, IL-13 R a 1, IL-13, Clq R1/CD93, Integrin a 4/CD49d, VE-Cadherin, Integrin β 2/CD18, CD31/PECAM-1, KLF4, CD36/SR-B3, LYVE-1, CD151, MCAM, CL-P1/COLEC12, Nectin-2/CD112, Coagulation Factor III/Tissue Factor, E-Selectin, D6, P-Selectin, DC-SIGNR/CD299, SLAM, EMMPRIN/CD 147, Tie-2, Endoglin/CD105, TNF RI/TNFRSF1A, EPCR, TNF RII/TNFRSF1B, Erythropoietin R, TRAIL RI/TNFRS-FIOA, ESAM, TRAIL R2/TNFRSF10B, FABP5, VCAM-1, ICAM-1/CD54, VEGF R2/Flk-1, ICAM-2/CD102, VEGF R3/Flt-4, IL-1 RI and VG5Q.

Clause 259A. An isolated polypeptide or the fusion protein according to any of the foregoing Clauses which agonizes at least one immune inhibitory effect of VSIG3 and/or VISTA.

Clause 260A. An isolated polypeptide or fusion protein according to Clause 259 which mediates at least one of the following effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-y production by T-cells, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases Inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said isolated or recombinant VISTA polypeptide or fusion protein may elicit an opposite effect to one or more of (i)-(xxviii).

Clause 261A. An isolated polypeptide or fusion protein according to any of the foregoing Clauses which antagonizes at least one immune inhibitory effect of VSIG3 and/or VISTA.

Clause 262A. An isolated polypeptide or fusion protein according to Clause 261 which mediates at least one of the following effects (i) increases immune response, (ii) increases T cell activation, (iii) increases cytotoxic T cell activity, (iv) increases NK cell activity, (v) alleviates T-cell suppression, (vi) increases pro-inflammatory cytokine secretion, (vii) increases IL-2 secretion; (viii) increases interferon-y production by T-cells, (ix) increases Th1 response, (x) decrease Th2 response, (xi) decreases or eliminates cell number and/or activity of at least one of regulatory T cells (Tregs), myeloid derived suppressor cells (MDSCs), iMCs, mesenchymal stromal cells, TIE2-expressing monocytes, (xii) reduces regulatory cell activity, and/or the activity of one or more of myeloid derived suppressor cells (MDSCs), iMCs, mesenchymal stromal cells, TIE2-expressing monocytes, (xiii) decreases or eliminates M2 macrophages, (xiv) reduces M2 macrophage pro-tumorigenic activity, (xv) decreases or eliminates N2 neutrophils, (xvi) reduces N2 neutrophils pro-tumorigenic activity, (xvii) reduces inhibition of T cell activation, (xviii) reduces inhibition of CTL activation, (xix) reduces inhibition of NK cell activation, (xx) reverses T cell exhaustion, (xxi) increases T cell response, (xxii) increases activity of cytotoxic cells, (xxiii) stimulates antigen-specific memory responses, (xxiv) elicits apoptosis or lysis of cancer cells, (xxv) stimulates cytotoxic or cytostatic effect on cancer cells, (xxiv) induces direct killing of cancer cells, (xxvi) increases Th17 activity and/or (xxvii) induces complement dependent cytotoxicity and/or antibody dependent cell-mediated cytotoxicity, with the proviso that said isolated or recombinant VISTA polypeptide or fusion protein may elicit an opposite effect to one or more of (i)-(xxvii).

Clause 263A. An isolated polypeptide or fusion protein according to any of the above Clauses which agonizes or antagonizes at least one effect of VSIG3 and/or VISTA on T cells, natural killer (NK) cells or the production of one or more proinflammatory cytokines.

Clause 264A. An isolated polypeptide or fusion protein according to any of the above Clauses which inhibits or promotes one or more of CTL activity, CD4+ T cell activation and/or CD4+ T cell proliferation and/or cell depletion or the secretion of proinflammatory cytokines.

Clause 265A. An isolated polypeptide or fusion protein according to any of the above Clauses which inhibits or promotes NK cell activity.

Clause 266A. An Isolated polypeptide or fusion protein according to any of the above Clauses which inhibits or promotes the differentiation, proliferation and/or activity of Tregs, MDSCs, iMCs, mesenchymal stromal cells, TIE2-expressing monocytes, and/or the infiltration of Tregs (Tregs), MDSCs iMCs, mesenchymal stromal cells, TIE2-expressing monocytes.

Clause 267A. The polypeptide or fusion protein of Clause 266, wherein said Tregs are inducible Tregs.

Clause 268A. An isolated polypeptide or fusion protein according to any of the foregoing Clauses which specifically binds to a receptor expressed by NK cells.

Clause 269A. An isolated polypeptide or fusion protein according to any of the foregoing Clauses which specifically binds to a receptor expressed by activated T cells or dendritic or myeloid suppressor or monocyte or neutrophil cells.

Clause 270A. A polynucleotide encoding an isolated polypeptide or fusion protein according to any of the foregoing Clauses.

Clause 271A. An expression vector or a virus, comprising at least one polynucleotide according to Clause 270.

Clause 272A. A recombinant cell comprising an expression vector according to Clause 270 or a virus containing a polynucleotide according to Clause 271, wherein the cell constitutively or inducibly expresses the polypeptide encoded by the DNA segment.

Clause 273A. A method of producing an isolated polypeptide or fusion protein according to any of Clauses 200-269, comprising culturing the recombinant cell according to Clause 272, under conditions whereby the cell expresses the polypeptide encoded by the DNA segment or nucleic acid and recovering said polypeptide.

Clause 274A. A pharmaceutical composition comprising the isolated protein or fusion protein of any of Clauses 200-269 or comprising a VISTA ECD protein set forth in SEQ ID NO:3 or SEQ ID NO:4 the polynucleotide of Clause 270, the expression vector or virus of Clause 271, or the recombinant cell of Clause 272.

Clause 275A. A pharmaceutical composition according to Clause 274, the isolated polypeptide or fusion protein of any of Clauses 200-269, the polynucleotide of Clause 270, the expression vector or virus of Clause 271, the recombinant cell of Clause 272, for use in treatment in a subject suffering from cancer.

Clause 276A. The pharmaceutical composition, cancer immunotherapy, the isolated polypeptide or fusion protein, the polynucleotide, the expression vector or virus, the recombinant cell or the use of Clause 275, for use in immunotherapy treatment of cancer.

Clause 277A. The pharmaceutical composition, cancer immunotherapy, the isolated polypeptide or fusion protein, the polynucleotide, the expression vector or virus, the recombinant cell or the use of Clauses 275 or 276, wherein the cancer does not express sufficient levels of VISTA protein at diagnosis or prior to the treatment.

Clause 278A. The pharmaceutical composition, cancer immunotherapy, the isolated polypeptide or fusion protein, the polynucleotide, the expression vector or virus, the recombinant cell or the use of Clauses 275 or 276, wherein the cancer does express sufficient levels of VISTA protein at diagnosis or prior to the treatment.

Clause 279A. The pharmaceutical composition, cancer immunotherapy, the isolated polypeptide or fusion protein, the polynucleotide, the expression vector or virus, the recombinant cell or the use of any of Clauses 275-278, wherein said pharmaceutical composition, isolated polypeptide, fusion protein, polynucleotide, expression vector, virus or cell is administered to the subject in need thereof in combination with a therapeutic agent useful for treatment of cancer.

Clause 280A. The pharmaceutical composition, cancer immunotherapy, the Isolated polypeptide or fusion protein, the polynucleotide, the expression vector or virus, the recombinant cell or the use of any of Clauses 275-279, for performing at least one of the following: (i) increasing immune response, (ii) increasing T cell activation, (iii) increasing cytotoxic T cell activity, (iv) increasing NK cell activity, (v) increasing Th17 activity, (vi) alleviating T-cell suppression, (vii) increasing pro-inflammatory cytokine secretion, (viii) increasing IL-2 secretion; (ix) increasing interferon-y production by T-cells, (x) increasing Th1 response, (xi) decreasing Th2 response, (xii) decreasing or eliminating at least one of regulatory T cells (Tregs), myeloid derived suppressor cells (MDSCs), iMCs, mesenchymal stromal cells, TIE2-expressing monocytes, (xiii) reducing regulatory cell activity and/or the activity of one or more of myeloid derived suppressor cells (MDSCs), iMCs, mesenchymal stromal cells, TIE2-expressing monocytes, (xiv) decreasing or eliminating M2 macrophages, (xv) reducing M2 macrophage pro-tumorigenic activity, (xvi) decreases or eliminates N2 neutrophils, (xvii) reduces N2 neutrophils pro-tumorigenic activity, (xviii) reducing inhibition of T cell activation, (xix) reducing inhibition of CTL activation, (xx) reducing inhibition of NK cell activation, (xxi) reversing T cell exhaustion, (xxii) increasing T cell response, (xxiii) increasing activity of cytotoxic cells, (xxiv) stimulating antigen-specific memory responses, (xxv) eliciting apoptosis or lysis of cancer cells, (xxvi) stimulating cytotoxic or cytostatic effect on cancer cells, (xxvii) inducing direct killing of cancer cells, and/or (xxviii) inducing complement dependent cytotoxicity and/or (xxix) inducing antibody dependent cell-mediated cytotoxicity.

Clause 281A. The pharmaceutical composition, cancer immunotherapy, the isolated polypeptide or fusion protein, the polynucleotide, the expression vector or virus, the recombinant cell or the use of any of Clauses 275-280, further comprising administering an additional therapy comprising one or more of radiotherapy, cryotherapy, antibody therapy, chemotherapy, photodynamic therapy, surgery, hormonal deprivation, targeted therapy agent, a cancer vaccine or combination therapy with conventional drugs.

Clause 282A. The pharmaceutical composition, cancer immunotherapy, the isolated polypeptide or fusion protein, the polynucleotide, the expression vector or virus, the recombinant cell or the use of any of Clauses 275-281, wherein the therapeutic agent or additional therapy is selected from the group consisting of cytotoxic drugs, tumor vaccines, antibodies, peptides, pepti-bodies, small molecules, chemotherapeutic agents, cytotoxic and cytostatic agents, immunological modifiers, interferons, interleukins, immunostimulatory growth hormones, cytokines, vitamins, minerals, aromatase inhibitors, RNAi, Histone Deacetylase Inhibitors, and proteasome inhibitors.

Clause 283A. The pharmaceutical composition, cancer immunotherapy, the isolated polypeptide or fusion protein, the polynucleotide, the expression vector or virus, the recombinant cell or the use of any of Clauses 275-282, administered to a subject simultaneously or sequentially in combination with one or more therapeutic agents, additional therapy or potentiating agents to obtain a therapeutic effect, wherein said one or more potentiating agents is selected from the group consisting of radiotherapy, conventional/classical anti-cancer therapy potentiating anti-tumor immune responses, Targeted therapy potentiating anti-tumor immune responses, Therapeutic agents targeting immunosuppressive cells Tregs and/or MDSCs, Immunostimulatory antibodies, Cytokine therapy, and Adoptive cell transfer.

Clause 284A. The pharmaceutical composition, cancer immunotherapy, the isolated polypeptide or fusion protein, the polynucleotide, the expression vector or virus, the recombinant cell or the use of any of Clauses 275-283, wherein the conventional/classical anti-cancer agent is selected from the group consisting of platinum based compounds, antibiotics with anti-cancer activity, Anthracyclines, Anthracenediones, alkylating agents, antimetabolites, Anti-mitotic agents, Taxanes, Taxoids, microtubule inhibitors, *Vinca* alkaloids, Folate antagonists, Topoisomerase inhibitors, Antiestrogens, Antiandrogens, Aromatase inhibitors, GnRh analogs, inhibitors of 5a-reductase, bisphosphonates and antibodies.

Clause 285A. The pharmaceutical composition, cancer immunotherapy, the isolated polypeptide or fusion protein, the polynucleotide, the expression vector or virus, the recombinant cell or the use of any of Clauses 275-284, wherein the Targeted therapy agent is selected from the group consisting of histone deacetylase (HDAC) inhibitors, proteasome inhibitors, mTOR pathway inhibitors, JAK2 inhibitors, tyrosine kinase inhibitors (TKIs), PI3K inhibitors, Protein kinase inhibitors, Inhibitors of serine/threonine kinases, inhibitors of intracellular signaling, inhibitors of Ras/Raf signaling, MEK inhibitors, AKT inhibitors, inhibitors of survival signaling proteins, cyclin dependent kinase inhibitors, therapeutic monoclonal antibodies, TRAIL pathway agonists, anti-angiogenic agents, metalloproteinase inhibitors, cathepsin inhibitors, inhibitors of urokinase plasminogen activator receptor function, immunoconjugates, antibody drug conjugates, antibody fragments, bispecific antibodies, bispecific T cell engagers (BiTEs).

Clause 286A. The pharmaceutical composition, cancer immunotherapy, the isolated polypeptide or fusion protein, the polynucleotide, the expression vector or virus, the recombinant cell or the use of any of Clauses 275-285, wherein the antibody is selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab tiuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Clause 287A. The pharmaceutical composition, cancer immunotherapy, the isolated polypeptide or fusion protein, the polynucleotide, the expression vector or virus, the recombinant cell or the use of any of Clauses 275-286, wherein the Therapeutic agent targeting immunosuppressive cells Tregs and/or MDSCs is selected from antimitotic drugs, cyclophosphamide, gemcitabine, mitoxantrone, fludarabine, thalidomide, thalidomide derivatives, COX-2 inhibitors, depleting or killing antibodies that directly target Tregs through recognition of Treg cell surface receptors, anti-CD25 daclizumab, basiliximab, ligand-directed toxins, denileukin diftitox (Ontak)—a fusion protein of human IL-2 and diphtheria toxin, or LMB-2—a fusion between an scFv against CD25 and the pseudomonas exotoxin, antibodies targeting Treg cell surface receptors, TLR modulators, agents that interfere with the adenosinergic pathway, ectonucleotidase inhibitors, or inhibitors of the A2A adenosine receptor, TGF-β inhibitors, chemokine receptor inhibitors, retinoic acid, all-trans retinoic acid (ATRA), Vitamin D3, phosphodiesterase 5 inhibitors, sildenafil, ROS inhibitors and nitroaspirin.

Clause 288A. The pharmaceutical composition, cancer immunotherapy, the isolated polypeptide or fusion protein, the polynucleotide, the expression vector or virus, the recombinant cell or the use of any of Clauses 275-287, wherein the Immunostimulatory antibody is selected from antagonistic antibodies targeting one or more of CTLA4, PD-1, PDL-1, LAG-3, TIM-3, BTLA, B7-H4, B7-H3, VISTA, and/or Agonistic antibodies targeting one or more of CD40, CD 137, OX40, GITR, CD27, CD28 or ICOS.

Clause 289A. The pharmaceutical composition, cancer immunotherapy, the isolated polypeptide or fusion protein, the polynucleotide, the expression vector or virus, the recombinant cell or the use of any of Clauses 275-288, wherein the therapeutic cancer vaccine is selected from exogenous cancer vaccines including proteins or peptides used to mount an immunogenic response to a tumor antigen, recombinant virus and bacteria vectors encoding tumor antigens, DNA-based vaccines encoding tumor antigens, proteins targeted to dendritic cell-based vaccines, whole tumor cell vaccines, gene modified tumor cells expressing GM-CSF, ICOS and/or Flt3-ligand, oncolytic virus vaccines.

Clause 290A. The pharmaceutical composition, cancer immunotherapy, the isolated polypeptide or fusion protein, the polynucleotide, the expression vector or virus, the recombinant cell or the use of any of Clauses 275-289, wherein the cytokine therapy is selected from one or more of the cytokines IL-2, IL-7, IL-12, IL-15, IL-17, IL-18 and IL-21, IL23, IL-27, GM-CSF, IFNa (interferon alpha), IFNa-2b, IFNβ, IFNγ, and their different strategies for delivery.

Clause 291A. The pharmaceutical composition, cancer immunotherapy, the isolated polypeptide or fusion protein, the polynucleotide, the expression vector or virus, the recombinant cell or the use of any of Clauses 275-290, wherein the adoptive cell transfer therapy is carried out following ex vivo treatment selected from expansion of the patient autologous naturally occurring tumor specific T cells or genetic modification of T cells to confer specificity for tumor antigens.

Clause 292A. An assay for diagnosing or aiding in the diagnosis of a disease in a subject, wherein the disease is selected from the group consisting of cancer, autoimmune disease, or an infectious disease, comprising the isolated polypeptide or fusion protein of any of the above Clauses and/or with VISTA ECD protein set forth in any of SEQ ID NO. 3 or SEQ ID NO. 4, and a detector for detecting specific binding of the isolated protein or fusion protein to a tissue sample taken from the subject.

Clause 293A. A diagnostic method for diagnosing or aiding in the diagnosis of a disease in a subject, wherein the disease is selected from the group consisting of cancer, autoimmune disease, or infectious disease, comprising using the assay of Clause 292 for performing the method.

Clause 294A. A diagnostic method for diagnosing or aiding in the diagnosis of a disease in a subject, wherein the disease is selected from the group consisting of cancer, autoimmune disease, or infectious disease, wherein the diagnostic method is performed ex vivo, and comprises contacting a tissue sample from the subject with the isolated polypeptide or fusion protein of any of the above Clauses and/or with VISTA ECD protein set forth in any of SEQ ID NO: 3 or SEQ ID NO:4 and detecting specific binding to the tissue sample.

Clause 295A. A diagnostic method for diagnosing or aiding in the diagnosis of a disease in a subject, wherein the disease is selected from the group consisting of cancer, autoimmune disease, or an infectious disease, wherein the diagnostic method is performed in vivo, comprising administering the isolated polypeptide or fusion protein of any of the above Clauses, and/or with VISTA ECD protein set forth in any of SEQ ID NO. 3 or SEQ ID NO. 4 to a subject and detecting specific binding to tissues.

Clause 296A. The method of any of Clauses 293-295, or use of the assay of Clause 292 wherein the diagnostic method is performed before therapy or treatment comprising administering the isolated polypeptide or fusion protein of any of Clauses 200-269, the polynucleotide of Clause 270, the expression vector or virus of Clause 271, the recombinant cell of Clause 272, the pharmaceutical composition of Clause 274, the use of Clause 275, or the protein, the polynucleotide, the expression vector or virus, the recombinant cell, the pharmaceutical composition, or the use of any of Clauses 276-291, to the subject.

Clause 297A. The method of any of Clauses 293-296, for screening for a disease, screening for VISTA-mediated immunosuppression, detecting a presence or a severity of a disease, providing prognosis of a disease, monitoring disease progression or relapse, as well as assessment of treatment efficacy and/or relapse of a disease, disorder or condition, as well as selecting a therapy and/or a treatment for a disease, optimization of a given therapy for a disease, monitoring the treatment of a disease, and/or predicting the suitability of a therapy for specific patients or subpopulations or determining the appropriate dosing of a therapeutic product in patients or subpopulations.

Clause 298A. The isolated polypeptide or fusion protein of any of Clauses 200-269, the polynucleotide of Clause 270, the expression vector or virus of Clause 271, the recombinant cell of Clause 272, the pharmaceutical composition of Clause 274, the use of Clause 275, or the protein, the polynucleotide, the expression vector or virus, the recombinant cell, the pharmaceutical composition, the use of any of Clauses 276-291, the assay of Clause 292 or the method of any of Clauses 94-98, wherein said cancer is selected from the group consisting of breast cancer, cervical cancer, ovary cancer, endometrial cancer, melanoma, uveal melanoma, bladder cancer, lung cancer, pancreatic cancer, colorectal cancer, prostate cancer, leukemia, acute lymphocytic leukemia, chronic lymphocytic leukemia, B-cell lymphoma, Burkitt's lymphoma, multiple myeloma, Non-Hodgkin's lymphoma, myeloid leukemia, acute myelogenous leukemia (AML), chronic myelogenous leukemia, thyroid cancer, thyroid follicular cancer, myelodysplastic syndrome (MDS), fibrosarcomas and rhabdomyosarcomas, teratocarcinoma, neuroblastoma, glioma, glioblastoma, benign tumor of the skin, keratoacanthomas, renal cancer, anaplastic large-cell lymphoma, esophageal cancer, follicular dendritic cell carcinoma, seminal vesicle tumor, epidermal carcinoma, spleen cancer, bladder cancer, head and neck cancer, stomach cancer, liver cancer, bone cancer, brain cancer, cancer of the retina, biliary cancer, small bowel cancer, salivary gland cancer, cancer of uterus, cancer of testicles, cancer of connective tissue, myelodysplasia, Waldenstrom's macroglobinaemia, nasopharyngeal, neuroendocrine cancer, mesothelioma, angiosarcoma, Kaposi's sarcoma, carcinoid, fallopian tube cancer, peritoneal cancer, papillary serous millierian cancer, malignant ascites, gastrointestinal stromal tumor (GIST), Li-Fraumeni syndrome and Von Hippel-Lindau syndrome (VHL), and cancer of unknown origin either primary or metastatic.

Clause 299A. The isolated protein, the fusion protein, the polynucleotide, the expression vector or virus, the recombinant cell, the pharmaceutical composition, the assay or the method of Clause 298, wherein said breast cancer is breast carcinoma, and is selected from the group consisting of ductal-carcinoma, infiltrating ductal carcinoma, lobular carcinoma, mucinous adenocarcinoma, intra duct and invasive ductal carcinoma, and Scirrhous adenocarcinoma.

Clause 300A. The isolated protein, the fusion protein, the polynucleotide, the expression vector or virus, the recombinant cell, the pharmaceutical composition, the assay or the method of Clause 298, wherein said colon cancer is selected from the group consisting of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, and Moderately Differentiated Mucinous adenocarcinoma of the rectum.

Clause 301A. The isolated protein, the fusion protein, the polynucleotide, the expression vector or virus, the recombinant cell, the pharmaceutical composition, the assay or the method of Clause 298, wherein said lung cancer is selected from the group consisting of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, and Small cell lung cancer, preferably Small cell lung carcinoma, more preferably undifferentiated Small cell lung carcinoma.

Clause 302A. The isolated protein, the fusion protein, the polynucleotide, the expression vector or virus, the recombinant cell, the pharmaceutical composition, the assay or the method of Clause 298, wherein said prostate cancer is prostate adenocarcinoma and is selected from the group consisting of Adenocarcinoma Gleason Grade 6 to 9, Infiltrating adenocarcinoma, High grade prostatic intraepithelial neoplasia, undifferentiated carcinoma.

Clause 303A. The isolated protein, the fusion protein, the polynucleotide, the expression vector or virus, the recombinant cell, the pharmaceutical composition, the assay or the method of Clause 298, wherein said stomach cancer is moderately differentiated gastric adenocarcinoma.

Clause 304A. The isolated protein, the fusion protein, the polynucleotide, the expression vector or virus, the recombinant cell, the pharmaceutical composition, the assay or the method of Clause 298, wherein said ovarian cancer is selected from the group consisting of cystadenocarcinoma, serous papillary cystic carcinoma, Serous papillary cystic carcinoma, and Invasive serous papillary carcinoma.

Clause 305A. The isolated protein, the fusion protein, the polynucleotide, the expression vector or virus, the recombinant cell, the pharmaceutical composition, the assay or the method of Clause 298, wherein said brain cancer is selected from the group consisting of Astrocytoma and Glioblastoma multiforme.

Clause 306A. The isolated protein, the fusion protein, the polynucleotide, the expression vector or virus, the recombinant cell, the pharmaceutical composition, the assay or the method of Clause 298, wherein said brain cancer is astrocytoma.

Clause 307A. The isolated protein, the fusion protein, the polynucleotide, the expression vector or virus, the recombinant cell, the pharmaceutical composition, the assay or the method of Clause 298, wherein said kidney cancer is clear cell renal cell carcinoma.

Clause 308A. The isolated protein, the fusion protein, the polynucleotide, the expression vector or virus, the recombinant cell, the pharmaceutical composition, the assay or the method of Clause 298, wherein liver cancer is Hepatocellular carcinoma.

Clause 309A. The isolated protein, the fusion protein, the polynucleotide, the expression vector or virus, the recombinant cell, the pharmaceutical composition, the assay or the method of Clause 308, wherein said Hepatocellular carcinoma is Low Grade hepatocellular carcinoma or Fibrolamellar Hepatocellular Carcinoma.

Clause 310A. The isolated protein, the fusion protein, the polynucleotide, the expression vector or virus, the recombinant cell, the pharmaceutical composition, the assay or the method of Clause 298, wherein said lymphoma is selected from the group consisting of Hodgkin's Lymphoma and High to low grade Non-Hodgkin's Lymphoma.

Clause 311A. The isolated protein, the fusion protein, the polynucleotide, the expression vector or virus, the recombinant cell, the pharmaceutical composition, the assay or the method of Clause 298, for treating a subject suffering from a disease selected from the group consisting of B-cell lymphoma, Burkitt's lymphoma, thyroid cancer, thyroid follicular cancer, myelodysplastic syndrome (MDS), fibrosarcomas and rhabdomyosarcomas, melanoma, uveal melanoma, teratocarcinoma, neuroblastoma, glioma, glioblastoma cancer, keratoacanthomas, anaplastic large-cell lymphoma, esophageal squamous cells carcinoma, hepatocellular carcinoma cancer, follicular dendritic cell carcinoma, muscle-invasive cancer, seminal vesicle tumor, epidermal carcinoma, cancer of the retina, biliary cancer, small bowel cancer, salivary gland cancer, cancer of connective tissue, myelodysplasia, Waldenstrom's macroglobinaemia, nasopharyngeal, neuroendocrine cancer, myelodysplastic syndrome, mesothelioma, angiosarcoma, Kaposi's sarcoma, carcinoid, esophagogastric, fallopian tube cancer, peritoneal cancer, papillary serous miillerian cancer, malignant ascites, gastrointestinal stromal tumor (GIST), Li-Fraumeni syndrome and Von Hippel-Lindau syndrome (VHL); endometrial cancer, Breast carcinoma, preferably any of ductal-carcinoma, infiltrating ductal carcinoma, lobular carcinoma, mucinous adenocarcinoma, intra duct and invasive ductal carcinoma, and Scirrhous adenocarcinoma, Colorectal adenocarcinoma, preferably any of Poorly to Well Differentiated invasive and noninvasive Adenocarcinoma, Poorly to Well Differentiated Adenocarcinoma of the cecum, Well to Poorly Differentiated Adenocarcinoma of the colon, Tubular adenocarcinoma, preferably Grade 2 Tubular adenocarcinoma of the ascending colon, colon adenocarcinoma Duke's stage CI, invasive adenocarcinoma, Adenocarcinoma of the rectum, preferably Grade 3 Adenocarcinoma of the rectum, Moderately Differentiated Adenocarcinoma of the rectum, Moderately Differentiated Mucinous adenocarcinoma of the rectum; Lung cancer, preferably any of Well to Poorly differentiated Non-small cell carcinoma, Squamous Cell Carcinoma, preferably well to poorly Differentiated Squamous Cell Carcinoma, keratinizing squamous cell carcinoma, adenocarcinoma, preferably poorly to well differentiated adenocarcinoma, large cell adenocarcinoma, Small cell lung cancer, preferably Small cell lung carcinoma, more preferably undifferentiated Small cell lung carcinoma; Prostate adenocarcinoma, preferably any of Adenocarcinoma Gleason Grade 6 to 9, Infiltrating adenocarcinoma, High grade prostatic intraepithelial neoplasia, undifferentiated carcinoma; Stomach adenocarcinoma, preferably moderately differentiated gastric adenocarcinoma; Ovary carcinoma, preferably any of cystadenocarcinoma, serous papillary cystic carcinoma, Serous papillary cystic carcinoma, Invasive serous papillary carcinoma; Brain cancer, preferably any of Astrocytoma and Glioblastoma multiforme; Kidney carcinoma, preferably Clear cell renal cell carcinoma; Liver cancer, preferably any of Hepatocellular carcinoma, preferably Low Grade hepatocellular carcinoma, Fibrolamellar Hepatocellular Carcinoma; Lymphoma, preferably any of, Hodgkin's Lymphoma and High to low grade Non-Hodgkin's Lymphoma.

Clause 312A. A pharmaceutical composition according to Clause 274, the isolated polypeptide or fusion protein of any of Clauses 200-269, the polynucleotide of Clause 270, the expression vector or virus of Clause 271, or the recombinant cell of Clause 272, for use in the treatment of an immune related condition in a subject suffering from same.

Clause 313A. The pharmaceutical composition, the isolated polypeptide or fusion protein, the polynucleotide, the expression vector or virus, the recombinant cell or the use of Clause 312, wherein said pharmaceutical composition, isolated polypeptide, fusion protein, polynucleotide, expression vector, virus or cell is administered to the subject in need thereof in combination with a therapeutic agent useful for treatment of an immune related condition.

Clause 314A. The pharmaceutical composition, the isolated polypeptide or fusion protein, the polynucleotide, the expression vector or virus, the recombinant cell or the use of Clauses 312 or 313, for treating an immune related condition, in a subject in need thereof.

Clause 315A. The pharmaceutical composition, the isolated polypeptide or fusion protein, the polynucleotide, the expression vector or virus, the recombinant cell or the use of any of Clauses 312-314, wherein said protein, said polynucleotide, said expression vector or virus, said recombinant cell, or said pharmaceutical composition is used for treatment of treatment of immune related diseases and/or for reducing the undesirable immune activation that follows gene or cell therapy, or transplantation of cells, tissues, and/or organs into a subject, and is capable of at least one of: inhibiting immune response, reducing T cell activity, reducing NK cell activity, enhancing regulatory cell activity, enhancing T-cell suppression, enhancing immune regulatory cell activity, inducing establishment of immune tolerance, reducing pro-inflammatory cytokine secretion, re-establishing Th1-Th2 immune balance, reducing immune memory responses to self-antigens, decreasing or eliminating pro-inflammatory immune cells, decreasing or eliminating autoreactive immune cells.

Clause 316A. The pharmaceutical composition, the isolated polypeptide or fusion protein, the polynucleotide, the expression vector or virus, the recombinant cell or the use of any of Clauses 312-315, for performing at least one of the following: (i) decreasing immune response, (ii) decreasing T cell activation, (iii) decreasing cytotoxic T cell activity, (iv) decreasing natural killer (NK) cell activity, (v) decreasing T-cell activity, (vi) decreasing Th17 activity, (vii) decreasing pro-inflammatory cytokine secretion, (viii) decreasing IL-2 secretion; (ix) decreasing interferon-γ production by T-cells, (x) decreasing Th1 response, (xi) decreasing Th2 response, (xii) increasing regulatory T cells and/or one or more of myeloid derived suppressor cells (MDSCs), iMCs, mesenchymal stromal cells, TIE2-expressing monocytes, (xiii) increasing regulatory cell activity and/or the activity of one or more of myeloid derived suppressor cells (MDSCs), iMCs, mesenchymal stromal cells, TIE2-expressing monocytes, (xiv) increasing M2 macrophages, (xv) increasing M2 macrophage activity, (xvi) increasing N2 neutrophils, (xvii) increasing N2 neutrophils activity, (xviii) increasing inhibition of T cell activation, (xix) increasing inhibition of CTL activation, (xx) increasing inhibition of NK cell activation, (xxi) increasing T cell exhaustion, (xxii) decreasing T cell response, (xxiii) decreasing activity of cytotoxic cells, (xxiv) reducing antigen-specific memory responses, (xxv) inhibiting apoptosis or lysis of cells, (xxvi) decreasing cytotoxic or cytostatic effect on cells, (xxvii) reducing direct killing of cells, and/or (xxviii) reducing complement dependent cytotoxicity and/or (xxix) reducing antibody dependent cell-mediated cytotoxicity.

Clause 317A. The pharmaceutical composition, the isolated polypeptide or fusion protein, the polynucleotide, the expression vector or virus, the recombinant cell or the use of any of Clauses 312-316, wherein said immune related condition is selected from the group consisting of autoimmune disease, transplant rejection, and graft versus host disease.

Clause 318A. The pharmaceutical composition, the isolated polypeptide or fusion protein, the polynucleotide, the expression vector or virus, the recombinant cell or the use of any of Clauses 312-316, wherein said autoimmune disease is selected from the group consisting of multiple sclerosis, psoriasis; rheumatoid arthritis; psoriatic arthritis, systemic lupus erythematosus (SLE); discoid lupus erythematosus, inflammatory bowel disease, ulcerative colitis; Crohn's disease; benign lymphocytic angiitis, thrombocytopenic purpura, idiopathic thrombocytopenia, idiopathic autoimmune hemolytic anemia, pure red cell aplasia, Sjogren's syndrome, rheumatic disease, connective tissue disease, inflammatory rheumatism, degenerative rheumatism, extra-articular rheumatism, juvenile rheumatoid arthritis, arthritis uratica, muscular rheumatism, chronic polyarthritis, cryoglobulinemic vasculitis, ANCA-associated vasculitis, antiphospholipid syndrome, myasthenia gravis, autoimmune hemolytic anaemia, Guillain-Barre syndrome, chronic immune polyneuropathy, autoimmune thyroiditis, insulin dependent diabetes mellitus, type I diabetes, Addison's disease, membranous glomerulonephropathy, Goodpasture's disease, autoimmune gastritis, autoimmune atrophic gastritis, pernicious anaemia, pemphigus, pemphigus vulgaris, cirrhosis, primary biliary cirrhosis, dermatomyositis, polymyositis, fibromyositis, myogelosis, celiac disease, immunoglobulin A nephropathy, Henoch-Schonlein purpura, Evans syndrome, Dermatitis, atopic dermatitis, psoriasis, psoriasis arthropathica, Graves' disease, Graves' ophthalmopathy, scleroderma, systemic scleroderma, progressive systemic scleroderma, asthma, allergy, primary biliary cirrhosis, Hashimoto's thyroiditis, primary myxedema, sympathetic ophthalmia, autoimmune uveitis, hepatitis, chronic action hepatitis, collagen diseases, ankylosing spondylitis, periarthritis humeroscapularis, panarteritis nodosa, chondrocalcinosis, Wegener's granulomatosis, microscopic polyangiitis, chronic urticaria, bullous skin disorders, pemphigoid, atopic eczema, bullous pemphigoid, cicatricial pemphigoid, vitiligo, atopic eczema, eczema, chronic urticaria, autoimmune urticaria, normocomplementemic urticarial vasculitis, hypocomplementemic urticarial vasculitis, autoimmune lymphoproliferative syndrome, Devic's disease, sarcoidosis, pernicious anemia, childhood autoimmune hemolytic anemia, idiopathic autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, periodontitis, pancreatitis, myocarditis, vasculitis, gastritis, gout, gouty arthritis, and inflammatory skin disorders, normocomplementemic urticarial vasculitis, pericarditis, idiopathic pericarditis, myositis, antisynthetase syndrome, scleritis, macrophage activation syndrome, Behcet's Syndrome, PAPA Syndrome, Blau's Syndrome, gout, adult and juvenile Still's disease, cryopyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, a rheumatic disease, polymyalgia rheumatica, mixed connective tissue disease, inflammatory rheumatism, degenerative rheumatism, extra-articular rheumatism, juvenile arthritis, juvenile rheumatoid arthritis, systemic juvenile idiopathic arthritis, arthritis uratica, muscular rheumatism, chronic polyarthritis, reactive arthritis, Reiter's syndrome, rheumatic fever, relapsing polychondritis, Raynaud's phenomenon, vasculitis, cryoglobulinemic vasculitis, temporal arteritis, giant cell arteritis, Takayasu arteritis, Behcet's disease, chronic inflammatory demyelinating polyneuropathy, autoimmune thyroiditis, insulin dependent diabetes mellitus, type I diabetes, Addison's disease, membranous glomerulonephropathy, polyglandular autoimmune syndromes, Goodpasture's disease, autoimmune gastritis, autoimmune atrophic gastritis, pernicious anaemia, pemphigus, pemphigus vulgaris, cirrhosis, primary biliary cirrhosis, idiopathic pulmonary fibrosis, myositis, dermatomyositis, juvenile dermatomyositis, polymyositis, fibromyositis, myogelosis, celiac disease, celiac sprue dermatitis, immunoglobulin A nephropathy, Henoch-Schonlein purpura, Evans syndrome, atopic dermatitis, psoriasis, psoriasis vulgaris, psoriasis arthropathica, Graves' disease, Graves' ophthalmopathy, scleroderma, systemic scleroderma, progressive systemic scleroderma, diffuse scleroderma, localized scleroderma, Crest syndrome, asthma, allergic asthma, allergy, primary biliary cirrhosis, fibromyalgia, chronic fatigue and immune dysfunction syndrome (CFIDS), autoimmune inner ear disease, Hyper IgD syndrome, Schnitzler's syndrome, autoimmune retinopathy, age-related macular degeneration, atherosclerosis, chronic prostatitis, alopecia, alopecia areata, alopecia universalis, alopecia totalis, utoimmune thrombocytopenic purpura, idiopathic thrombocytopenic purpura, pure red cell aplasia, and TNF receptor-associated periodic syndrome (TRAPS).

Clause 319A. The pharmaceutical composition, the isolated polypeptide or fusion protein, the polynucleotide, the expression vector or virus, the recombinant cell or the use of any of Clauses 312-317, for treating an autoimmune disease selected from relapsing-remitting multiple sclerosis, primary progressive multiple sclerosis, secondary progressive multiple sclerosis; progressive relapsing multiple sclerosis, chronic progressive multiple sclerosis, transitional/progressive multiple sclerosis, rapidly worsening multiple sclerosis, clinically-definite multiple sclerosis, malignant multiple sclerosis, also known as Marburg's Variant, acute multiple sclerosis, conditions relating to multiple sclerosis, psoriatic arthritis, gout and pseudo-gout, juvenile idiopathic arthritis, Still's disease, rheumatoid vasculitis, conditions relating to rheumatoid arthritis, discoid lupus, lupus arthritis, lupus pneumonitis, lupus nephritis, conditions relating to systemic lupus erythematosus include osteoarticular tuberculosis, antiphospholipid antibody syndrome, inflammation of various parts of the heart, such as pericarditis, myocarditis, and endocarditis, Lung and pleura inflammation, pleuritis, pleural effusion, chronic diffuse interstitial lung disease, pulmonary hypertension, pulmonary emboli, pulmonary hemorrhage, and shrinking lung syndrome, lupus headache, Guillain-Barre syndrome, aseptic meningitis, demyelinating syndrome, mononeuropathy, mononeuritis multiplex, myelopathy, cranial neuropathy, polyneuropathy, vasculitis, Collagenous colitis, Lymphocytic colitis, Ischaemic colitis, Diversion colitis, Behcet's disease, Indeterminate colitis, thrombocytopenic purpura, idiopathic autoimmune hemolytic anemia, pure red cell aplasia, cryoglobulinemic vasculitis, ANCA-associated vasculitis, antiphospholipid syndrome, autoimmune hemolytic anaemia, Guillain-Barre syndrome, chronic immune polyneuropathy, autoimmune thyroiditis, idiopathic diabetes, juvenile type I diabetes, maturity onset diabetes of the young, latent autoimmune diabetes in adults, gestational diabetes, conditions relating to type 1 diabetes, membranous glomerulonephropathy, autoimmune gastritis, pemphigus vulgaris, cirrhosis, fibromyositis, celiac disease, immunoglobulin A nephropathy, Henoch-Schonlein purpura, Evans syndrome, atopic dermatitis, psoriasis, Graves' ophthalmopathy, systemic scleroderma, asthma, allergy, anterior uveitis (or iridocyclitis), intermediate uveitis (pars planitis), posterior uveitis (or chorioretinitis), panuveitic form, hepatitis, Wegener's granulomatosis, microscopic polyangiitis, chronic urticaria, bullous skin disorders, pemphigoid, atopic eczema, Devic's disease, childhood autoimmune hemolytic anemia, Refractory or chronic Autoimmune Cytopenias, Prevention of development of Autoimmune Anti-Factor VIII Antibodies in Acquired Hemophilia A, Cold Agglutinin Disease, Neuromyelitis Optica, Stiff Person Syndrome, gingivitis, perodontitis, pancreatitis, myocarditis, vasculitis, gastritis, gout, gouty arthritis, and inflammatory skin disorders, selected from the group consisting of psoriasis, Nonpustular Psoriasis including Psoriasis vulgaris and Psoriatic erythroderma (erythrodermic psoriasis), Pustular psoriasis including Generalized pustular psoriasis (pustular psoriasis of von Zumbusch), Pustulosis palmaris et plantaris (persistent palmoplanar pustulosis, pustular psoriasis of the Barber type, pustular psoriasis of the extremities), Annular pustular psoriasis, Acrodermatitis continua, Impetigo herpetiformis, drug-induced psoriasis, Inverse psoriasis, Napkin psoriasis, Seborrheic-like psoriasis, Guttate psoriasis, Nail psoriasis, Psoriatic arthritis, atopic dermatitis, eczema, rosacea, urticaria, and acne, normocomplementemic urticarial vasculitis, pericarditis, anti-synthetase syndrome, scleritis, macrophage activation syndrome, Behcet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, autoimmune retinopathy, age-related macular degeneration, atherosclerosis, chronic prostatitis and TNF receptor-associated periodic syndrome (TRAPS).

Clause 320A. The pharmaceutical composition, the isolated polypeptide or fusion protein, the polynucleotide, the expression vector or virus, the recombinant cell or the use of any of Clauses 312-319, wherein the treatment is combined with another moiety useful for treating said condition.

Clause 321A. The pharmaceutical composition, the isolated polypeptide or fusion protein, the polynucleotide, the expression vector or virus, the recombinant cell or the use of any of Clauses 312-320, wherein said other moiety useful for treating immune related condition is selected from immunosuppressants such as corticosteroids, cyclosporin, cyclophosphamide, prednisone, azathioprine, methotrexate, rapamycin, tacrolimus, leflunomide or an analog thereof; mizoribine; mycophenolic acid; mycophenolate mofetil; 15-deoxyspergualine or an analog thereof; biological agents such as TNF-alpha blockers or antagonists, or any other biological agent targeting any inflammatory cytokine, non-steroidal antiinflammatory drugs/Cox-2 inhibitors, hydroxychloroquine, sulfasalazine, gold salts, etanercept, infliximab, mycophenolate mofetil, basiliximab, atacicept, rituximab, Cytoxan® (cyclophosphamide), interferon beta-Ia, interferon beta-Ib, glatiramer acetate, mitoxantrone hydrochloride, anakinra and/or other biologies and/or intravenous immunoglobulin (IVIG), interferons such as IFN-beta-Ia (REBIF®. AVONEX® and CINNOVEX®) and IFN-beta-Ib) (BETASERON®); EXTAVIA®, BETASERON®, ZIFERON®); glatiramer acetate (COPAXONE®), a polypeptide; natalizumab (TYSABRI®), mitoxantrone (NOVANTRONE®), a cytotoxic agent, a calcineurin inhibitor; cyclosporin A; FK506; an immunosuppressive macrolide; rapamycin; a rapamycin derivative; 40-O-(2-hydroxy)ethyl-rapamycin, a lymphocyte homing agent, FTY720; an analog of FTY720; corticosteroids; cyclophosphamide; azathioprine; methotrexate; leflunomide or an analog thereof; mizoribine; mycophenolic acid; mycophenolate mofetil; 15-deoxyspergualine or an analog thereof; immunosuppressive monoclonal antibodies, monoclonal antibodies to leukocyte receptors, monoclonal antibodies to MHC, CD2, CD3, CD4, CDI Ia/CD18, CD7, CD25, CD27, B7, CD40, CD45, CD58, CD137, ICOS, CD150 (SLAM), OX40, 4-1BB or their ligands; or other immunomodulatory compounds, CTLA4-Ig (abatacept, ORENCIA®, belatacept), CD28-Ig, B7-H4-Ig, or other costimulatory agents, or adhesion molecule inhibitors, mAbs or low molecular weight inhibitors, LFA-1 antagonists, Selectin antagonists and VLA-4 antagonists, or another immunomodulatory agent.

Clause 322A. A pharmaceutical composition according to Clause 274, the isolated polypeptide or fusion protein of any of Clauses 200-269, the polynucleotide of Clause 270, the expression vector or virus of Clause 271, or the recombinant cell of Clause 272, for use in treatment of Infectious disease in a subject suffering from same.

Clause 323A. The pharmaceutical composition, the isolated polypeptide or fusion protein, the polynucleotide, the expression vector or virus, the recombinant cell or the use of Clause 322, wherein said protein, said polynucleotide, said expression vector or virus, said recombinant cell, said pharmaceutical composition or said use is used for treatment of infectious disease and is capable of at least one of the following: (i) increasing immune response, (ii) increasing T cell activation, (iii) increasing cytotoxic T cell activity, (iv) increasing NK cell activity, (v) increasing Th17 activity, (vi) alleviating T-cell suppression, (vii) increasing pro-inflammatory cytokine secretion, (viii) increasing IL-2 secretion; (ix) increasing interferon-y production by T-cells, (x) increasing Th1 response, (xi) decreasing Th2 response, (xii) decreasing or eliminating at least one of regulatory T cells (Tregs), myeloid derived suppressor cells (MDSCs), iMCs, mesenchymal stromal cells, TIE2-expressing monocytes, (xiii) reducing regulatory cell activity and/or the activity of one or more of myeloid derived suppressor cells (MDSCs), iMCs, mesenchymal stromal cells, TIE2-expressing monocytes, (xiv) decreasing or eliminating M2 macrophages, (xv) reducing M2 macrophage pro-tumorigenic activity, (xvi) decreasing N2 neutrophils, (xvii) decreasing N2 neutrophils activity, (xviii) reducing inhibition of T cell activation, (xix) reducing inhibition of CTL activation, (xx) reducing inhibition of NK cell activation, (xxi) reversing T cell exhaustion, (xxii) increasing T cell response, (xxiii) increasing activity of cytotoxic cells, (xxiv) stimulating antigen-specific memory responses, (xxv) eliciting apoptosis or lysis of cancer cells, (xxvi) stimulating cytotoxic or cytostatic effect on cancer cells, (xxvii) Inducing direct killing of cancer cells, and/or (xxviii) inducing complement dependent cytotoxicity and/or (xxix) inducing antibody dependent cell-mediated cytotoxicity.

Clause 324A. The pharmaceutical composition, the isolated polypeptide or fusion protein, the polynucleotide, the expression vector or virus, the recombinant cell or the use of any of Clauses 321-323, wherein said infectious disease is chronic infectious disease and is selected from the disease caused by bacterial infection, viral infection, fungal infection and/or other parasite infection.

Clause 325A. The pharmaceutical composition, the isolated polypeptide or fusion protein, the polynucleotide, the expression vector or virus, the recombinant cell or the use of any of Clauses 321-324, wherein said infectious disease results in sepsis.

Clause 326A. The pharmaceutical composition, the isolated polypeptide or fusion protein, the polynucleotide, the expression vector or virus, the recombinant cell or the use of any of Clauses 321-324, wherein the infectious disease is selected from hepatitis B, hepatitis C, infectious mononucleosis, AIDS, tuberculosis, malaria and schistosomiasis.

Clause 327A. The pharmaceutical composition, the isolated polypeptide or fusion protein, the polynucleotide, the expression vector or virus, the recombinant cell or the use of any of Clauses 321-326, wherein the treatment is combined with another moiety useful for treating infectious disease, or with another moiety useful for reducing the undesirable immune activation that follows gene therapy, in a subject in need thereof.

Clause 328A. The pharmaceutical composition, the isolated polypeptide or fusion protein, the polynucleotide, the expression vector or virus, the recombinant cell or the use of any of Clauses 321-327, wherein said other moiety is a therapeutic agent useful for treating bacterial infection, viral infection, fungal infection, parasitic infection or sepsis.

Clause 329A. A compound, composition, method or use according to any of the foregoing Clauses which further includes a VISTA agonist or antagonist compound which is separate or is conjugated to a VISTA agonist or antagonist compound.

Clause 330A. A fusion protein, pharmaceutical composition, isolated polypeptide, polynucleotide, expression vector or virus, recombinant cell or method or use according to any of the foregoing Clauses which further includes a VSIG3 agonist or antagonist which is separate or conjugated to a VISTA agonist or antagonist compound which preferably comprises an anti-VISTA antibody, VISTA protein or VISTA fusion protein.

Clause 331A. Method of using a VISTA fusion protein, pharmaceutical composition, isolated polypeptide, polynucleotide, expression vector or virus, recombinant cell or method or use according to any of the foregoing Clauses, in therapy, preferably for use in inhibiting T cell or NK immunity, e.g., in treating any of autoimmunity, allergy, inflammatory conditions, transplant or sepsis alone or in combination with any of the other therapeutics or actives disclosed herein, especially immune inhibitors.

Clause 332A. Method of using a VISTA fusion protein, pharmaceutical composition, isolated polypeptide, polynucleotide, expression vector or virus, recombinant cell or method or use according to any of the foregoing Clauses, in therapy, preferably for use in inhibiting T cell or NK immunity, e.g., in treating any of autoimmunity, allergy, inflammatory conditions, transplant or sepsis alone or in combination with any of the other therapeutics or actives disclosed herein, especially immune inhibitors.

What is claimed is:

1. An anti-VSIG3 antibody or antigen binding fragment thereof, wherein the anti-VSIG3 antibody comprises:
   - a light chain comprising SEQ ID NO: 85 and a heavy chain comprising SEQ ID NO: 90; or
   - a light chain comprising SEQ ID NO: 86 and a heavy chain comprising SEQ ID NO: 91; or
   - a light chain comprising SEQ ID NO: 87 and a heavy chain comprising SEQ ID NO:92; or
   - a light chain comprising SEQ ID NO: 88 and a heavy chain comprising SEQ ID NO: 93; or
   - a light chain comprising SEQ ID NO: 89 and a heavy chain comprising SEQ ID NO: 94; or
   - a light chain comprising SEQ ID NO: 95 and a heavy chain comprising SEQ ID NO: 101; or
   - a light chain comprising SEQ ID NO: 96 and a heavy chain comprising SEQ ID NO: 102); or
   - a light chain comprising SEQ ID NO: 97 and a heavy chain comprising SEQ ID NO: 103; or
   - a light chain comprising SEQ ID NO: 98 and a heavy chain comprising SEQ D NO:104; or
   - a light chain comprising SEQ ID: 99 and a heavy chain comprising SEQ ID NO:105; or
   - a light chain comprising SEQ ID NO:100 and a heavy chain comprising SEQ ID NO:106.

2. An anti-VSIG3 antibody or antigen binding fragment thereof, wherein the anti-VSIG3 antibody or antigen binding fragment thereof comprises:
- a light chain variable region comprising a CDR1 comprising SEQ ID NO: 7, a CDR2 comprising SEQ ID NO: 18, and a CDR3 comprising SEQ ID NO: 29 and a heavy chain variable region comprising a CDR1 comprising SEQ ID NO: 40, a CDR2 comprising SEQ ID NO: 51, and a CDR3 comprising SEQ ID NO: 62; or
- a light chain variable region comprising a CDR1 comprising SEQ ID NO: 8, a CDR2 comprising SEQ ID NO: 19, and a CDR3 comprising SEQ ID NO: 30 and a heavy chain variable region comprising a CDR1 comprising SEQ ID NO: 41, a CDR2 comprising SEQ ID NO: 52, and a CDR3 comprising SEQ ID NO: 63; or
- a light chain variable region comprising a CDR1 comprising SEQ ID NO:9, a CDR2 comprising SEQ ID NO: 20, and a CDR3 comprising SEQ ID NO: 31 and a heavy chain variable region comprising a CDR1 comprising SEQ ID NO: 42, a CDR2 comprising SEQ ID NO: 53, and a CDR3 comprising SEQ ID NO: 64; or
- a light chain variable region comprising a CDR1 comprising SEQ ID NO: 10, a CDR2 comprising SEQ ID NO: 21, and a CDR3 comprising SEQ ID NO: 32 and a heavy chain variable region comprising a CDR1 comprising SEQ ID NO: 43, a CDR2 comprising SEQ ID NO: 54, and a CDR3 comprising SEQ ID NO: 65; or
- a light chain variable region comprising a CDR1 comprising SEQ ID NO: 11, a CDR2 comprising SEQ ID NO: 22, and a CDR3 comprising SEQ ID NO: 33 and a heavy chain variable region comprising a CDR1 comprising SEQ ID NO: 44, a CDR2 comprising SEQ ID NO: 55, and a CDR3 comprising SEQ ID NO: 66; or
- a light chain variable region comprising a CDR1 comprising SEQ ID NO: 12, a CDR2 comprising SEQ ID NO: 23, and a CDR3 comprising SEQ ID NO: 34 and a heavy chain variable region comprising a CDR1 comprising SEQ ID NO: 45, a CDR2 comprising SEQ ID NO: 56, and a CDR3 comprising SEQ ID NO: 67; or
- a light chain variable region comprising a CDR1 comprising SEQ ID NO: 13, a CDR2 comprising SEQ ID NO: 24, and a CDR3 comprising SEQ ID NO: 35 and a heavy chain variable region comprising a CDR1 comprising SEQ ID NO:46, a CDR2 comprising SEQ ID NO: 57, and a CDR3 comprising SEQ ID NO: 68; or
- a light chain variable region comprising a CDR1 comprising SEQ ID NO: 14, a CDR2 comprising SEQ ID NO: 25, and a CDR3 comprising SEQ ID NO: 36 and a heavy chain variable region comprising a CDR1 comprising SEQ ID NO:47, a CDR2 comprising SEQ ID NO: 58, and a CDR3 comprising SEQ ID NO: 69; or
- a light chain variable region comprising a CDR1 comprising SEQ ID NO: 15, a CDR2 comprising SEQ ID NO: 26, and a CDR3 comprising SEQ ID NO: 37 and a heavy chain variable region comprising a CDR1 comprising SEQ ID NO: 48, a CDR2 comprising SEQ ID NO: 59, and a CDR3 comprising SEQ ID NO: 70; or
- a light chain variable region comprising a CDR1 comprising SEQ ID NO: 16, a CDR2 comprising SEQ ID NO: 27, and a CDR3 comprising SEQ ID NO: 38 and a heavy chain variable region comprising a CDR1 comprising SEQ ID NO: 49, a CDR2 comprising SEQ ID NO: 60, and a CDR3 comprising SEQ ID NO: 71; or
- a light chain variable region comprising a CDR1 comprising SEQ ID NO: 17, a CDR2 comprising SEQ ID NO: 28, and a CDR3 comprising SEQ ID NO: 39 and a heavy chain variable region comprising a CDR1 comprising SEQ ID NO: 50, a CDR2 comprising SEQ ID NO: 61, and a CDR3 comprising SEQ ID NO: 72.

3. The anti-VSIG3 antibody or antigen binding fragment thereof of claim 1, wherein the antibody or antigen binding fragment thereof antagonizes the interaction of VISTA and VSIG3.

4. The anti-VSIG3 antibody or antigen binding fragment thereof of claim 2, wherein the antibody antagonizes the interaction of VISTA and VSIG3.

5. The anti-VSIG3 antibody or antigen binding fragment thereof of claim 4, wherein the antibody or antigen binding fragment thereof abrogates the binding of VISTA and VSIG3, or VISTA signaling, or both.

6. The anti-VSIG3 antibody or antigen binding fragment thereof of claim 5, wherein abrogation of VISTA signaling comprises abrogation of at least one of CD3-induced IL-2 production, CD3-induced IFN-γ production, CD3-induced RANTES production, CD3-induced MIP-1 alpha production, CD3-induced IL-17 production, and CD3-induced CXCL11 production.

7. A composition comprising an anti-VSIG3 antibody or antigen binding fragment thereof of claim 2.

8. The composition of claim 7, wherein the composition comprises two or more anti-VSIG3 antibodies, and the two or more anti-VSIG3 antibodies bind to different epitopes.

9. A composition of claim 7, wherein the composition blocks at least one of a VSIG3-VISTA interaction, a VSIG3-VISTA8 interaction, and multimerization of VSIG3.

10. The anti-VSIG3 antibody or antigen binding fragment thereof of claim 2, wherein the anti-VSIG3 antibody or antigen binding fragment thereof comprises:
- a light chain variable region comprising SEQ ID NO: 85, or SEQ ID NO: 85 having one, two, three, four, five, or six amino acid substitutions thereof; or
- a heavy chain variable region comprising SEQ ID NO: 90, or SEQ ID NO: 90 having one, two, three, four, five, or six amino acid substitutions thereof; or
- a light chain variable region comprising SEQ ID NO: 85, or SEQ ID NO: 85 having one, two, three, four, five, or six amino acid substitutions thereof, and a heavy chain variable region comprising SEQ ID NO: 90, or SEQ ID NO: 90 having one, two, three, four, five, or six amino acid substitutions thereof.

11. The anti-VSIG3 antibody or antigen binding fragment thereof of claim 2, wherein the anti-VSIG3 antibody or antigen binding fragment thereof comprises:
- a light chain variable region comprising SEQ ID NO: 85, or SEQ ID NO: 85 having one, two, three, four, five, or six amino acid substitutions thereof;
  wherein the light chain comprises a CDR1 comprising SEQ ID NO: 7, a CDR2 comprising SEQ ID NO: 18, and a CDR3 comprising SEQ ID NO: 29;
- a heavy chain variable region comprising SEQ ID NO: 90, or SEQ ID NO: 90 having one, two, three, four, five, or six amino acid substitutions thereof; and wherein the heavy chain comprises a CDR1 comprising SEQ ID NO: 40, a CDR2 comprising SEQ ID NO: 51, and a CDR3 comprising SEQ ID NO: 62.

12. The anti-VSIG3 antibody or antigen binding fragment thereof of claim 2, wherein the anti-VSIG3 antibody or antigen binding fragment thereof comprises a humanized antibody, or a chimeric antibody.

13. The anti-VSIG3 antibody or antigen binding fragment thereof of claim 1, wherein the anti-VSIG3 antibody or antigen binding fragment thereof comprises a humanized antibody, or a chimeric antibody.

14. The anti-VSIG3 antibody or antigen binding fragment thereof of claim 1, wherein the antibody or antigen binding fragment thereof blocks at least one of a VSIG3-VISTA interaction, a VSIG3-VISTA8 interaction, and multimerization of VSIG3.

15. A composition comprising an anti-VSIG3 antibody or antigen binding fragment thereof of claim 1.

16. The composition of claim 15, wherein the composition comprises two or more anti-VSIG3 antibodies, and the two or more anti-VSIG3 antibodies bind to different epitopes.

17. The anti-VSIG3 antibody or antigen binding fragment thereof of claim 2, wherein the antibody or antigen binding fragment thereof blocks at least one of a VSIG3-VISTA interaction, a VSIG3-VISTA8 interaction, and multimerization of VSIG3.

18. The anti-VSIG3 antibody or antigen binding fragment thereof of claim 3, wherein the antibody or antigen binding fragment thereof abrogates the binding of VISTA and VSIG3, or VISTA signaling, or both.

19. The anti-VSIG3 antibody or antigen binding fragment thereof of claim 18, wherein abrogation of VISTA signaling comprises abrogation of at least one of CD3-induced IL-2 production, CD3-induced IFN-γ production, CD3-induced RANTES production, CD3-induced MIP-1 alpha production, CD3-induced IL-17 production, and CD3-induced CXCL11 production.

20. A composition of claim 15, wherein the composition blocks at least one of a VSIG3-VISTA interaction, a VSIG3-VISTA8 interaction, and multimerization of VSIG3.

21. The anti-VSIG3 antibody or antigen binding fragment thereof of claim 2, wherein the anti-VSIG3 antibody or antigen binding fragment thereof comprises:
  a light chain variable region comprising SEQ ID NO: 86, or SEQ ID NO: 86 having one, two, three, four, five, or six amino acid substitutions thereof, and a heavy chain variable region comprising SEQ ID NO: 91, or SEQ ID NO: 91 having one, two, three, four, five, or six amino acid substitutions thereof, wherein the light chain comprises a CDR1 comprising SEQ ID NO: 8, a CDR2 comprising SEQ ID NO: 19, and a CDR3 comprising SEQ ID NO: 30, and wherein the heavy chain comprises a CDR1 comprising SEQ ID NO: 41, a CDR2 comprising SEQ ID NO: 52, and a CDR3 comprising SEQ ID NO: 63; or
  a light chain variable region comprising SEQ ID NO: 87, or SEQ ID NO: 87 having one, two, three, four, five, or six amino acid substitutions thereof, and a heavy chain variable region comprising SEQ ID NO: 92, or SEQ ID NO: 92 having one, two, three, four, five, or six amino acid substitutions thereof, wherein the light chain comprises a CDR1 comprising SEQ ID NO: 9, a CDR2 comprising SEQ ID NO: 20, and a CDR3 comprising SEQ ID NO: 31, and wherein the heavy chain comprises a CDR1 comprising SEQ ID NO: 42, a CDR2 comprising SEQ ID NO: 53, and a CDR3 comprising SEQ ID NO: 64; or
  a light chain variable region comprising SEQ ID NO: 88, or SEQ ID NO: 88 having one, two, three, four, five, or six amino acid substitutions thereof, and a heavy chain variable region comprising SEQ ID NO: 93, or SEQ ID NO: 93 having one, two, three, four, five, or six amino acid substitutions thereof, wherein the light chain comprises a CDR1 comprising SEQ ID NO: 10, a CDR2 comprising SEQ ID NO: 21, and a CDR3 comprising SEQ ID NO: 32, and wherein the heavy chain comprises a CDR1 comprising SEQ ID NO: 43, a CDR2 comprising SEQ ID NO: 54, and a CDR3 comprising SEQ ID NO: 65; or
  a light chain variable region comprising SEQ ID NO: 89, or SEQ ID NO: 89 having one, two, three, four, five, or six amino acid substitutions thereof, and a heavy chain variable region comprising SEQ ID NO: 94, or SEQ ID NO: 94 having one, two, three, four, five, or six amino acid substitutions thereof, wherein the light chain comprises a CDR1 comprising SEQ ID NO: 11, a CDR2 comprising SEQ ID NO: 22 and a CDR3 comprising SEQ ID NO: 33, and wherein the heavy chain comprises a CDR1 comprising SEQ ID NO: 44, a CDR2 comprising SEQ ID NO: 55, and a CDR3 comprising SEQ ID NO: 66; or
  a light chain variable region comprising SEQ ID NO: 73, or SEQ ID NO: 73 having one, two, three, four, five, or six amino acid substitutions thereof, and a heavy chain variable region comprising SEQ ID NO: 80, or SEQ ID NO: 80 having one, two, three, four, five, or six amino acid substitutions thereof, wherein the light chain comprises a CDR1 comprising SEQ ID NO: 12, a CDR2 comprising SEQ ID NO: 23, and a CDR3 comprising SEQ ID NO: 34, and wherein the heavy chain comprises a CDR1 comprising SEQ ID NO: 45, a CDR2 comprising SEQ ID NO: 56, and a CDR3 comprising SEQ ID NO: 67; or
  a light chain variable region comprising SEQ ID NO: 74, or SEQ ID NO: 74 having one, two, three, four, five, or six amino acid substitutions thereof, and a heavy chain variable region comprising SEQ ID NO: 80, or SEQ ID NO: 80 having one, two, three, four, five, or six amino acid substitutions thereof, wherein the light chain comprises a CDR1 comprising SEQ ID NO: 13, a CDR2 comprising SEQ ID NO: 24, and a CDR3 comprising SEQ ID NO: 35, and wherein the heavy chain comprises a CDR1 comprising SEQ ID NO: 46, a CDR2 comprising SEQ ID NO: 57, and a CDR3 comprising SEQ ID NO: 68; or
  a light chain variable region comprising SEQ ID NO: 75, or SEQ ID NO: 75 having one, two, three, four, five, or six amino acid substitutions thereof, and a heavy chain variable region comprising SEQ ID NO: 81, or SEQ ID NO: 81 having one, two, three, four, five, or six amino acid substitutions thereof, wherein the light chain comprises a CDR1 comprising SEQ ID NO: 14, a CDR2 comprising SEQ ID NO: 25, and a CDR3 comprising SEQ ID NO: 36, and wherein the heavy chain comprises a CDR1 comprising SEQ ID NO: 47, a CDR2 comprising SEQ ID NO: 58, and a CDR3 comprising SEQ ID NO: 69; or
  a light chain variable region comprising SEQ ID NO: 76, or SEQ ID NO: 76 having one, two, three, four, five, or six amino acid substitutions thereof, and a heavy chain variable region comprising SEQ ID NO: 82, or SEQ ID NO: 82 having one, two, three, four, five, or six amino acid substitutions thereof, wherein the light chain comprises a CDR1 comprising SEQ ID NO: 15, a CDR2 comprising SEQ ID NO: 26, and a CDR3 comprising SEQ ID NO: 37, and wherein the heavy chain comprises a CDR1 comprising SEQ ID NO: 48, a CDR2 comprising SEQ ID NO: 59, and a CDR3 comprising SEQ ID NO: 70; or a light chain variable region comprising SEQ ID NO: 77, or SEQ ID NO: 77 having one, two, three, four, five, or six amino acid substitutions thereof, and a heavy chain variable region comprising SEQ ID NO: 83, or SEQ ID NO: 83 having one, two, three, four, five, or six amino acid substitutions thereof, wherein the light chain comprises a CDR1 comprising SEQ ID NO: 16, a CDR2 comprising SEQ ID NO: 27, and a CDR3 comprising SEQ ID NO: 38, and wherein the heavy chain comprises a CDR1 comprising SEQ ID NO: 49, a CDR2 comprising SEQ ID NO: 60, and a CDR3 comprising SEQ ID NO: 71; or a light chain variable region comprising SEQ ID NO: 78, or SEQ ID NO: 78 having one, two, three, four, five, or six amino acid substitutions thereof, and a heavy chain variable region comprising SEQ ID NO: 84, or SEQ ID NO: 84 having one, two, three, four, five, or six amino acid substitutions thereof, wherein the light chain comprises a CDR1 comprising SEQ ID NO: 17, a CDR2 comprising SEQ ID NO: 28, and a CDR3 comprising SEQ ID NO: 39, and wherein the heavy chain comprises a CDR1 comprising SEQ ID NO: 50, a CDR2 comprising SEQ ID NO: 61, and a CDR3 comprising SEQ ID NO: 72.

\* \* \* \* \*

SEQUENCE LISTING

```
<160> NUMBER OF SEQ ID NOS: 106

<210> SEQ ID NO 1
<211> LENGTH: 431
<212> TYPE: PRT
<213> ORGANISM: homo sapiens

<400> SEQUENCE: 1

Met Thr Ser Gln Arg Ser Pro Leu Ala Pro Leu Leu Leu Ser Leu
1               5                   10                  15

His Gly Val Ala Ala Ser Leu Glu Val Ser Glu Ser Pro Gly Ser Ile
                20                  25                  30

Gln Val Ala Arg Gly Gln Pro Ala Val Leu Pro Cys Thr Phe Thr Thr
            35                  40                  45

Ser Ala Ala Leu Ile Asn Leu Asn Val Ile Trp Met Val Thr Pro Leu
    50                  55                  60

Ser Asn Ala Asn Gln Pro Glu Gln Val Ile Leu Tyr Gln Gly Gly Gln
65                  70                  75                  80

Met Phe Asp Gly Ala Pro Arg Phe His Gly Arg Val Gly Phe Thr Gly
                85                  90                  95

Thr Met Pro Ala Thr Asn Val Ser Ile Phe Ile Asn Asn Thr Gln Leu
            100                 105                 110

Ser Asp Thr Gly Thr Tyr Gln Cys Leu Val Asn Asn Leu Pro Asp Ile
        115                 120                 125

Gly Gly Arg Asn Ile Gly Val Thr Gly Leu Thr Val Leu Val Pro Pro
    130                 135                 140

Ser Ala Pro His Cys Gln Ile Gln Gly Ser Gln Asp Ile Gly Ser Asp
145                 150                 155                 160

Val Ile Leu Leu Cys Ser Ser Glu Glu Gly Ile Pro Arg Pro Thr Tyr
                165                 170                 175

Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
        195                 200                 205

Ser Ser Gly Leu Tyr Gln Cys Val Ala Ser Asn Ala Ile Gly Thr Ser
    210                 215                 220

Thr Cys Leu Leu Asp Leu Gln Val Ile Ser Pro Gln Pro Arg Asn Ile
```

```
                225                 230                 235                 240
        Gly Leu Ile Ala Gly Ala Ile Gly Thr Gly Ala Val Ile Ile Ile Phe
                            245                 250                 255

Cys Ile Ala Leu Ile Leu Gly Ala Phe Phe Tyr Trp Arg Ser Lys Asn
                            260                 265                 270

Lys Glu Glu Glu Glu Glu Ile Pro Asn Glu Ile Arg Glu Asp Asp
                            275                 280                 285

Leu Pro Pro Lys Cys Ser Ser Ala Lys Ala Phe His Thr Glu Ile Ser
                290                 295                 300

Ser Ser Asp Asn Asn Thr Leu Thr Ser Ser Asn Ala Tyr Asn Ser Arg
        305                 310                 315                 320

Tyr Trp Ser Asn Asn Pro Lys Val His Arg Asn Thr Glu Ser Val Ser
                            325                 330                 335

His Phe Ser Asp Leu Gly Gln Ser Phe Ser Phe His Ser Gly Asn Ala
                            340                 345                 350

Asn Ile Pro Ser Ile Tyr Ala Asn Gly Thr His Leu Val Pro Gly Gln
                        355                 360                 365

His Lys Thr Leu Val Val Thr Ala Asn Arg Gly Ser Ser Pro Gln Val
                        370                 375                 380

Met Ser Arg Ser Asn Gly Ser Val Ser Arg Lys Pro Arg Pro His
        385                 390                 395                 400

Thr His Ser Tyr Thr Ile Ser His Ala Thr Leu Glu Arg Ile Gly Ala
                            405                 410                 415

Val Pro Val Met Val Pro Ala Gln Ser Arg Ala Gly Ser Leu Val
                        420                 425                 430

<210> SEQ ID NO 2
<211> LENGTH: 245
<212> TYPE: PRT
<213> ORGANISM: homo sapiens

<400> SEQUENCE: 2

Met Thr Ser Gln Arg Ser Pro Leu Ala Pro Leu Leu Leu Leu Ser Leu
1               5                   10                  15

His Gly Val Ala Ala Ser Leu Glu Val Ser Glu Ser Pro Gly Ser Ile
                    20                  25                  30

Gln Val Ala Arg Gly Gln Thr Ala Val Leu Pro Cys Thr Phe Thr Thr
                35                  40                  45

Ser Ala Ala Leu Ile Asn Leu Asn Val Ile Trp Met Val Thr Pro Leu
            50                  55                  60

Ser Asn Ala Asn Gln Pro Glu Gln Val Ile Leu Tyr Gln Gly Gly Gln
65                  70                  75                  80

Met Phe Asp Gly Ala Pro Arg Phe His Gly Arg Val Gly Phe Thr Gly
                    85                  90                  95

Thr Met Pro Ala Thr Asn Val Ser Ile Phe Ile Asn Asn Thr Gln Leu
                100                 105                 110

Ser Asp Thr Gly Thr Tyr Gln Cys Leu Val Asn Asn Leu Pro Asp Ile
            115                 120                 125

Gly Gly Arg Asn Ile Gly Val Thr Gly Leu Thr Val Leu Val Pro Pro
        130                 135                 140

Ser Ala Pro His Cys Gln Ile Gln Gly Ser Gln Asp Ile Gly Ser Asp
145                 150                 155                 160

Val Ile Leu Leu Cys Ser Ser Glu Glu Gly Ile Pro Arg Pro Thr Tyr
                    165                 170                 175
```

```
Leu Trp Glu Lys Leu Asp Asn Thr Leu Lys Leu Pro Pro Thr Ala Thr
            180                 185                 190

Gln Asp Gln Val Gln Gly Thr Val Thr Ile Arg Asn Ile Ser Ala Leu
        195                 200                 205

Ser Ser Gly Leu Tyr Gln Cys Val Ala Ser Asn Ala Ile Gly Thr Ser
        210                 215                 220

Thr Cys Leu Leu Asp Leu Gln Val Ile Ser Pro Gln Pro Arg Asn Ile
225                 230                 235                 240

Gly Leu Ile Ala Gly
                245

<210> SEQ ID NO 3
<211> LENGTH: 460
<212> TYPE: PRT
<213> ORGANISM: homo sapiens

<400> SEQUENCE: 3

Leu Glu Val Ser Glu Ser Pro Gly Ser Ile Gln Val Ala Arg Gly Gln
1               5                   10                  15

Thr Ala Val Leu Pro Cys Thr Phe Thr Thr Ser Ala Ala Leu Ile Asn
            20                  25                  30

Leu Asn Val Ile Trp Met Val Thr Pro Leu Ser Asn Ala Asn Gln Pro
        35                  40                  45

Glu Gln Val Ile Leu Tyr Gln Gly Gly Gln Met Phe Asp Gly Ala Pro
    50                  55                  60

Arg Phe His Gly Arg Val Gly Phe Thr Gly Thr Met Pro Ala Thr Asn
65                  70                  75                  80

Val Ser Ile Phe Ile Asn Asn Thr Gln Leu Ser Asp Thr Gly Thr Tyr
                85                  90                  95

Gln Cys Leu Val Asn Asn Leu Pro Asp Ile Gly Gly Arg Asn Ile Gly
            100                 105                 110

Val Thr Gly Leu Thr Val Leu Val Pro Pro Ser Ala Pro His Cys Gln
        115                 120                 125

Ile Gln Gly Ser Gln Asp Ile Gly Ser Asp Val Ile Leu Leu Cys Ser
    130                 135                 140

Ser Glu Glu Gly Ile Pro Arg Pro Thr Tyr Leu Trp Glu Lys Leu Asp
145                 150                 155                 160

Asn Thr Leu Lys Leu Pro Pro Thr Ala Thr Gln Asp Gln Val Gln Gly
                165                 170                 175

Thr Val Thr Ile Arg Asn Ile Ser Ala Leu Ser Ser Gly Leu Tyr Gln
            180                 185                 190

Cys Val Ala Ser Asn Ala Ile Gly Thr Ser Thr Cys Leu Leu Asp Leu
        195                 200                 205

Gln Val Ile Ser Pro Gln Pro Arg Asn Ile Gly Leu Ile Ala Gly Ile
    210                 215                 220

Glu Gly Arg Met Asp Pro Lys Ser Cys Asp Lys Thr His Thr Cys Pro
225                 230                 235                 240

Pro Cys Pro Ala Pro Glu Ala Glu Gly Ala Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300
```

```
Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Ala Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460

<210> SEQ ID NO 4
<211> LENGTH: 311
<212> TYPE: PRT
<213> ORGANISM: homo sapiens

<400> SEQUENCE: 4

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
```

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
            245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
            275                 280                 285

Pro Gly Pro Gly Asp Val Phe Phe Pro Ser Leu Asp Pro Val Pro Asp
290                 295                 300

Ser Pro Asn Phe Glu Val Ile
305                 310

<210> SEQ ID NO 5
<211> LENGTH: 198
<212> TYPE: PRT
<213> ORGANISM: homo sapiens

<400> SEQUENCE: 5

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Val Asp Lys Gly His
50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
            85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
            115                 120                 125

Phe Ser Ile Thr Met Arg Asn Leu Thr Leu Leu Asp Ser Gly Leu Tyr
            130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
            165                 170                 175

Asn Cys Val Val Tyr Pro Ser Ser Ser Gln Glu Ser Glu Asn Ile Thr
            180                 185                 190

Ala Ala Ile Glu Gly Arg
            195

<210> SEQ ID NO 6
<211> LENGTH: 399
<212> TYPE: PRT
<213> ORGANISM: homo sapiens

<400> SEQUENCE: 6

Phe Lys Val Ala Thr Pro Tyr Ser Leu Tyr Val Cys Pro Glu Gly Gln
1               5                   10                  15

Asn Val Thr Leu Thr Cys Arg Leu Leu Gly Pro Val Asp Lys Gly His

```
                20                  25                  30
Asp Val Thr Phe Tyr Lys Thr Trp Tyr Arg Ser Ser Arg Gly Glu Val
                35                  40                  45
Gln Thr Cys Ser Glu Arg Arg Pro Ile Arg Asn Leu Thr Phe Gln Asp
                50                  55                  60
Leu His Leu His His Gly Gly His Gln Ala Ala Asn Thr Ser His Asp
65                  70                  75                  80
Leu Ala Gln Arg His Gly Leu Glu Ser Ala Ser Asp His His Gly Asn
                85                  90                  95
Phe Ser Ile Thr Met Arg Asn Leu Thr Leu Leu Asp Ser Gly Leu Tyr
                100                 105                 110
Cys Cys Leu Val Val Glu Ile Arg His His Ser Glu His Arg Val
                115                 120                 125
His Gly Ala Met Glu Leu Gln Val Gln Thr Gly Lys Asp Ala Pro Ser
                130                 135                 140
Asn Cys Val Val Tyr Pro Ser Ser Ser Gln Glu Ser Glu Asn Ile Thr
145                 150                 155                 160
Ala Ala Ile Glu Gly Arg Met Asp Pro Lys Ser Cys Asp Lys Thr His
                165                 170                 175
Thr Cys Pro Pro Cys Pro Ala Pro Glu Ala Glu Gly Ala Pro Ser Val
                180                 185                 190
Phe Leu Phe Pro Pro Lys Pro Lys Asp Thr Leu Met Ile Ser Arg Thr
                195                 200                 205
Pro Glu Val Thr Cys Val Val Val Asp Val Ser His Glu Asp Pro Glu
                210                 215                 220
Val Lys Phe Asn Trp Tyr Val Asp Gly Val Glu Val His Asn Ala Lys
225                 230                 235                 240
Thr Lys Pro Arg Glu Glu Gln Tyr Asn Ser Thr Tyr Arg Val Val Ser
                245                 250                 255
Val Leu Thr Val Leu His Gln Asp Trp Leu Asn Gly Lys Glu Tyr Lys
                260                 265                 270
Cys Lys Val Ser Asn Lys Ala Leu Pro Ala Pro Ile Glu Lys Thr Ile
                275                 280                 285
Ser Lys Ala Lys Gly Gln Pro Arg Glu Pro Gln Val Tyr Thr Leu Pro
                290                 295                 300
Pro Ser Arg Asp Glu Leu Thr Lys Asn Gln Val Ser Leu Thr Cys Leu
305                 310                 315                 320
Val Lys Gly Phe Tyr Pro Ser Asp Ile Ala Val Glu Trp Glu Ser Asn
                325                 330                 335
Gly Gln Pro Glu Asn Asn Tyr Lys Ala Thr Pro Pro Val Leu Asp Ser
                340                 345                 350
Asp Gly Ser Phe Phe Leu Tyr Ser Lys Leu Thr Val Asp Lys Ser Arg
                355                 360                 365
Trp Gln Gln Gly Asn Val Phe Ser Cys Ser Val Met His Glu Ala Leu
                370                 375                 380
His Asn His Tyr Thr Gln Lys Ser Leu Ser Leu Ser Pro Gly Lys
385                 390                 395

<210> SEQ ID NO 7
<211> LENGTH: 10
<212> TYPE: PRT
<213> ORGANISM: artificial
<220> FEATURE:
<223> OTHER INFORMATION: antibody fragment
```

```
<400> SEQUENCE: 7

Arg Ala Ser Ser Ser Val Ser Tyr Met His
1               5                   10

<210> SEQ ID NO 8
<211> LENGTH: 16
<212> TYPE: PRT
<213> ORGANISM: artificial
<220> FEATURE:
<223> OTHER INFORMATION: antibody fragment

<400> SEQUENCE: 8

Lys Ser Ser Gln Ser Leu Leu Asp Ser Asp Gly Lys Thr Tyr Leu Asn
1               5                   10                  15

<210> SEQ ID NO 9
<211> LENGTH: 11
<212> TYPE: PRT
<213> ORGANISM: artificial
<220> FEATURE:
<223> OTHER INFORMATION: antibody fragment

<400> SEQUENCE: 9

Lys Ala Ser Gln Asp Ile His Lys Tyr Val Ala
1               5                   10

<210> SEQ ID NO 10
<211> LENGTH: 11
<212> TYPE: PRT
<213> ORGANISM: artificial
<220> FEATURE:
<223> OTHER INFORMATION: antibody fragment

<400> SEQUENCE: 10

Arg Ala Ser Glu Asn Ile Asn Ser Tyr Leu Ala
1               5                   10

<210> SEQ ID NO 11
<211> LENGTH: 11
<212> TYPE: PRT
<213> ORGANISM: artificial
<220> FEATURE:
<223> OTHER INFORMATION: antibody fragment

<400> SEQUENCE: 11

Arg Thr Ser Glu Asn Ile Asn Ser Tyr Leu Ala
1               5                   10

<210> SEQ ID NO 12
<211> LENGTH: 10
<212> TYPE: PRT
<213> ORGANISM: artificial
<220> FEATURE:
<223> OTHER INFORMATION: antibody fragment

<400> SEQUENCE: 12

Ser Ala Ser Ser Ser Val Ser Phe Met Tyr
1               5                   10

<210> SEQ ID NO 13
<211> LENGTH: 10
<212> TYPE: PRT
<213> ORGANISM: artificial
<220> FEATURE:
<223> OTHER INFORMATION: antibody fragment

<400> SEQUENCE: 13
```

```
Ser Ala Ser Ser Ser Val Ser Tyr Met Asn
1               5                   10

<210> SEQ ID NO 14
<211> LENGTH: 10
<212> TYPE: PRT
<213> ORGANISM: artificial
<220> FEATURE:
<223> OTHER INFORMATION: antibody fragment

<400> SEQUENCE: 14

Arg Ala Ser Ser Ser Val Ser Tyr Ile His
1               5                   10

<210> SEQ ID NO 15
<211> LENGTH: 15
<212> TYPE: PRT
<213> ORGANISM: artificial
<220> FEATURE:
<223> OTHER INFORMATION: antibody fragment

<400> SEQUENCE: 15

Arg Ala Ser Lys Ser Val Ser Thr Ser Gly Tyr Ser Tyr Met His
1               5                   10                  15

<210> SEQ ID NO 16
<211> LENGTH: 16
<212> TYPE: PRT
<213> ORGANISM: artificial
<220> FEATURE:
<223> OTHER INFORMATION: antibody fragment

<400> SEQUENCE: 16

Arg Ser Ser Gln Ser Ile Val His Ser Asn Gly Asn Thr Tyr Leu Glu
1               5                   10                  15

<210> SEQ ID NO 17
<211> LENGTH: 11
<212> TYPE: PRT
<213> ORGANISM: artificial
<220> FEATURE:
<223> OTHER INFORMATION: antibody fragment

<400> SEQUENCE: 17

Arg Ala Ser Gln Ser Ile Ser Asn Asn Leu His
1               5                   10

<210> SEQ ID NO 18
<211> LENGTH: 7
<212> TYPE: PRT
<213> ORGANISM: artificial
<220> FEATURE:
<223> OTHER INFORMATION: antibody fragment

<400> SEQUENCE: 18

Ala Thr Ser Asn Leu Ala Ser
1               5

<210> SEQ ID NO 19
<211> LENGTH: 7
<212> TYPE: PRT
<213> ORGANISM: artificial
<220> FEATURE:
<223> OTHER INFORMATION: antibody fragment

<400> SEQUENCE: 19
```

Leu Val Ser Lys Leu Asp Ser
1               5

<210> SEQ ID NO 20
<211> LENGTH: 7
<212> TYPE: PRT
<213> ORGANISM: artificial
<220> FEATURE:
<223> OTHER INFORMATION: antibody fragment

<400> SEQUENCE: 20

Tyr Thr Ser Thr Leu Gln Pro
1               5

<210> SEQ ID NO 21
<211> LENGTH: 7
<212> TYPE: PRT
<213> ORGANISM: artificial
<220> FEATURE:
<223> OTHER INFORMATION: antibody fragment

<400> SEQUENCE: 21

Asn Ala Lys Thr Leu Ala Glu
1               5

<210> SEQ ID NO 22
<211> LENGTH: 7
<212> TYPE: PRT
<213> ORGANISM: artificial
<220> FEATURE:
<223> OTHER INFORMATION: antibody fragment

<400> SEQUENCE: 22

Asn Ala Lys Thr Leu Ala Glu
1               5

<210> SEQ ID NO 23
<211> LENGTH: 7
<212> TYPE: PRT
<213> ORGANISM: artificial
<220> FEATURE:
<223> OTHER INFORMATION: antibody fragment

<400> SEQUENCE: 23

Leu Thr Ser Asn Leu Ala Ser
1               5

<210> SEQ ID NO 24
<211> LENGTH: 7
<212> TYPE: PRT
<213> ORGANISM: artificial
<220> FEATURE:
<223> OTHER INFORMATION: antibody fragment

<400> SEQUENCE: 24

Leu Thr Ser Asn Leu Ala Ser
1               5

<210> SEQ ID NO 25
<211> LENGTH: 7
<212> TYPE: PRT
<213> ORGANISM: artificial
<220> FEATURE:
<223> OTHER INFORMATION: antibody fragment

<400> SEQUENCE: 25

Ala Thr Ser Asn Leu Ala Ser

```
1               5

<210> SEQ ID NO 26
<211> LENGTH: 7
<212> TYPE: PRT
<213> ORGANISM: artificial
<220> FEATURE:
<223> OTHER INFORMATION: antibody fragment

<400> SEQUENCE: 26

Leu Ala Ser Asn Leu Glu Ser
1               5

<210> SEQ ID NO 27
<211> LENGTH: 7
<212> TYPE: PRT
<213> ORGANISM: artificial
<220> FEATURE:
<223> OTHER INFORMATION: antibody fragment

<400> SEQUENCE: 27

Lys Val Ser Asn Arg Phe Ser
1               5

<210> SEQ ID NO 28
<211> LENGTH: 7
<212> TYPE: PRT
<213> ORGANISM: artificial
<220> FEATURE:
<223> OTHER INFORMATION: antibody fragment

<400> SEQUENCE: 28

Tyr Ala Ser Gln Ser Ile Ser
1               5

<210> SEQ ID NO 29
<211> LENGTH: 9
<212> TYPE: PRT
<213> ORGANISM: artificial
<220> FEATURE:
<223> OTHER INFORMATION: antibody fragment

<400> SEQUENCE: 29

Gln Gln Trp Ser Ser Asp Pro Pro Thr
1               5

<210> SEQ ID NO 30
<211> LENGTH: 9
<212> TYPE: PRT
<213> ORGANISM: artificial
<220> FEATURE:
<223> OTHER INFORMATION: antibody fragment

<400> SEQUENCE: 30

Trp Gln Gly Thr His Phe Pro Tyr Thr
1               5

<210> SEQ ID NO 31
<211> LENGTH: 9
<212> TYPE: PRT
<213> ORGANISM: artificial
<220> FEATURE:
<223> OTHER INFORMATION: antibody fragment

<400> SEQUENCE: 31

Leu Gln Tyr Asp Asn Leu Leu Phe Thr
1               5
```

```
<210> SEQ ID NO 32
<211> LENGTH: 9
<212> TYPE: PRT
<213> ORGANISM: artificial
<220> FEATURE:
<223> OTHER INFORMATION: antibody fragment

<400> SEQUENCE: 32

Gln His His Tyr Gly Thr Pro Pro Thr
1               5

<210> SEQ ID NO 33
<211> LENGTH: 9
<212> TYPE: PRT
<213> ORGANISM: artificial
<220> FEATURE:
<223> OTHER INFORMATION: antibody fragment

<400> SEQUENCE: 33

Gln His His Tyr Gly Thr Pro Pro Thr
1               5

<210> SEQ ID NO 34
<211> LENGTH: 9
<212> TYPE: PRT
<213> ORGANISM: artificial
<220> FEATURE:
<223> OTHER INFORMATION: antibody fragment

<400> SEQUENCE: 34

Gln Gln Trp Ser Ser Asn Pro Leu Thr
1               5

<210> SEQ ID NO 35
<211> LENGTH: 9
<212> TYPE: PRT
<213> ORGANISM: artificial
<220> FEATURE:
<223> OTHER INFORMATION: antibody fragment

<400> SEQUENCE: 35

Gln Gln Trp Ser Ser Asn Pro Leu Thr
1               5

<210> SEQ ID NO 36
<211> LENGTH: 9
<212> TYPE: PRT
<213> ORGANISM: artificial
<220> FEATURE:
<223> OTHER INFORMATION: antibody fragment

<400> SEQUENCE: 36

Gln Gln Trp Ser Ser Asn Pro Phe Thr
1               5

<210> SEQ ID NO 37
<211> LENGTH: 9
<212> TYPE: PRT
<213> ORGANISM: artificial
<220> FEATURE:
<223> OTHER INFORMATION: antibody fragment

<400> SEQUENCE: 37

Gln His Ser Arg Glu Leu Pro Tyr Thr
1               5
```

```
<210> SEQ ID NO 38
<211> LENGTH: 9
<212> TYPE: PRT
<213> ORGANISM: artificial
<220> FEATURE:
<223> OTHER INFORMATION: antibody fragment

<400> SEQUENCE: 38

Phe Gln Gly Ser His Val Pro Pro Thr
1               5

<210> SEQ ID NO 39
<211> LENGTH: 9
<212> TYPE: PRT
<213> ORGANISM: artificial
<220> FEATURE:
<223> OTHER INFORMATION: antibody fragment

<400> SEQUENCE: 39

Gln Gln Ser Asn Ser Trp Pro Leu Thr
1               5

<210> SEQ ID NO 40
<211> LENGTH: 5
<212> TYPE: PRT
<213> ORGANISM: artificial
<220> FEATURE:
<223> OTHER INFORMATION: antibody fragment

<400> SEQUENCE: 40

Ser Tyr Ser Met Ser
1               5

<210> SEQ ID NO 41
<211> LENGTH: 5
<212> TYPE: PRT
<213> ORGANISM: artificial
<220> FEATURE:
<223> OTHER INFORMATION: antibody fragment

<400> SEQUENCE: 41

Ser Tyr Ser Met Ser
1               5

<210> SEQ ID NO 42
<211> LENGTH: 5
<212> TYPE: PRT
<213> ORGANISM: artificial
<220> FEATURE:
<223> OTHER INFORMATION: antibody fragment

<400> SEQUENCE: 42

Ser Phe Gly Met His
1               5

<210> SEQ ID NO 43
<211> LENGTH: 6
<212> TYPE: PRT
<213> ORGANISM: artificial
<220> FEATURE:
<223> OTHER INFORMATION: antibody fragment

<400> SEQUENCE: 43

Ser Asp Tyr Ala Trp Asn
1               5
```

```
<210> SEQ ID NO 44
<211> LENGTH: 6
<212> TYPE: PRT
<213> ORGANISM: artificial
<220> FEATURE:
<223> OTHER INFORMATION: antibody fragment

<400> SEQUENCE: 44

Ser Asp Tyr Ala Trp Asn
1               5

<210> SEQ ID NO 45
<211> LENGTH: 5
<212> TYPE: PRT
<213> ORGANISM: artificial
<220> FEATURE:
<223> OTHER INFORMATION: antibody fragment

<400> SEQUENCE: 45

Thr Tyr Thr Ile His
1               5

<210> SEQ ID NO 46
<211> LENGTH: 5
<212> TYPE: PRT
<213> ORGANISM: artificial
<220> FEATURE:
<223> OTHER INFORMATION: antibody fragment

<400> SEQUENCE: 46

Ser Tyr Thr Met His
1               5

<210> SEQ ID NO 47
<211> LENGTH: 5
<212> TYPE: PRT
<213> ORGANISM: artificial
<220> FEATURE:
<223> OTHER INFORMATION: antibody fragment

<400> SEQUENCE: 47

Ser Tyr Ser Met Ser
1               5

<210> SEQ ID NO 48
<211> LENGTH: 5
<212> TYPE: PRT
<213> ORGANISM: artificial
<220> FEATURE:
<223> OTHER INFORMATION: antibody fragment

<400> SEQUENCE: 48

Ser Tyr Gly Met Ser
1               5

<210> SEQ ID NO 49
<211> LENGTH: 5
<212> TYPE: PRT
<213> ORGANISM: artificial
<220> FEATURE:
<223> OTHER INFORMATION: antibody fragment

<400> SEQUENCE: 49

Asp Tyr Val Ile Thr
1               5

<210> SEQ ID NO 50
```

```
<211> LENGTH: 5
<212> TYPE: PRT
<213> ORGANISM: artificial
<220> FEATURE:
<223> OTHER INFORMATION: antibody fragment

<400> SEQUENCE: 50

Gly Tyr Tyr Met His
1               5

<210> SEQ ID NO 51
<211> LENGTH: 17
<212> TYPE: PRT
<213> ORGANISM: artificial
<220> FEATURE:
<223> OTHER INFORMATION: antibody fragment

<400> SEQUENCE: 51

Tyr Ile Ser Asn Gly Gly Gly Ser Thr Tyr Tyr Pro Asp Thr Val Lys
1               5                   10                  15
Gly

<210> SEQ ID NO 52
<211> LENGTH: 17
<212> TYPE: PRT
<213> ORGANISM: artificial
<220> FEATURE:
<223> OTHER INFORMATION: antibody fragment

<400> SEQUENCE: 52

Tyr Ile Ser Asn Gly Gly Gly Ser Pro Tyr Tyr Pro Asp Thr Val Lys
1               5                   10                  15
Gly

<210> SEQ ID NO 53
<211> LENGTH: 17
<212> TYPE: PRT
<213> ORGANISM: artificial
<220> FEATURE:
<223> OTHER INFORMATION: antibody fragment

<400> SEQUENCE: 53

Tyr Ile Ser Ser Gly Ser Thr Thr Ile Tyr Tyr Ala Asp Thr Val Lys
1               5                   10                  15
Gly

<210> SEQ ID NO 54
<211> LENGTH: 16
<212> TYPE: PRT
<213> ORGANISM: artificial
<220> FEATURE:
<223> OTHER INFORMATION: antibody fragment

<400> SEQUENCE: 54

Tyr Ile Ser Tyr Ser Gly Tyr Ala Ile Tyr Asn Pro Ser Leu Lys Ser
1               5                   10                  15

<210> SEQ ID NO 55
<211> LENGTH: 16
<212> TYPE: PRT
<213> ORGANISM: artificial
<220> FEATURE:
<223> OTHER INFORMATION: antibody fragment

<400> SEQUENCE: 55
```

Tyr Ile Ser Tyr Ser Gly Tyr Thr Thr Tyr Asn Pro Ser Leu Lys Ser
1               5                   10                  15

<210> SEQ ID NO 56
<211> LENGTH: 17
<212> TYPE: PRT
<213> ORGANISM: artificial
<220> FEATURE:
<223> OTHER INFORMATION: antibody fragment

<400> SEQUENCE: 56

Tyr Ile Asn Pro Ser Ser Gly Tyr Thr Glu Tyr Asn Gln Lys Phe Lys
1               5                   10                  15
Asp

<210> SEQ ID NO 57
<211> LENGTH: 17
<212> TYPE: PRT
<213> ORGANISM: artificial
<220> FEATURE:
<223> OTHER INFORMATION: antibody fragment

<400> SEQUENCE: 57

Tyr Ile Asn Pro Ser Ser Gly Tyr Thr Glu Tyr Asn Gln Lys Phe Lys
1               5                   10                  15
Asp

<210> SEQ ID NO 58
<211> LENGTH: 17
<212> TYPE: PRT
<213> ORGANISM: artificial
<220> FEATURE:
<223> OTHER INFORMATION: antibody fragment

<400> SEQUENCE: 58

Tyr Ile Ser Asn Gly Gly Gly Ser Thr Tyr Tyr Pro Asp Thr Val Lys
1               5                   10                  15
Gly

<210> SEQ ID NO 59
<211> LENGTH: 17
<212> TYPE: PRT
<213> ORGANISM: artificial
<220> FEATURE:
<223> OTHER INFORMATION: antibody fragment

<400> SEQUENCE: 59

Ile Ile Ser Ser Gly Gly Ser Tyr Thr Tyr Tyr Pro Asp Ser Val Lys
1               5                   10                  15
Gly

<210> SEQ ID NO 60
<211> LENGTH: 17
<212> TYPE: PRT
<213> ORGANISM: artificial
<220> FEATURE:
<223> OTHER INFORMATION: antibody fragment

<400> SEQUENCE: 60

Glu Ile Tyr Pro Arg Ser Gly Ser Thr Tyr Tyr Asn Glu Asn Phe Lys
1               5                   10                  15
Gly

```
<210> SEQ ID NO 61
<211> LENGTH: 17
<212> TYPE: PRT
<213> ORGANISM: artificial
<220> FEATURE:
<223> OTHER INFORMATION: antibody fragment

<400> SEQUENCE: 61

Tyr Ile Ser Cys Ser Asn Gly Ala Ser Thr Tyr Asn Gln Lys Phe Lys
1               5                   10                  15
Gly

<210> SEQ ID NO 62
<211> LENGTH: 10
<212> TYPE: PRT
<213> ORGANISM: artificial
<220> FEATURE:
<223> OTHER INFORMATION: antibody fragment

<400> SEQUENCE: 62

His Asp Gly Asn Tyr Pro Trp Phe Ala Tyr
1               5                   10

<210> SEQ ID NO 63
<211> LENGTH: 12
<212> TYPE: PRT
<213> ORGANISM: artificial
<220> FEATURE:
<223> OTHER INFORMATION: antibody fragment

<400> SEQUENCE: 63

Leu Leu Asp Ser Ser Gly Tyr Val Trp Phe Ser Tyr
1               5                   10

<210> SEQ ID NO 64
<211> LENGTH: 14
<212> TYPE: PRT
<213> ORGANISM: artificial
<220> FEATURE:
<223> OTHER INFORMATION: antibody fragment

<400> SEQUENCE: 64

Gly Ser Tyr Tyr Arg Tyr Asp Leu Tyr Tyr Ala Met Asp Tyr
1               5                   10

<210> SEQ ID NO 65
<211> LENGTH: 8
<212> TYPE: PRT
<213> ORGANISM: artificial
<220> FEATURE:
<223> OTHER INFORMATION: antibody fragment

<400> SEQUENCE: 65

Ser Gly Gly Ser Trp Phe Ala Tyr
1               5

<210> SEQ ID NO 66
<211> LENGTH: 8
<212> TYPE: PRT
<213> ORGANISM: artificial
<220> FEATURE:
<223> OTHER INFORMATION: antibody fragment

<400> SEQUENCE: 66

Ser Gly Gly Ser Trp Phe Ala Tyr
1               5
```

```
<210> SEQ ID NO 67
<211> LENGTH: 11
<212> TYPE: PRT
<213> ORGANISM: artificial
<220> FEATURE:
<223> OTHER INFORMATION: antibody fragment

<400> SEQUENCE: 67

Arg Glu Val Tyr Gly Ser Gly Ser Met Asp Tyr
1               5                   10

<210> SEQ ID NO 68
<211> LENGTH: 11
<212> TYPE: PRT
<213> ORGANISM: artificial
<220> FEATURE:
<223> OTHER INFORMATION: antibody fragment

<400> SEQUENCE: 68

Arg Glu Val Tyr Gly Ser Gly Ala Met Asp Tyr
1               5                   10

<210> SEQ ID NO 69
<211> LENGTH: 11
<212> TYPE: PRT
<213> ORGANISM: artificial
<220> FEATURE:
<223> OTHER INFORMATION: antibody fragment

<400> SEQUENCE: 69

His Gly Asp Gly Tyr Tyr Pro Trp Phe Ala Tyr
1               5                   10

<210> SEQ ID NO 70
<211> LENGTH: 14
<212> TYPE: PRT
<213> ORGANISM: artificial
<220> FEATURE:
<223> OTHER INFORMATION: antibody fragment

<400> SEQUENCE: 70

Leu Ser Tyr Tyr Tyr Gly Ser Ser Pro Tyr Ala Met Asp Tyr
1               5                   10

<210> SEQ ID NO 71
<211> LENGTH: 3
<212> TYPE: PRT
<213> ORGANISM: artificial
<220> FEATURE:
<223> OTHER INFORMATION: antibody fragment

<400> SEQUENCE: 71

Gly Asp Tyr
1

<210> SEQ ID NO 72
<211> LENGTH: 8
<212> TYPE: PRT
<213> ORGANISM: artificial
<220> FEATURE:
<223> OTHER INFORMATION: antibody fragment

<400> SEQUENCE: 72

Ser Gly Glu Thr Pro Phe Ala Tyr
1               5
```

<210> SEQ ID NO 73
<211> LENGTH: 140
<212> TYPE: PRT
<213> ORGANISM: artificial
<220> FEATURE:
<223> OTHER INFORMATION: antibody fragment

<400> SEQUENCE: 73

```
Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Ser Val Ser Phe Met Tyr Trp Tyr His Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

Arg Ala Asp Ala Ala Pro Thr Val Ser Ile Phe Pro
    130                 135                 140
```

<210> SEQ ID NO 74
<211> LENGTH: 140
<212> TYPE: PRT
<213> ORGANISM: artificial
<220> FEATURE:
<223> OTHER INFORMATION: antibody fragment

<400> SEQUENCE: 74

```
Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
        35                  40                  45

Ser Ser Val Ser Tyr Met Asn Trp Tyr Gln Gln Lys Pro Arg Ser Ser
    50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
        115                 120                 125

Arg Ala Asp Ala Ala Pro Thr Val Ser Ile Phe Pro
    130                 135                 140
```

<210> SEQ ID NO 75
<211> LENGTH: 140
<212> TYPE: PRT
<213> ORGANISM: artificial
<220> FEATURE:

<223> OTHER INFORMATION: antibody fragment

<400> SEQUENCE: 75

Met Asp Phe Gln Val Gln Ile Phe Ser Phe Leu Leu Ile Ser Ala Ser
1               5                   10                  15

Val Val Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asn Pro Phe Thr Phe Ala Ser Gly Thr Lys Leu Glu Ile Lys
        115                 120                 125

Arg Ala Asp Ala Ala Pro Thr Val Ser Ile Phe Pro
    130                 135                 140

<210> SEQ ID NO 76
<211> LENGTH: 143
<212> TYPE: PRT
<213> ORGANISM: artificial
<220> FEATURE:
<223> OTHER INFORMATION: antibody fragment

<400> SEQUENCE: 76

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Met His Trp Tyr Gln Gln Lys Pro
    50                  55                  60

Gly Gln Ser Pro Lys Leu Leu Ile Tyr Leu Ala Ser Asn Leu Glu Ser
65                  70                  75                  80

Gly Val Pro Ala Arg Cys Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

Gln His Ser Arg Glu Leu Pro Tyr Thr Phe Gly Gly Gly Thr Lys Leu
        115                 120                 125

Glu Ile Lys Arg Ala Asp Ala Ala Pro Thr Val Ser Ile Phe Pro
    130                 135                 140

<210> SEQ ID NO 77
<211> LENGTH: 143
<212> TYPE: PRT
<213> ORGANISM: artificial
<220> FEATURE:
<223> OTHER INFORMATION: antibody fragment

<400> SEQUENCE: 77

Met Lys Leu Pro Val Arg Leu Leu Val Leu Met Phe Trp Ile Pro Ala

```
                1               5                  10                 15
            Ser Ser Ser Asp Val Leu Met Thr Gln Thr Pro Leu Ser Leu Pro Val
                           20                  25                 30

Ser Leu Gly Asp Gln Ala Ser Ile Ser Cys Arg Ser Ser Gln Ser Ile
                           35                  40                 45

Val His Ser Asn Gly Asn Thr Tyr Leu Glu Trp Tyr Leu Gln Lys Pro
                50                          55                             60

Gly Gln Ser Pro Lys Leu Leu Ile Tyr Lys Val Ser Asn Arg Phe Ser
            65                          70                  75                         80

Gly Val Pro Asp Arg Phe Ser Gly Ser Gly Ser Gly Thr Asp Phe Thr
                                   85                  90                 95

Leu Lys Ile Ser Arg Val Glu Ala Glu Asp Leu Gly Val Tyr Tyr Cys
                          100                 105                110

Phe Gln Gly Ser His Val Pro Pro Thr Phe Gly Gly Gly Thr Lys Leu
                          115                 120                125

Glu Ile Lys Arg Ala Asp Ala Ala Pro Thr Val Ser Ile Phe Pro
                          130                 135                140

<210> SEQ ID NO 78
<211> LENGTH: 139
<212> TYPE: PRT
<213> ORGANISM: artificial
<220> FEATURE:
<223> OTHER INFORMATION: antibody fragment

<400> SEQUENCE: 78

Met Val Phe Thr Pro Gln Ile Leu Gly Leu Met Leu Phe Trp Ile Ser
            1                5                  10                 15

Ala Ser Arg Gly Asp Ile Val Leu Thr Gln Ser Pro Ala Thr Leu Ser
                           20                  25                 30

Val Thr Pro Gly Asp Ser Val Ser Leu Ser Cys Arg Ala Ser Gln Ser
                           35                  40                 45

Ile Ser Asn Asn Leu His Trp Tyr Gln Gln Lys Ser His Glu Ser Pro
                50                          55                             60

Arg Leu Leu Ile Lys Tyr Ala Ser Gln Ser Ile Ser Gly Ile Pro Ser
            65                          70                  75                         80

Arg Phe Ser Gly Ser Gly Ser Gly Thr Asp Phe Thr Leu Ser Ile Asn
                                   85                  90                 95

Ser Val Glu Thr Glu Asp Phe Gly Met Tyr Phe Cys Gln Gln Ser Asn
                          100                 105                110

Ser Trp Pro Leu Thr Phe Gly Ala Gly Thr Lys Leu Glu Leu Lys Arg
                          115                 120                125

Ala Asp Ala Ala Pro Thr Val Ser Ile Phe Pro
                          130                 135

<210> SEQ ID NO 79
<211> LENGTH: 166
<212> TYPE: PRT
<213> ORGANISM: artificial
<220> FEATURE:
<223> OTHER INFORMATION: antibody fragment

<400> SEQUENCE: 79

Met Glu Arg His Trp Ile Phe Leu Phe Leu Ser Val Thr Ala Gly
            1                5                  10                 15

Val His Ser Gln Val Gln Leu Gln Gln Ser Ala Ala Glu Leu Ala Arg
                           20                  25                 30
```

Pro Gly Ala Ser Val Lys Met Ser Cys Lys Ala Ser Gly Tyr Thr Phe
            35                  40                  45

Ala Thr Tyr Thr Ile His Trp Val Lys Gln Arg Pro Gly Gln Gly Leu
    50                  55                  60

Glu Trp Ile Gly Tyr Ile Asn Pro Ser Ser Gly Tyr Thr Glu Tyr Asn
65                  70                  75                  80

Gln Lys Phe Lys Asp Lys Thr Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Glu Val Tyr Gly Ser Gly Ser Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys
            165

<210> SEQ ID NO 80
<211> LENGTH: 166
<212> TYPE: PRT
<213> ORGANISM: artificial
<220> FEATURE:
<223> OTHER INFORMATION: antibody fragment

<400> SEQUENCE: 80

Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Ala Arg
            20                  25                  30

Pro Gly Ala Ser Val Lys Met Ser Cys Lys Ala Ser Gly Tyr Thr Phe
        35                  40                  45

Thr Ser Tyr Thr Met His Trp Val Lys Gln Arg Pro Gly Gln Gly Leu
    50                  55                  60

Glu Trp Ile Gly Tyr Ile Asn Pro Ser Ser Gly Tyr Thr Glu Tyr Asn
65                  70                  75                  80

Gln Lys Phe Lys Asp Lys Thr Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Glu Val Tyr Gly Ser Gly Ala Met Asp Tyr
        115                 120                 125

Trp Gly Gln Gly Thr Ser Val Thr Val Ser Ser Ala Lys Thr Thr Pro
    130                 135                 140

Pro Ser Val Tyr Pro Leu Ala Pro Gly Ser Ala Ala Gln Thr Asn Ser
145                 150                 155                 160

Met Val Thr Leu Gly Cys
            165

<210> SEQ ID NO 81
<211> LENGTH: 166
<212> TYPE: PRT
<213> ORGANISM: artificial
<220> FEATURE:
<223> OTHER INFORMATION: antibody fragment

<400> SEQUENCE: 81

```
Met Asn Phe Gly Leu Ser Met Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
            35                  40                  45

Ser Ser Tyr Ser Met Ser Trp Val Arg Gln Thr Pro Glu Lys Arg Leu
    50                  55                  60

Glu Trp Val Ala Tyr Ile Ser Asn Gly Gly Ser Thr Tyr Tyr Pro
65                  70                  75                  80

Asp Thr Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
                100                 105                 110

Tyr Tyr Cys Ala Arg His Gly Asp Gly Tyr Tyr Pro Trp Phe Ala Tyr
            115                 120                 125

Trp Gly Gln Gly Thr Leu Val Thr Val Ser Ala Ala Lys Thr Thr Pro
            130                 135                 140

Pro Ser Val Tyr Pro Leu Ala Pro Gly Cys Gly Asp Thr Thr Gly Ser
145                 150                 155                 160

Ser Val Thr Leu Gly Cys
                165

<210> SEQ ID NO 82
<211> LENGTH: 169
<212> TYPE: PRT
<213> ORGANISM: artificial
<220> FEATURE:
<223> OTHER INFORMATION: antibody fragment

<400> SEQUENCE: 82

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
            35                  40                  45

Asn Ser Tyr Gly Met Ser Trp Val Arg Gln Thr Pro Asp Lys Arg Leu
    50                  55                  60

Glu Trp Val Ala Ile Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
                100                 105                 110

Tyr Tyr Cys Ala Arg Leu Ser Tyr Tyr Gly Ser Ser Pro Tyr Ala
            115                 120                 125

Met Asp Tyr Trp Gly Gln Gly Thr Ser Val Thr Ile Ser Ser Ala Lys
130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys
                165

<210> SEQ ID NO 83
```

<211> LENGTH: 157
<212> TYPE: PRT
<213> ORGANISM: artificial
<220> FEATURE:
<223> OTHER INFORMATION: antibody fragment

<400> SEQUENCE: 83

Met Glu Trp Arg Ile Phe Leu Phe Ile Leu Ser Gly Thr Ala Gly Val
1               5                   10                  15

His Ser Gln Val Gln Leu Gln Gln Ser Gly Pro Glu Leu Val Lys Pro
            20                  25                  30

Gly Ala Ser Val Lys Met Ser Cys Lys Ala Ser Gly Tyr Thr Phe Thr
        35                  40                  45

Asp Tyr Val Ile Thr Trp Val Lys Gln Arg Thr Gly Gln Gly Leu Glu
    50                  55                  60

Trp Ile Gly Glu Ile Tyr Pro Arg Ser Gly Ser Thr Tyr Tyr Asn Glu
65                  70                  75                  80

Asn Phe Lys Gly Lys Ala Thr Leu Thr Ala Asp Lys Ser Ser Asn Thr
                85                  90                  95

Ala Tyr Met Gln Leu Ser Ser Leu Thr Ser Glu Asp Ser Ala Val Tyr
            100                 105                 110

Phe Cys Ala Arg Gly Asp Tyr Trp Gly Gln Gly Thr Thr Leu Thr Val
        115                 120                 125

Ser Ser Ala Lys Thr Thr Pro Pro Ser Val Tyr Pro Leu Ala Pro Gly
    130                 135                 140

Cys Gly Asp Thr Thr Gly Ser Ser Val Thr Leu Gly Cys
145                 150                 155

<210> SEQ ID NO 84
<211> LENGTH: 163
<212> TYPE: PRT
<213> ORGANISM: artificial
<220> FEATURE:
<223> OTHER INFORMATION: antibody fragment

<400> SEQUENCE: 84

Met Gly Trp Ile Trp Ile Phe Leu Phe Leu Leu Ser Gly Thr Ala Gly
1               5                   10                  15

Val His Ser Glu Val Gln Val Gln Gln Ser Gly Pro Glu Leu Val Lys
            20                  25                  30

Thr Gly Ala Ser Val Lys Ile Ser Cys Lys Ala Ser Gly Tyr Ser Phe
        35                  40                  45

Thr Gly Tyr Tyr Met His Trp Val Lys Gln Ser His Gly Met Ser Leu
    50                  55                  60

Glu Trp Ile Gly Tyr Ile Ser Cys Ser Asn Gly Ala Ser Thr Tyr Asn
65                  70                  75                  80

Gln Lys Phe Lys Gly Lys Ala Thr Phe Thr Val Asp Thr Ser Ser Ser
                85                  90                  95

Thr Ala Tyr Met Gln Phe Asn Ser Leu Thr Ser Glu Asp Ser Ala Val
            100                 105                 110

Tyr Tyr Cys Ala Arg Ser Gly Glu Thr Pro Phe Ala Tyr Trp Gly Gln
        115                 120                 125

Gly Thr Leu Val Thr Val Ser Ala Ala Lys Thr Pro Pro Ser Val
    130                 135                 140

Tyr Pro Leu Ala Pro Gly Cys Gly Asp Thr Thr Gly Ser Ser Val Thr
145                 150                 155                 160

Leu Gly Cys

<210> SEQ ID NO 85
<211> LENGTH: 234
<212> TYPE: PRT
<213> ORGANISM: artificial
<220> FEATURE:
<223> OTHER INFORMATION: antibody fragment

<400> SEQUENCE: 85

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Ser Asp Pro Pro Thr Phe Gly Arg Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu
225                 230

<210> SEQ ID NO 86
<211> LENGTH: 238
<212> TYPE: PRT
<213> ORGANISM: artificial
<220> FEATURE:
<223> OTHER INFORMATION: antibody fragment

<400> SEQUENCE: 86

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp

```
                65                  70                  75                  80
Ser Gly Val Pro Asp Arg Phe Thr Gly Ser Gly Ser Gly Thr Asp Phe
                    85                  90                  95

Thr Leu Lys Ile Ser Arg Val Glu Ala Glu Asp Leu Gly Val Tyr Tyr
                100                 105                 110

Cys Trp Gln Gly Thr His Pro Tyr Thr Phe Gly Gly Gly Thr Lys
                115                 120                 125

Leu Glu Ile Lys Arg Ala Asp Ala Ala Pro Thr Val Ser Ile Phe Pro
            130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu
225                 230                 235
```

<210> SEQ ID NO 87
<211> LENGTH: 233
<212> TYPE: PRT
<213> ORGANISM: artificial
<220> FEATURE:
<223> OTHER INFORMATION: antibody fragment

<400> SEQUENCE: 87

```
Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
                20                  25                  30

Ala Ser Leu Gly Gly Lys Val Thr Ile Thr Cys Lys Ala Ser Gln Asp
            35                  40                  45

Ile His Lys Tyr Val Ala Trp Tyr Gln His Lys Pro Gly Lys Gly Pro
        50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Ser Asp Tyr Ser Phe Ser Ile Ser
                85                  90                  95

Asn Leu Glu Pro Ala Asp Ile Ala Ser Tyr Tyr Cys Leu Gln Tyr Asp
                100                 105                 110

Asn Leu Leu Phe Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
```

-continued

```
                195                 200                 205
His Asn Ser Tyr Thr Cys Glu Ala Thr His Lys Thr Ser Thr Ser Pro
    210                 215                 220

Ile Val Lys Ser Phe Asn Arg Asn Glu
225                 230

<210> SEQ ID NO 88
<211> LENGTH: 233
<212> TYPE: PRT
<213> ORGANISM: artificial
<220> FEATURE:
<223> OTHER INFORMATION: antibody fragment

<400> SEQUENCE: 88

Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Asn Ser Tyr Leu Ala Trp Tyr Gln Gln Lys Gln Gly Lys Ser Pro
    50                  55                  60

Gln Leu Leu Val Tyr Asn Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His His Tyr
            100                 105                 110

Gly Thr Pro Pro Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu
225                 230

<210> SEQ ID NO 89
<211> LENGTH: 233
<212> TYPE: PRT
<213> ORGANISM: artificial
<220> FEATURE:
<223> OTHER INFORMATION: antibody fragment

<400> SEQUENCE: 89

Met Ser Val Pro Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
            20                  25                  30
```

```
Ala Ser Val Gly Glu Thr Val Asn Ile Thr Cys Arg Thr Ser Glu Asn
         35                  40                  45

Ile Asn Ser Tyr Leu Ala Trp Tyr Gln Gln Lys Gln Gly Lys Ser Pro
 50                  55                  60

Gln Leu Leu Val Tyr Asn Ala Lys Thr Leu Ala Glu Gly Val Pro Ser
 65                  70                  75                  80

Arg Phe Ser Gly Ser Gly Ser Gly Thr Gln Phe Ser Leu Lys Ile Asn
                 85                  90                  95

Ser Leu Gln Pro Glu Asp Phe Gly Ser Tyr Tyr Cys His His Tyr
             100                 105                 110

Gly Thr Pro Pro Thr Phe Gly Gly Gly Thr Lys Leu Glu Ile Lys Arg
         115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                 165                 170                 175

Asn Gly Val Leu Asn Ser Trp Thr Asp Gln Asp Ser Lys Asp Ser Thr
             180                 185                 190

Tyr Ser Met Ser Ser Thr Leu Thr Leu Thr Lys Asp Glu Tyr Glu Arg
         195                 200                 205

His Asn Ser Tyr Thr Cys Glu Ala Thr His Lys Thr Ser Thr Ser Pro
     210                 215                 220

Ile Val Lys Ser Phe Asn Arg Asn Glu
225                 230

<210> SEQ ID NO 90
<211> LENGTH: 414
<212> TYPE: PRT
<213> ORGANISM: artificial
<220> FEATURE:
<223> OTHER INFORMATION: antibody fragment
<220> FEATURE:
<221> NAME/KEY: MISC_FEATURE
<222> LOCATION: (406)..(406)
<223> OTHER INFORMATION: Xaa can be any naturally occurring amino acid

<400> SEQUENCE: 90

Met Asn Phe Gly Leu Ser Trp Ile Phe Leu Val Pro Val Leu Lys Gly
 1               5                  10                  15

Val Leu Cys Glu Val Lys Leu Val Glu Ser Gly Arg Gly Leu Val Gln
                 20                  25                  30

Pro Gly Gly Ser Leu Lys Leu Ser Cys Ala Ala Ser Gly Phe Thr Phe
         35                  40                  45

Ser Ser Tyr Ser Met Ser Trp Val Arg Gln Thr Pro Glu Lys Arg Leu
 50                  55                  60

Glu Trp Val Ala Tyr Ile Ser Asn Gly Gly Ser Thr Tyr Tyr Pro Asp
 65                  70                  75                  80

Asp Thr Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
             100                 105                 110

Tyr Tyr Cys Ala Arg His Asp Gly Asn Tyr Pro Trp Phe Ala Tyr Trp
         115                 120                 125

Gly Gln Gly Thr Leu Val Thr Val Ser Ala Ala Lys Thr Thr Pro Pro
130                 135                 140
```

```
Ser Val Tyr Pro Leu Ala Pro Gly Cys Gly Asp Thr Thr Gly Ser Ser
145                 150                 155                 160

Val Thr Leu Gly Cys Leu Val Lys Gly Tyr Phe Pro Glu Ser Leu Glu
            165                 170                 175

Pro Ser Gly Pro Ile Ser Thr Ile Asn Pro Cys Pro Cys Lys Glu
        180                 185                 190

Cys His Lys Cys Pro Ala Pro Asn Leu Glu Gly Gly Pro Ser Val Phe
        195                 200                 205

Ile Phe Pro Pro Asn Ile Lys Asp Val Leu Met Ile Ser Leu Thr Pro
210                 215                 220

Lys Val Thr Cys Val Val Val Asp Val Ser Glu Asp Asp Pro Asp Val
225                 230                 235                 240

Gln Ile Ser Trp Phe Val Asn Asn Val Glu Val His Thr Ala Gln Thr
            245                 250                 255

Gln Thr His Arg Glu Asp Tyr Asn Ser Thr Ile Arg Val Val Ser Thr
            260                 265                 270

Leu Pro Ile Gln His Gln Asp Trp Met Ser Gly Lys Glu Phe Lys Cys
        275                 280                 285

Lys Val Asn Asn Lys Asp Leu Pro Ser Pro Ile Glu Arg Thr Ile Ser
290                 295                 300

Lys Ile Lys Gly Leu Val Arg Ala Pro Gln Val Tyr Ile Leu Pro Pro
305                 310                 315                 320

Pro Ala Glu Gln Leu Ser Arg Lys Asp Val Ser Leu Thr Cys Leu Val
            325                 330                 335

Val Gly Phe Asn Pro Gly Asp Ile Ser Val Glu Trp Thr Ser Asn Gly
            340                 345                 350

His Thr Glu Glu Asn Tyr Lys Asp Thr Ala Pro Val Leu Asp Ser Asp
        355                 360                 365

Gly Ser Tyr Phe Ile Tyr Ser Lys Leu Asn Met Lys Thr Ser Lys Trp
370                 375                 380

Glu Lys Thr Asp Ser Phe Ser Cys Asn Val Arg His Glu Gly Leu Lys
385                 390                 395                 400

Asn Tyr Tyr Leu Lys Xaa Thr Ile Ser Arg Ser Pro Gly Lys
                405                 410
```

```
<210> SEQ ID NO 91
<211> LENGTH: 404
<212> TYPE: PRT
<213> ORGANISM: artificial
<220> FEATURE:
<223> OTHER INFORMATION: antibody fragment

<400> SEQUENCE: 91
```

```
Met Asn Phe Gly Leu Ser Leu Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Ser Met Ser Trp Val Arg Leu Thr Pro Gly Lys Arg Leu
50                  55                  60

Glu Trp Val Ala Tyr Ile Ser Asn Gly Gly Ser Pro Tyr Tyr Pro
65                  70                  75              80

Asp Thr Val Lys Gly Arg Phe Thr Ile Ser Arg Asp Asn Ala Asn Asn
            85                  90                  95
```

```
Thr Leu Tyr Leu Gln Met Ser Ser Leu Lys Ser Glu Asp Thr Ala Met
                100                 105                 110

Tyr Phe Cys Thr Arg Leu Leu Asp Ser Ser Gly Tyr Val Trp Phe Ser
            115                 120                 125

Tyr Trp Gly Gln Gly Thr Leu Val Thr Val Ser Ala Ala Lys Thr Thr
130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Ile Val Pro Arg Asp Cys Gly Cys Lys Pro Cys Ile Cys Thr Val Pro
            180                 185                 190

Glu Val Ser Ser Val Phe Ile Phe Pro Pro Lys Pro Lys Asp Val Leu
        195                 200                 205

Thr Ile Thr Leu Thr Pro Lys Val Thr Cys Val Val Val Asp Ile Ser
    210                 215                 220

Lys Asp Asp Pro Glu Val Gln Phe Ser Trp Phe Val Asp Asp Val Glu
225                 230                 235                 240

Val His Thr Ala Gln Thr Gln Pro Arg Glu Glu Gln Phe Asn Ser Thr
                245                 250                 255

Phe Arg Ser Val Ser Glu Leu Pro Ile Met His Gln Asp Trp Leu Asn
            260                 265                 270

Gly Lys Glu Phe Lys Cys Arg Val Asn Ser Ala Ala Phe Pro Ala Pro
        275                 280                 285

Ile Glu Lys Thr Ile Ser Lys Thr Lys Gly Arg Pro Lys Ala Pro Gln
    290                 295                 300

Val Tyr Thr Ile Pro Pro Pro Lys Glu Gln Met Ala Lys Asp Lys Val
305                 310                 315                 320

Ser Leu Thr Cys Met Ile Thr Asp Phe Phe Pro Glu Asp Ile Thr Val
                325                 330                 335

Glu Trp Gln Trp Asn Gly Gln Pro Ala Glu Asn Tyr Lys Asn Thr Gln
            340                 345                 350

Pro Ile Met Asp Thr Asp Gly Ser Tyr Phe Val Tyr Ser Lys Leu Asn
        355                 360                 365

Val Gln Lys Ser Asn Trp Glu Ala Gly Asn Thr Phe Thr Cys Ser Val
    370                 375                 380

Leu His Glu Gly Leu His Asn His His Thr Glu Lys Ser Leu Ser His
385                 390                 395                 400

Ser Pro Gly Lys

<210> SEQ ID NO 92
<211> LENGTH: 418
<212> TYPE: PRT
<213> ORGANISM: artificial
<220> FEATURE:
<223> OTHER INFORMATION: antibody fragment

<400> SEQUENCE: 92

Met Asp Ser Arg Leu Asn Leu Val Phe Leu Val Leu Ile Leu Lys Gly
1               5                   10                  15

Val Gln Cys Asp Val Gln Leu Val Glu Ser Gly Gly Gly Leu Val Gln
                20                  25                  30

Pro Gly Gly Ser Arg Lys Leu Ser Cys Ala Ala Ser Gly Phe Thr Phe
            35                  40                  45
```

```
Ser Ser Phe Gly Met His Trp Val Arg Gln Ala Pro Glu Lys Gly Leu
 50                  55                  60

Glu Trp Val Ala Tyr Ile Ser Ser Gly Ser Thr Thr Ile Tyr Tyr Ala
 65                  70                  75                  80

Asp Thr Val Lys Gly Arg Phe Thr Ile Ser Arg Asp Asn Pro Lys Asn
                 85                  90                  95

Thr Leu Phe Leu Gln Met Thr Ser Leu Arg Ser Glu Asp Thr Ala Met
                100                 105                 110

Tyr Tyr Cys Thr Arg Gly Ser Tyr Tyr Arg Tyr Asp Leu Tyr Tyr Ala
            115                 120                 125

Met Asp Tyr Trp Gly Gln Gly Thr Ser Val Thr Val Ser Ser Ala Lys
130                 135                 140

Thr Thr Pro Pro Ser Val Tyr Pro Leu Ala Pro Gly Cys Gly Asp Thr
145                 150                 155                 160

Thr Gly Ser Ser Val Thr Leu Gly Cys Leu Val Lys Gly Tyr Phe Pro
                165                 170                 175

Glu Ser Leu Glu Pro Ser Gly Pro Ile Ser Thr Ile Asn Pro Cys Pro
                180                 185                 190

Pro Cys Lys Glu Cys His Lys Cys Pro Ala Pro Asn Leu Glu Gly Gly
            195                 200                 205

Pro Ser Val Phe Ile Phe Pro Pro Asn Ile Lys Asp Val Leu Met Ile
210                 215                 220

Ser Leu Thr Pro Lys Val Thr Cys Val Val Asp Val Ser Glu Asp
225                 230                 235                 240

Asp Pro Asp Val Gln Ile Ser Trp Phe Val Asn Asn Val Glu Val His
                245                 250                 255

Thr Ala Gln Thr Gln Thr His Arg Glu Asp Tyr Asn Ser Thr Ile Arg
                260                 265                 270

Val Val Ser Thr Leu Pro Ile Gln His Gln Asp Trp Met Ser Gly Lys
            275                 280                 285

Glu Phe Lys Cys Lys Val Asn Asn Lys Asp Leu Pro Ser Pro Ile Glu
290                 295                 300

Arg Thr Ile Ser Lys Ile Lys Gly Leu Val Arg Ala Pro Gln Val Tyr
305                 310                 315                 320

Ile Leu Pro Pro Pro Ala Glu Gln Leu Ser Arg Lys Asp Val Ser Leu
                325                 330                 335

Thr Cys Leu Val Val Gly Phe Asn Pro Gly Asp Ile Ser Val Glu Trp
            340                 345                 350

Thr Ser Asn Gly His Thr Glu Glu Asn Tyr Lys Asp Thr Ala Pro Val
355                 360                 365

Leu Asp Ser Asp Gly Ser Tyr Phe Ile Tyr Ser Lys Leu Asn Met Lys
370                 375                 380

Thr Ser Lys Trp Glu Lys Thr Asp Ser Phe Ser Cys Asn Val Arg His
385                 390                 395                 400

Glu Gly Leu Lys Asn Tyr Tyr Leu Lys Lys Thr Ile Ser Arg Ser Pro
                405                 410                 415

Gly Lys
```

<210> SEQ ID NO 93
<211> LENGTH: 399
<212> TYPE: PRT
<213> ORGANISM: artificial
<220> FEATURE:
<223> OTHER INFORMATION: antibody fragment

<400> SEQUENCE: 93

```
Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Ser Tyr Ser Gly Tyr Ala Ile Tyr Asn Pro
65                  70                  75                  80

Ser Leu Lys Ser Arg Ile Ser Ile Thr Arg Asp Thr Ser Lys Asn His
                85                  90                  95

Phe Phe Leu Gln Leu Asn Ser Val Thr Thr Glu Asp Thr Ala Thr Tyr
            100                 105                 110

Tyr Cys Ala Arg Ser Gly Gly Ser Trp Phe Ala Tyr Trp Gly Gln Gly
        115                 120                 125

Thr Leu Val Thr Val Ser Ala Ala Lys Thr Thr Pro Pro Ser Val Tyr
130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Ile Val Pro Arg Asp
                165                 170                 175

Cys Gly Cys Lys Pro Cys Ile Cys Thr Val Pro Glu Val Ser Ser Val
            180                 185                 190

Phe Ile Phe Pro Pro Lys Pro Lys Asp Val Leu Thr Ile Thr Leu Thr
        195                 200                 205

Pro Lys Val Thr Cys Val Val Val Asp Ile Ser Lys Asp Asp Pro Glu
    210                 215                 220

Val Gln Phe Ser Trp Phe Val Asp Asp Val Glu Val His Thr Ala Gln
225                 230                 235                 240

Thr Gln Pro Arg Glu Glu Gln Phe Asn Ser Thr Phe Arg Ser Val Ser
                245                 250                 255

Glu Leu Pro Ile Met His Gln Asp Trp Leu Asn Gly Lys Glu Phe Lys
            260                 265                 270

Cys Arg Val Asn Ser Ala Ala Phe Pro Ala Pro Ile Glu Lys Thr Ile
        275                 280                 285

Ser Lys Thr Lys Gly Arg Pro Lys Ala Pro Gln Val Tyr Thr Ile Pro
    290                 295                 300

Pro Pro Lys Glu Gln Met Ala Lys Asp Lys Val Ser Leu Thr Cys Met
305                 310                 315                 320

Ile Thr Asp Phe Phe Pro Glu Asp Ile Thr Val Glu Trp Gln Trp Asn
                325                 330                 335

Gly Gln Pro Ala Glu Asn Tyr Lys Asn Thr Gln Pro Ile Met Asp Thr
            340                 345                 350

Asp Gly Ser Tyr Phe Val Tyr Ser Lys Leu Asn Val Gln Lys Ser Asn
        355                 360                 365

Trp Glu Ala Gly Asn Thr Phe Thr Cys Ser Val Leu His Glu Gly Leu
    370                 375                 380

His Asn His His Thr Glu Lys Ser Leu Ser Asn Ser Pro Gly Lys
385                 390                 395
```

<210> SEQ ID NO 94

```
<211> LENGTH: 411
<212> TYPE: PRT
<213> ORGANISM: artificial
<220> FEATURE:
<223> OTHER INFORMATION: antibody fragment

<400> SEQUENCE: 94
```

| | | | | | | | | | | | | | | | |
|---|---|---|---|---|---|---|---|---|---|---|---|---|---|---|---|
| Met | Arg | Val | Leu | Ile | Leu | Leu | Trp | Leu | Phe | Thr | Ala | Phe | Pro | Gly | Met |
| 1 | | | | 5 | | | | | 10 | | | | | 15 | |
| Leu | Ser | Asp | Val | Gln | Leu | Gln | Glu | Ser | Gly | Pro | Gly | Leu | Val | Lys | Pro |
| | | | 20 | | | | | 25 | | | | | 30 | | |
| Ser | Gln | Ser | Leu | Ser | Leu | Ile | Cys | Thr | Val | Thr | Gly | Tyr | Ser | Ile | Thr |
| | | 35 | | | | | 40 | | | | | 45 | | | |
| Ser | Asp | Tyr | Ala | Trp | Asn | Trp | Ile | Arg | Gln | Phe | Pro | Gly | Asn | Lys | Leu |
| | 50 | | | | | 55 | | | | | 60 | | | | |
| Glu | Trp | Met | Gly | Tyr | Ile | Ser | Tyr | Ser | Gly | Tyr | Thr | Thr | Tyr | Asn | Pro |
| 65 | | | | | 70 | | | | | 75 | | | | | 80 |
| Ser | Leu | Lys | Ser | Arg | Ile | Ser | Ile | Thr | Arg | Asp | Thr | Ser | Lys | Asn | Gln |
| | | | | 85 | | | | | 90 | | | | | 95 | |
| Phe | Phe | Leu | Gln | Leu | Asn | Ser | Val | Thr | Thr | Glu | Asp | Thr | Ala | Thr | Tyr |
| | | | 100 | | | | | 105 | | | | | 110 | | |
| Tyr | Cys | Ala | Ile | Ser | Gly | Gly | Ser | Trp | Phe | Ala | Tyr | Trp | Gly | Gln | Gly |
| | | 115 | | | | | 120 | | | | | 125 | | | |
| Thr | Leu | Val | Thr | Val | Ser | Ala | Ala | Lys | Thr | Thr | Pro | Pro | Ser | Val | Tyr |
| 130 | | | | | 135 | | | | | 140 | | | | | |
| Pro | Leu | Ala | Pro | Gly | Cys | Gly | Asp | Thr | Thr | Gly | Ser | Ser | Val | Thr | Leu |
| 145 | | | | | 150 | | | | | 155 | | | | | 160 |
| Gly | Cys | Leu | Val | Lys | Gly | Tyr | Phe | Pro | Glu | Ser | Leu | Glu | Pro | Ser | Gly |
| | | | | 165 | | | | | 170 | | | | | 175 | |
| Pro | Ile | Ser | Thr | Ile | Asn | Pro | Cys | Pro | Pro | Cys | Lys | Glu | Cys | His | Lys |
| | | | 180 | | | | | 185 | | | | | 190 | | |
| Cys | Pro | Ala | Pro | Asn | Leu | Glu | Gly | Gly | Pro | Ser | Val | Phe | Ile | Phe | Pro |
| | | 195 | | | | | 200 | | | | | 205 | | | |
| Pro | Asn | Ile | Lys | Asp | Val | Leu | Met | Ile | Ser | Leu | Thr | Pro | Lys | Val | Thr |
| | 210 | | | | | 215 | | | | | 220 | | | | |
| Cys | Val | Val | Val | Asp | Val | Ser | Glu | Asp | Asp | Pro | Asp | Val | Gln | Ile | Ser |
| 225 | | | | | 230 | | | | | 235 | | | | | 240 |
| Trp | Phe | Val | Asn | Asn | Val | Glu | Val | His | Thr | Ala | Gln | Thr | Gln | Thr | His |
| | | | | 245 | | | | | 250 | | | | | 255 | |
| Arg | Glu | Asp | Tyr | Asn | Ser | Thr | Ile | Arg | Val | Val | Ser | Thr | Leu | Pro | Ile |
| | | | 260 | | | | | 265 | | | | | 270 | | |
| Gln | His | Gln | Asp | Trp | Met | Ser | Gly | Lys | Glu | Phe | Lys | Cys | Lys | Val | Asn |
| | | 275 | | | | | 280 | | | | | 285 | | | |
| Asn | Lys | Asp | Leu | Pro | Ser | Pro | Ile | Glu | Arg | Thr | Ile | Ser | Lys | Ile | Lys |
| | 290 | | | | | 295 | | | | | 300 | | | | |
| Gly | Leu | Val | Arg | Ala | Pro | Gln | Val | Tyr | Ile | Leu | Pro | Pro | Pro | Ala | Glu |
| 305 | | | | | 310 | | | | | 315 | | | | | 320 |
| Gln | Leu | Ser | Arg | Lys | Asp | Val | Ser | Leu | Thr | Cys | Leu | Val | Val | Gly | Phe |
| | | | | 325 | | | | | 330 | | | | | 335 | |
| Asn | Pro | Gly | Asp | Ile | Ser | Val | Glu | Trp | Thr | Ser | Asn | Gly | His | Thr | Glu |
| | | | 340 | | | | | 345 | | | | | 350 | | |
| Glu | Asn | Tyr | Lys | Asp | Thr | Ala | Pro | Val | Leu | Asp | Ser | Asp | Gly | Ser | Tyr |
| | | 355 | | | | | 360 | | | | | 365 | | | |
| Phe | Ile | Tyr | Ser | Lys | Leu | Asn | Met | Lys | Thr | Ser | Lys | Trp | Glu | Lys | Thr |
| | 370 | | | | | 375 | | | | | 380 | | | | |

```
Asp Ser Phe Ser Cys Asn Val Arg His Glu Gly Leu Lys Asn Tyr Tyr
385                 390                 395                 400

Leu Lys Lys Thr Ile Ser Arg Ser Pro Gly Lys
            405                 410

<210> SEQ ID NO 95
<211> LENGTH: 234
<212> TYPE: PRT
<213> ORGANISM: artificial
<220> FEATURE:
<223> OTHER INFORMATION: antibody fragment

<400> SEQUENCE: 95

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
            35                  40                  45

Ser Ser Val Ser Phe Met Tyr Trp Tyr His Gln Lys Pro Arg Ser Ser
50                  55                  60

Pro Lys Pro Trp Ile Tyr Leu Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Ser Asn Pro Leu Thr Phe Gly Ala Gly Thr Lys Leu Glu Leu Lys
            115                 120                 125

Arg Ala Asp Ala Ala Pro Thr Val Ser Ile Phe Pro Pro Ser Ser Glu
        130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
            195                 200                 205

Arg His Asn Ser Tyr Thr Cys Glu Ala Thr His Lys Thr Ser Thr Ser
        210                 215                 220

Pro Ile Val Lys Ser Phe Asn Arg Asn Glu
225                 230

<210> SEQ ID NO 96
<211> LENGTH: 233
<212> TYPE: PRT
<213> ORGANISM: artificial
<220> FEATURE:
<223> OTHER INFORMATION: antibody fragment

<400> SEQUENCE: 96

Met Asp Phe Gln Val Gln Ile Phe Ser Phe Leu Leu Met Ser Ala Ser
1               5                   10                  15

Val Ile Met Ser Arg Gly Gln Ile Val Leu Thr Gln Ser Pro Ala Leu
            20                  25                  30

Met Ser Ala Ser Pro Gly Glu Lys Val Thr Met Thr Cys Ser Ala Ser
```

```
                35                  40                  45
Ser Ser Val Ser Tyr Met Trp Tyr Gln Gln Lys Pro Arg Ser Ser Pro
 50                  55                  60

Lys Pro Trp Ile Tyr Leu Thr Ser Asn Leu Ala Ser Gly Val Pro Ala
 65                  70                  75                  80

Arg Phe Ser Gly Ser Gly Ser Gly Thr Ser Tyr Ser Leu Thr Ile Ser
                 85                  90                  95

Ser Met Glu Ala Glu Asp Ala Ala Thr Tyr Tyr Cys Gln Gln Trp Ser
                100                 105                 110

Ser Asn Pro Leu Thr Phe Gly Ala Gly Thr Lys Leu Glu Leu Lys Arg
                115                 120                 125

Ala Asp Ala Ala Pro Thr Val Ser Ile Phe Pro Pro Ser Ser Glu Gln
                130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
                195                 200                 205

His Asn Ser Tyr Thr Cys Glu Ala Thr His Lys Thr Ser Thr Ser Pro
                210                 215                 220

Ile Val Lys Ser Phe Asn Arg Asn Glu
225                 230

<210> SEQ ID NO 97
<211> LENGTH: 234
<212> TYPE: PRT
<213> ORGANISM: artificial
<220> FEATURE:
<223> OTHER INFORMATION: antibody fragment

<400> SEQUENCE: 97

Met Asp Phe Gln Val Gln Ile Phe Ser Phe Leu Leu Ile Ser Ala Ser
 1               5                  10                  15

Val Val Met Ser Arg Gly Gln Ile Val Leu Ser Gln Ser Pro Ala Ile
                 20                  25                  30

Leu Ser Ala Ser Pro Gly Glu Lys Val Thr Met Thr Cys Arg Ala Ser
                 35                  40                  45

Ser Ser Val Ser Tyr Ile His Trp Tyr Gln Gln Lys Pro Gly Ser Ser
 50                  55                  60

Pro Lys Pro Trp Ile Tyr Ala Thr Ser Asn Leu Ala Ser Gly Val Pro
 65                  70                  75                  80

Ala Arg Phe Ser Gly Ser Gly Ser Gly Thr Ser Tyr Ser Leu Thr Ile
                 85                  90                  95

Ser Arg Val Glu Ala Glu Asp Ala Ala Thr Tyr Tyr Cys Gln Gln Trp
                100                 105                 110

Ser Ser Asn Pro Phe Thr Phe Ala Ser Gly Thr Lys Leu Glu Ile Lys
                115                 120                 125

Arg Ala Asp Ala Ala Pro Thr Val Ser Ile Phe Pro Pro Ser Ser Glu
                130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
```

```
                165                 170                 175
Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
            195                 200                 205

Arg His Asn Ser Tyr Thr Cys Glu Ala Thr His Lys Thr Ser Thr Ser
            210                 215                 220

Pro Ile Val Lys Ser Phe Asn Arg Asn Glu
225                 230
```

<210> SEQ ID NO 98
<211> LENGTH: 237
<212> TYPE: PRT
<213> ORGANISM: artificial
<220> FEATURE:
<223> OTHER INFORMATION: antibody fragment

<400> SEQUENCE: 98

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Lys Ser
        35                  40                  45

Val Ser Thr Ser Gly Tyr Ser Tyr Met His Trp Tyr Gln Gln Lys Pro
    50                  55                  60

Gly Gln Ser Pro Lys Leu Leu Ile Tyr Leu Ala Ser Asn Leu Glu Ser
65                  70                  75                  80

Gly Val Pro Ala Arg Cys Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ser Arg Glu Leu Pro Tyr Thr Phe Gly Gly Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu
225                 230                 235
```

<210> SEQ ID NO 99
<211> LENGTH: 237
<212> TYPE: PRT
<213> ORGANISM: artificial
<220> FEATURE:
<223> OTHER INFORMATION: antibody fragment

<400> SEQUENCE: 99

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Pro Thr Phe Gly Gly Gly Thr Lys Leu
        115                 120                 125

Glu Ile Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu
225                 230                 235

<210> SEQ ID NO 100
<211> LENGTH: 233
<212> TYPE: PRT
<213> ORGANISM: artificial
<220> FEATURE:
<223> OTHER INFORMATION: antibody fragment

<400> SEQUENCE: 100

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
            20                  25                  30

Val Thr Pro Gly Asp Ser Val Ser Leu Ser Cys Arg Ala Ser Gln Ser
        35                  40                  45

Ile Ser Asn Asn Leu His Trp Tyr Gln Gln Lys Ser His Glu Ser Pro
    50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Thr Glu Asp Phe Gly Met Tyr Phe Cys Gln Gln Ser Asn
            100                 105                 110

Ser Trp Pro Leu Thr Phe Gly Ala Gly Thr Lys Leu Glu Leu Lys Arg
        115                 120                 125
```

```
Ala Asp Ala Ala Pro Thr Val Ser Ile Phe Pro Ser Ser Glu Gln
130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
210                 215                 220

Ile Val Lys Ser Phe Asn Arg Asn Glu
225                 230
```

<210> SEQ ID NO 101
<211> LENGTH: 463
<212> TYPE: PRT
<213> ORGANISM: artificial
<220> FEATURE:
<223> OTHER INFORMATION: antibody fragment

<400> SEQUENCE: 101

```
Met Glu Arg His Trp Ile Phe Leu Phe Leu Leu Ser Val Thr Ala Gly
1               5                   10                  15

Val His Ser Gln Val Gln Leu Gln Gln Ser Ala Ala Glu Leu Ala Arg
                20                  25                  30

Pro Gly Ala Ser Val Lys Met Ser Cys Lys Ala Ser Gly Tyr Thr Phe
            35                  40                  45

Ala Thr Tyr Thr Ile His Trp Val Lys Gln Arg Pro Gly Gln Gly Leu
        50                  55                  60

Glu Trp Ile Gly Tyr Ile Asn Pro Ser Ser Gly Tyr Thr Glu Tyr Asn
65                  70                  75                  80

Gln Lys Phe Lys Asp Lys Thr Thr Leu Thr Ala Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Arg Glu Val Tyr Gly Ser Gly Ser Met Asp Tyr
            115                 120                 125

Trp Gly Gln Gly Thr Ser Val Thr Val Ser Ser Ala Lys Thr Thr Pro
130                 135                 140

Pro Ser Val Tyr Pro Leu Ala Pro Gly Ser Ala Ala Gln Thr Asn Ser
145                 150                 155                 160

Met Val Thr Leu Gly Cys Leu Val Lys Gly Tyr Phe Pro Glu Pro Val
                165                 170                 175

Thr Val Thr Trp Asn Ser Gly Ser Leu Ser Ser Gly Val His Thr Phe
                180                 185                 190

Pro Ala Val Leu Gln Ser Asp Leu Tyr Thr Leu Ser Ser Ser Val Thr
            195                 200                 205

Val Pro Ser Ser Thr Trp Pro Ser Glu Thr Val Thr Cys Asn Val Ala
210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
                245                 250                 255
```

-continued

```
Phe Ile Phe Pro Pro Lys Pro Lys Asp Val Leu Thr Ile Thr Leu Thr
            260             265                 270
Pro Lys Val Thr Cys Val Val Asp Ile Ser Lys Asp Asp Pro Glu
        275                 280             285
Val Gln Phe Ser Trp Phe Val Asp Asp Val Glu Val His Thr Ala Gln
        290                 295             300
Thr Gln Pro Arg Glu Glu Gln Phe Asn Ser Thr Phe Arg Ser Val Ser
305             310                 315                 320
Glu Leu Pro Ile Met His Gln Asp Trp Leu Asn Gly Lys Glu Phe Lys
            325                 330                 335
Cys Arg Val Asn Ser Ala Ala Phe Pro Ala Pro Ile Glu Lys Thr Ile
            340                 345             350
Ser Lys Thr Lys Gly Arg Pro Lys Ala Pro Gln Val Tyr Thr Ile Pro
        355                 360             365
Pro Pro Lys Glu Gln Met Ala Lys Asp Lys Val Ser Leu Thr Cys Met
        370                 375             380
Ile Thr Asp Phe Phe Pro Glu Asp Ile Thr Val Glu Trp Gln Trp Asn
385             390                 395                 400
Gly Gln Pro Ala Glu Asn Tyr Lys Asn Thr Gln Pro Ile Met Asp Thr
            405                 410                 415
Asp Gly Ser Tyr Phe Val Tyr Ser Lys Leu Asn Val Gln Lys Ser Asn
            420                 425                 430
Trp Glu Ala Gly Asn Thr Phe Thr Cys Ser Val Leu His Glu Gly Leu
            435                 440             445
His Asn His His Thr Glu Lys Ser Leu Ser His Ser Pro Gly Lys
450                 455                 460

<210> SEQ ID NO 102
<211> LENGTH: 462
<212> TYPE: PRT
<213> ORGANISM: artificial
<220> FEATURE:
<223> OTHER INFORMATION: antibody fragment

<400> SEQUENCE: 102

Met Glu Arg His Trp Ile Phe Leu Phe Leu Ser Val Thr Ala Gly
1               5                   10                  15
Val His Ser Gln Val Gln Leu Gln Gln Ser Ala Ala Glu Leu Ala Arg
            20                  25                  30
Pro Gly Ala Ser Val Lys Met Ser Cys Lys Ala Ser Gly Tyr Thr Phe
        35                  40                  45
Thr Ser Tyr Thr Met His Trp Val Lys Gln Arg Pro Gly Gln Gly Leu
    50                  55                  60
Glu Trp Ile Gly Tyr Ile Asn Pro Ser Ser Gly Tyr Thr Glu Tyr Asn
65                  70                  75                  80
Gln Lys Phe Lys Asp Lys Thr Thr Leu Thr Ala Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Arg Glu Val Tyr Gly Ser Gly Ala Met Asp Tyr
        115                 120                 125
Trp Gly Gln Gly Thr Ser Val Thr Val Ser Ser Ala Lys Thr Thr Pro
    130                 135                 140
Pro Ser Val Tyr Pro Leu Ala Pro Gly Ser Ala Ala Gln Thr Asn Ser
145                 150                 155                 160
```

Met Val Thr Leu Gly Cys Leu Val Lys Gly Tyr Phe Pro Glu Pro Val
            165                 170                 175

Thr Val Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
            195                 200                 205

Val Pro Ser Ser Thr Trp Pro Ser Glu Thr Val Thr Cys Asn Val Ala
210                 215                 220

His Pro Ala Ser Ser Thr Lys Val Asp Lys Lys Ile Val Pro Arg Asp
225                 230                 235                 240

Cys Gly Cys Lys Pro Cys Ile Cys Thr Val Pro Glu Val Ser Ser Val
            245                 250                 255

Phe Ile Phe Pro Pro Lys Pro Lys Asp Val Leu Thr Ile Thr Leu Thr
            260                 265                 270

Pro Lys Val Thr Cys Val Val Val Asp Ile Ser Lys Asp Asp Pro Glu
            275                 280                 285

Val Gln Phe Ser Trp Phe Val Asp Asp Val Glu Val His Thr Ala Gln
            290                 295                 300

Thr Gln Pro Arg Glu Glu Gln Phe Asn Ser Thr Phe Arg Ser Val Ser
305                 310                 315                 320

Glu Leu Pro Ile Met His Gln Asp Trp Leu Asn Gly Lys Glu Phe Lys
            325                 330                 335

Cys Arg Val Asn Ser Ala Ala Pro Ala Pro Ile Glu Lys Thr Ile Ser
            340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
            405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
            450                 455                 460

<210> SEQ ID NO 103
<211> LENGTH: 475
<212> TYPE: PRT
<213> ORGANISM: artificial
<220> FEATURE:
<223> OTHER INFORMATION: antibody fragment

<400> SEQUENCE: 103

Met Asn Phe Gly Leu Ser Met Ile Phe Leu Val Leu Val Leu Lys Gly
1               5                   10                  15

Val Leu Cys Glu Val Lys Leu Val Glu Ser Gly Gly Gly Leu Val Gln
            20                  25                  30

Pro Gly Gly Ser Leu Lys Leu Ser Cys Ala Ala Ser Gly Phe Thr Phe
        35                  40                  45

Ser Ser Tyr Ser Met Ser Trp Val Arg Gln Thr Pro Glu Lys Arg Leu
    50                  55                  60

-continued

```
Glu Trp Val Ala Tyr Ile Ser Asn Gly Gly Ser Thr Tyr Tyr Pro
 65                  70                  75                  80

Asp Thr Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
            100                 105                 110

Tyr Tyr Cys Ala Arg His Gly Asp Gly Tyr Tyr Pro Trp Phe Ala Tyr
            115                 120                 125

Trp Gly Gln Gly Thr Leu Val Thr Val Ser Ala Ala Lys Thr Thr Pro
130                 135                 140

Pro Ser Val Tyr Pro Leu Ala Pro Gly Cys Gly Asp Thr Thr Gly Ser
145                 150                 155                 160

Ser Val Thr Leu Gly Cys Leu Val Lys Gly Tyr Phe Pro Glu Ser Val
                165                 170                 175

Thr Val Thr Trp Asn Ser Gly Ser Leu Ser Ser Ser Val His Thr Phe
            180                 185                 190

Pro Ala Leu Leu Gln Ser Gly Leu Tyr Thr Met Ser Ser Ser Val Thr
            195                 200                 205

Val Pro Ser Ser Thr Trp Pro Ser Gln Thr Val Thr Cys Ser Val Ala
210                 215                 220

His Pro Ala Ser Ser Thr Thr Val Asp Lys Lys Leu Glu Pro Ser Gly
225                 230                 235                 240

Pro Ile Ser Thr Ile Asn Pro Cys Pro Pro Cys Lys Glu Cys His Lys
                245                 250                 255

Cys Pro Ala Pro Asn Leu Glu Gly Gly Pro Ser Val Phe Ile Phe Pro
            260                 265                 270

Pro Asn Ile Lys Asp Val Leu Met Ile Ser Leu Thr Pro Lys Val Thr
            275                 280                 285

Cys Val Val Asp Val Ser Glu Asp Asp Pro Asp Val Gln Ile Ser
290                 295                 300

Trp Phe Val Asn Asn Val Glu Val His Thr Ala Gln Thr Gln Thr His
305                 310                 315                 320

Arg Glu Asp Tyr Asn Ser Thr Ile Arg Val Val Ser Thr Leu Pro Ile
                325                 330                 335

Gln His Gln Asp Trp Met Ser Gly Lys Glu Phe Lys Cys Lys Val Asn
            340                 345                 350

Asn Lys Asp Leu Pro Ser Pro Ile Glu Arg Thr Ile Ser Lys Ile Lys
            355                 360                 365

Gly Leu Val Arg Ala Pro Gln Val Tyr Ile Leu Pro Pro Ala Glu
370                 375                 380

Gln Leu Ser Arg Lys Asp Val Ser Leu Thr Cys Leu Val Val Gly Phe
385                 390                 395                 400

Asn Pro Gly Asp Ile Ser Val Glu Trp Thr Ser Asn Gly His Thr Glu
                405                 410                 415

Glu Asn Tyr Lys Asp Thr Ala Pro Val Leu Asp Ser Asp Gly Ser Tyr
            420                 425                 430

Phe Ile Tyr Ser Lys Leu Asn Met Lys Thr Ser Lys Trp Glu Lys Thr
            435                 440                 445

Asp Ser Phe Ser Cys Asn Val Arg His Glu Gly Leu Lys Asn Tyr Tyr
450                 455                 460

Leu Lys Lys Thr Ile Ser Arg Ser Pro Gly Lys
465                 470                 475
```

-continued

```
<210> SEQ ID NO 104
<211> LENGTH: 466
<212> TYPE: PRT
<213> ORGANISM: artificial
<220> FEATURE:
<223> OTHER INFORMATION: antibody fragment

<400> SEQUENCE: 104
```

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Asn Ser Tyr Gly Met Ser Trp Val Arg Gln Thr Pro Asp Lys Arg Leu
    50                  55                  60

Glu Trp Val Ala Ile Ile Ser Ser Gly Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Leu Ser Tyr Tyr Gly Ser Ser Pro Tyr Ala
        115                 120                 125

Met Asp Tyr Trp Gly Gln Gly Thr Ser Val Thr Ile Ser Ser Ala Lys
    130                 135                 140

Thr Thr Pro Pro Ser Val Tyr Pro Leu Ala Pro Gly Ser Ala Ala Gln
145                 150                 155                 160

Thr Asn Ser Met Val Thr Leu Gly Cys Leu Val Lys Gly Tyr Phe Pro
                165                 170                 175

Glu Pro Val Thr Val Thr Trp Asn Ser Gly Ser Leu Ser Ser Gly Val
            180                 185                 190

His Thr Phe Pro Ala Val Leu Gln Ser Asp Leu Tyr Thr Leu Ser Ser
        195                 200                 205

Ser Val Thr Val Pro Ser Ser Thr Trp Pro Ser Glu Thr Val Thr Cys
    210                 215                 220

Asn Val Ala His Pro Ala Ser Ser Thr Lys Val Asp Lys Lys Ile Val
225                 230                 235                 240

Pro Arg Asp Cys Gly Cys Lys Pro Cys Ile Cys Thr Val Pro Glu Val
                245                 250                 255

Ser Ser Val Phe Ile Phe Pro Pro Lys Pro Lys Asp Val Leu Thr Ile
            260                 265                 270

Thr Leu Thr Pro Lys Val Thr Cys Val Val Val Asp Ile Ser Lys Asp
        275                 280                 285

Asp Pro Glu Val Gln Phe Ser Trp Phe Val Asp Asp Val Glu Val His
    290                 295                 300

Thr Ala Gln Thr Gln Pro Arg Glu Glu Gln Phe Asn Ser Thr Phe Arg
305                 310                 315                 320

Ser Val Ser Glu Leu Pro Ile Met His Gln Asp Trp Leu Asn Gly Lys
                325                 330                 335

Glu Phe Lys Cys Arg Val Asn Ser Ala Ala Phe Pro Ala Pro Ile Glu
            340                 345                 350

Lys Thr Ile Ser Lys Thr Lys Gly Arg Pro Lys Ala Pro Gln Val Tyr
        355                 360                 365

Thr Ile Pro Pro Pro Lys Glu Gln Met Ala Lys Asp Lys Val Ser Leu

-continued

```
            370                 375                 380
Thr Cys Met Ile Thr Asp Phe Phe Pro Glu Asp Ile Thr Val Glu Trp
385                 390                 395                 400

Gln Trp Asn Gly Gln Pro Ala Glu Asn Tyr Lys Asn Thr Gln Pro Ile
                405                 410                 415

Met Asp Thr Asp Gly Ser Tyr Phe Val Tyr Ser Lys Leu Asn Val Gln
            420                 425                 430

Lys Ser Asn Trp Glu Ala Gly Asn Thr Phe Thr Cys Ser Val Leu His
        435                 440                 445

Glu Gly Leu His Asn His His Thr Glu Lys Ser Leu Ser His Ser Pro
    450                 455                 460

Gly Lys
465

<210> SEQ ID NO 105
<211> LENGTH: 466
<212> TYPE: PRT
<213> ORGANISM: artificial
<220> FEATURE:
<223> OTHER INFORMATION: antibody fragment

<400> SEQUENCE: 105

Met Glu Trp Arg Ile Phe Leu Phe Ile Leu Ser Gly Thr Ala Gly Val
1               5                   10                  15

His Ser Gln Val Gln Leu Gln Gln Ser Gly Pro Glu Leu Val Lys Pro
                20                  25                  30

Gly Ala Ser Val Lys Met Ser Cys Lys Ala Ser Gly Tyr Thr Phe Thr
            35                  40                  45

Asp Tyr Val Ile Thr Trp Val Lys Gln Arg Thr Gly Gln Gly Leu Glu
        50                  55                  60

Trp Ile Gly Glu Ile Tyr Pro Arg Ser Gly Ser Thr Tyr Tyr Asn Glu
65                  70                  75                  80

Asn Phe Lys Gly Lys Ala Thr Leu Thr Ala Asp Lys Ser Ser Asn Thr
                85                  90                  95

Ala Tyr Met Gln Leu Ser Ser Leu Thr Ser Glu Asp Ser Ala Val Tyr
            100                 105                 110

Phe Cys Ala Arg Gly Asp Tyr Trp Gly Gln Gly Thr Thr Leu Thr Val
        115                 120                 125

Ser Ser Ala Lys Thr Thr Pro Pro Ser Val Tyr Pro Leu Ala Pro Gly
130                 135                 140

Cys Gly Asp Thr Thr Gly Ser Ser Val Thr Leu Gly Cys Leu Val Lys
145                 150                 155                 160

Gly Tyr Phe Pro Glu Ser Val Thr Val Thr Trp Asn Ser Gly Ser Leu
                165                 170                 175

Ser Ser Ser Val His Thr Phe Pro Ala Leu Leu Gln Ser Gly Leu Tyr
            180                 185                 190

Thr Met Ser Ser Ser Val Thr Val Pro Ser Ser Thr Trp Pro Ser Gln
        195                 200                 205

Thr Val Thr Cys Ser Val Ala His Pro Ala Ser Ser Thr Thr Val Asp
    210                 215                 220

Lys Lys Leu Glu Pro Ser Gly Pro Ile Ser Thr Ile Asn Pro Cys Pro
225                 230                 235                 240

Pro Cys Lys Glu Cys His Lys Cys Pro Ala Pro Asn Leu Glu Gly Gly
                245                 250                 255

Pro Ser Val Phe Ile Phe Pro Pro Asn Ile Lys Asp Val Leu Met Ile
```

```
                       260                 265                 270
Ser Leu Thr Pro Lys Val Thr Cys Val Val Asp Val Ser Glu Asp
            275                 280                 285
Asp Pro Asp Val Gln Ile Ser Trp Phe Val Asn Asn Val Glu Val His
            290                 295                 300
Thr Ala Gln Thr Gln Thr His Arg Glu Asp Tyr Asn Ser Thr Ile Arg
305                 310                 315                 320
Val Val Ser Thr Leu Pro Ile Gln His Gln Asp Trp Met Ser Gly Lys
            325                 330                 335
Glu Phe Lys Cys Lys Val Asn Asn Lys Asp Leu Pro Ser Pro Ile Glu
            340                 345                 350
Arg Thr Ile Ser Lys Ile Lys Gly Leu Val Arg Ala Pro Gln Val Tyr
            355                 360                 365
Ile Leu Pro Pro Pro Ala Glu Gln Leu Ser Arg Lys Asp Val Ser Leu
            370                 375                 380
Thr Cys Leu Val Val Gly Phe Asn Pro Gly Asp Ile Ser Val Glu Trp
385                 390                 395                 400
Thr Ser Asn Gly His Thr Glu Glu Asn Tyr Lys Asp Thr Ala Pro Val
            405                 410                 415
Leu Asp Ser Asp Gly Ser Tyr Phe Ile Tyr Ser Lys Leu Asn Met Lys
            420                 425                 430
Thr Ser Lys Trp Glu Lys Thr Asp Ser Phe Ser Cys Asn Val Arg His
            435                 440                 445
Glu Gly Leu Lys Asn Tyr Tyr Leu Lys Lys Thr Ile Ser Arg Ser Pro
            450                 455                 460
Gly Lys
465

<210> SEQ ID NO 106
<211> LENGTH: 472
<212> TYPE: PRT
<213> ORGANISM: artificial
<220> FEATURE:
<223> OTHER INFORMATION: antibody fragment

<400> SEQUENCE: 106

Met Gly Trp Ile Trp Ile Phe Leu Phe Leu Leu Ser Gly Thr Ala Gly
1               5                   10                  15
Val His Ser Glu Val Gln Val Gln Gln Ser Gly Pro Glu Leu Val Lys
            20                  25                  30
Thr Gly Ala Ser Val Lys Ile Ser Cys Lys Ala Ser Gly Tyr Ser Phe
            35                  40                  45
Thr Gly Tyr Tyr Met His Trp Val Lys Gln Ser His Gly Met Ser Leu
            50                  55                  60
Glu Trp Ile Gly Tyr Ile Ser Cys Ser Asn Gly Ala Ser Thr Tyr Asn
65                  70                  75                  80
Gln Lys Phe Lys Gly Lys Ala Thr Phe Thr Val Asp Thr Ser Ser Ser
            85                  90                  95
Thr Ala Tyr Met Gln Phe Asn Ser Leu Thr Ser Glu Asp Ser Ala Val
            100                 105                 110
Tyr Tyr Cys Ala Arg Ser Gly Glu Thr Pro Phe Ala Tyr Trp Gly Gln
            115                 120                 125
Gly Thr Leu Val Thr Val Ser Ala Ala Lys Thr Thr Pro Pro Ser Val
            130                 135                 140
Tyr Pro Leu Ala Pro Gly Cys Gly Asp Thr Thr Gly Ser Ser Val Thr
```

```
145                 150                 155                 160
Leu Gly Cys Leu Val Lys Gly Tyr Phe Pro Glu Ser Val Thr Val Thr
                165                 170                 175
Trp Asn Ser Gly Ser Leu Ser Ser Val His Thr Phe Pro Ala Leu
            180                 185                 190
Leu Gln Ser Gly Leu Tyr Thr Met Ser Ser Val Thr Val Pro Ser
            195                 200                 205
Ser Thr Trp Pro Ser Gln Thr Val Thr Cys Ser Val Ala His Pro Ala
    210                 215                 220
Ser Ser Thr Thr Val Asp Lys Lys Leu Glu Pro Ser Gly Pro Ile Ser
225                 230                 235                 240
Thr Ile Asn Pro Cys Pro Pro Cys Lys Glu Cys His Lys Cys Pro Ala
                245                 250                 255
Pro Asn Leu Glu Gly Gly Pro Ser Val Phe Ile Phe Pro Pro Asn Ile
                260                 265                 270
Lys Asp Val Leu Met Ile Ser Leu Thr Pro Lys Val Thr Cys Val Val
                275                 280                 285
Val Asp Val Ser Glu Asp Asp Pro Asp Val Gln Ile Ser Trp Phe Val
                290                 295                 300
Asn Asn Val Glu Val His Thr Ala Gln Thr Gln Thr His Arg Glu Asp
305                 310                 315                 320
Tyr Asn Ser Thr Ile Arg Val Val Ser Thr Leu Pro Ile Gln His Gln
                325                 330                 335
Asp Trp Met Ser Gly Lys Glu Phe Lys Cys Lys Val Asn Asn Lys Asp
                340                 345                 350
Leu Pro Ser Pro Ile Glu Arg Thr Ile Ser Lys Ile Lys Gly Leu Val
                355                 360                 365
Arg Ala Pro Gln Val Tyr Ile Leu Pro Pro Ala Glu Gln Leu Ser
                370                 375                 380
Arg Lys Asp Ala Ser Leu Thr Cys Leu Val Val Gly Phe Asn Pro Gly
385                 390                 395                 400
Asp Ile Ser Val Glu Trp Thr Ser Asn Gly His Thr Glu Glu Asn Tyr
                405                 410                 415
Lys Asp Thr Ala Pro Val Leu Asp Ser Asp Gly Ser Tyr Phe Ile Tyr
                420                 425                 430
Ser Lys Leu Asn Met Lys Thr Ser Lys Trp Glu Lys Thr Asp Ser Phe
                435                 440                 445
Ser Cys Asn Val Arg His Glu Gly Leu Lys Asn Tyr Tyr Leu Lys Lys
    450                 455                 460
Thr Ile Ser Arg Ser Pro Gly Lys
465                 470
```